(12) United States Patent
Bellott et al.

(10) Patent No.: US 8,008,088 B2
(45) Date of Patent: Aug. 30, 2011

(54) SMMR (SMALL MOLECULE METABOLITE REPORTERS) FOR USE AS IN VIVO GLUCOSE BIOSENSORS

(75) Inventors: Emile M. Bellott, Beverly, MA (US); Dongsheng Bu, Piscataway, NJ (US); James J. Childs, Bolton, MA (US); Christopher Lambert, Hudson, MA (US); Hubert A. Nienaber, Newburyport, MA (US); Shirley J. Shi, Lexington, MA (US); Zhaolin Wang, Wellesley, MA (US); Jerome J. Workman, Madison, WI (US); Alex R. Zelenchuk, Stoughton, MA (US)

(73) Assignee: Masimo Laboratories, Inc., Irvine, CA (US)

( * ) Notice: Subject to any disclaimer, the term of this patent is extended or adjusted under 35 U.S.C. 154(b) by 0 days.

(21) Appl. No.: 11/475,784

(22) Filed: Jun. 26, 2006

(65) Prior Publication Data

US 2007/0110672 A1   May 17, 2007

Related U.S. Application Data

(63) Continuation of application No. PCT/US2004/043087, filed on Dec. 23, 2004.

(60) Provisional application No. 60/532,667, filed on Dec. 24, 2003, provisional application No. 60/571,170, filed on May 14, 2004.

(51) Int. Cl.
G01N 33/00 (2006.01)
A61K 49/00 (2006.01)

(52) U.S. Cl. ......... 436/95; 436/172; 436/164; 436/518; 436/546; 424/9.6; 424/9.1

(58) Field of Classification Search .................... 436/95, 436/172, 518, 546, 68, 164, 516; 549/223; 252/582; 600/316; 424/9.6, 9.1
See application file for complete search history.

(56) References Cited

U.S. PATENT DOCUMENTS

| | | | |
|---|---|---|---|
| H227 H | 3/1987 | Tracy et al. | |
| 4,810,636 A * | 3/1989 | Corey | 435/14 |
| 5,208,332 A | 5/1993 | Marrone et al. | |
| 5,362,628 A | 11/1994 | Haughland et al. | |
| 5,451,343 A * | 9/1995 | Neckers et al. | 252/582 |
| 5,503,770 A | 4/1996 | James et al. | |
| 5,512,246 A | 4/1996 | Russell et al. | |
| 5,605,152 A | 2/1997 | Slate et al. | |
| 5,624,847 A * | 4/1997 | Lakowicz et al. | 436/68 |
| 5,936,087 A * | 8/1999 | Benson et al. | 546/33 |
| 6,002,954 A | 12/1999 | Van Antwerp et al. | |
| 6,011,984 A | 1/2000 | Van Antwerp et al. | |
| 6,040,194 A | 3/2000 | Chick et al. | |
| 6,130,101 A * | 10/2000 | Mao et al. | 436/546 |
| 6,150,097 A | 11/2000 | Tyagi et al. | |
| 6,162,931 A * | 12/2000 | Gee et al. | 549/223 |
| 6,304,766 B1 | 10/2001 | Colvin, Jr. | |
| 6,319,540 B1 | 11/2001 | Van Antwerp et al. | |
| 6,330,464 B1 | 12/2001 | Colvin, Jr. et al. | |
| 6,344,360 B1 | 2/2002 | Colvin et al. | |
| 6,360,888 B1 | 3/2002 | McIvor et al. | |
| 6,368,274 B1 | 4/2002 | Van Antwerp et al. | |
| 6,377,721 B1 | 4/2002 | Walt et al. | |
| 6,399,392 B1 * | 6/2002 | Haugland et al. | 436/172 |
| 6,400,974 B1 | 6/2002 | Lesho | |
| 6,484,045 B1 | 11/2002 | Holker et al. | |
| 6,485,703 B1 | 11/2002 | Cote et al. | |
| 6,558,320 B1 | 5/2003 | Causey, III et al. | |
| 6,673,625 B2 | 1/2004 | Satcher, Jr. et al. | |
| 6,682,938 B1 | 1/2004 | Satcher, Jr. et al. | |
| 6,711,423 B2 | 3/2004 | Colvin | |
| 6,750,311 B1 | 6/2004 | Van Antwerp et al. | |
| 6,766,183 B2 | 7/2004 | Walsh et al. | |
| 6,794,195 B2 | 9/2004 | Colvin, Jr. | |
| 6,800,451 B2 | 10/2004 | Daniloff | |
| 6,804,544 B2 | 10/2004 | Van Antwerp et al. | |
| 6,806,089 B1 | 10/2004 | Lakowicz et al. | |
| 6,927,246 B2 | 8/2005 | Noronha et al. | |
| 6,940,590 B2 | 9/2005 | Colvin, Jr. et al. | |
| 7,003,336 B2 | 2/2006 | Holker et al. | |
| 7,016,714 B2 | 3/2006 | Colvin, Jr. | |
| 7,045,361 B2 | 5/2006 | Heiss et al. | |
| 7,060,503 B2 | 6/2006 | Colvin, Jr. | |
| 7,078,554 B2 | 7/2006 | Daniloff et al. | |
| 7,135,342 B2 | 11/2006 | Colvin, Jr. et al. | |
| 7,157,723 B2 | 1/2007 | Colvin et al. | |
| 7,166,074 B2 | 1/2007 | Reghabi et al. | |

(Continued)

FOREIGN PATENT DOCUMENTS

WO   WO 97/19188   5/1997

(Continued)

OTHER PUBLICATIONS

Kataoka et al, Novel sensing system for glucose based on the complex formation between phenylborate and fluorescent diol compound, J. Biochem., 1995, 117:1145-1147.

Sandanayake et al., Molecular fluorescence sensor for Saccharides based on amino coumarin, Chemistry Letters, 1995, 139-140.

Koschinsky, T. et al., Sensors for glucose monitoring: technical and clinical aspects. Diabetes Metab. Res. Rev., vol. 17, pp. 113-123, 2001.

Connor, J.A., Digital imaging of free calcium changes and of spatial gradients in growing processes in single, mammalian central nervous system cells. Proc. Natl. Acad. Sci. USA, 83: 6179-6183, 1986.

(Continued)

*Primary Examiner* — Walter D Griffin
*Assistant Examiner* — Christine T Mui
(74) *Attorney, Agent, or Firm* — Knobbe, Martens, Olson & Bear, LLP

(57) ABSTRACT

Small Molecule Metabolite Reporters (SMMRs) for use as in vivo glucose biosensors, sensor compositions, and methods of use, are described. The SMMRs include boronic acid-containing xanthene, coumarin, carbostyril and phenalene-based small molecules which are used for monitoring glucose in vivo, advantageously on the skin.

6 Claims, 53 Drawing Sheets

U.S. PATENT DOCUMENTS

| | | |
|---|---|---|
| 7,190,445 B2 | 3/2007 | Colvin, Jr. et al. |
| 7,227,156 B2 | 6/2007 | Colvin, Jr. et al. |
| 7,247,138 B2 | 7/2007 | Reghabi et al. |
| 7,289,836 B2 | 10/2007 | Colvin, Jr. |
| 7,384,397 B2 | 6/2008 | Zhang et al. |
| 7,405,387 B2 | 7/2008 | Colvin, Jr. et al. |
| 2002/0043651 A1 | 4/2002 | Darrow et al. |
| 2002/0123675 A1 | 9/2002 | Trautman et al. |
| 2002/0193672 A1* | 12/2002 | Walsh et al. .......... 600/316 |
| 2003/0008405 A1* | 1/2003 | Lippard et al. .......... 436/73 |
| 2004/0064086 A1 | 4/2004 | Gottlieb et al. |
| 2004/0206916 A1 | 10/2004 | Colvin, Jr. et al. |
| 2004/0229370 A1 | 11/2004 | Colvin, Jr. |
| 2005/0191761 A1* | 9/2005 | Heiss et al. .......... 436/518 |
| 2005/0227242 A1 | 10/2005 | Colvin, Jr., et al. |
| 2006/0281185 A1 | 12/2006 | Colvin |
| 2007/0014726 A1 | 1/2007 | Merical et al. |
| 2007/0059210 A1 | 3/2007 | Colvin, Jr., et al. |
| 2008/0064944 A1 | 3/2008 | Van Antwerp et al. |
| 2008/0108885 A1 | 5/2008 | Colvin, Jr |
| 2008/0145944 A1 | 6/2008 | Colvin et al. |
| 2009/0039286 A1 | 2/2009 | Colvin, , Jr. et al. |

FOREIGN PATENT DOCUMENTS

| | | |
|---|---|---|
| WO | WO0014515 | 3/2000 |

OTHER PUBLICATIONS

Wachtler J. et al., Glucose availability alters ischaemia-induced changes in intracellular pH and calcium of isolated rat spinal roots. Brain Research, 725: 30-36, 1996.

International Preliminary Report on Patentability (5 pgs.), 2006.

International Search Report (8 pgs.), 2006.

\* cited by examiner

SEQUENCE #

ADDITIONAL RING SUBSTRUCTURES

JAMES AND SHINKAI

JAMES AND SHINKAI

JAMES AND SHINKAI

DRUECKHAMMER

EGGERT ET AL.

CYCLIC DECAPEPTIDE A

WGSGGYGSGG

CYCLIC DECAPEPTIDE B

WGSGGKGSGG

CROWN ETHER WITH BORONIC ACID FLUOROPHORES AND AUXILIARY BINDING SIDE CHAINS

SMMR (SMALL MOLECULE METABOLITE REPORTERS) FOR USE AS IN VIVO GLUCOSE BIOSENSORS

RELATED APPLICATIONS

This application is a continuation of International Application No. PCT/US2004/043087, filed Dec. 23, 2004, which claims priority under 35 U.S.C. §119(e) to Provisional Application Nos. 60/532,667, filed Dec. 24, 2003 and 60/571,170, filed May 14, 2004.

FIELD OF THE INVENTION

This invention provides compositions and methods for designing small molecule metabolite reporters (SMMRs) for optical reporting of cell metabolism and intracellular or extracellular metabolite or analyte concentrations. The specific application of this work is to design molecules that are able to optically report the concentration of the biologically active molecule D-glucose, including other small molecule analytes or metabolic processes, in or near human keratinocytes located within the viable epidermis of human or mammalian skin. The skin glucose levels are then used to infer blood glucose levels. In particular, this invention provides compositions and methods for several non-invasive techniques to determine in vivo blood glucose levels based upon the direct measurement of glucose levels present in the skin.

BACKGROUND OF THE INVENTION

Identifying and understanding the risk factors associated with diabetes is invaluable for the development and evaluation of effective intervention strategies. Lacking normal regulatory mechanisms, diabetics are encouraged to strive for optimal control through a modulated life style approach that focuses on dietary control, exercise, and glucose self-testing with the timely administration of insulin or oral hypoglycemic medications. Invasive forms of self-testing are painful and fraught with a multitude of psychosocial hurdles, and are resisted by most diabetics. Alternatives to the currently available invasive blood glucose testing are highly desirable.

Conventional approaches seek to reduce or eliminate the skin trauma, pain, and blood waste associated with traditional invasive glucose monitoring technologies. In general, non-invasive optical blood glucose monitoring requires no samples and involves external irradiation with electromagnetic radiation and measurement of the resulting optical flux. Glucose levels are derived from the spectral information following comparison to reference spectra for glucose and background interferants, reference calibrants, and/or application of advanced signal processing mathematical algorithms. Candidate radiation-based technologies include: 1) mid-infrared (MIR) spectroscopy, 2) near-infrared (NIR) spectroscopy, 3) far-infrared (FIR) spectroscopy, 4) radio wave impedance, 5) infrared photoacoustic spectroscopy and 6) Raman spectroscopy. Each of these methods uses optical sensors, and relies on the premise that the absorption pattern of infrared light (700-3000 nm) can be quantitatively related to the glucose concentration. Other substances such as water, protein, and hemoglobin are known to absorb infrared light at these wavelengths and easily obscure the relatively weak glucose signal.

Other approaches are based on microvascular changes in the retina; acoustical impedance, NMR spectroscopy and optical hydrogels that quantify glucose levels in tear fluid. While putatively non-invasive, these technologies have yet to be demonstrated as viable in clinical testing.

Nearly non-invasive techniques tend to rely on interstitial fluid extraction from skin. This can be accomplished using permeability enhancers, sweat inducers, and/or suction devices with or without the application of electrical current. One device recently approved by the FDA relies on reverse iontophoresis, utilizing an electrical current applied to the skin. The current pulls out salt, which carries water, which in turn carries glucose. The glucose concentration of this extracted fluid is measured and is proportional to that of blood. This technology, in keeping with its nearly non-invasive description, is commonly associated with some discomfort and requires at least twice daily calibrations against conventional blood glucose measurements (e.g., invasive lancing).

Other nearly non-invasive blood glucose monitoring techniques similarly involve transcutaneous harvesting for interstitial fluid measurement. Other technologies for disrupting the skin barrier to obtain interstitial fluid include: 1) dissolution with chemicals; 2) microporation with a laser, sound, or electrical stimulation; 3) penetration with a thin needle; and/or 4) suction with a pump. Minimally invasive blood glucose monitoring can also involve the insertion of an indwelling glucose monitor under the skin to measure the interstitial fluid glucose concentration. These monitors typically rely on optical or enzymatic sensors. Technologically innovative, these in situ sensors have had limited success. Implantable glucose oxidase sensors have been limited by local factors causing unstable signal output, whereas optical sensors must overcome signal obfuscation by blood constituents as well as interference by substances with absorption spectra similar to glucose. Moreover, inflammation associated with subcutaneous monitoring may contribute to systematic errors requiring repositioning, recalibration or replacement, and more research is needed to evaluate the effects of variable local inflammation at the sensor implantation site on glucose concentration and transit time.

Interstitial fluid glucose concentrations have previously been shown to be similar to simultaneously measured fixed or fluctuating blood glucose concentrations (Bantle et al., *Journal of Laboratory and Clinical Medicine* 130:436-441, 1997; Sternberg et al., *Diabetes Care* 18:1266-1269, 1995). Such studies helped validate non-invasive/minimally invasive technologies for blood glucose monitoring, insofar as many of these technologies measure glucose in blood as well as interstitial fluid.

A non-invasive glucose monitor that is portable, simple and rapid to use, and that provides accurate clinical information is highly desirable. In particular, the ability to derive primary and secondary order information regarding real time, dynamic glucose metabolism (such as the direction and rate of change of bioavailable glucose distributed within the blood and interstitial fluid space) is highly desirable.

SUMMARY OF THE INVENTION

In vivo fluorescence (autofluorescence) has been used for a number of years to determine the metabolic state and to monitor pharmaceutical effects in cells and tissues (Dellinger et al., *Biotechnol Appl Biochem*, 28(Pt. 1): 25-32, 1998). Consideration of the photophysics involved in autofluorescence rapidly leads one to the conclusion that the use of autofluorescence alone as the analytic probe imposes some severe limitations on any measurement technique.

Fluorescence techniques are capable of detecting molecular species at picomole levels or less. This sensitivity arises because of the simplicity of detecting single photons against a dark background. This advantage disappears if there are other fluorescent species in the detection volume. Fluorescence intensity is also not an absolute technique and must be referenced to some internal standard using a ratiometric or comparative method.

It has been shown that fluorophores, or colored dyes utilizing absorption spectroscopy can be used to measure glucose in solution or serum by using series of separate reagents. These generic reagents include glucose oxidase (which oxidizes glucose forming hydrogen peroxide); peroxidase (generally, horseradish peroxidase: HRP) used to create an oxidizing reaction in the presence of hydrogen peroxide with the dye or fluorophore; and a dye reagent or fluorophore, which changes its color or fluorescence spectrum when brought in contact with hydrogen peroxide, and peroxidase. The resultant colored or fluorescent species is measured with a calorimeter or fluorimeter and the amount of glucose in solution is calculated. In addition, other analytical techniques have been shown to be commercially useful for measuring hydrogen peroxide generated from the reaction of glucose oxidase and glucose.

The methods and compositions of the present invention effectively determine the glucose concentration in blood for a living organism by non-invasive, in vivo measurement of the glucose level in skin by means of fluorescence measurements of metabolic indicators/reporters of glucose metabolism. Disclosed are dyes used as metabolic indicators that allow for specific in vivo monitoring of metabolites, which are used as indicators of metabolic activity. Dyes characterized by this invention are referred to herein as a small molecule metabolite reporters ("SMMRs") or alternatively, "small molecule multi-domain reporters ("SMMDRs".) In many cases the description in the specification will apply to both terms.

The invention relates in one aspect to SMMRs which comprise novel xanthene-based boronic acid compounds. The SMMRs may be used in sensor compositions for, e.g., direct measurement of glucose, and in other diagnostic or analytical methods as described herein. In an embodiment these compounds are of the following formula (I):

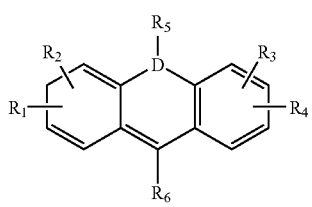

wherein
D is a heteroatom;
$R_1$ and $R_2$ are different and are selected from the group consisting of H, OH, $NH_2$, $NO_2$, $OCH_3$, $N(CH_3)_2$, A, or, $R_1$ and $R_2$, taken together with the ring to which they are attached, form $R_7$;
$R_3$ and $R_4$ are different and are selected from the group consisting of H,

OH, $B(OH)_2$, M, or $R_3$ and $R_4$, taken together with the ring to which they are attached, form $R_8$;
$R_5$ and $R_6$ are different and are selected from the group consisting of H or

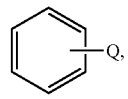

wherein Q is H, COOH, $B(OH)_2$, or M;
A is OH, $NH_3$,

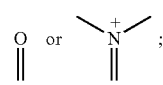

$R_7$ is

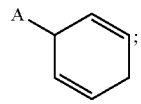

$R_8$ is

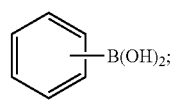

M is

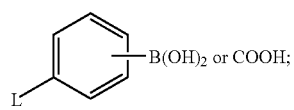

L, when present, is an amino-containing linking moiety;
$R_1$ and $R_2$, and $R_3$ and $R_4$, are adjacent to each other on the rings on which they reside; and
at least one boronic acid moiety is present; and salts thereof.

"Amino-containing linking moieties" may include moieties comprising a substituted or unsubstituted amino group, an amido group or a sulfonamido group. In an embodiment, xanthene-based boronic acid compounds of the invention include those of the formula (II):

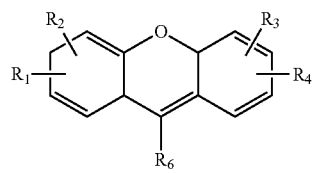

wherein
$R_1$ and $R_2$ are different and may be A, or, $R_1$ and $R_2$, taken together with the ring to which they are attached, form $R_7$;

$R_3$ and $R_4$ are different and are selected from the group consisting of H,

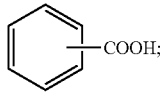

OH, $B(OH)_2$, M, or $R_3$ and $R_4$, taken together with the ring to which they are attached, form $R_8$;

$R_6$ is

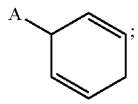

A is

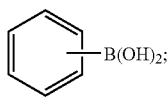

$R_7$ is

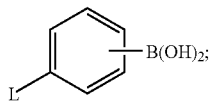

$R_8$ is

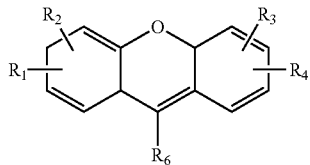

M is

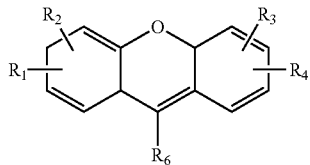

L, when present, is an amino-containing linking moiety; and $R_1$ and $R_2$, and $R_3$ and $R_4$, are adjacent to each other on the rings on which they reside; and salts thereof.

In another embodiment, xanthene-based boronic acid compounds of the invention include those of the formula (III):

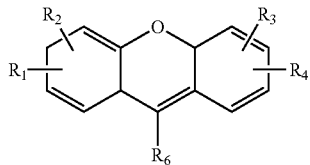

(III)

wherein $R_1$ and $R_2$ are different and are selected from the group consisting of H, OH, $NH_2$, $NO_2$, $OCH_3$, $N(CH_3)_2$, A, or, $R_1$ and $R_2$, taken together with the ring to which they are attached, form $R_7$;

$R_3$ and $R_4$ are different and are selected from the group consisting of H,

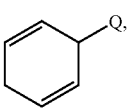

OH, M, or $R_3$ and $R_4$, taken together with the ring to which they are attached, form $R_8$;

$R_5$ and $R_6$ are different and are selected from the group consisting of H or

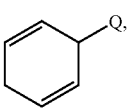

wherein Q is H or M;

A is

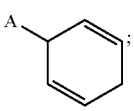

$R_7$ is

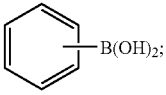

$R_8$ is

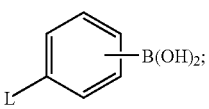

M is

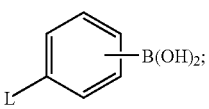

L, when present, is an amino-containing linking moiety; and $R_1$ and $R_2$, and $R_3$ and $R_4$, are adjacent to each other on the rings on which they reside; and salts thereof.

Examples of xanthene-based SMMRs of the invention include:
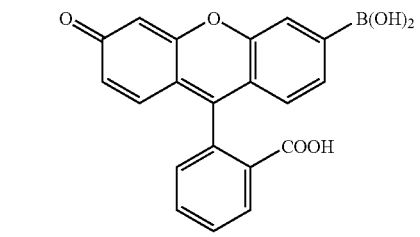
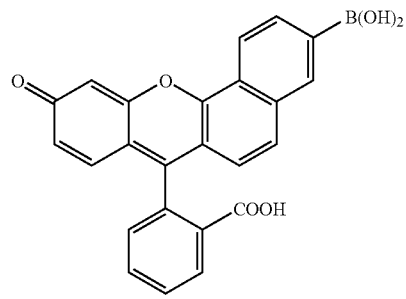
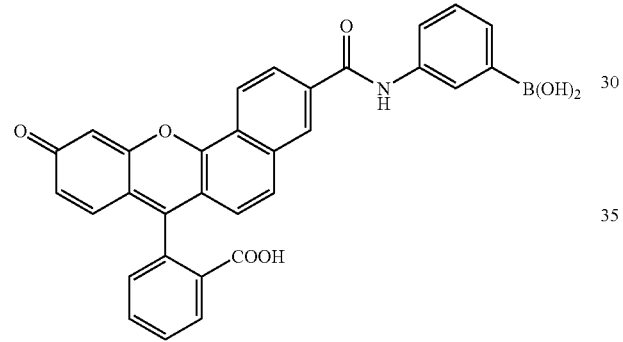
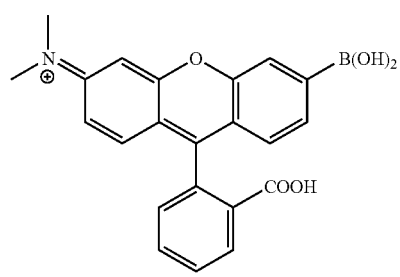
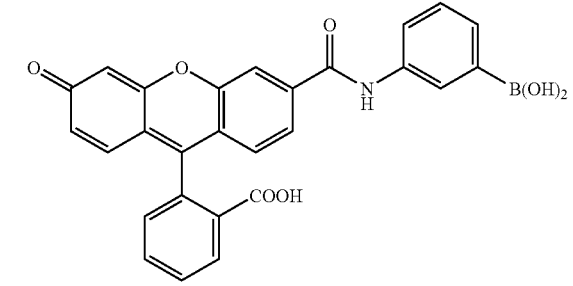
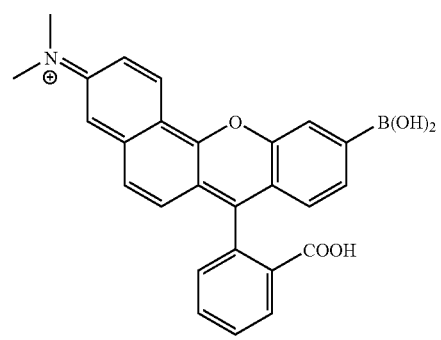
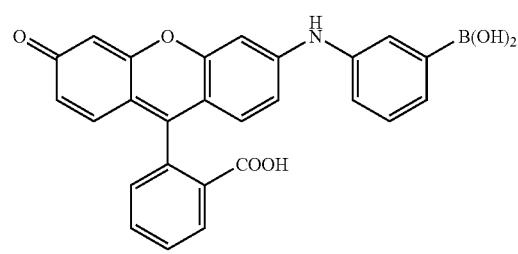
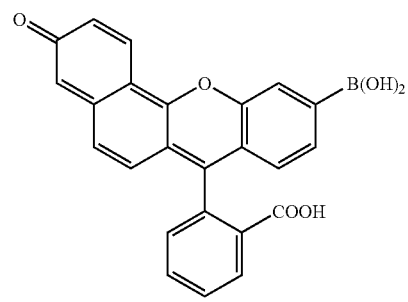
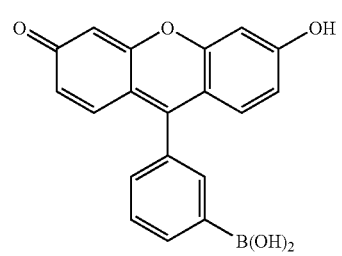
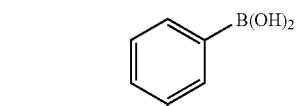
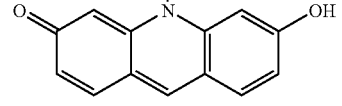
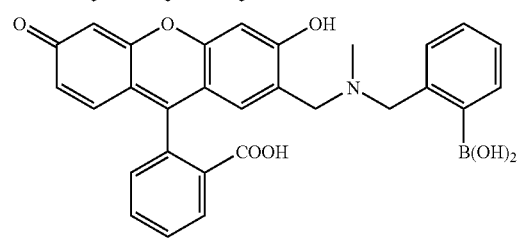

-continued

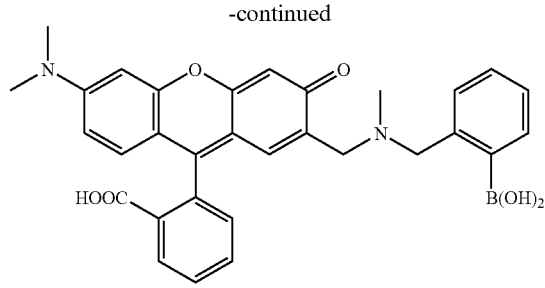

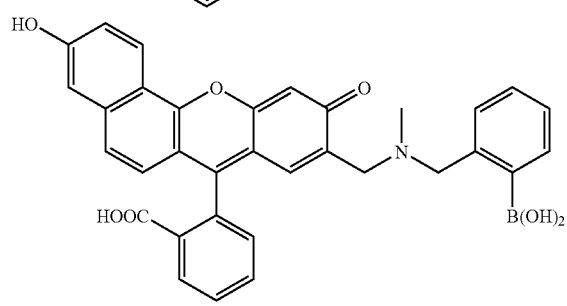

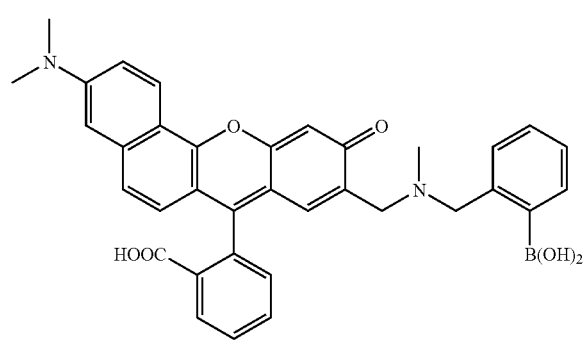

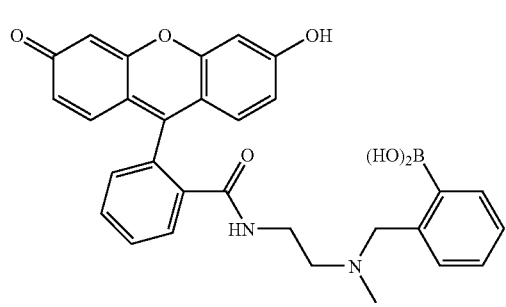

The invention relates in another aspect to SMMRs which comprise novel phenalene-based boronic acid compounds. In an embodiment these compounds are phenalene-1-one compounds of the following formula (IV):

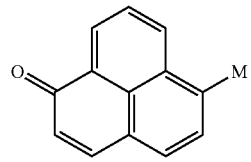

(IV)

wherein

M is

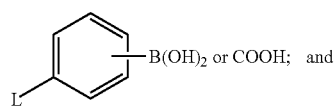

—B(OH)₂ or COOH; and

L, when present, is an amino-containing linking moiety; and salts thereof.

Examples of such phenalene-based boronic acid compounds include:

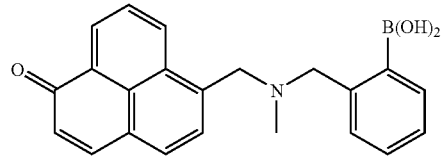

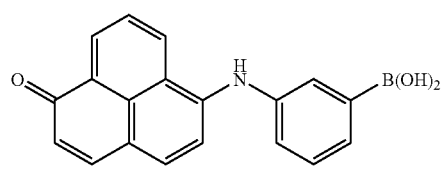

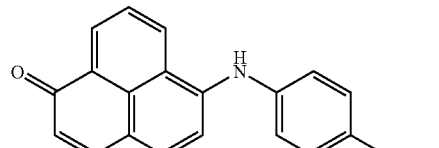

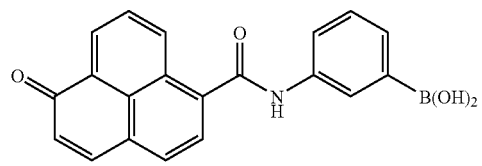

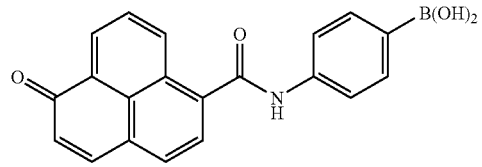

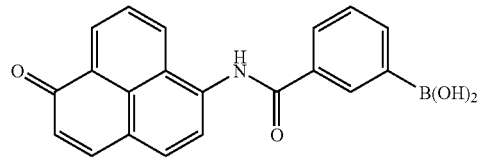

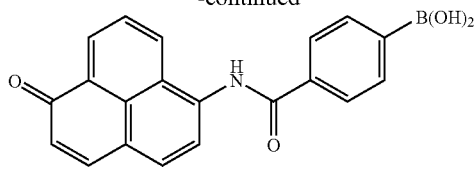

The invention relates in another aspect to SMMRs which comprise novel boronic acid-containing coumarin or carbostyril derivative compounds. In an embodiment these compounds include those of the following formula (V):

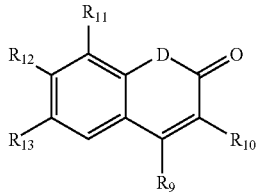

wherein

D is a heteroatom (e.g., O or N);

$R_9$ is H, OH, $CH_3$, $CF_3$, M, or an amino or substituted amino group;

$R_{10}$ is H, $CH_3$, or M;

$R_{11}$, $R_{12}$, and $R_{13}$ are individually H, OH, alkoxy, M, or an amino or substituted amino group;

$R_{14}$, when present, is H or $CH_3$;

M is

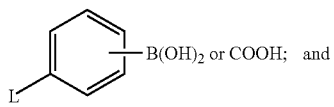

at least one boronic acid moiety is present; and salts thereof.

A substituted amino group may include where $R_{11}$, $R_{12}$, and $R_{13}$, taken together with the ring to which they are attached, form a nitrogen-containing polycycle. Examples of such boronic acid-containing coumarin or carbostyril SMMRs include:

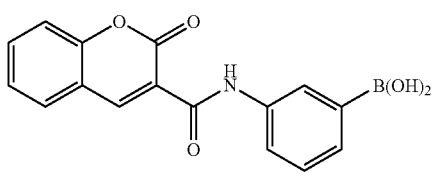

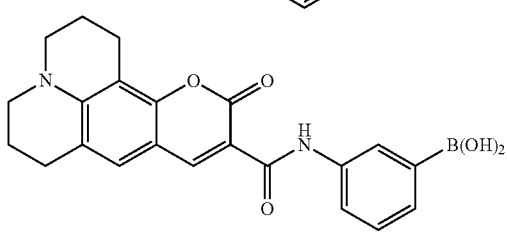

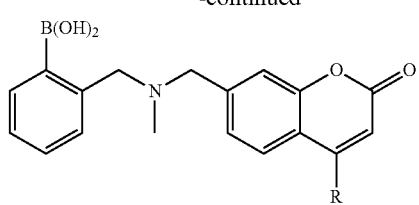

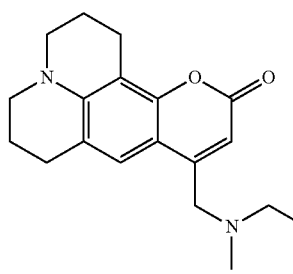

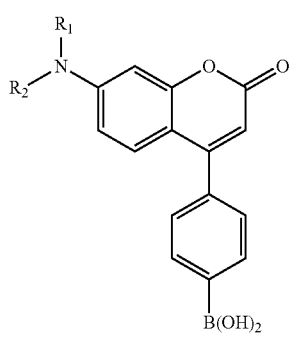

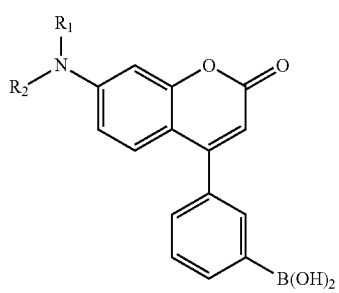

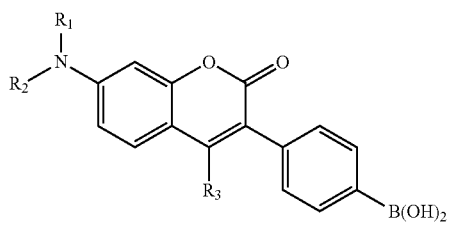

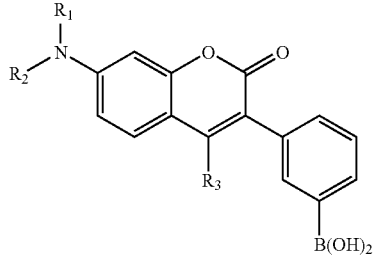

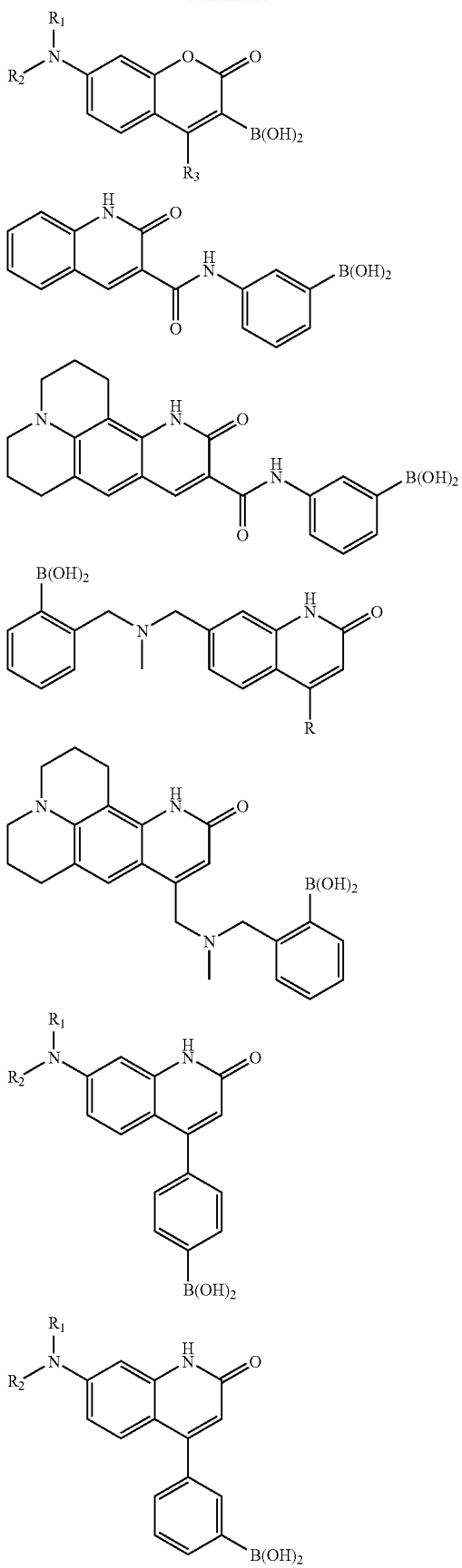

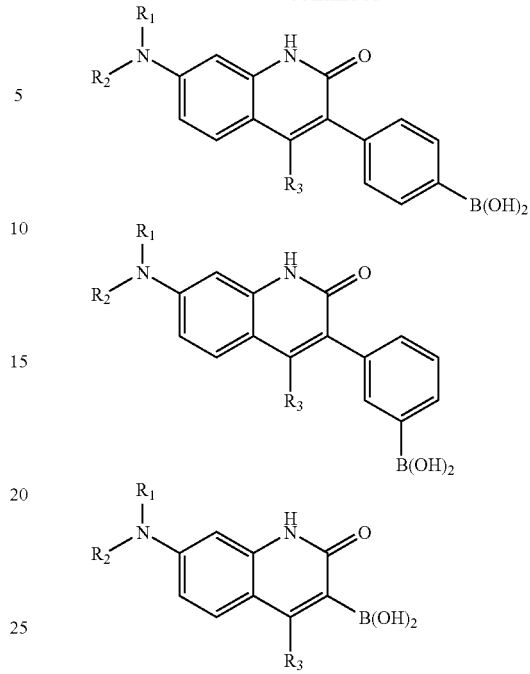

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Alkenes can include either the E- or Z-geometry, where appropriate. Tautomeric forms of compounds of the invention are also intended to be included within the scope of the invention, unless indicated otherwise.

In another aspect, a chromophore of the following rational design structure is disclosed:

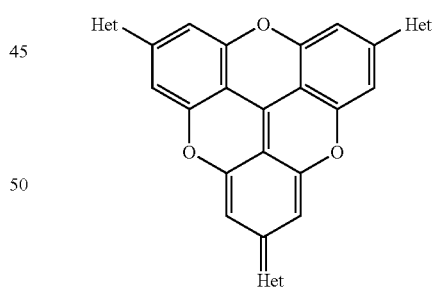

wherein Het represents a heteroatomic group, e.g., containing N, O, or S; $B(OH)_2$; M or $R_8$ (as set forth in Formula (I)); or mono or di-substituted N, $NO_2$ or $N(CH_3)_2$; which groups may be identical or different. Heteroatomic groups may include amino, amido, carbonyl, hydroxyl, thiol, and thio.

This invention also provides for fluorescence measurements of extracellular and intracellular reporter molecules placed into the cytosol, nucleus, or organelles of cells within intact, living, tissue that track the concentration of blood glucose in an organism. When any one of a series of metabolites is measured using this technique, the molar concentration of blood glucose can be calculated. Direct or indirect fluorescence measurements of glucose using one or more of the following measurements is described: pH (as lactate/$H^+$), membrane reduction-oxidation electric potential, NAD(P)H (nicotinamide adenine dinucleotide (phosphate), reduced form) for energy transfer, $FAD^+$ (flavin adenine dinucleotide, oxidized form) for energy transfer, ATP/ADP ratio, $Ca^{2+}$-pumping rate, $Mg^{2+}$-pumping rate, $Na^+$-pumping rate, $K^+$-pumping rate, and vital mitochondrial membrane stains/dyes/molecules fluorescence response. These analytes, measured in skin using the techniques taught herein, are used to provide a complete picture of epidermal skin glycolytic metabolism where local epidermal analyte (glucose) quantities are proportional to the concentration of glucose in systemic blood, specifically the capillary fields within the papillary layer of the dermis (corium). Temperature and/or nitric oxide measurement may also be combined with the above measurements for better calibration and determination of glucose concentrations.

The invention further provides sensor compositions that are applied to at least one surface of living tissue, organs, interstitial fluid, and whole organisms and transported into the tissue at an effective concentration. The sensor composition can include at least one SMMR at an effective concentration such that when the at least one SMMR is brought in contact with one or more specific metabolites or analytes, a change in fluorescence or absorption occurs, thereby allowing quantification of the change in fluorescence or absorption.

The primary embodiment of this invention utilizes a series of molecules (SMMRs) specifically designed for topical delivery onto tissue, such as the viable epidermis, which when applied to the tissue will report glucose concentration using any one or more of several reporting mechanisms. The most significant advantage of the present invention is increased sensitivity in reporting glucose concentration, while eliminating the requirement to draw body fluid from the skin as is required by current conventional techniques.

The in vivo information obtained when the SMMR is brought in contact with the one or more metabolites or analytes can include, but is not limited to, assessment of metabolic function; diagnosis of metabolic disease state; monitoring and control of disease state; stress status of cells, tissues and organs; determination of vitality and viability of cells based on metabolic function; critical care monitoring; diagnosis and monitoring of cardiovascular diseases, autoimmune disorders, neurological disorders, degenerative diseases; determination of metabolic concentration; and cancer diagnosis, detection, staging and prognosis.

For example, the in vivo information obtained may provide detailed information on glucose metabolism, fructose metabolism and galactose metabolism; advanced-glycosylated end products; monitoring and control of diseases such as diabetes, cancer, stress and organ transplantation.

The sensor compositions used in these methods for monitoring the concentration of one or more metabolite(s) or analyte(s) can be formulated as, but are not limited to, emulsions, ointments, disposable gel film patches, reservoir devices, creams, paints, polar solvents, non-polar solvents, or any combination thereof.

Penetration of the sensor composition can be accomplished using an active transport technique or a passive transport technique, such as, for example, electroporation, laser poration, sonic poration, ultrasonic poration, iontophoresis, mechanical-poration, solvent transport, tattooing, wicking, microneedle or pressurized delivery. In addition, penetration of the sensor composition to the desired depth can be accomplished by combining the composition with various molecular size attachments.

Typically, the quantification of the change in fluorescence or absorption is monitored using fluorescence or absorption spectroscopy.

An effective concentration of the sensor composition is, for example, at least between 0.01 to 500 µg/ml, between 0.1 to 500 µg/ml, between 1.0 to 150 µg/ml, between 1 to 100 µg/ml, and between 10 to 100 µg/ml. The SMMR can be introduced in a low concentration in a range from 10 µM to 1000 µM and in a volume from 200 µL to 0.1 µL, respectively (e.g., introducing the SMMR at a concentration in the range of 200 µL of a 10 µM SMMR solution to 0.1 µl of a 1000 µM SMMR solution). One specific application of the sensor composition is, for example, a 5 µL volume of a 400 µM SMMR solution, or a 10 µL volume at 200 µM concentration.

Once one or more SMMRs are activated as a result of placement within the skin, fluorescence measurements monitor the response of the skin cells to glucose. As described herein, the fluorescence mechanism used is either a direct or indirect indication of the glucose concentration in the target cell environment. Fluorescence is typically measured using an optical reader. The optical reader calculates the skin response to glucose, applies first principles mathematical models to the response, and provides a determination of the blood glucose levels. Choosing the particular commercially available or custom designed optical reader that is compatible for use with the methods and compositions of this invention is within the ability of one skilled in the art.

One embodiment of this invention utilizes indirect means to measure skin and blood glucose in vivo by placing one or more SMMRs into the viable epidermis to form a fluorescent product. This fluorescent product is provided by one of many specifically described reporting mechanisms, whereby the SMMR fluorescent signal changes with respect to the effects of glucose concentration on cell metabolism. The quantity of fluorescence, or the fluorescent ratio at two or more emission wavelengths, is indicative of the total glucose concentration within the skin, either intracellular or extracellular as described here. The skin glucose thus determined is used to infer blood glucose levels as calibrated and described herein.

In another embodiment, a method for monitoring in vivo blood glucose levels uses SMMRs that directly bind or respond to glucose itself. The mechanisms of glucose reporting thus does not use cell metabolism, as in the first embodiment, but rather the SMMR responds to glucose by one of several direct mechanisms to produce a fluorescent product. The measured fluorescence is thus a direct reporter of the interstitial fluid or extracellular glucose concentrations. Thus, the skin glucose level directly determined in vivo is used to infer blood glucose levels as calibrated and described within this invention text.

This invention describes the unique physicochemical, photochemical, photophysical and biological properties of SMMR molecules, as well as their design, synthesis, and application. The use of an SMMR enables fluorescence measurements from picomolar through millimolar in vivo glucose levels in living skin tissue, or interstitial fluid, either of which are indicative of the blood glucose levels. The invention described here relates to the indirect or direct determination of skin glucose levels for use in the monitoring and control of diabetes mellitus. Embodiments of the invention use SMMR fluorescence to measure skin glucose levels without withdrawing bodily fluids. When the SMMR-based skin glucose measurements are made, the blood glucose levels are directly inferred.

The quantity of glucose in the epidermis is supplied by mass transport from the blood vessels and capillary fields located within the dermis, immediately beneath the epidermis. The movement of glucose from the blood stream to the epidermis is concentration dependent and non-insulin regulated providing the basis for measurement of blood glucose as a direct inference from skin glucose measurement. The rate of glucose transport into the epidermis is indicative of the differential concentration between skin glucose and blood glucose levels. The rate of transport into the extracellular spaces between human skin cells allows an accurate first principles mathematical extrapolation of blood glucose levels. Once modeled, the kinetics of blood glucose transport to the skin from the blood enables the determination of the precise first principles mathematical relationship between the rate of change of skin glucose and the rate of change of blood glucose. Thus rapid blood glucose concentration changes up or down can be accurately tracked by knowing the skin glucose mean concentration levels and the rate of change of skin glucose levels. First principles mathematical models can be developed for the individual case, preferably for small local populations, and most preferably for a universal patient case.

The SMMR-derived fluorescence reports glucose levels within or surrounding human keratinocyte cells as an indication of blood glucose levels. The movement of glucose from the interstitial fluid surrounding the keratinocytes into the keratinocytes of the epidermis is concentration dependent and non-insulin regulated. That is, the glucose is transported into these cells via non-insulin regulated glucose transporter GluT1 (GenBank Accession Number: K03195), not insulin regulated glucose transporter GluT4 (GenBank Accession Number: M91463). This transport mechanism provides the basis for measurement of blood glucose as a direct inference from intracellular keratinocyte glucose measurement.

Also provided are noninvasive methods for monitoring in vivo blood glucose levels. According to these methods at least one small molecule metabolic reporter is applied to at least one surface of skin for a predetermined period of time causing penetration of the one or more SMMRs to a depth of about 10 μm, wherein the depth corresponds with the bottom of the dead stratum corneum layer, to about 175 μm, wherein the depth corresponds with the top of the dermal layer, into the epidermis. The one or more SMMRs come in contact with one or more metabolites or analytes and a change in the concentration of the one or more metabolites or analytes is monitored by detecting changes in the SMMRs using an optical reader. The change in the concentration of the one or more metabolites or analytes is then correlated with in vivo blood glucose levels.

Also included in the invention is a reagent strip for use in a glucose measuring instrument comprising a polymer strip and a known concentration of at least one small molecule metabolic reporter, wherein when a sample of a biological fluid containing an amount of glucose is interacted with the reagent strip, a change in fluorescence or absorption of the one or more molecular sensor proteins occurs, and the change is measured by the glucose measuring instrument, thereby detecting the glucose concentration of the biological fluid.

The change in fluorescence or absorption can be monitored using fluorescence or absorption spectroscopy. Those of ordinary skill in the art will recognize that any fluorescence or absorption spectroscopic techniques can be used in accordance with the invention.

The invention also provides sensor systems that include a device having a component that transmits radiation to a material or tissue, a component that detects radiation emitted from a material or tissue, and a component to display the detection results, each component are operably linked. The sensor systems further include an applicator that delivers the sensor composition of the invention to the material or tissue. Typically, there is an air interface between the device and the material or tissue, wherein the air interface measures a resulting excitation radiation emitted from the irradiated sensor composition.

The device included in the sensor system can emit radiation at one or more wavelengths that have been chosen to specifically excite the SMMR mixture that is applied to the material or tissue. The sensor composition can include a reporter dye and a marker dye, or alternatively, a dye exhibiting a wavelength shift in absorption or fluorescence emission in the presence of a metabolite. The sensor composition can be present at a depth from the surface of the skin of about 10 μm to about 175 μm in the epidermis in a concentration that is effective for detection of one or more metabolites or analytes in a biological sample.

The sensor system can detect radiation at one or more wavelengths that have been chosen to specifically identify fluorescence emission that has been scattered back to the system from the sensor composition.

DETAILED DESCRIPTION OF THE INVENTION

Figure 1:
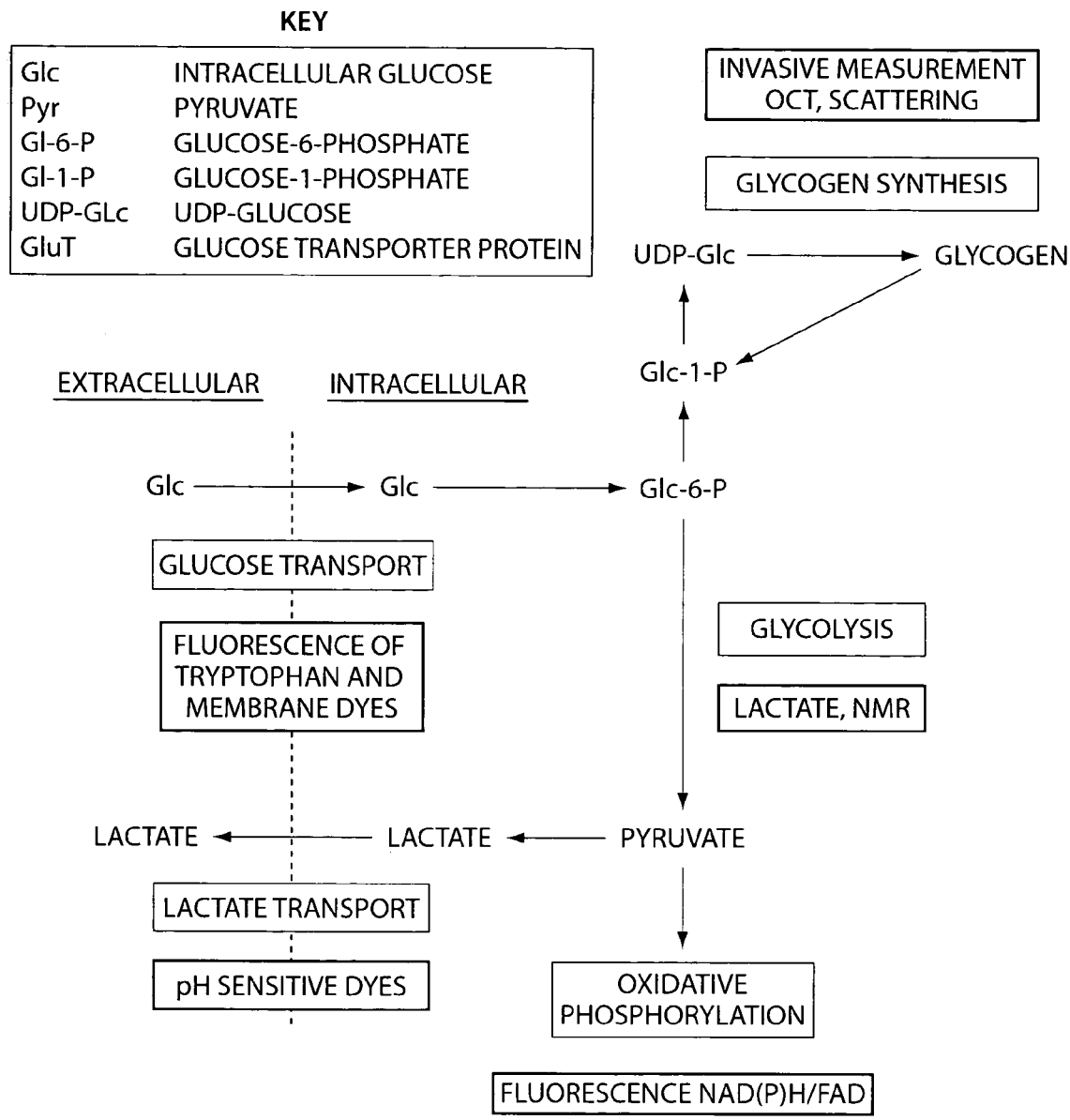
FIG. 1. Glucose pathway of living cells
Figure 2:
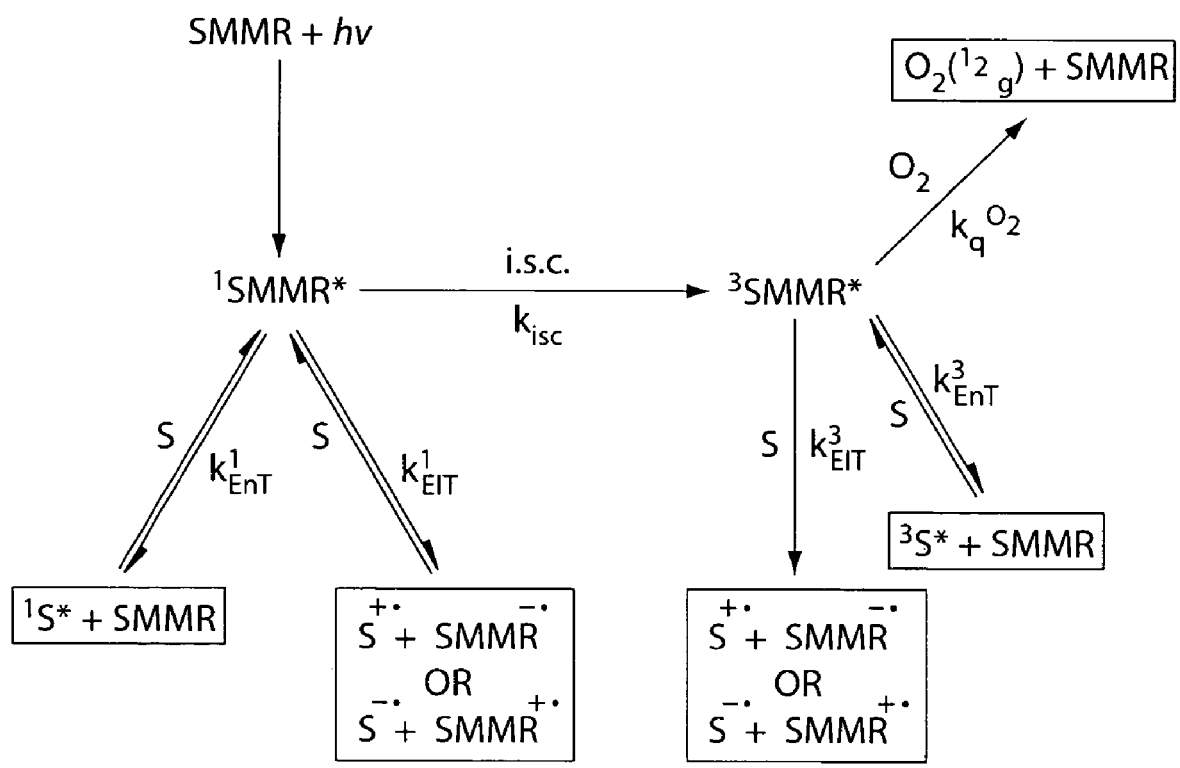
FIG. 2. Summary of photochemical reaction pathways

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

Definitions

The singular forms "a", "and" and "the" include plural referents unless the context clearly dictates otherwise. For example, the term small molecule metabolic reporter "SMMR" and/or "small molecule multi-domain reporter "SMMDR" includes one or more small molecule metabolic reporters "SMMRs" and/or "small molecule multi-domain reporters "SMMDRs". Those skilled in the art will recognize that the terms "SMMR" and "SMMRs", and "SMMDR" and "SMMDRs" are used interchangeably herein.

The term "biologically active molecule" includes, but is not limited to, enzymes, coenzymes, metabolites, analytes, reactive species, polypeptides, proteins, cofactors, small molecules and other macromolecules of physiological significance including mixtures or active fragments or subunits thereof. A "small molecule" includes a molecule from 100 Da to 250 kDa. Molecules of this molecular weight range have a demonstrated ability for use as quantitative reporters of glucose activity.

The terms "small molecule metabolic reporter(s)", "SMMR(s)", "analyte enhancing molecules", "reporter" and "reporters" include, but are not limited to, fluorophores, protein-labeled fluorophores, proteins with a photooxidizable cofactor (such as FADH contained in a glucose oxidase), and proteins with another intercalated fluorophore.

A "chromophore" includes a molecule exhibiting specific absorption or fluorescence emission when excited by energy from an external source. This is a more generic term than fluorophore.

A "fluorophore" includes a molecule exhibiting specific fluorescence emission when excited by energy from an external source.

An "intercalated fluorophore" includes fluorophores that will fluoresce when intercalated with a molecule. For example, Glucose Oxidase-Intercalated Fluorophore (GO-IF) is a molecule with specific glucose binding sites. The fluorescent properties will change when glucose binds to the molecule, causing a measurable change.

A "dye" includes molecules having large absorptivity or high fluorescence quantum yield and which demonstrates affinity for certain materials or organic (cellular) structures.

A "xanthene dye" includes a molecule having a xanthene-like skeletal structure, which exhibits large absorptivity and high fluorescence quantum yield and which demonstrates affinity for certain materials or organic (cellular) structures.

The phrase "energy transfer from reducing equivalents (e.g., NAD/NADH, NAD(P)/NAD(P)H, FAD/FADH$_2$) indicating SMMRs" refers to a use of SMMRs whereby the presence of these reducing equivalents molecules, is detected by excitation of the reducing equivalents molecules from an external source, energy transfer from the reducing equivalents molecule(s) to an SMMR, and detection of the fluorescence emission at the SMMR emission wavelength.

The phrase "absorption/diffuse reflection or fluorescence spectrum" refers to two types of spectra measured independently. The absorption/diffuse reflection spectrum refers to the energy reflection spectrum from a material reported in either the dimensions of reflectance or absorbance versus wavelength. The fluorescence spectrum is measured independently as the fluorescence emission intensity or the fluorescence lifetime of a fluorophore following excitation from an external source.

The phrase "molecular size attachment" refers to the molecular size in Angstroms (Å), which is related to molecular weight in Daltons (Da), of an attachment added as an adjunct to an SMMR. As used herein, "molecular size attachments" includes adducts to the fluorescent moieties of SMMRs that include, but are not limited to, structural modifications of fluorescence SMMRs as the additions to the fluorescence structure of: acetoxy methyl esters, chloro-methyl derivatives, alkyl chain adducts, highly charged moieties, enzyme substrate mimics, enzyme cofactor tethers, and membrane binding tethers.

As used herein, a "reporter" includes an SMMR having the property of optical or fluorescence signal related to the quantity of analyte in the immediate vicinity of the SMMR. Thus, as the analyte quantity increases, the fluorescence signal changes (up or down) in proportion.

As used herein, a "marker" includes a molecule having the property of yielding a fluorescence signal that is constant when applied to target cells or tissues. Its main purpose is for use as a reference signal channel. As such, it is applied in a ratiometric measurement for correction of a reporter signal. The variation in physiological and optical characteristics of individual subjects requires a reference channel signal to correct or normalize a reporter channel signal when the ratio of reporter to marker is used for quantitative applications.

As used herein, a "sensor" includes a handheld device capable of making absorption or fluorescence measurements at one or more wavelengths, and converting the ratios and sums of these measurements into analyte concentrations. These analyte concentrations are used to infer the rate or quantity of a specific metabolic process.

As used herein, a "metabolite" includes a substance produced by a metabolic process, such as glycolysis, which can be quantitatively measured as an indication of the rate or quantity of a specific metabolic process.

As used herein, an "analyte" includes a measurable parameter, using analytical chemistry, which can be quantitatively measured as an indication of the rate and quantity of a specific metabolic process. The term analyte is a generic term describing such concepts as metabolites, ions, processes, conditions, physico-chemical parameters, or metabolic results that can be used to infer the rate or quantity of specific metabolic processes.

As used herein, a "response range" includes an analyte range (lower and upper limits) over which a metabolic process, and its measured absorption or fluorescence signal, follow a linear or defined mathematical function.

The phrase "physico-chemical parameter" refers to a subset of broadly defined analyte parameters specifically related to the physical chemistry constants of materials. These constants can be used in combination with the measurement of other analytes to infer the rate or quantity of specific metabolic processes. Such constants refer specifically to, e.g., atomic mass, Faraday constant, Boltzmann constant, molar volume, dielectric properties, and the like.

As used herein, "wicking" includes the flow of a liquid into a solid material via the pull of gravity, Brownian motion, adhesion, mass transport, or capillary action such that a natural movement of a liquid occurs into a solid material.

The phrases "direct metabolic reporters," and "indirect metabolic reporters" refer to the mechanism of action of SMMR for reporting glucose concentration. Direct metabolic reporters report the concentration of glucose directly, whereas indirect metabolic reporters report the concentration of analytes used to infer the concentration of glucose.

As used herein, an "octanol-water coefficient ($K_{ow}$)" includes a measure of the extent to which a solute molecule is distributed between water and octanol in a mixture. The octanol-water partition coefficient is the ratio of a chemical's solubility (concentration) in octanol to that in water using a two-phase mixture at equilibrium.

As used herein, "toxicity" includes the degree or quality of being toxic or hazardous to the health and well being of human and other mammalian organisms, organs, tissues, and cells.

The phrase "specialized tattoo" or more precisely the "active viewing window" refers to an area of tissue treated with an SMMR. That area is used for viewing the fluorescence ratio measurements of the SMMR interaction with tissue, in order to directly measure, calculate, or otherwise infer the concentration of skin and blood glucose or other metabolites of interest.

As used herein, "organ" includes a structure that contains at least two different types of tissue functioning together for a common purpose. Examples of organs in the body include, but are not limited to, the brain, heart, liver, kidneys, pancreas, stomach, intestines, lungs, and skin.

As used herein, a "keratinocyte" includes a living cell comprising the majority of the epidermis of mammalian skin. The keratinocyte is unique in both its proximity to the surface of an organism as well as in its glycolytic behavior. The keratinocyte metabolizes glucose in such a way as to produce a number of analytes whereby the glucose concentration within the cell can be inferred.

As used herein, a "mammal" includes both a human and a non-human mammal (e.g., rabbit, mouse, rat, gerbil, cow, horse, sheep, etc.). Transgenic animals are also encompassed within the scope of the term.

The non-invasive devices, compositions, and methods of the present invention directly yield in vivo information for the assessment of intracellular and extracellular metabolic state, as well as the stress status of cells, tissues, and organisms. In a preferred embodiment, the devices, compositions and methods of the invention can be used to monitor and determine metabolite concentration levels, and more specifically, determine blood glucose concentration levels.

The invention provides non-invasive sensor compositions that comprise one or more small molecule metabolic reporters ("SMMRs" or "reporters"). When applied topically to skin, peripheral tissues, or organs, these reporters are able to penetrate the upper tissue layers and interact with a specific biologically active molecule in such a way as to report metabolic or health status, while not interfering with metabolic function. The reporters provide a metabolic signal that can be used for multiple purposes including, but not limited to, assessment of metabolic function (e.g., particularly as related to glucose metabolism); diagnosis of metabolic disease states (e.g., as related to advanced glycosylated end-products); monitoring and control of disease state; stress status of cells, tissues and organs; determination of vitality and viability of cells based on metabolic function; critical care monitoring; diagnosis and monitoring of cardiovascular diseases, autoimmune disorders, neurological disorders, degenerative diseases; determination of metabolic concentration; and cancer diagnosis, detection, staging and prognosis. Specifically, applying the reporters of the invention to living peripheral or epithelial tissue provides detailed information on the state of multiple metabolic pathways in living organisms that can be analyzed using low-cost, hand held instrumentation.

The invention provides techniques whereby one or more reporters are applied to solid tissue (i.e., are introduced to the upper cell layers of tissues and organisms following local and/or topical administration). The reporters are added in trace quantities (from about 10 to about 1000 μL of 0.1 to 200 μM, preferably from about 5 to about 100 μL), using a substance that is transparent to visible light and that has a pre-specified temporary residence at the application site (e.g., 2 days-up to 30 days, 24-48 hours, preferably 2-6 hours, more preferably 30 seconds to 5 minutes, and most preferably 5 seconds to 5 minutes). Contemplated diffusion times include periods less than 48 hrs, 24 hrs, 10 hrs, 6 hrs, 2 hrs, 1 hr, 30 min, 15 min, 10 min, 5 min, 1 min, 30 sec, 10 sec, or 1 sec. Reporters that are placed on skin are able to penetrate the skin and be transported to a depth from the surface of from about 10 μm to about 300 μm into the tissue and are brought in contact with a specific metabolite, wherein a change in fluorescence or absorption (e.g., measured using fluorescence or absorption spectroscopy) of the one or more reporters occurs, thereby allowing quantification of the change in fluorescence or absorption that provides detailed in vivo information regarding picomolar through millimolar cellular metabolite and precursor levels for living tissue, organs, interstitial fluid, and whole organisms.

The reporters can be monitored non-invasively using any low-cost instrumentation capable of directly analyzing the metabolic state in tissue (e.g., using optical instrumentation). The reporters are chosen to specifically enhance the signal of pre-specified analytes in order to assess metabolic state of a tissue or organism and to yield detailed, real-time information regarding the state of intracellular and extracellular metabolism.

Discussion of Properties of SMMR Compounds: Physicochemical, Photochemical, Photophysical and Biological SMMR compounds consist of elements of molecular substructure which confer the special properties required to fulfill their specific metabolic reporter function:

1. A fluorescent reporter, with specific photophysical properties,
2. Chemical functional groups that confer affinity to metabolites, enzymes, cell organelles, membranes, or glucose itself,
3. Structural features that confer specificity between the target of interest and similar targets, which are present in the biological medium (e.g., glucose versus fructose).

The chemistry of small molecule metabolic reporter (SMMR) compounds combines a number of parameters that, in general, results in the following characteristics: SMMR compounds are non-toxic; they have high molar absorption coefficients, and a high quantum yield of fluorescence. They have a large Stokes shift; they are readily taken up by cells, and are retained in the active form at the target tissue. They undergo a large change in fluorescence in response to the metabolism monitored, they are photostable, they do not exhibit excited state chemistry, and they are eventually lost from the body by shedding of the stratum corneum. The molecular design behind these characteristics is the subject of this invention.

Toxicity

The metabolic impact of the compounds to be used as SMMRs is low because of a number of properties that are common to these molecules. When minute quantities may be absorbed into the body they are readily eliminated from the system via biotransformation (metabolism) of the aromatic rings through hydroxylation by a variety of nonspecific enzymes contained within the microsomes of the liver endoplasmic reticulum. Small, more water soluble metabolites result, which are then eliminated from the body by passing through the glomeruli into the proximal tubules of the kidney and into the urine. SMMRs have strict requirements relative to toxicity. Four main criteria must be met: (1) they do not bind to DNA, (2) they do not disrupt cell membranes, (3) they are used at low concentration (e.g., 50 μL of 250 μM), and (4) the SMMR is delivered to a limited volume of tissue, typically the viable epidermis.

The Activity Index (A.I.) of the SMMR compounds is an indication of the effective dose required to elicit an appropriate response to a metabolic signal or glucose. It is indicated by the ratio of the Toxic Dose (T.D.) to the Effective Dose (E.D.) as in equation (1). Note that the A.I. for any proposed SMMR must be greater than 1.0 and ideally should be 10,000 or more.

$$A.I. = \frac{T.D.}{E.D.} \qquad (EQ. 1)$$

A better indication of the safety of the SMMR would be indicated by the Minimum Activity Index ($A.I._{min}$) as the ratio of the Maximum Tolerated Dose ($T.D._{max}$) for 100 percent of the tested group, indicating a maximum dose at which no adverse effects occur, to the Maximum Effective Dose used ($E.D._{max}$), whereby the maximum signal occurs as equation (2). The larger the $A.I._{min}$ the better toxicity to effective signal characteristics the SMMR possesses. This number must always exceed 1.0 with values greater than 5.0 considered optimum.

$$A.I._{min} = \frac{T.D._{max}}{E.D._{max}} \quad \text{(EQ. 2)}$$

SMMR molecules with quantum yield ($\phi_F$) values substantially less than unity (e.g., less than 0.3) or those with longer fluorescent lifetimes may show phototoxicity via a photodynamic effect, a process that is unrelated to the inherent toxicity of the SMMR. Phototoxicity arises from reactions of an excited state or from a reactive intermediate generated by the excited state. Phototoxicity can be minimized by using low light doses combined with high quantum yields (e.g., less than 5 mW excitation with a $\phi_F$ greater than 0.6), thereby decreasing the energy available to form damaging oxygen radicals, and the number of excited states generated, respectively.

As a general rule, exogenous materials such as drugs or, with reference to this embodiment, SMMRs that interact with more than one metabolic pathway have a reduced likelihood of becoming clinically significant due to the availability of compensatory pathways if one is inhibited. Interactions, and hence toxicity, are likely to be increased if the SMMR is an inhibitor or inducer of a particular enzyme, if the response of the SMMR is critically dependent on the concentration and particularly if turnover of the SMMR occurs via a single specific pathway (see for example, Johnson, M. D. et al. Clinically significant drug interactions. *Postgraduate Medicine* 1999; 105(2): 193-222).

To a large extent the rationale for SMMR design has avoided many of these problems by targeting normal overall changes in the chemistry of the cell rather than the concentration or activity of a specific metabolite. For example, the monitoring of reducing equivalents within a cell by energy transfer does not affect the overall intracellular concentration of those equivalents nor are there interactions between the enzymes responsible for metabolism and the SMMRs. For some molecules, the toxicity or carcinogenicity is not related to the parent molecule but the metabolite of the molecule. This is often a result of activity of the liver on the molecule. For example, metabolites of benzene are formed by the action of cytochrome P450 in the liver to form, epoxides, phenol, catechol and muconaldehyde. Many of these compounds are extremely reactive and toxic and they may be metabolized further to other toxic materials.

Molar Absorption Coefficient

The molar absorption coefficient ($\in$) of a typical SMMR is high (greater than 50,000 dm$^3$ mol$^{-1}$ cm$^{-1}$). This implies that the probability of a transition from $S_0 \rightarrow S_1$ is high. The amount of light absorbed is given by the Beer-Lambert law as equation (3).

$$\log \frac{I_0}{I_t} = A = \varepsilon c l \quad \text{(EQ. 3)}$$

Where, $I_0$ is the intensity of the incident light, $I_t$ is the intensity of the transmitted light, A is the absorbance, $\in$ is the molar absorption coefficient, c is the concentration and l is the pathlength. This expression can also be rearranged to give the fraction of incident light that is absorbed ($I_a$) as described in equation (4).

$$I_a = 1 - 10^{-A} \quad \text{(EQ. 4)}$$

For an SMMR concentration of 10 μM in a sample thickness of 100 μm (typical skin thickness for skin epidermis), a molar absorption coefficient of 50,000 dm$^3$ mol$^{-1}$ cm$^{-1}$ results in 11% of the incident light being absorbed. Ultimately, the more light absorbed the more will be converted into fluorescence. In designing an SMMR a high molar absorption coefficient ($\in$) is important; practically this means values greater than 50,000 dm$^3$ mol$^{-1}$ cm$^{-1}$.

The probability of the $S_0 \rightarrow S_1$ transition occurring can be explained in molecular terms by consideration of the type of bonding that is present in the SMMR. A high probability for the transition requires good overlap between the orbitals in the ground and excited state. Such overlap is found for $\pi$-$\pi$* transitions and charge transfer states. Transitions involving non-bonding electrons, i.e., n-$\pi$* are not as probable and hence the molar absorption coefficients are lower for these type of transitions. However, the electrons in a non-bonding orbital are higher in energy than electrons in a bonding orbital and therefore the n-$\pi$* transition occurs at lower energy than the $\pi$-$\pi$* transition.

Because of the low probability of the n-$\pi$* transition the excited state generated by such a transition is expected to be longer lived. Since the balance between the rate constants for radiative and non-radiative decay determines fluorescence quantum yield a long lifetime, in general, allows a greater probability for radiationless decay to occur. Hence, n-$\pi$* transitions tend to be non-fluorescent.

Fluorescence Quantum Yield

Following absorption of a photon the SMMR is promoted to an electronically excited state. The molecule undergoes vibrational changes and interactions with the solvent that result in relaxation to the state from which fluorescence occurs. If this state only undergoes spontaneous emission then the yield of fluorescence is high ($\phi_F$=1). If the state undergoes any other process, such as internal conversion or other photophysical change, then $\phi_F$<1. The fluorescence quantum yield ($\phi_F$) of an ideal SMMR is close to unity. Compounds with $\phi_F$ less than unity are likely to be less photostable and more photoreactive. The factors that are common in the design of an SMMR that result in a high quantum yield are:

1. Rigidity of the molecule. Constraining a molecule limits the number of vibrational modes by which the excited state can be deactivated. Binding of ethidium bromide to DNA for example, increases the quantum yield of the molecule by 30 times.
2. Lack of heavy atom effect. Heavy atom substituents, such as iodine or bromine, cause spin orbit coupling in a molecule and facilitate intersystem crossing. The excited singlet state for such a molecule can readily form a triplet state. Not only does this process decrease the fluorescence quantum yield but it also generates a potentially long-lived reactive state.
3. Bonding character. As mentioned above, n-$\pi$* transitions are, in general, not only weakly absorbing but also non-fluorescent. $\pi$-$\pi$* transitions have high molar absorption coefficients and are fluorescent. For molecules that have both an electron donating and withdrawing group attached to the $\pi$ system, the transitions that can occur are described as charge transfer. Typical electron donating groups include amine and hydroxyl groups and withdrawing groups include carbonyl and nitro groups. The transitions are intense and if the transition is of the lowest energy, they are also fluorescent.

From this discussion, it is apparent that the intensity or brightness of fluorescence is determined by the product of the molar absorption coefficient and the quantum yield ($\in \phi_F$). If brightness is sufficiently high, then even at low concentration, the SMMR absorbs excitation light strongly and efficiently converts this energy to fluorescence. As a general rule then the minimum requirement for an SMMR is that $\in > 50,000$ dm$^3$ mol$^{-1}$ cm$^{-1}$ and $\phi_F > 0.2$; thus brightness or $\in \phi_F \geq 25,000$ dm$^3$ mol$^{-1}$ cm$^{-1}$.

Stokes Shift

The Stokes shift is the difference in energy between the lowest energy absorption and the highest energy emission of a molecule. The advantage in having a large Stokes shift is that it is much easier, from a practical standpoint, to optically eliminate the influence of the excitation light on the detected light, i.e., the bandpass filter requirements are simplified.

Consideration of a Jablonski diagram (below) would imply that for an $S_0$ to $S_1$ transition, involving only the lowest vibrational levels, the energy of the fluorescence should be the same as the absorption. This is almost never precisely the case. The main reasons are threefold:

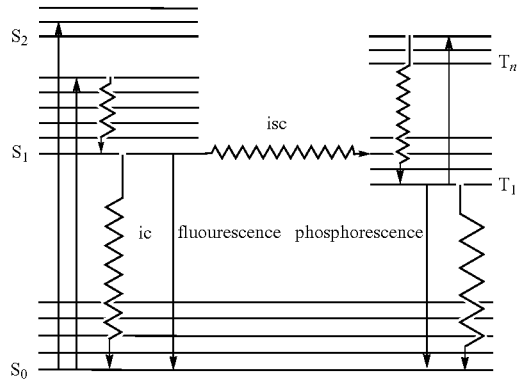

1. Consideration of the bond order in the transition. In a π-π* transition the electron distribution in the excited state involves non-bonding orbitals. As a result the bond length and the magnitude of the vibration in that bond increases. This process results in a loss of energy and therefore the fluorescent transition occurs from an excited state slightly lower in energy that the state generated by the absorption.
2. The lower bond order in the excited state literally causes the molecule to expand. This change in volume is measurable using photoacoustic spectroscopy. For a molecule in solution to expand requires work to be done in pushing back the solvent. This work results in a loss of energy in the excited state and an increase in the Stokes shift. The volume change increases as the size of the π system increases.
3. The greater the degree of flexibility in the molecule the more the number of vibrational modes available to the molecule. For a complex molecule energy may be lost from parts of the molecule not associated with the chromophore. Any mechanism that causes the molecule to lose energy, including solvent and intermolecular interactions, will lead to a decrease in the energy of the observed fluorescence.

It is noted that factors that serve to increase the magnitude of the Stokes shift also serve to lower the overall fluorescence quantum yield. A novel method to increase the separation of the excitation and emission wavelengths for an SMMR is to covalently link two fluorescent probes together. In practice the molecule that absorbs the light need not even be fluorescent provided its excited state lifetime is long enough to transfer energy to the acceptor molecule that fluoresces. This kind of system increases the design flexibility of the SMMR. Proposed examples to monitor pH include a molecule where both the donor and acceptor are sensitive to pH and because of electrostatic changes associated with pH changes, the energy transfer process is also sensitive. ratiometric measurements of the donor and acceptor fluorescence show very large changes as a function of pH.

An ideal SMMR has a Stokes shift of about 50 nm or more. Xanthene dyes typically have a Stokes shift of 5-15 nm but this value is also dependent on the pKa of the molecule. As an example, BeXan type dyes exhibit Stokes shifts of about 40 nm for the acid form and 60 nm for the basic forms of the dye.

Predicting Spectroscopic Properties from Molecular Structure

The prediction of spectroscopic properties such as absorption and emission spectra are very difficult. The absorption of a photon involves the promotion of an electron from a ground to excited state. There is currently no molecular calculation algorithm nor automated software package that can take into account the chemical microenvironment of a molecule. The position of the $S_1 \leftarrow S_o$ transition is calculated by considering the energy of the molecule in its ground equilibrium configuration and the energy of the excited state in the same geometry, which is not an equilibrium conformation for the excited state. This is a consequence of the fact that an electronic transition occurs with no change in the geometry of the molecule during the transition (the Born-Oppenheimer approximation). The intensity of the absorption is dependent on the probability of the transition. In general π*←π transitions are intense and have molar absorption coefficients of $10^5$ dm$^3$ mol$^{-1}$ cm$^{-1}$ or greater. High probability is favored by strong overlap between the ground and excited state orbitals.

Affinity to Target Site

Designing SMMR compounds to have an affinity for specified cellular locations, membranes, or structures helps reduce noise in an SMMR measurement. When the SMMR is targeted to specific cell locations, both the immediate chemical microenvironment of the SMMR molecule as well as its location for optical measurement can be more closely controlled. SMMRs can be designed to have high affinity for membranes, organelles, charged structures including specific membrane layers, biopolymers, protein or enzyme binding sites, and regions of the cell that are particularly hydrophobic or hydrophilic. Absolute specificity may be conferred on an SMMR by binding it to a variety of other membrane specific binding substituents including the use of antibodies.

Examples of an SMMR structure designed to confer target affinity are given here:

Membrane affinity: Amphipathic molecules have a high affinity for membranes. Hydrophilic molecules become amphipathic when an alkyl chain is linked to the structure. This linkage is not necessarily covalent in nature. Electrostatic complexes of cationic detergents and methyl viologen, for example, are stable and bind strongly to membranes. In binding to a membrane, the alkyl chain is solubilized in the hydrophobic core of the membrane and the hydrophilic head group is located at the surface of the membrane. This type of molecule is particularly effective at monitoring changes at the interface between the bulk phase and the membrane that include membrane potential and pH changes, either of which may be used to track glucose concentration at the cell.

Enzyme binding site affinity: SMMR affinity for an enzyme-binding site may be conferred by covalently linking a model enzyme substrate or enzyme cofactor to the SMMR, e.g., as disclosed in pending U.S. Application No. 60/438,837, entitled "Method for Non-invasive, in vivo monitoring of Blood Glucose Levels," filed Jan. 9, 2003, that discusses the binding of an SMMR to the FAD cofactor of glucose oxidase, the entire disclosure of which is incorporated herein by reference.

Skin Uptake

One of the most important functions of skin is to protect the essential tissues of the body from the outside environment. The layer of skin that forms the physical barrier for the body, preventing moisture loss, infection and regulating temperature is the stratum corneum. This cell layer is both hydrophobic as well as acidic, and thus presents a number of problems to transdermal drug delivery. The problem is exacerbated in SMMR technology, since the goal of delivering an SMMR to the epidermis is to have the dye pass through the stratum corneum but to localize in the living epidermal layer. The factors that affect skin uptake include molecular size, hydrophobicity and volatility.

The ideal characteristics of an SMMR, useful to penetrate the stratum corneum, include a low molecular weight (less than 600 g mol$^{-1}$), a partition coefficient of about 10, yielding good solubility in lipid and water phases and a low melting point (see for example, "Novel mechanisms and devices to enable successful transdermal drug delivery," B. W. Barry. Eur. J. Pharm. Sci. (2001) 14 101-114). A low melting point correlates with high solubility since there is little interaction between the molecules.

For an SMMR that will eventually localize in the cytoplasm or the interstitial fluid, the molecule must have good water solubility. However, a hydrophilic molecule will have difficulty in passing the hydrophobic environment of the stratum corneum. These opposing properties of the molecule imply that the design of the molecule has to be altered to accommodate both environments, that the molecule is amphipathic or that the delivery system can accommodate both polar and non-polar molecules. Delivery systems are customized for individual SMMR properties, and the preparation/formulation of such delivery systems are within the skill of one of ordinary skill in the art, taken with the disclosure herein. It is well known that mixed solvent systems using mixed organic solvents for the organic phase have a significantly greater range of properties. Other solvent systems include the use of surface-active agents to expand the range of properties of the vehicle.

Cellular Uptake

To a certain extent the factors that affect uptake in the skin are the same as those that affect cellular uptake. Overall, there has to be a balance between movement of the SMMR into the stratum corneum, diffusion into the epidermis, and then the competing processes of SMMR uptake by the epidermal cells and loss of the dye into the dermis. All of these processes may be considered to be reversible. The most important factors that facilitate cellular uptake of a small molecule include the partition coefficient (P), and the molecular size and the diffusion coefficient in the lipid matrix (D). Diffusion across a biological membrane is dependent on three factors: the diffusion of the SMMR from the aqueous phase to the lipid phase, diffusion within the lipid phase and diffusion from the lipid phase back into an aqueous phase. For a molecule whose flux across the membrane is proportional to the concentration gradient the proportionality constant is called the permeability coefficient (Cp) and it is directly dependent on the three factors above. The permeability coefficient is given by the expression in equation (5).

$$C_p = \frac{DP}{x} \quad (EQ. 5)$$

Where x is the distance across the membrane, or more accurately the distance across the concentration gradient, the other terms are as defined above. For most SMMRs the permeability is directly proportional to the partition coefficient although this relationship does not hold for very small molecules.

The $pK_a$ is important, since this will determine the overall charge of the molecule at a particular pH and hence the partition coefficient. For many pH indicating xanthene compounds there are two $pK_a$ values of importance. As an example, fluorescein

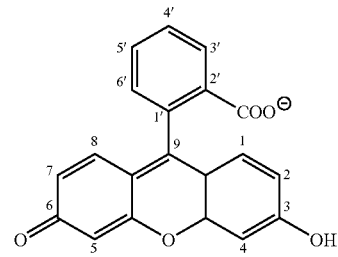

will be considered. The pKa of fluorescein is 6.4. Below this pH, the hydroxyl group drawn at position 3 is protonated. In practice, the oxygen atoms at positions 3 and 6 are equivalent, and above pH 6.4 the xanthene ring is negatively charged with electron density shared between these two positions. The carboxylic acid at the 2' position is unprotonated until the pH drops to about pH 4.2. Below a pH of 2.2, the carboxylic acid ring closes at position 9, there is a hydrogen shift onto the carbonyl at position 6 and the quinoid structure no longer exists. Under these conditions the compound is colorless. The relevance of this parameter to drug delivery in the skin is that this type of compound displays many of the characteristics that facilitate SMMR delivery.

SMMRs designed with acidic functionality have greater potential for skin and cellular uptake. In skin, the stratum corneum is acidic and the surface of cell membranes is also acidic. Therefore the use of SMMRs with acidic substitutions result in a significant fraction of compound molecules being uncharged at pH 5 (close to the values reported in the stratum corneum and at the cell surface). These molecules are therefore more hydrophobic, may cross the barrier and once inside the cell, at ~pH 7 become deprotonated again. Suitable groups include carboxylic acids (pKa ~4-5) and aromatic thiols (pKa ~8). Both of these groups are electrostatically neutral when protonated.

Cellular uptake and retention may be improved by the use of polyoxyethylene chains or polylysine chains. The purpose of these substitutions are to give the SMMRs both hydrophobic and hydrophilic properties. The molecule behaves as a cross-linked micelle changing its conformation and degree of order depending on its environment. The chromophore itself is hydrophilic but it can be solubilized in non-polar environments by the long alkyl chain. In a hydrophobic environment, the chain wraps around the molecule and, if a poly-oxaethylene is used the chain is configured to present the oxygen atoms of the chain towards the interior of the complex. In a hydrophilic environment, the chain unwraps and the SMMR is exposed.

SMMR species connected by flexible saturated chains behave as individual chromophores when located in environments where the monomer is soluble. Under conditions where the monomer is not soluble, the dimer will fold to present the smallest volume of the molecule to the environment. This approach has previously been used to deliver photodynamic therapeutic (PDT) agents to tissues. The folded dimer, which is often non-fluorescent, may cross the cell membrane and unfold when it reaches its cytoplasm related target. The unfolded dimer is again photochemically active.

An example of a dimeric BeXan type molecule is shown below:

Molecules with molecular weights of greater than 600 g mol$^{-1}$ will be retained to a much higher degree than smaller molecules. Negatively charged species are electrostatically repelled from cell membranes. Cell membranes have a high pH gradient near the surface. Negatively charged surfaces attract cationic species, which include the highly mobile hydrogen ion, in a layer called the Stern layer. This layer, located near the membrane surface, may be as much as two pH units lower than the phase of the bulk membrane. Therefore, to maintain charge in the vicinity of a membrane, it is important that at least some of the protonatable groups on the molecule have pKa values less than pH 5.

Quantitatively, leakage from the cell may be measured by monitoring the fluorescence of the interstitial fluid or medium in which the cells are bathed. The leakage is dependent on the concentration gradient and therefore leakage will be higher in a cell culture type measurement than in a skin type system.

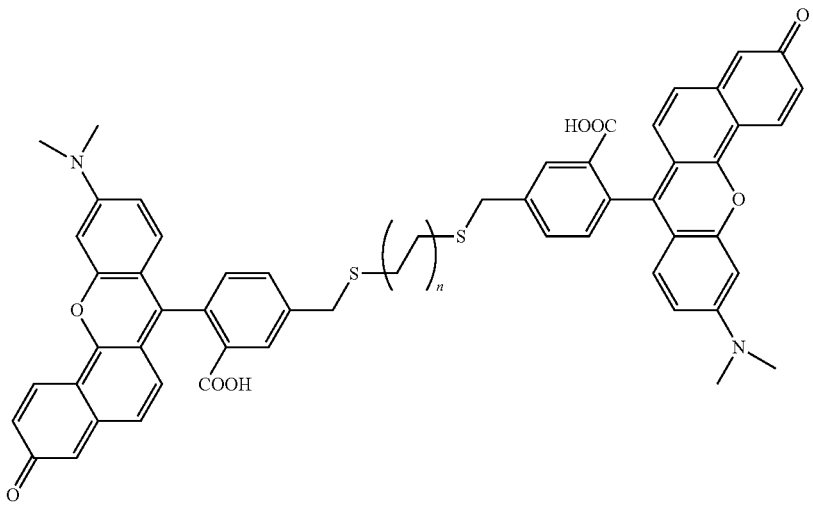

It is readily synthesized from the chloromethyl derivative of the monomer reacting with a dithioalkane. Thioethers are known to be biologically stable molecules (see, e.g., Effect of linker variation on the stability, potency, and efficacy of carcinoma-reactive BR64-doxorubicin immunoconjugates. P. A. Trail, D. Willner, J. Knipe, A. J. Henderson, S. J. Lasch, M. E. Zoeckler, M. D. TrailSmith, T. W. Doyle, H. D. King, A. M. Casazza, G. R. Braslawsky, J. Brown, S. J. Hofstead, R. S. Greenfield, R. A. Firestone, K. Mosure, K. F. Kadow, M. B. Yang, K. E. Hellstrom and I. Hellstrom. Cancer Research, (1997) 57(1) 100-105; and Enhancing selectivity, stability, and bioavailability of peptidomimetic estrogen receptor modulators F. Spatola, A. K. Galande, F. M. Brunel, K. S. Bramlett, and T. P. Burris, Presented at the 18$^{th}$ American Peptide Symposium, Jul. 19-23, 2003, Boston, Mass.).

Cellular Retention

The compounds used as SMMRs must be retained inside the cell so that repeated applications are not necessary for an SMMR monitoring device to function over extended periods from 1 hour to 30 days. Many of the same factors that determine how well an SMMR will cross the membrane also determine whether the compound will leak out of the cell. The principal factors that influence compound retention include: charge, size, polarity, pKa, and the presence of groups that interact with cellular components. Assuming that the principal mechanism for leakage out of the cell is diffusion across the membrane, the SMMR compound should be large, hydrophilic and preferably negatively charged to prevent leakage.

For example, if a 35 mm diameter dish confluent with keratinocytes and bathed with 1 ml of medium is compared to the same number of cells stacked as the cells in the epidermis, then the apparent leakage rate would be at least 30 times higher in the cell culture system. The leakage rate may ultimately be compared to the target site affinity (T.S.A.) parameter (equation 3):

$$T.S.A. = \frac{SMMR_{active}}{SMMR_{delivered}} \quad (EQ. 3)$$

The T.S.A. value is related not only to the leakage rate but also to the rate at which the SMMR is metabolized or photobleached within the cell. These are the same parameters that would have prevented the compound entering the cell initially. Therefore, ideally the SMMR should be converted to this type of molecule after it has entered the cell. This conversion has been accomplished in a number of ways.

Esterification of an SMMR leads to a hydrophobic molecule that can cross the cell membrane. Once inside the cell, the ester is cleaved off by esterase enzymes, generating a charged molecule that cannot readily pass back out of the cell across the membrane. Reduced compounds such as dihydrorhadamines are hydrophobic and may be oxidized inside the cell to form the fluorescent, hydrophilic form of the compound. Other methods that have been used include substitution of a chloromethyl group that interacts with thiol groups leading to conjugation with proteins or hydrophilic moieties preventing leakage from the cell.

The affinity of the SMMR to the target tissue is also given as the Target Site Affinity (T.S.A.). The T.S.A. indicates the percent of SMMR that remains active at the target site after physical delivery to the site. It is reported as a time dependent phenomenon relative to 1 hour, 24 hours, and 72 hours. The T.S.A. for any time period is given in equation (3) as the ratio of moles of SMMR delivered to moles of SMMR active at the delivery site.

Metabolic Monitoring (Indirect Glucose Measurement)

SMMR technology is designed to specifically target metabolic pathways. For SMMRs designed to track glucose these pathways have a direct relationship with the in vivo glucose concentration. For the most part biological pathways do not stand in isolation from other processes that occur in the body. It is therefore possible to improve the sensitivity of monitoring by targeting more than one pathway at the same time. For example, it is useful to know the percentage of metabolism that occurs by oxidative phosphorylation, and the fraction that occurs by anaerobic metabolism. This knowledge allows different cell types or cells under different conditions to be compared. Increasing the number of pathways monitored increases the specificity of the measurements, the dynamic range (since measurements can be made under a wider array of conditions) and decreases the influence of competing processes. As an example of the use of SMMR technology to monitor glucose concentration, the pathways that would be targeted are shown in FIG. 1. The technique to monitor each pathway is given.

SMMR technology is able to monitor glucose transport through the use of membrane bound reporters that respond to the activity of the glucose transporter molecule (GluT). It has previously been shown that the kinetics of GluT may be monitored from the autofluorescence of tryptophan residues in the protein. SMMR technology can monitor the GluT protein either by energy transfer from tryptophan to the dye, or by monitoring membrane dynamics in the vicinity of the GluT protein.

Under conditions where there is excess glucose, cells can convert glucose to glycogen. Glycogen is stored within the cytoplasm of cells as small granules. The size of these granules is fairly uniform and is on the order of tens of nanometers in diameter. As the amount of glycogen stored increases the number of granules increases not the size of the granules. Glycogen synthesis is measured in tissue biopsies using the absorption of the glycogen:iodine complex at 460 mm. Thus, this aspect of the glucose metabolism pathway is measurable using optical means.

In tissue that undergoes primarily anaerobic metabolism, the products of the glycolysis reaction pathway are lactate and adenosine triphosphate (ATP). ATP is synthesized from ADP, the diphosphate analog, and inorganic phosphate. Lactate is generated as a waste product of the pathway. The lactate concentration within the cell is dependent on lactate transport out of the cell and the rate of glycolysis. The extracellular lactate concentration is dependent on lactate transport and diffusion of lactate into the blood stream. Published work has correlated the production of lactate with intracellular pH. Both intra and extracellular pH is measured using SMMR technology with ratiometric monitoring. To monitor the pH values simultaneously, dyes with different spectroscopic properties are used. To use SMMRs with overlapping spectra requires the SMMRs to be applied to different regions of the skin and then repetitive measurements to be made at each site.

Photostability

The photostability of a fluorophore is a function of the magnitude of the quantum yield. If the excited state of the SMMR undergoes any process other than radiative or decay via a vibrational cascade the possibility for a photochemical reaction to take place and an attendant loss of photostability. The loss of fluorescence is the result of a photochemical reaction, often involving the excited state of the compound, and the generation of a photoproduct. This process is generally called photobleaching, which means literally the loss of color. Photobleaching is often an oxidation process and the degree of photobleaching may be proportional to the number of excited states generated. Therefore, photobleaching can be minimized by using low intensity excitation light, a low oxygen concentration and by increasing antioxidant concentrations.

Excited State Chemistry

The processes that can lead to a photochemical reaction include: energy transfer from the excited singlet state ($S_1$), electron transfer from $S_1$ energy transfer from the excited triplet state ($T_1$), electron transfer from $T_1$ formation and subsequent reaction of singlet oxygen ($O_2(^1\Delta_g)$). These reactions are summarized in the following Figure (2) where:

SMMR+hv represents the absorption of a photon
$^1$SMMR* is the first excited singlet state
$^3$SMMR* is the first excited triplet state
S represents some biological substrate
+• and •− represent a semioxidized and semireduced species respectively
$O_2(^1\Delta_g)$ is singlet oxygen
i.s.c is intersystem crossing.

The k terms in the diagram are the rate constants for each process. Elt and Ent refer to electron transfer and energy transfer respectively. For an SMMR to have a high quantum yield the rate constant for fluorescence has to compete with all of these processes.

Turnover

The turnover of the SMMR is related to a number of factors including: photostability, localization, metabolic activity involving reaction with the SMMR, leakage out of cells, uptake into the blood stream, migration into the stratum corneum and loss to the environment. Some SMMR turnover is an advantage since the process reduces the potential for a photobleached compound or compounds to migrate into a non-active region of the tissue. Turnover due to photochemical effects has been discussed earlier.

SMMR Reporting Activity

The activity of an SMMR is dependent on its response to the metabolic pathway to which it is targeted as well as its ability to reach the site of that pathway. The chemical properties of the compound that determine its potency include pKa, excited state energy levels, $\phi_F$, $\in$, octanol:water partition coefficient, and the selectivity of the SMMR for the targeted pathway.

The design of a suitable SMMR involves the correlation of the chemical properties of the SMMR with the biological reporting activity of the compound. To be able to do this it is critical that the reporting activity of the compound be quantified so that different compounds can be compared and a correlation derived.

There are several parameters that can be determined to measure the efficacy of an SMMR. These parameters include: minimum concentration that can be detected using fluorescence, smallest change in analyte concentration that results in a measurable spectroscopic change, and dynamic range in the SMMR response.

In a series of papers published in the 1960's, Hansch and co-workers described how certain aspects of a drug structure could be related to its activity. (Comparison of parameters currently used in the study of structure-activity relationships. A. Leo, C. Hansch and C. Church. *J. Med. Chem.* (1969) 12(5) 766-771; Homolytic constants in the correlation of chloramphenicol structure with activity. C. Hansch, E. Kutter and A. Leo. *J. Med. Chem.* (1969) 12(5) 746-749; Passive permeation of organic compounds through biological tissue: a non-steady-state theory. J. T. Penniston, L. Beckett, D. L. Bentley and C. Hansch. *Mol. Pharmacol.* (1969) 5(4) 333-341; The linear free-energy relationship between partition coefficients and the binding and conformational perturbation of macromolecules by small organic compounds. F. Helmer, K. Kiehs, and C. Hansch. *Biochemistry.* 1968 7(8) 2858-2863; Correlation of ratios of drug metabolism by microsomal subfractions with partition coefficients. E. J. Lien and C. Hansch. *J. Pharm. Sci.* (1968) 57(6) 1027-1028.) In particular, the hydrophobicity of a molecule described how it could partition between tissue and bodily fluid.

A similar approach for SMMR design may be used to provide a semi-empirical approach to SMMR design. Two examples are given, one for an SMMR that monitors a biological pathway, such as glycolysis, via a change in intracellular pH; and one for an SMMR that is used to monitor a biological pathway, such as glycolysis, via the overall reduction potential of the cell through energy transfer.

SMMR Reporting Glycolysis Via a Change in Intracellular pH

Using an analogous rationale to that described by Hansch, an empirical equation (4) that would allow the prediction of the smallest concentration of an SMMR that could be detected from its fluorescence following application to the skin is provided as follows.

$$\log\left(\frac{1}{[C]}\right) = k_1 \log A\phi_F + k_2 \log P - k_3 (\log P)^2 + k_4 pK_a + k_5 \quad \text{(EQ. 4)}$$

Where:
C is the smallest concentration that is detectable in the skin,
A is the absorbance of the solution,
$\phi_F$ is the quantum yield of the compound,
P is the octanol water coefficient,
$pK_a$ is the pKa of the compound,
the constants $k_1$ through $k_5$ are empirically determined constants obtained through linear regression.

The determination of the unknown parameters in this equation requires that at least five times the number of observations be made, as there are terms in the equation. In the example given here at least twenty-five observations would have to be made.

The term $k_1 \log A\phi_F$ describes the probability of the SMMR absorbing a photon and reemitting it as fluorescence. The higher the absorbance and the quantum yield, the more likely is the absorption of a photon and the generation of fluorescence. The term $k_2 \log P - k_3 (\log P)^2$ describes the partition between hydrophobic and hydrophilic phases within an organism. P is the octanol water partition coefficient and has been shown to describe the distribution of a solute between the bulk aqueous phase and the hydrophobic phase of a lipid bilayer such as a cell membrane. The optimum value of P is some intermediate value. Hydrophilic molecules remain in the bulk phase while hydrophobic molecules are not solubilized and therefore are not carried to the cell membrane.

The $pK_a$ is included in this equation because it is related to the partition coefficient of the SMMR. Protonation of basic groups and deprotonation of acidic groups lead to an increase of charge in the molecule and hence increased hydrophilicity. Equation (5) is a relatively simple equation that merely describes the factors that control the uptake of a molecule into a cell membrane. For an SMMR to be effective, the molecule must be retained in the cell or tissue. To a certain extent, retention is described by the same factors that describe uptake of the compound. An equation that describes the response of an SMMR to a change in pH caused by the activity of a metabolic pathway is given here:

$$\log R = k_w \log\left(\frac{A^{DH}\phi_F^{DH}}{A^D\phi_F^D}\right) + k_x pK_a + k_y \log P + k_z \quad \text{(EQ. 5)}$$

Where:
R is the difference in the fluorescence under the extreme conditions of the metabolic pathway, maximum and minimum activity.
The superscript DH and D refer to the protonated and deprotonated forms of the compound respectively.
All other terms are as in equation (1) and the constants $k_w$ through $k_z$ are determined empirically as before. Essentially the first two terms in this equation form the Henderson-Hasselbalch equation (Die Berechnung der Wasserstoffzahl des Blutes auf der freien und gebundenen Kohlensaure desselben, und die Sauerstoffbindung des Blutes als Funktion der Wasserstoffzahl. K. A. Hasselbalch. Biochem. Z. (1916) 78, 112-144). The log P term appears because the SMMR must localize in a similar region of the cell as the location of the biochemical pathway.

Further discussion of the design concept, and compounds and related constructs are described in the following examples.

EXAMPLE 1

Using pH to Track D-Glucose Concentration in Living Cells

For human keratinocytes, the carefully measured intracellular pH (as a measure of lactate production) is directly proportional to the concentration of D-glucose entering the cell. Thus, a decrease of intracellular pH is indicative of an increase in glucose concentration. The lactate formation within the cell is in direct proportion to the quantity of glycolysis occurring within the cell, and this glycolysis is 'fueled' by D-glucose and other simple sugars, such as fructose and galactose. This example demonstrates the protocol for precise pH measurement within viable cells, which is directly related to the D-glucose concentration within viable human keratinocytes.

A-431 cells obtained from ATCC (#CRL-1555) are seeded at $5 \times 10^5$ cells in 35 mm culture dishes (Falcon #353801) containing a #2 25 mm cover glass (VWR#48382-085). Cells are incubated in 2 mL Dulbecco's Modified Eagle's Medium at 100 mg/dL D-glucose (Gibco #11966-025) at 90% and Fetal Bovine Serum (Gibco#26140-087) at 10%. Cells are allowed to reach near confluence in 6% $CO_2$ 37° C. incubator, over a period of 3 to 5 days.

The glass cover slip with cells is dipped and rinsed in Dulbecco's Phosphate-Buffered Saline (D-PBS) (Invitrogen, Catalog #14040) or pH 7.2 HEPES buffer with composition (mM): NaCl 150, KCl 4.5, $MgCl_2$ 1, $CaCl_2$ 1.8. The cover slip is then mounted slip on a Sykes-Moore Chamber (#1943-11111, Bellco Glass, Vineland, N.J.) to form a study chamber.

The chamber is always sat on a hot plate at 36.5±0.5° C. A-431 cells are washed three times with the buffer. After wash, 1 ml buffer solution with 1 mM (18 mg/dL) D-glucose is added into the chamber. The background spectrum of A431 cells in buffer solution is then measured by in-house developed clinical development breadboard (CBB).

A ratiometric pH reporting dye is used as the in vitro intracellular pH indicator. 1 mM stock of the ratiometric pH reporting dye in DMSO is prepared and stored under −20° C. Cells are loaded in the presence of 0.4~2 µM of the dye in HEPES buffers (pH should be calibrated to 7.22 at 35° C.), plus 1 mM D-glucose under 36~37° C. for 1 hour. During the time, the cell chamber is shaken gently three times for homogenous loading. The cell is then washed four times with same buffer solution. Washing solution should be kept in the cell chamber for 3 minutes and then decanted. After washing, 1 ml buffer solution with 1 mM D-glucose is added into the cell chamber.

Two cell chambers are required for a complete study. One cell line is for pH change from neutral to acidic and the other is for the change to basic. About 12 minutes after dye loading, 5 spectra of cell chamber 1 are measured on the CBB as intracellular pH measurements. The whole solution is next replaced by 1 ml buffer solution with 15 µM nigericin (15 µL of 10 mM nigericin), and 5 spectra of pH 7.22 are measured 3 to 5 minutes later. For pH changes from neutral to pH 6, 10 µL pH 1.18 HEPES buffer is added continuously into 1 mL solution contains cells and nigericin. Each addition provides about 0.2 pH unit decrease. Five spectra at different pH are measured about 3 to 5 minutes after adding 10 µL pH 1.2 HEPES buffer. The procedure is repeated about 5 times. For measurements at pH 5, 2.5 uL 1 M HCl in distilled water is added into the chamber.

For the pH measurement from neutral to basic, the same procedure as used for intracellular pH and pH 7.22 are measured on cell chamber 2. For pH changes from neutral to pH 8.2, 10 µL pH 12.3 HEPES buffer is added continuously into 1 mL solution containing cells and nigericin. Each addition provides an increase of approximately 0.2 pH unit. Five spectra at different pH are measured about 3~5 minutes after adding 10 µL pH 12.3 HEPES buffer. The procedure is repeated about 4 times. For pH 9 measurements, 5 uL 1 M NaOH in DW is added in the chamber. The exact pH of 1 ml 7.22 HEPES buffer by adding certain amount of pH 1.2 or pH12.3 buffer should be calibrated by pH meter.

The basic assumption for the Henderson-Hasselbalch model to apply is: the fluorescence intensity of each form (protonated and deprotonated) of the dye is linearly proportional to that form's concentrations. The application of the modified model, the quantum yield and photobleaching of two forms should not be affected differently by environmental effects.

The governing equation for this model is $$pH = pK_a - \log\left[\frac{r - r_B}{r_A - r} \times \frac{F_{\lambda_2}^B}{F_{\lambda_2}^A}\right] \quad (EQ. 6)$$

where r is the ratio of fluorescence intensity at $\lambda_1$ to that at $\lambda_2$, $r_A$ is the ratio for the fluorescence of the protonated form, $r_B$ is the ratio for the deprotonated form, and $F_{\lambda_2}^{A,B}$ is the fluorescence intensity of the protonated and deprotonated forms, respectively, at $\lambda_2$. The $pK_a$ in Equation 1 is true pK and it can be expressed as $$pK_a = pK_{app} + \log\left[\frac{F_{\lambda_2}^B}{F_{\lambda_2}^A}\right] \quad (EQ. 7)$$

where $pK_{app}$ is the apparent pK at the ratio of $\lambda_1$ over $\lambda_2$.

Figure 3:
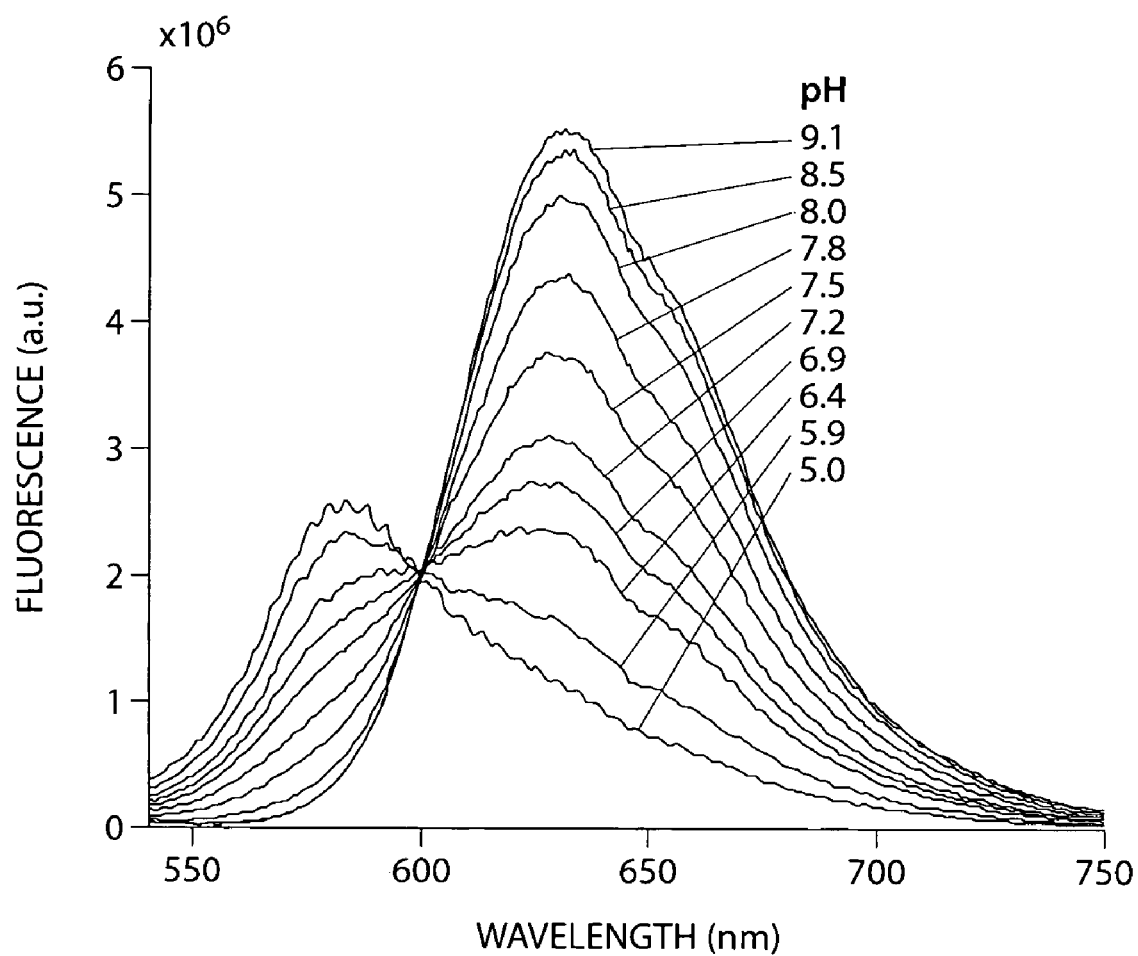
FIG. 3. Absorption and emission spectra for 5 uM of an example ratiometric pH reporting dye in PBS. Fluorescence spectra were measured using 532 nm to excite the dye.
Figure 4:
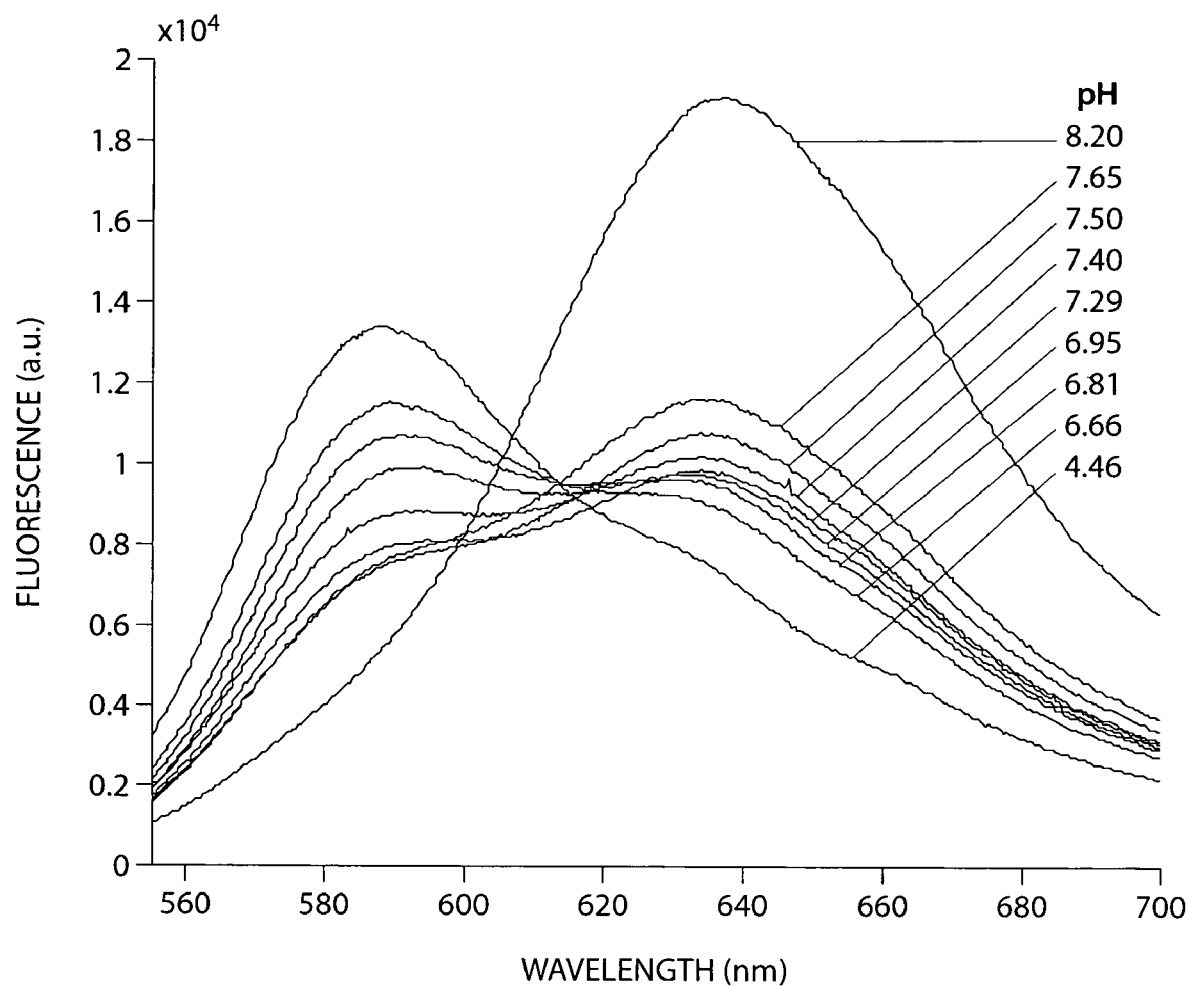
FIG. 4. Fluorescence emission spectra of an example ratiometric pH reporting dye loaded into the A-431 cells. Nigericin is present and allows intracellular pH to equilibrate extracellular pH.
Figure 5:
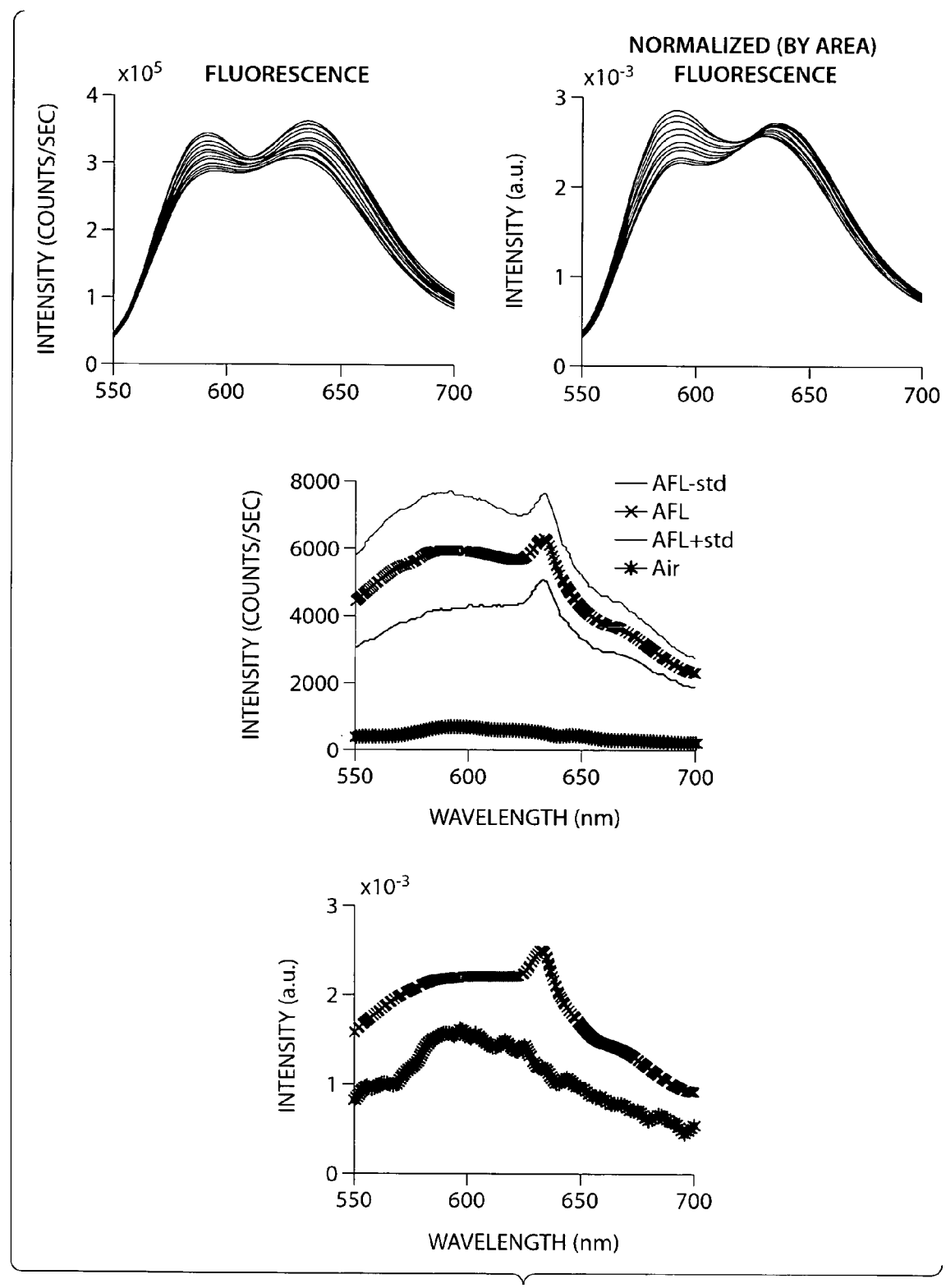
FIG. 5. "Absolute" and normalized Fluorescence, auto-Fluorescence and Air spectra.
Figure 6:
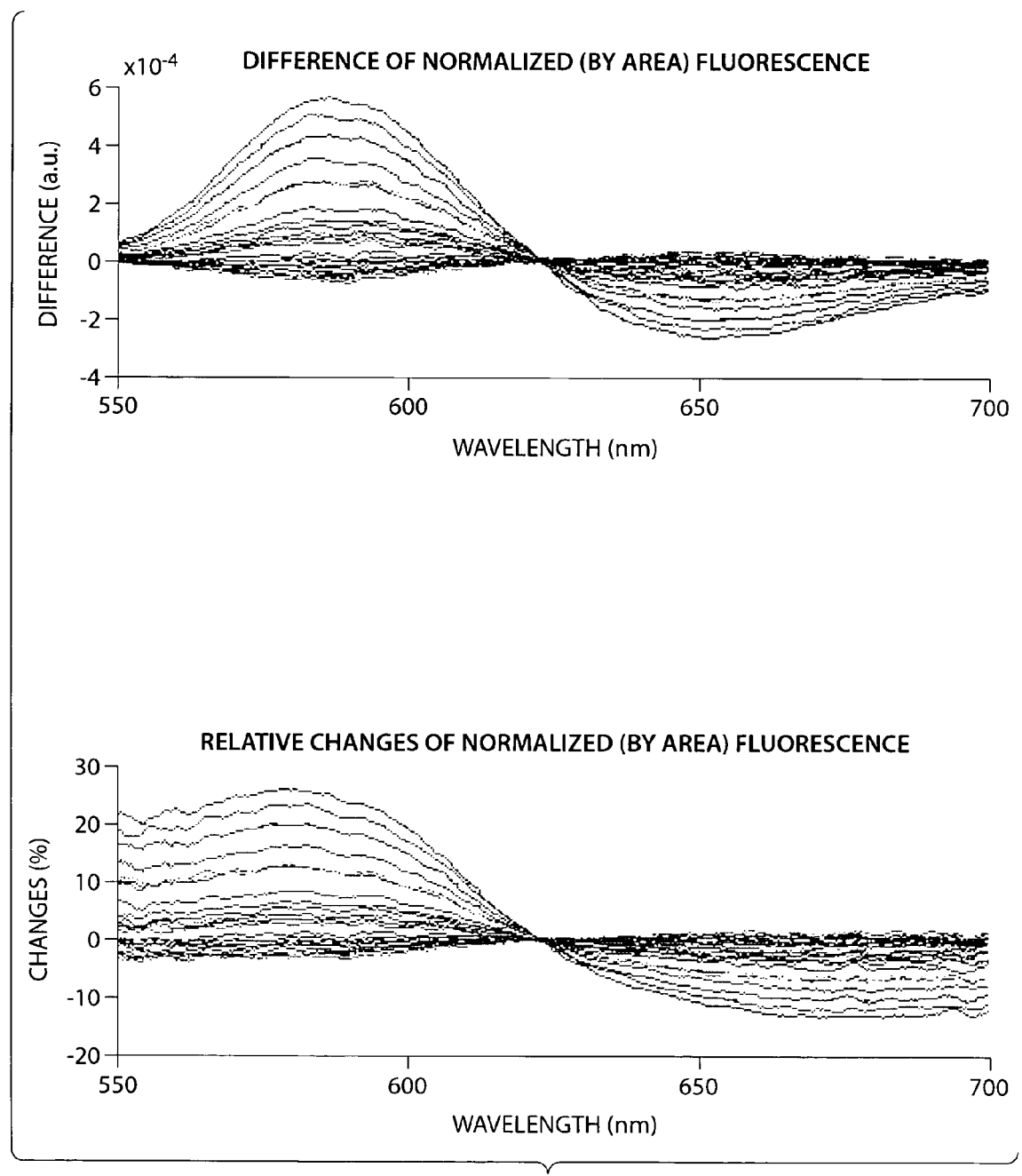
FIG. 6. Difference and relative spectra of normalized Fluorescence spectra.
Figure 7:
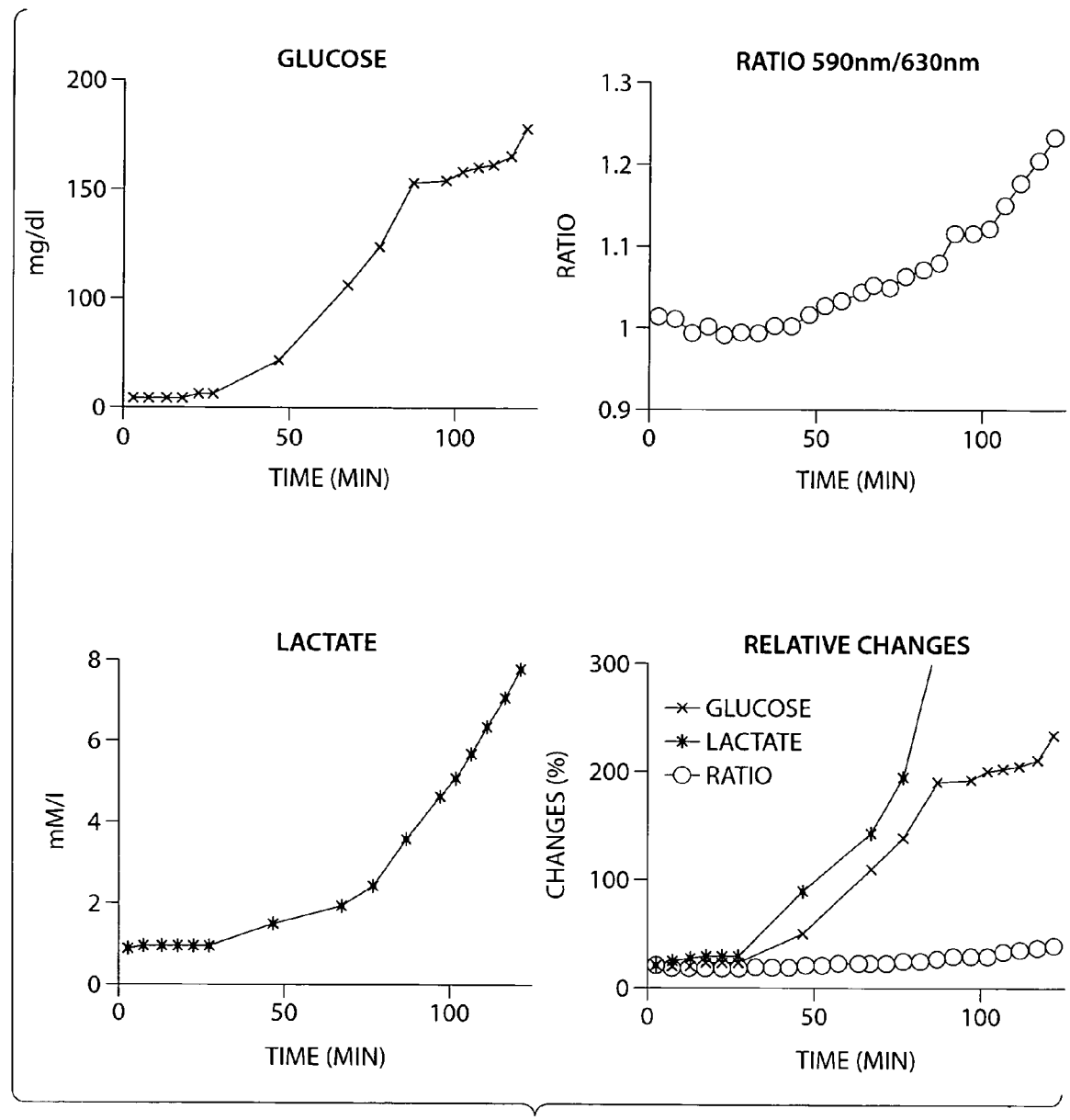
FIG. 7. Glucose, Lactate and SMMR measured ratio kinetics.
Figure 8:
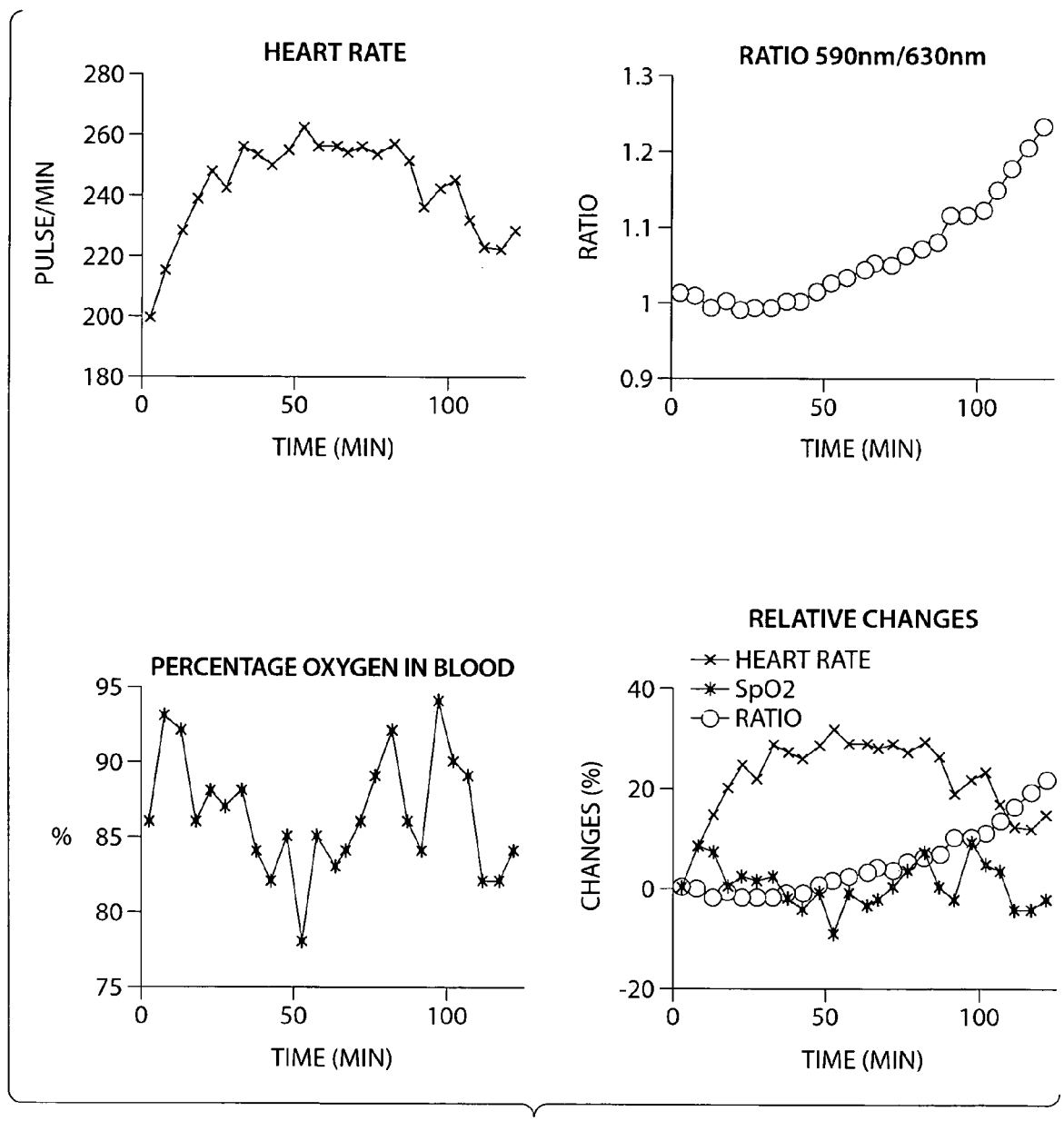
FIG. 8. Kinetics of physiological parameters and ratio.

The ratiometric pH reporting dye has a pale color in dimethyl sulfoxide (DMSO). Aqueous solution of the ratiometric pH reporting dye will actually exhibit different visible colors at pH 8 to 9. The absorption spectra of the ratiometric pH reporting dye (5 µM in 0.1 M phosphate buffer) are measured on an HP 8453 UV/Vis spectrometer, an example of which is shown in FIG. 3. Fluorescence emission spectra excited at 532 nm were measured on a Fluorolog® spectrometer (Jobin Yvon Inc., 3880 Park Avenue, Edison, N.J. 08820-3012 USA) and data are shown in FIG. 4. Samples were prepared from a series of combinations of 0.1 M monobasic sodium phosphate and 0.1 M dibasic sodium phosphate. Both sodium phosphate solutions contain the ratiometric pH reporting dye at 5 µM.

For the SMMR dynamic study, 12 minutes after SMMR loading, five spectra of one cell line are measured at 1 spec/min. Preheated (in water bath) 10 µL 10 g/dL D-glucose or same volume of control solution is added to the chamber. Twenty five spectra are measured after solution adding. The first 10 are at 30-second intervals, and then change to 1 minute. A set of cell lines (4 to 6) is followed above procedure by adding D-glucose and control solution.

For the statistical study, 12 minutes after dye loading, with a 30 second gap, half of total (~8) cell lines are added with 10 µL D-glucose, and another half with 10 µL control solution. Several rounds of measurements of all cell lines are carried out at appropriate intervals. The difference between adding D-glucose and control solution (L-glucose or buffer) will be studied statistically. The cell viability is assessed and recorded using fluorescence light microscopy.

Example 2

Using External, In Vivo pH Measurement to Track Blood Glucose or Blood Lactate

The rationale for measuring blood glucose levels or blood lactate levels using external, in vivo optical measurements of SMMR activity within skin is demonstrated. Fluorescence measurements in vivo of SMMR placed within the skin during glucose clamp studies were designed to improve the observation of the correlation between glucose levels and measured pH changes.

After improvements of fluorescence measurements, additional clamp studies with better control over anesthesia were done to demonstrate the consistency and reliability for the correlation between glucose levels in blood and the reporter dye fluorescence ratio.

This description demonstrates the results of additional glucose clamp studies during which fluorescence signals were measured in vivo after dye injections using low-cost components comprising a fluorescence sensing device.

An example ratiometric pH reporting dye was prepared as described by diluting a 1 mM stock aliquot (frozen at −20° C. in DMSO). The final concentration typically used for placement into the skin was 20 µM in PBS. The SMMR was delivered by shallow injection (or topical passive diffusion) into hairless rats using 100 µL of solution. Multi-injections at the same location were repeated 4 times at intervals of 1 hour. Clamps were started on the next day (15-20 hours after last injection) after the preliminary pre-heating of the rat, i.e., rat had laid on heated stage about 20 minutes before measurements. During bottom measurement of the rat the average temperature of the stage was about 36.5° C., and the standard deviation of the stage temperature during a single experiment did not exceed 0.5° C.

During this study the influence of anesthesia was minimized. Results of in vivo measurements are shown as in FIGS. 5-8.

Figure 9:
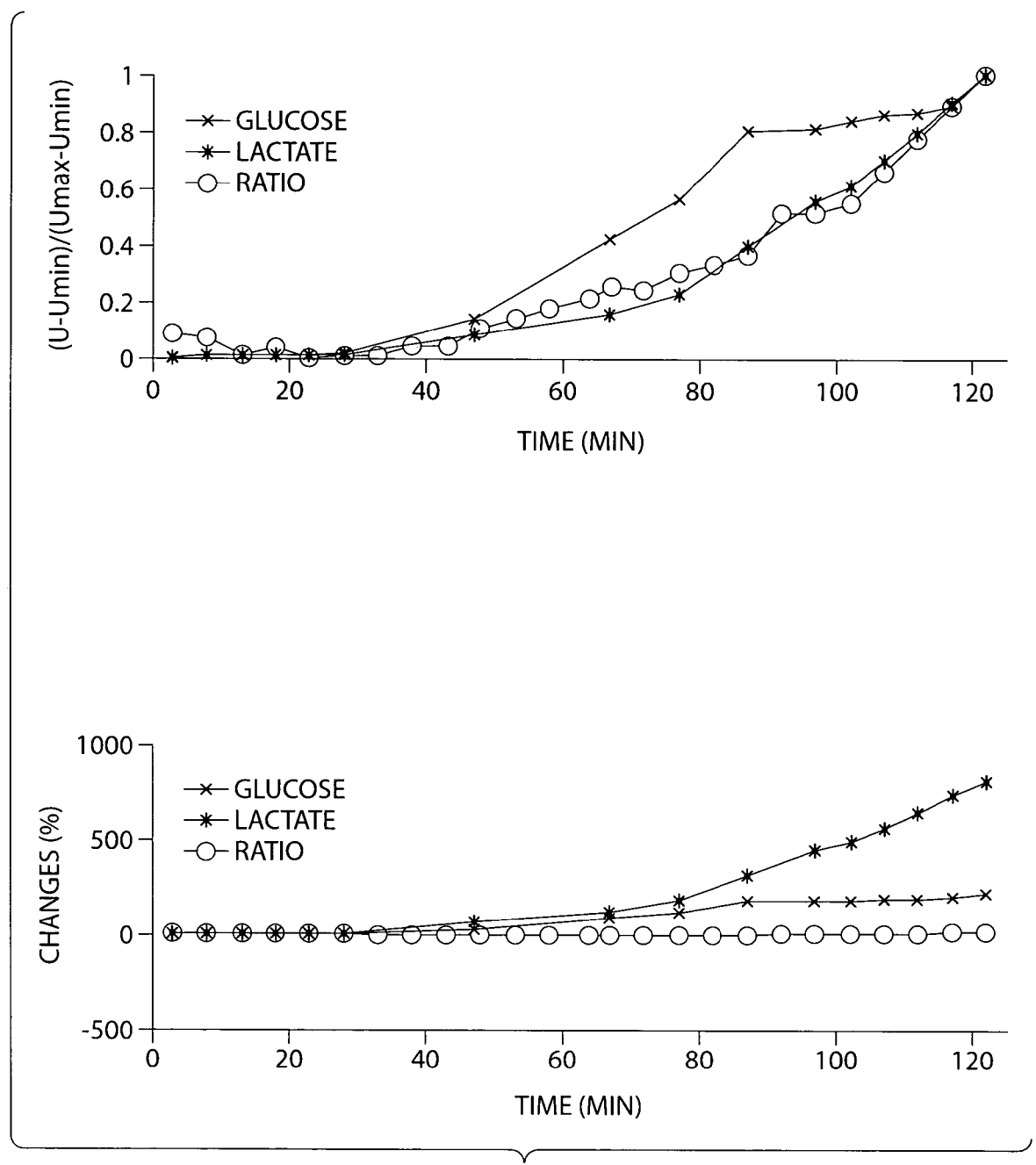
FIG. 9. Normalized and relative changes of ratio, glucose, and lactate in time.

Changes of intensity were not substantial during the experiments. Anesthesia (0.19 cc of ketamine) was administered by injection to each rat 75 minutes before measurements. Relative changes in time of parameter U can be defined as 100 [U(t)−U(0)]/U(0), where t is time (in minutes), and 0 denotes time at the beginning of measurements. As noted from FIG. 1d, observed relative changes for glucose and lactate are substantially greater than the corresponding changes of the fluorescence ratio. To provide a more meaningful visual comparison between glucose, lactate and fluorescence ratio changes, a normalization expression of the independent data are used as: $(U-U_{min}/U_{max}-U_{min})$, which refers to the difference between given value of ratio, lactate, or glucose and it minimum value divided by the difference between its maximum value and its minimum value. FIG. 9 shows the normalized and relative changes for the independent data sets over time: fluorescence ratio, lactate, and glucose.

The experimental data allows estimating the sensitivity coefficients of ratio change to glucose change and lactate change as given in equation (8).

$$\Delta R = \alpha \Delta G + \beta \Delta L \quad (EQ. 8)$$

Noting that the expression, $\Delta R/\Delta G = 5 \times 10^{-4}$ dL/mg and $\Delta R/\Delta L = 2 \times 10^{-2}$ dL/mM, where: L has units mM/dL and G has units mg/dL.

Figure 10:
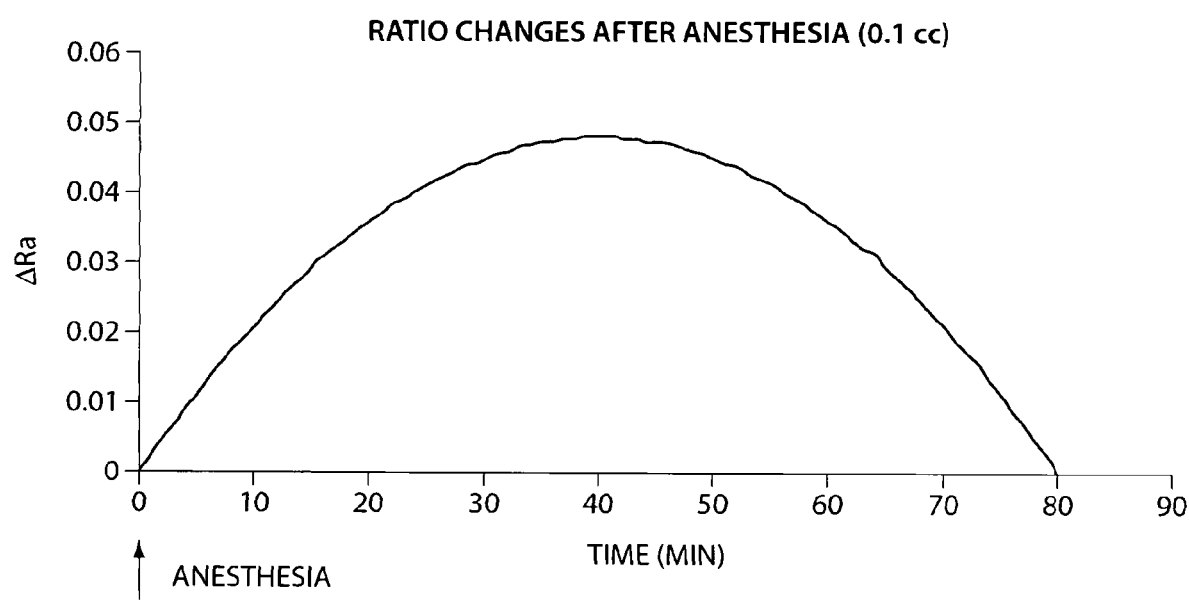
FIG. 10. Fluorescence ratio changes after anesthesia (0.1 cc of ketamine).

Previous clamps with anesthesia (0.1 cc of ketamine) during measurement provided estimates of the average kinetic changes in fluorescence ratio, which are shown in FIG. 10.

Taking into account the influence of three major factors, namely: anesthesia, lactate and glucose it is possible to compare experimentally observed changes during clamp studies with calculated values using an expression such as equation (9):

$$\Delta R = \alpha \Delta G + \beta \Delta L + \Delta R_a(t-t_a)A \quad (EQ. 9)$$

Where $t_a$ is the moment of time when anesthesia was administered; $\Delta R_a(t-t_a)$ is the experimentally defined ratio changes due to anesthesia with 0.1 cc of ketamine; and A is amount of ketamine (in 0.1 cc units).

Figure 11A:
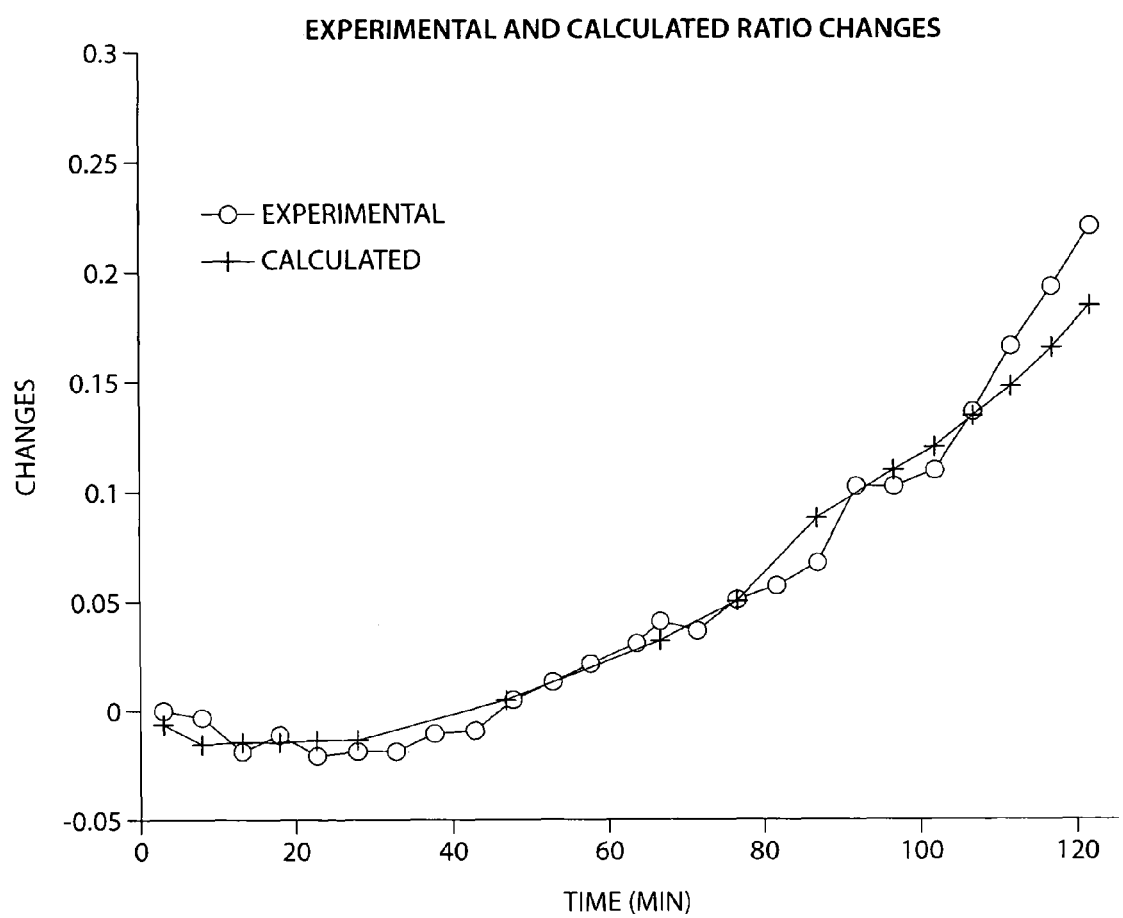
FIG. 11a. Data from a clamp study, comparison between experimental (YSI values) and calculated values of $\Delta R$ (from the equation $\Delta R = \alpha \Delta G + \beta \Delta L$ using the coefficients $\alpha$ and $\beta$ from above.
Figure 11B:
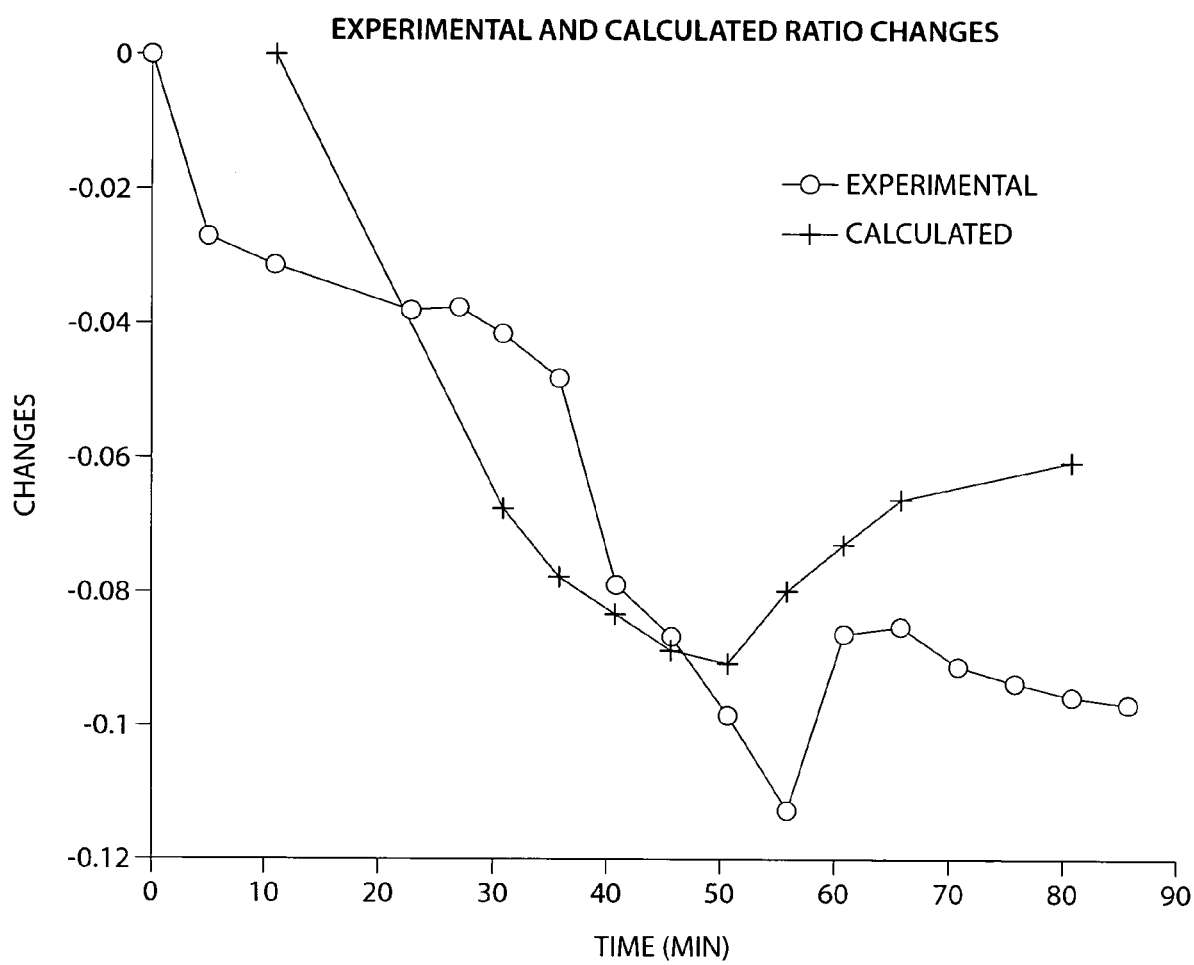
FIG. 11b. Data from another clamp study, comparison between experimental (YSI values) and calculated values of $\Delta R$ (from the equation $\Delta R = \alpha \Delta G + \beta \Delta L + \Delta R_a(t-t_a)$ A using the coefficients $\alpha$, $\beta$ and $\Delta R_a(t-t_a)$ from above.
Figure 11C:
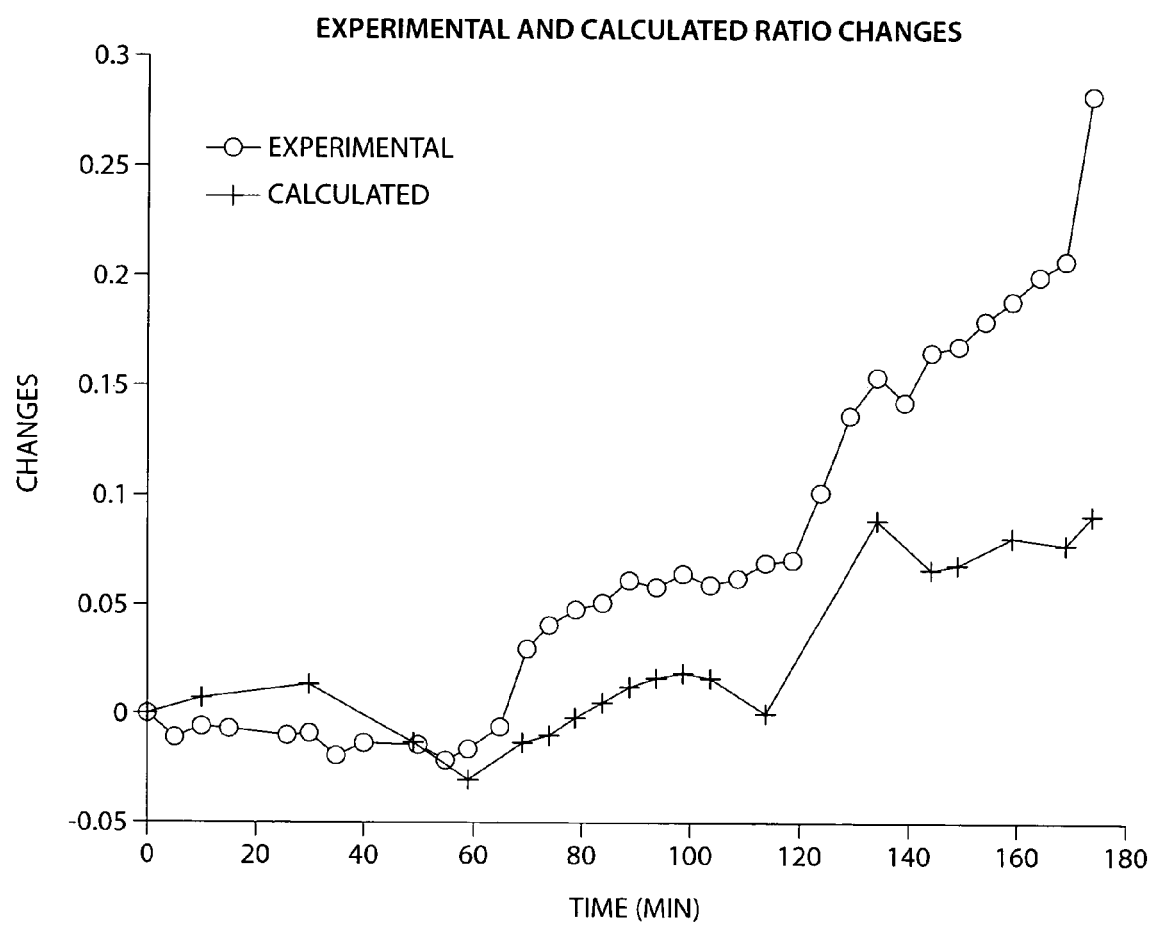
FIG. 11c. Data from yet another clamp study, comparison between experimental (YSI values) and calculated values of $\Delta R$ (from the $\Delta R = \alpha \Delta G + \beta \Delta L + \Delta R_a(t-t_a)$ A using the coefficients $\alpha$, $\beta$ and $\Delta R_a(t-t_a)$ from above.

FIGS. 11a-c show these results. From these results, the positive correlation between the fluorescence SMMR ratio measurements and changes in glucose and lactate are demonstrated.

SMMR Operating Through Energy Transfer

Assuming that SMMRs can be delivered to the sites at which energy transfer takes place (as described by equation (4) above, then a new expression can be derived for the efficiency of an SMMR monitoring the overall reduction potential of the cell by energy transfer, i.e., $$^1NAD(P)H^* + SMMR \rightarrow NAD(P)H + {}^1SMMR^*$$

In this process, the excited state of the reduced nicotinamide interacts with the SMMR to generate the excited state. The $\phi_F$ of NAD(P)H is less than 0.1. If an SMMR is chosen with a quantum yield close to unity, then the yield of fluorescence is increased by at least one order of magnitude, provided the energy transfer process is efficient, equation (10).

$$\log F = k_a \log \frac{k_T}{(\tau_D^{-1} + k_T)} + k_b \log P + k_c \quad (EQ. 10)$$

Where:
F is the fluorescence response to the change in intracellular reduction potential,
$k_T$ is the rate of energy transfer,
$\tau_D^{-1}$ is the reciprocal of the fluorescence lifetime,
P is the partition coefficient,
and $k_a$, $k_b$ and $k_c$ are the determined empirical constants as described previously.

The rate constant of energy transfer is given by the expression in equation (11).

$$k_T = \left(\frac{\phi_F \kappa^2}{\tau r^6 C n^4}\right) J(\lambda) \quad (EQ. 11)$$

Where:
$\kappa$ is known as the orientation factor,
$\tau$ is the fluorescence lifetime of the donor,
$\phi_F$ is the fluorescence quantum yield of the donor,
C is a collection of constants,
$J(\lambda)$ is known as the overlap integral,
and n is the refractive index of the medium.

The orientation factor describes how the transition dipoles of the donor and acceptor molecules align. For two molecules moving randomly in solution, the value of $\kappa^2$ is about 0.66, and for two dipoles perpendicular to each other the value is 0.

The term $k_T/(\tau_D^{-1}+k_T)$ in equation (6) is the efficiency of energy transfer. In words, it is the number of energy transfer events as a fraction of all decay events. The energy transfer rate constant must be significantly greater than the sum of all the rate constants attributed to all other decay routes for the energy transfer to be efficient.

The log P (or log $P_{o/w}$) value reflects the relative solubility of any drug in octanol (representing the lipid bilayer of a cell membrane) and water (the matrix fluid within the cell and in blood).

Example 3

Using NADH Fluorescence to Track D-Glucose Concentration in Living Cells

Figure 12:
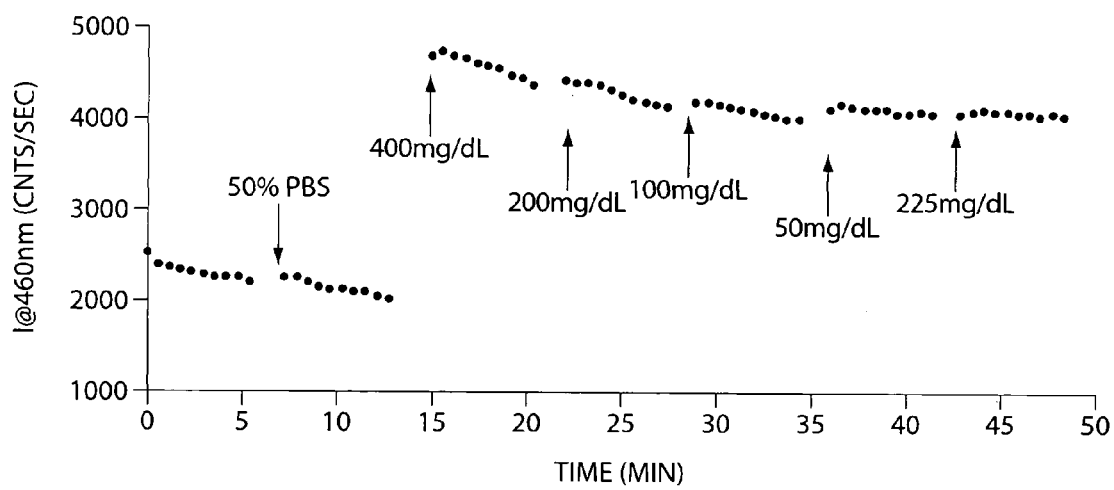
FIG. 12. NADH peak fluorescence signals versus time as glucose concentration is changed. Glucose concentrations are annotated in the Figure. The first annotation with 50% PBS is a control measurement.
Figure 13:
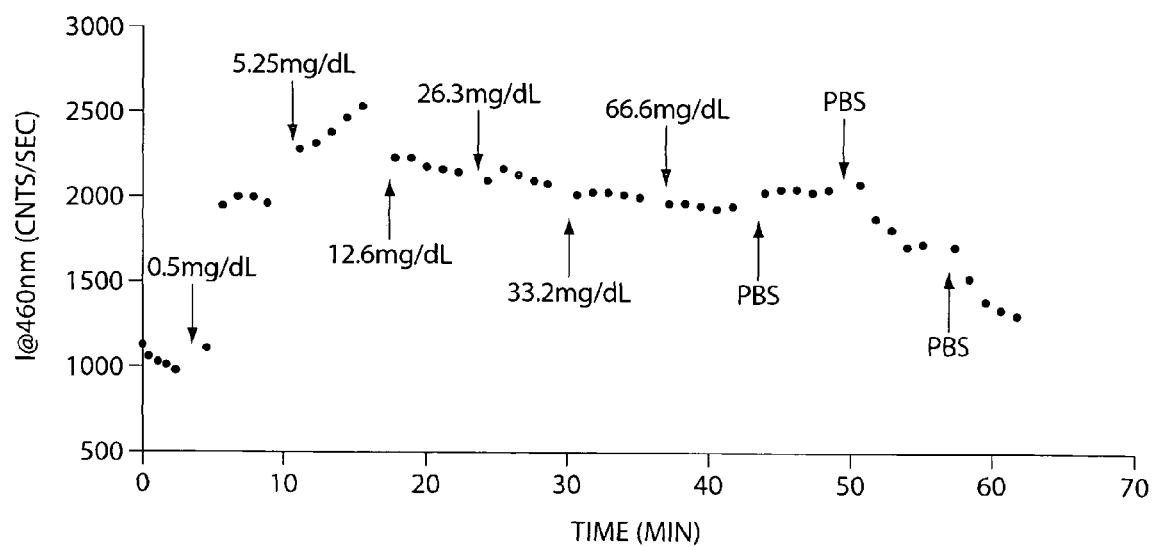
FIG. 13. Glucose concentration is varied from 0 to 66 mg/dL and the NADH peak signals exhibit corresponding changes in intensity.

A set of demonstration experiments for living cells has shown the expected trend in NADH signals with respect to a change in glucose concentration, as shown in FIG. 12 (glucose from 0 to 400 mg/dL) and FIG. 13 (glucose from 0 to 66 mg/dL). All glucose concentrations above ~5 mg/dL were well above the saturation limit as can be seen by the lack of any further change in signals.

Figure 14:
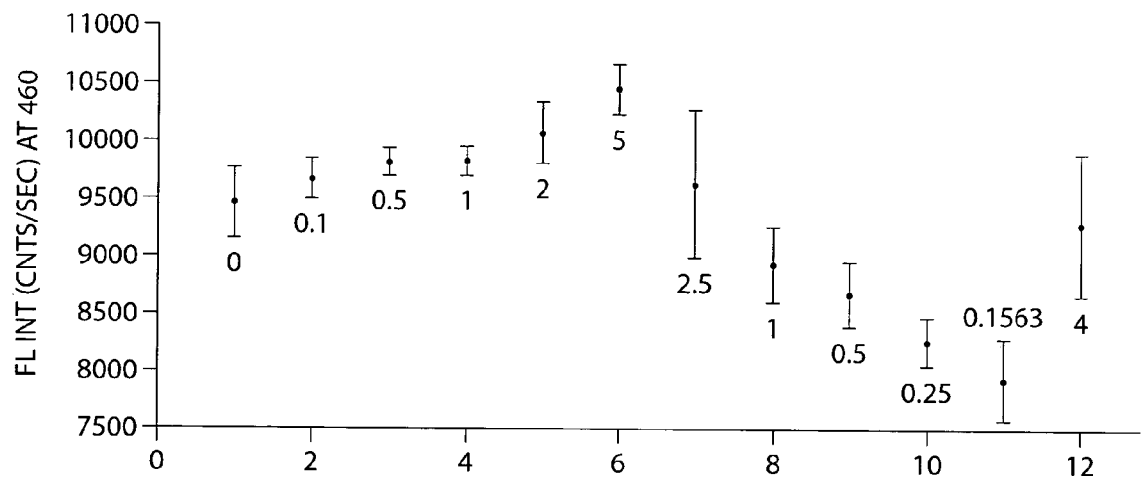
FIG. 14. NADH measurements versus sequence number. The glucose values (in mg/dL) for each data point are (from left to right): 0, 0.1, 0.5, 1.0, 2.0, 5.0, 2.5, 1.0, 0.5, 0.25, 0.16, and 4.0 mg/dL. Each point represents the mean and standard deviation of 5 data points. NOTE: The x-axis label sequence number.
Figure 15:
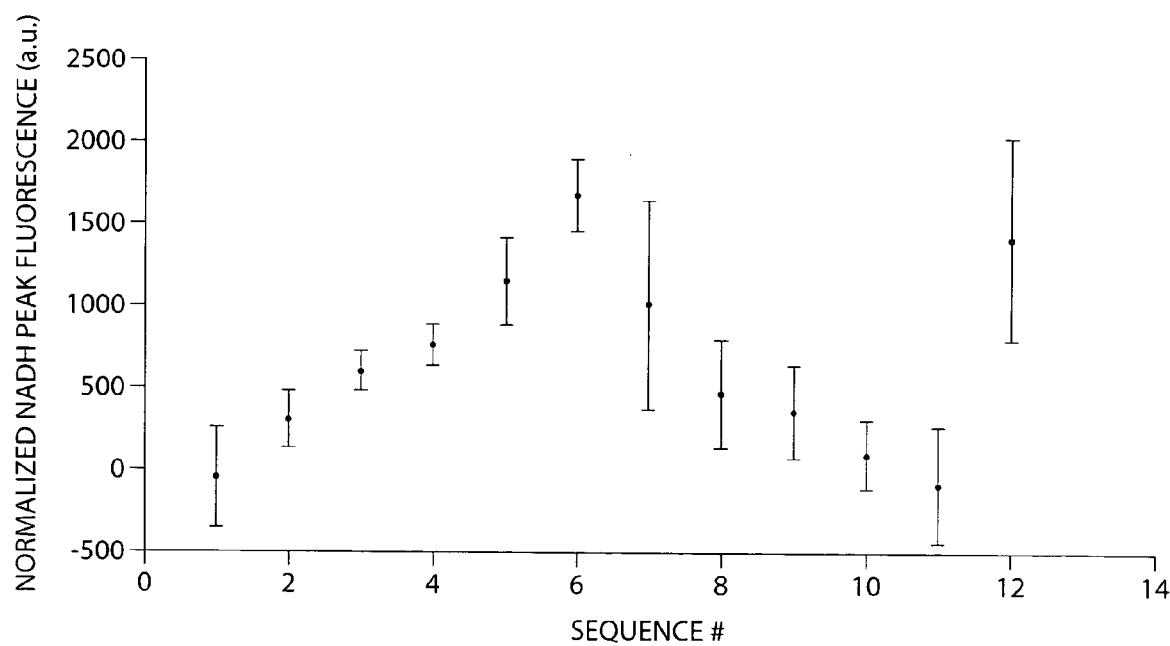
FIG. 15. Corrected NADH Signal of FIG. 14 for each data point (as from left to right), corresponding to a concentration 0, 0.1, 0.5, 1.0, 2.0, 5.0, 2.5, 1.0, 0.5, 0.25, 0.16, and 4.0.
Figure 16:
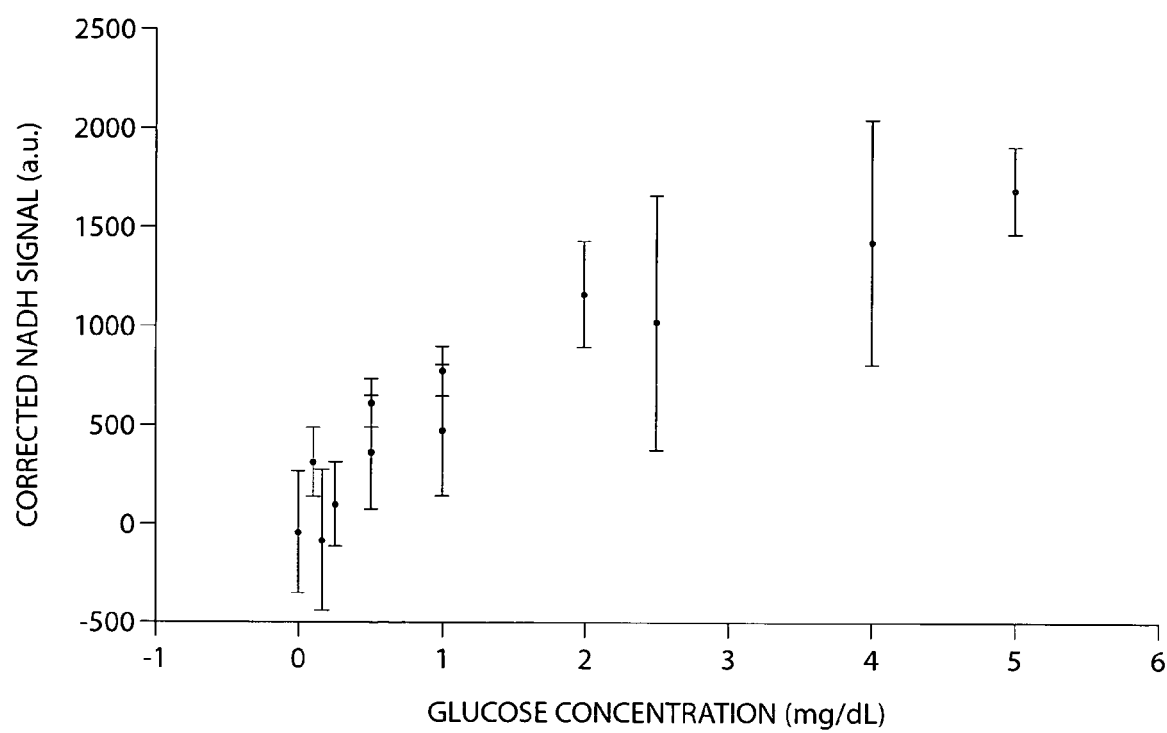
FIG. 16. Corrected NADH Signal versus Glucose concentration for upward trend and downward trend data together.

A second set of demonstration experiments was designed to determine the saturation limit by varying glucose concentration from 0 to 5 mg/dL and back to zero. The saturation point is expected to have a value between 0.0 and 2 mg/dL.) As shown in FIG. 14 an approximate linear increase in NADH fluorescence is observed with glucose concentration from 0 to 5 mg/dL (0.28 mM). FIG. 15 is a plot of a background subtracted NADH signal where the background changed linearly as determined from the first zero glucose signal and the last (near) zero glucose signal (sequence #11). FIG. 16 shows the NADH signal trend versus concentration for living cells.

Example 4

Using Membrane Potential to Track D-Glucose Concentration in Living Cells

Figure 17:
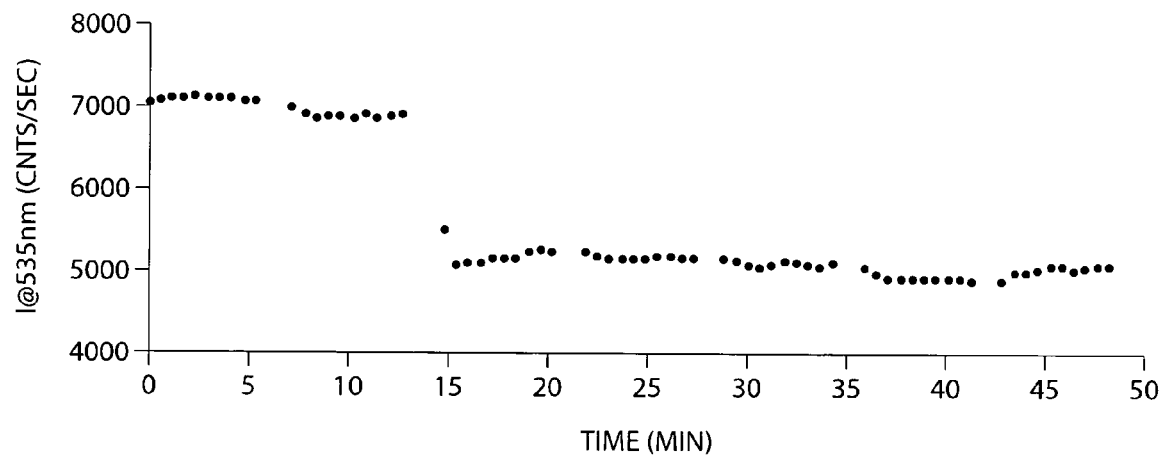
FIG. 17. A membrane-bound Rh123 peak fluorescence signal change (decrease in signal as an indication of membrane potential change) versus time as glucose concentration is changed. Glucose concentrations were increased at the 15-minute point in the Figure. The first annotation with 50% PBS is a control measurement.
Figure 18:
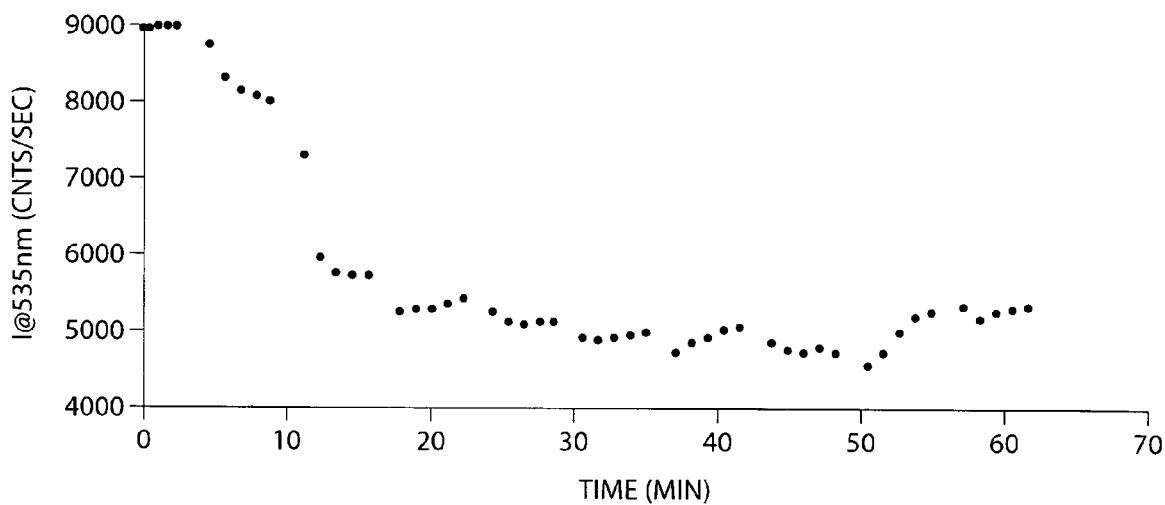
FIG. 18. Glucose concentration is varied from 0 to 66 mg/dL and the Rh123 (bottom plot) peak signals exhibit corresponding changes in intensity due to membrane potential changes.

A set of demonstration experiments showed the expected trend in Rh123 fluorescence quenching. The fluorescence quenching is an indication of membrane potential changes within living cells with respect to an increase in glucose concentration, as shown in FIG. 17 (glucose from 0 to 400 mg/dL) and FIG. 18 (glucose from 0 to 66 mg/dL).

Figure 19:
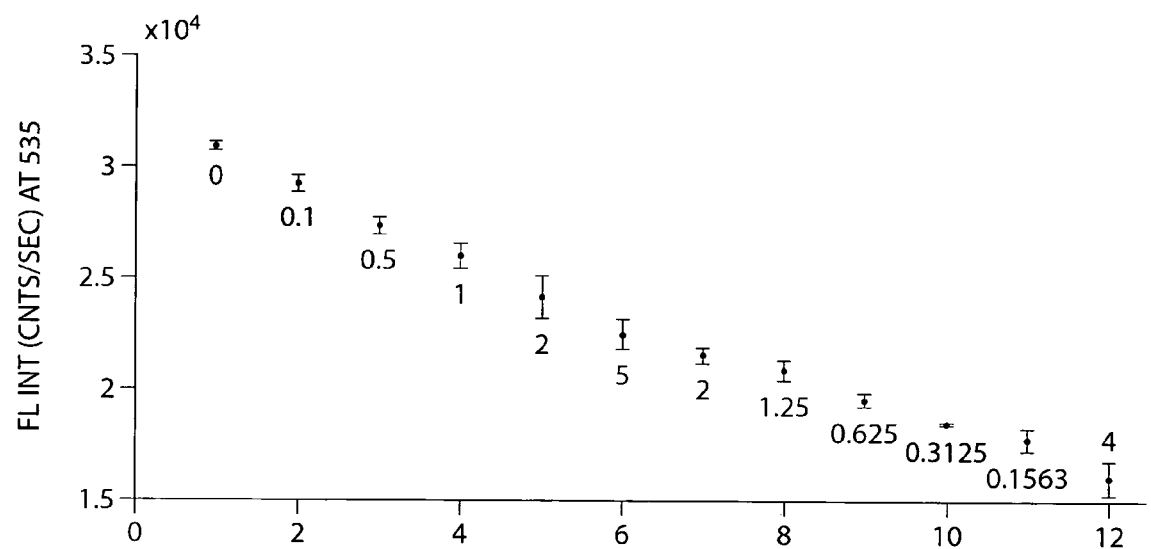
FIG. 19. Rh123 fluorescence quenching (as an indication of membrane potential changes) versus sequence number and glucose concentration. The glucose values (in mg/dL) for each data point is (from left to right): 0, 0.1, 0.5, 1.0, 2.0, 5.0, 2.5, 1.0, 0.5, 0.25, 0.16, and 4.0. Each point represents the mean and standard deviation of 5 data points. The x-axis label is sequence number.

A second set of demonstration experiments was designed to determine the saturation limit for membrane potential-based glucose analysis by varying glucose 0 to 5 mg/dL and back to zero. The saturation point value was expected to be between 0.0 and 2 mg/dL. As shown in FIG. 19 an approximate linear decrease in Rh123 fluorescence with increasing glucose levels was observed from 0 to 5 mg/dL (0.28 mM).

SMMR Fluorophore-Reporter for Glucose and Diol Measurement

For this application of direct glucose sensing SMMRs, the objective is to detect and quantify glucose via a small molecule fluorescent reporter whose photophysical properties are modulated by binding with D-glucose or other simple sugars or diol molecules. Such SMMRs report glucose using a reversible binding process and the molecular structure-activity consists of three mechanistic parts.

1) A fluorophore with suitable photochemical characteristics;
2) A chemical affinity group that binds reversibly with glucose and similar molecular species (e.g., a boronic acid-containing component);
3) Additional substructural features to favor specificity for glucose over fructose, galactose, and other biologically active saccharides, which may be physiologically present near target cells (i.e., near the intercellular or interstitial spaces of the viable epidermis).

Boronic acids are frequently used in saccharide reporter molecules to provide affinity. Boronic acids undergo reversible binding with glucose or another sugar or diol-containing molecule to form a boronate ester with high affinity. (Scheme 3):

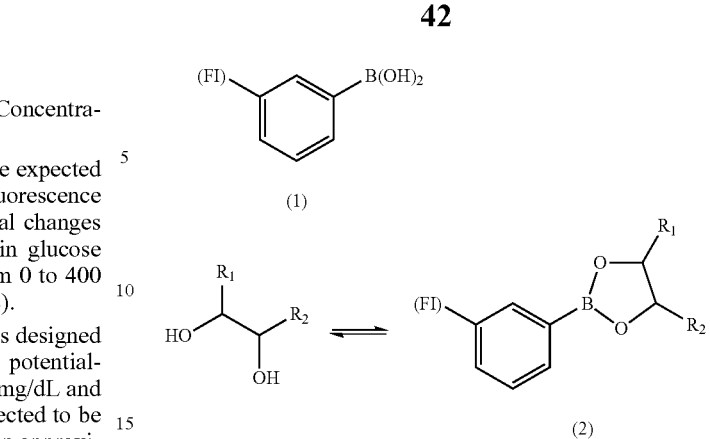

In the literature, signal transduction of the boronic acid+sugar-binding phenomenon has been accomplished in two ways:
1) Modulation of Photoinduced Electron Transfer (PET) quenching, and
2) Modulation of Internal Charge Transfer (ICT).

The PET mechanism of signal transduction is illustrated schematically in Scheme 4, in the case of an anthracene fluorophore [See for example, T. D. James, K. R. A. Samankumara Sandanayake, R. Iguchi, and S. Shinkai, "Novel Saccharide-Photoinduced Electron Transfer Sensors Based on the Interaction of Boronic Acid and Amine", J. Amer. Chem. Soc., 117, 8982 (1995)]. In this example, the fluorophore-boronic acid is present in a pH dependent equilibrium, represented by species (1) and (3). For this example, as pH is increased, the fraction of (3) present increases. In this form, the electrons of the nitrogen lone pair are available for fluorescence quenching of the anthracene moiety. At lower pH, the boron atom participates in a coordinate covalent bond, making the nitrogen lone pair electrons unavailable for quenching, resulting in higher fluorescent intensity.

The presence of a sugar molecule perturbs the (1)-(3) equilibrium. The boronate ester (2) exhibits a different pKa from boronic acid (1). Thus, at a given pH the fluorescent-to-quenched state equilibrium is shifted, resulting in a net increase or decrease of observed fluorescence intensity, depending on the pH of the experiment and the relative pKa of the boronic acids (1) and (2)

Scheme 4.

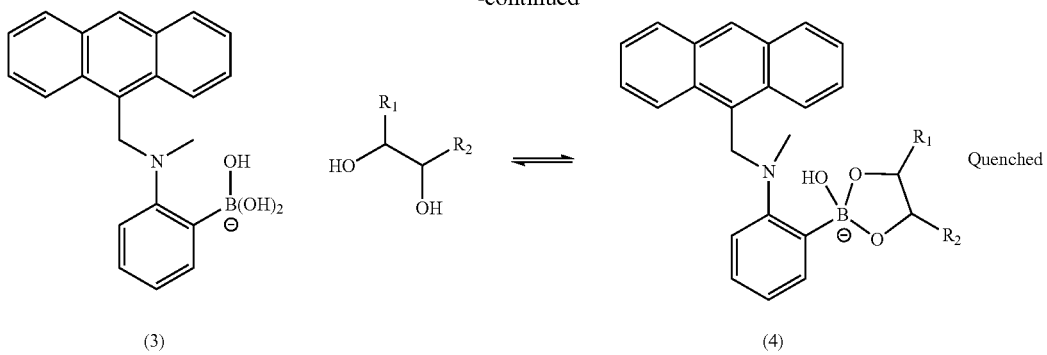

(3)                                           (4)

Illustrative example of the PET mechanism of Boronic acid signal transduction in the presence of a saccharide molecule. (T. D. James, K. R. A. Samankurama Sandanayake, R. Iguchi, and S. Shinkai, "Novel Saccharide-Photoinduced Electron Transfer Sensors Based on the Interaction of Boronic Acid and Amine", J. Amer. Chem. Soc., 117, 8982 (1995)).

The ICT mechanism of signal transduction is illustrated schematically in Scheme 5. In this instance the pH dependent equilibrium (1)-(3) is perturbed by the presence of a sugar molecule. At a given value of pH, this results in a different proportion of the fluorophores (boronic acids and boronate esters) being present in the hydroxylated form, thus modulating the electron-withdrawing characteristics of that end of the molecule. In the case of the boronic chalcone molecule (1), in Scheme 5, this is manifested as a change in relative fluorescent intensity and only a slight wavelength shift.

Another example of the ICT mechanism from Lakowicz's laboratory is shown in Scheme 6. In the case of the N-phenyl-3-nitro-1,8-naphthalimide, the ICT phenomenon manifests itself in a change in relative fluorescent intensity at two wavelengths, resulting in a ratiometric probe. The starting point for these authors' design was the knowledge that suitable N-phenylnaphthalimides exhibit fluorescent emission at two wavelengths and that the longer wavelength emission band shows solvatochromic behavior.

Scheme 5.

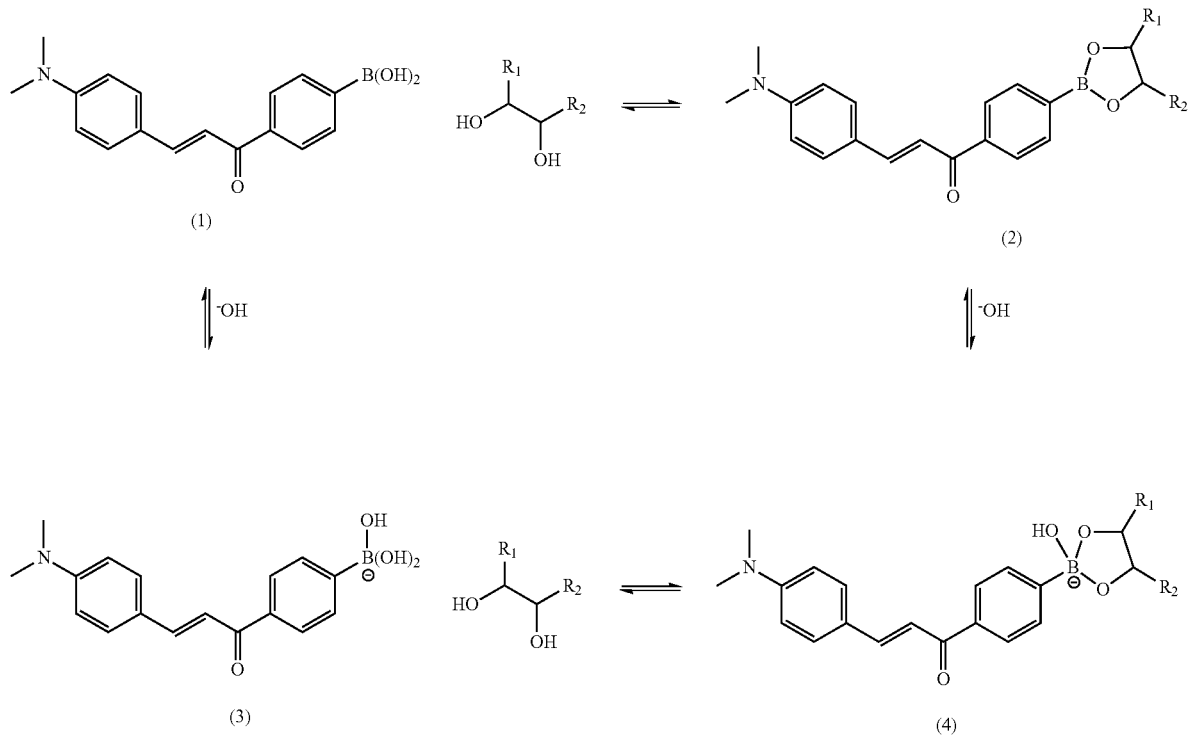

Illustration of the ICT mechanism of Boronic Acid flourescent signal transduction. (N. DiCesare and J. R. Lakowicz, "Chalcone-Analog Fluorescent Probes For Saccharides Signaling Using the Boronic Acid Group", Tetrahedron Letters, 43, 2615 (2002); and H. Cao, D. I. Diaz, N. DiCesare, J. R. Lakowicz, and M. D. Heagy, "Monoboronic Acid Sensor That Displays Anomalous Fluorescence Sensitivity to Glucose", Organic Letters, 4, 1503 (2002)).

Scheme 6.

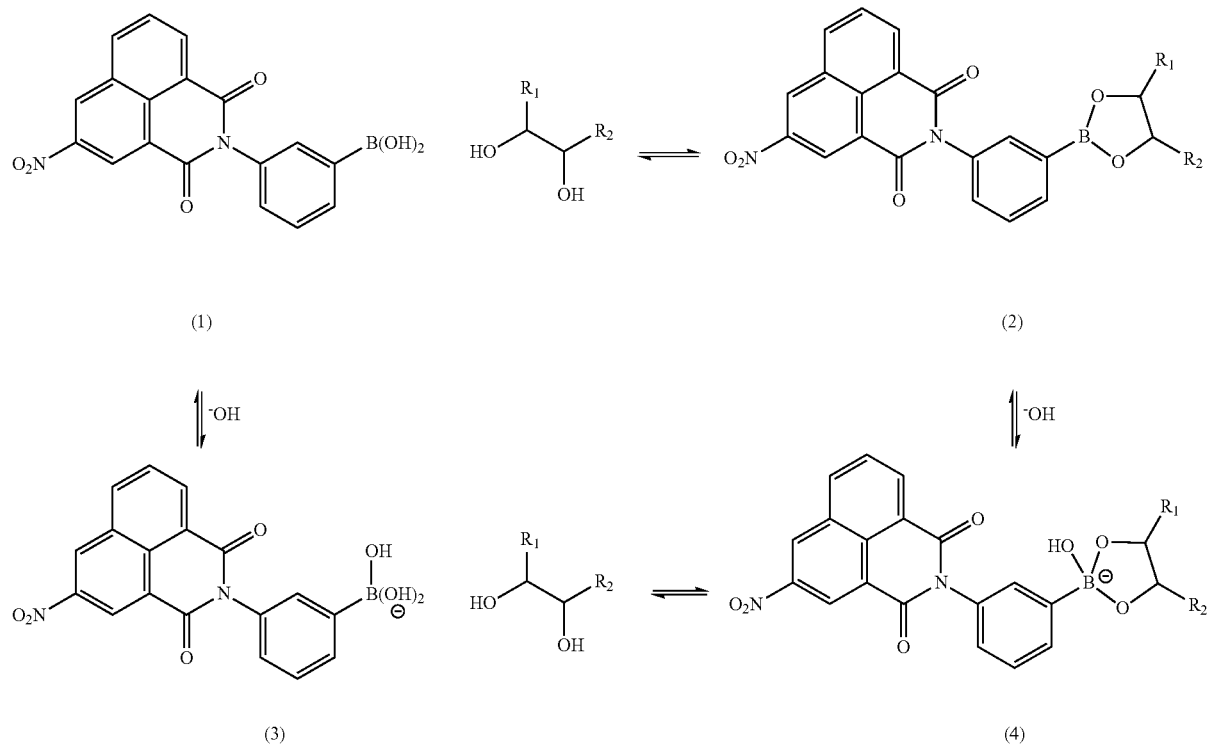

Schematic illustration of the ICT mechanism (N. DiCesare and J. R. Lakowicz, "Chalcone-Analog Fluorescent Probes For Saccharides Signaling Using the Boronic Acid Group," Tetrahedron Letters, 43, 2615 (2002); and H. Cao, D. I. Diaz, N. DiCesare, J. R. Lacowicz, and M. D. Heagy, "Monoboronic Acid Sensor That Displays Anomalous Fluorescence Sensitivity to Glucose", Organic Letters, 4, 1503 (2002)).

Designing the Fluorophore-Boronic Acid Reporter

This compound consists of a fluorophore with long wavelength excitation and emission and high quantum yield. The phenylboronic acid moiety is incorporated in the molecular structure as an essential requirement to add binding affinity for glucose and other diol-containing compounds. Solvatochromic properties may be defined. The photochemistry of the fluorophore is sensitive to its microchemical environment and solvent polarity. Boronic acid can directly affect photochemical properties such as quantum yield and wavelength if it is attached to the fluorophore and serves as the e-withdrawing portion of a "push-pull" system. This can be direct (when boron is connected directly to the fluorophore), or indirect (when the phenylboronic acid exerts a "through-bonds" electron-withdrawing inductive effect).

Prosthetic group selection is critical for fine-tuning molecular selectivity. Naturally occurring enzyme active sites and receptors exhibit exquisite selectivity, even among closely-related compounds. This is possible due to the receptor's high degree of spatial and electrostatic complementarity relative to the molecule in question.

In the case of glucose-binding proteins, for example, the selectivity of the enzyme glucose oxidase is achieved by hydrogen-bonding and close contacts between a glucose molecule and more than six amino-acid side chains present in the active site.

In the realm of small-molecule synthetic glucose reporters, some reported compounds achieve a relatively good specificity for glucose over fructose—as much as 10-fold, considering that there is very little in the way of molecular features (of the synthetic receptor) to distinguish one from the other. When designing a synthetic receptor, several strategies can be employed to improve specificity, namely:

1. Multiple Boronic Acid Binding Sites

Spatial disposition and distance will provide some selectivity among competing saccharide molecules, due to geometric constraints. (T. D. James, K. R. A. Samankumara Sandanayake, R. Iguchi, and S. Shinkai, "Novel Saccharide-Photoinduced Electron Transfer Sensors Based on the Interaction of Boronic Acid and Amine", J. Amer. Chem. Soc., 117, 8982 (1995)). Using two or more boronic acid binding complicates the picture due to the high affinity of the reversible formation of covalent bonds in the boronate ester. The equilibrium-binding constant of a single boronic acid based receptor is in the millimolar (mM) range for glucose. The corresponding binding constant is micromolar (μM) in the two-boronic acid case. Thus, at normal physiological concentrations, the two-boronic probe would be saturated.

2. Adjacent H-Bond Donors and Acceptors

Additional H-bond donors and acceptors contribute only about 6 kcal/Mol., each, to ligand-receptor binding. Design of a synthetic probe to include H-bonding sites provides a means to provide a binding advantage to molecules, which present H-bondable groups in the appropriate spatial orientation. Thus the position and orientation can be designed in by reference to molecular models, to enhance glucose specificity relative to other saccharides.

3. Adjacent Non-Bonded Interactions

Specificity can be enhanced by model driven choice of other chemical groups, such as alkyl side chains, which do not add to binding affinity, but operate by spatial exclusion.

Several examples of novel boronic acid compounds based on various fluorophores are given in the following examples.

Example 5

Xanthene Dyes Used to Report Glucose by the ICT Mechanism or Electronic Perturbation of the Fluorophore

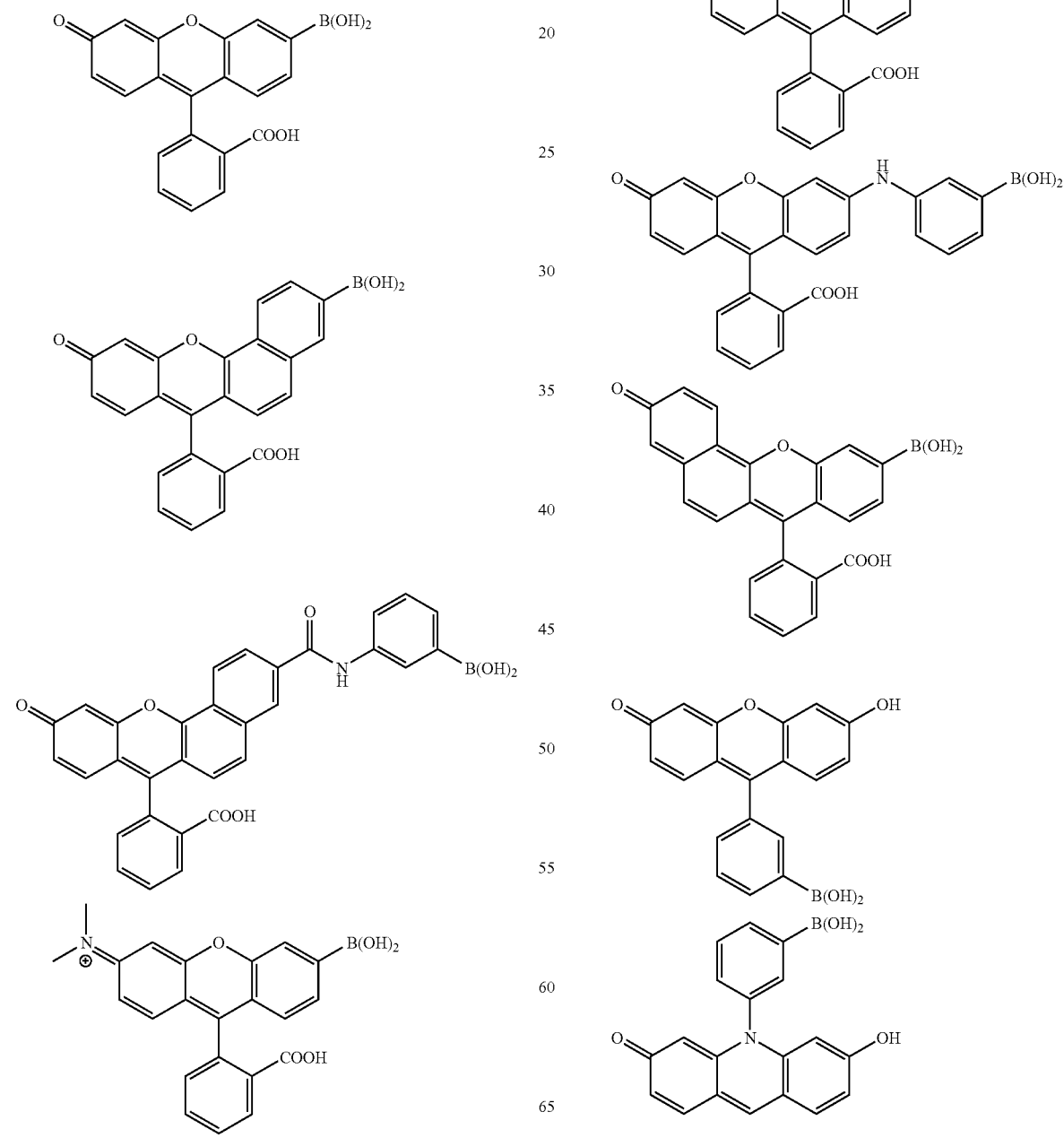

Example 6

Xanthene Dyes Used to Report Glucose by the Pet Mechanism

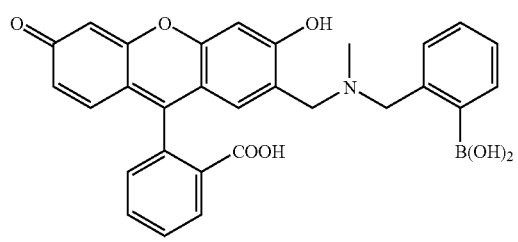

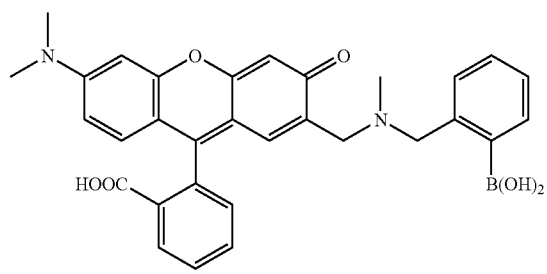

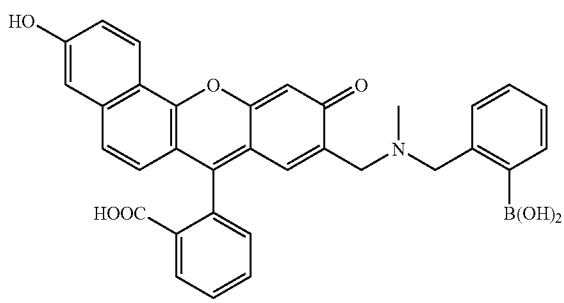

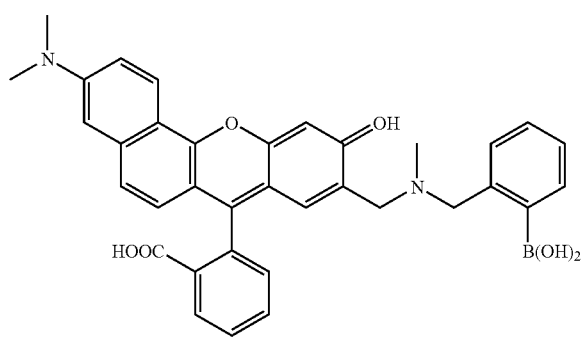

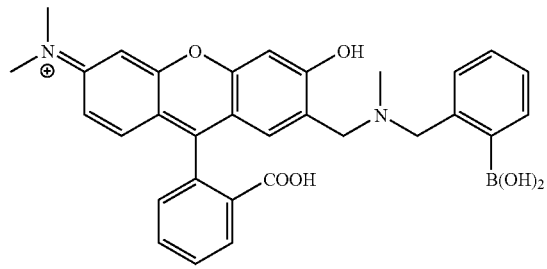

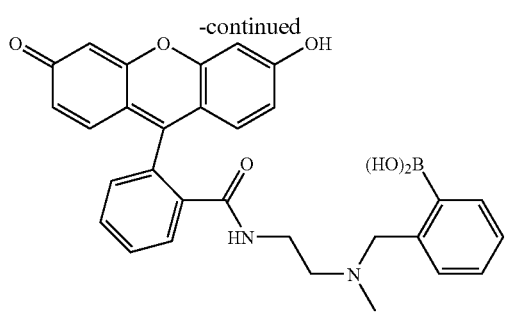

Designing Xanthene-Based Reporters

A library of xanthene dyes is proposed to form a basis for Structure-Activity studies with respect to emission wavelength, ratiometric behavior, and quantum yield. The library of compounds is made in a combinatorial synthesis paradigm, wherein each xanthene compound is a result of a cross-product of suitable building blocks. Substituents are chosen with emphasis on final products that incorporate electron-donating and electron-withdrawing groups as well as H-bond donors and acceptors. Thus the library members will include compounds with push-pull characteristics and solvatochromic sensitivity The library compounds are generated according to the reaction sequence outlined in Scheme 7, below. These reactions employ standard chemical methods. The final reaction yields the nominal product and byproducts corresponding to disproportionation and recombination of the building blocks. Final products are isolated after standard purification techniques such as flash chromatography and semi-preparative HPLC.

Scheme 7. A method for the synthesis of a Xanthene Combinatorial Library

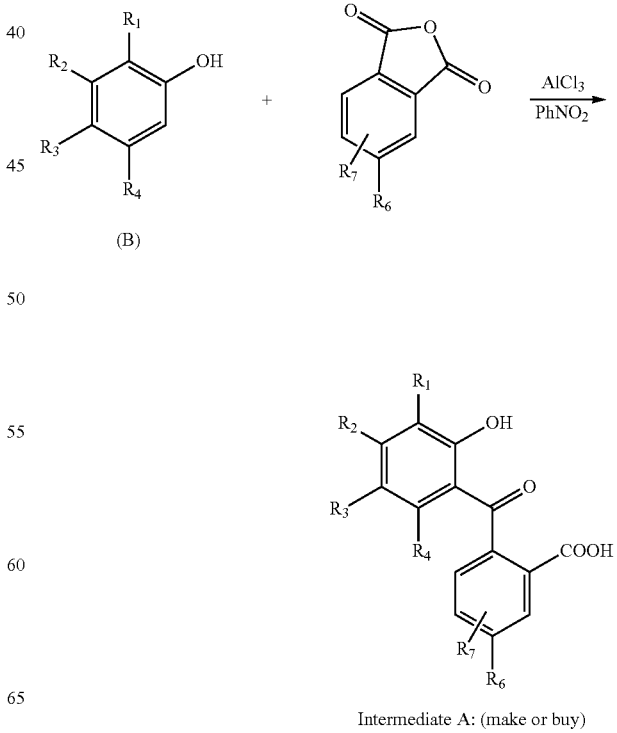

Intermediate A: (make or buy)

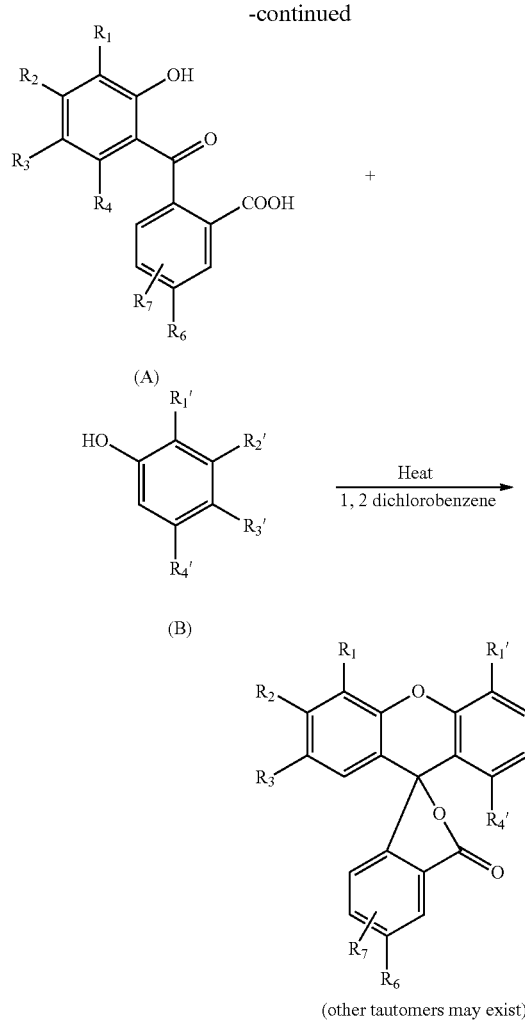

(A)

(B)

(other tautomers may exist)

Figure 20:
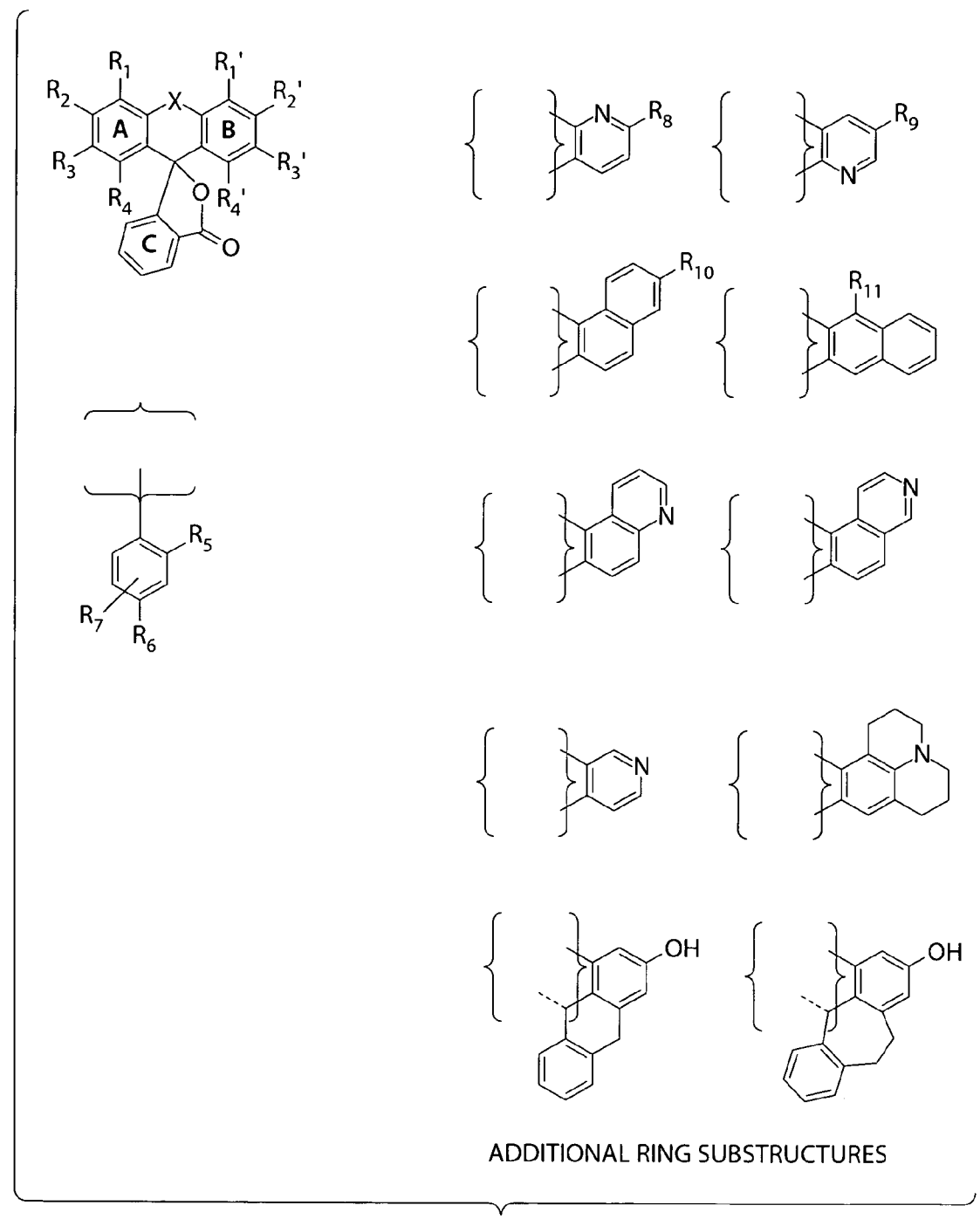
FIG. 20. Schematic representation of the products of the xanthene library in terms of Markush structures and some specific sub structures.

The possible products comprising this library are delineated schematically in FIG. 20 and the accompanying Tables 1, 2, and 3 as demonstrated.

Tabulated Substituents on Building Blocks Used in the Xanthene Library.

TABLE 1

Xanthene Building Blocks Incorporating R1, R2, R3, R4, and X

| | Building Block | | | | |
|---|---|---|---|---|---|
| | R1 | R2 | R3 | R4 | X |
| 1 | | OH | | | O |
| 2 | | N(CH$_3$)$_2$ | | | O |
| 3 | | OH | | | S |
| 4 | | SH | | | S |
| 5 | | SH | | | O |
| 6 | | OCH$_3$ | | | O |
| 7 | | CF$_3$ | | | O |
| 8 | OCH$_3$ | OH | | | O |
| 9 | NH$_2$ | OH | | | O |
| 10 | NO$_2$ | OH | | | O |
| 11 | CF$_3$ | OH | | | O |
| 12 | CH$_3$ | OH | | | O |
| 13 | Cl | OH | | | O |
| 14 | CN | OH | | | O |
| 15 | CH$_3$ | OH | | CH3 | O |
| 16 | Br | | | | O |

TABLE 1-continued

Xanthene Building Blocks Incorporating R1, R2, R3, R4, and X

| | Building Block | | | | |
|---|---|---|---|---|---|
| | R1 | R2 | R3 | R4 | X |
| 17 | COOH | | | | O |
| 18 | NO$_2$ | | | | O |
| 19 | OCH$_3$ | | | | O |
| 20 | OH | | | CH3 | O |
| 21 | OAc | | | | O |
| 22 | N—Me$_2$ | | | | O |
| 23 | NH$_2$ | | | | O |

TABLE 2

Xanthene Building Blocks incorporating R5, R6, and R7

| | Building Block | | |
|---|---|---|---|
| | R5 | R6 | R7 |
| 1 | COOH | — | — |
| 2 | COOH | — | COOH |
| 3 | — | OH | — |
| 4 | CH$_3$ | NHAc | |
| 5 | — | OH | — |

TABLE 3

Xanthene Building Blocks Incorporating R8, R9, R10, R11, and X

| | Building Block | | | | |
|---|---|---|---|---|---|
| | R8 | R9 | R10 | R11 | X |
| 1 | OH | — | — | — | O |
| 2 | — | OH | — | — | O |
| 3 | — | — | OH | — | O |
| 4 | — | — | N—Me$_2$ | — | O |
| 5 | — | — | — | Br | O |
| 6 | — | — | — | COOH | O |

Appendix 1. List of Building Blocks for the Xanthene Library Composition

A Components

Fluoresceins

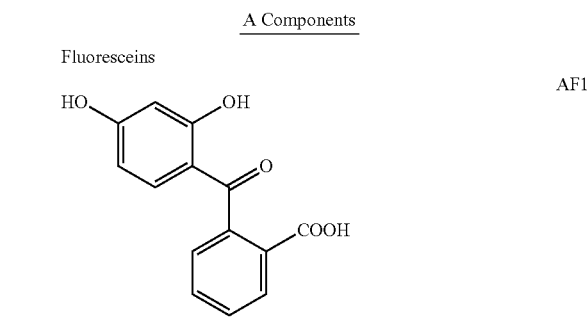

AF1

Rhodamines

AR1

AR2

Thio derivatives

AT1

AT2

Rigidified xanthenes

ARg1

ARg2

Quinoid chromophores

AQ1

Push-Pull xanthenes
Push

APus1

APus2

-continued
Pull
APul1
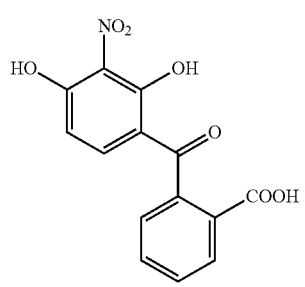
APul2
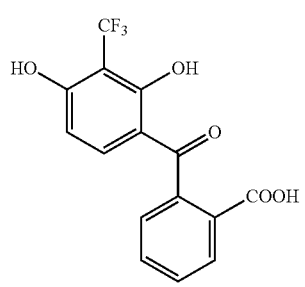
Naphtho xanthenes
AN1
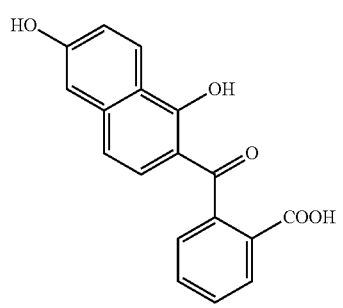
AN2
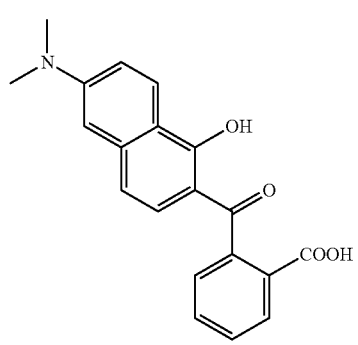
Miscellaneous
AM1
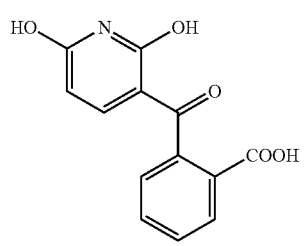
-continued
Xanthene analogs
AX1
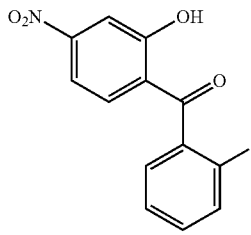
AX2
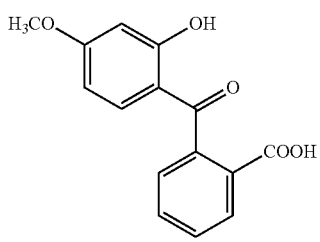
B Components
Fluoresceins
BF1
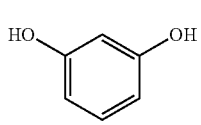
BF2
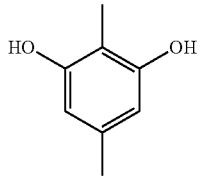
BF3
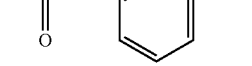
BF4
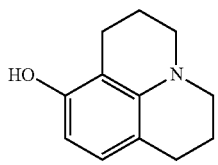
Rhodamines
BR1
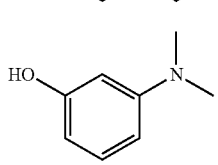
BR2
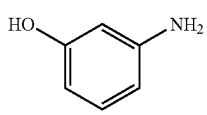
BR3

Thiol derivatives
BT1
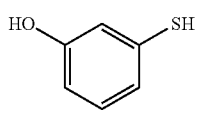
BT2
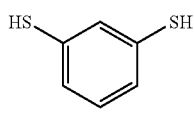
Heterocyclic analogs
BN1
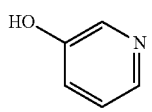
BN2
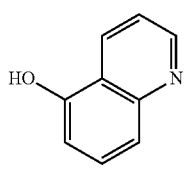
BN3
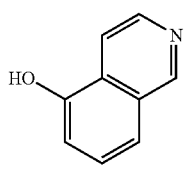
BN4
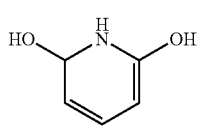
BN5
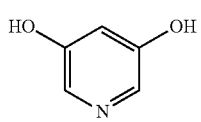
Naphtho xanthenes
BNap 1
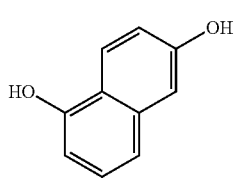
BNap 2
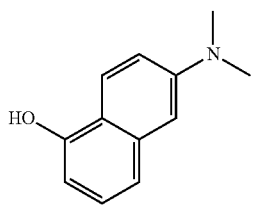
Push-Pull derivatives
Push
BPus1
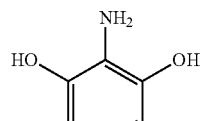
BPus2
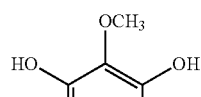
BPus3
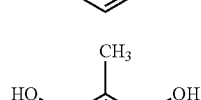
BPus4
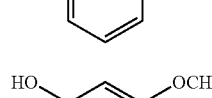
Pull
BPul1
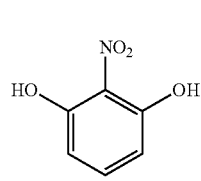
BPul2
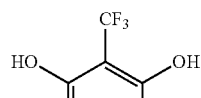
BPul3
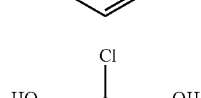
BPul4
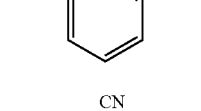
BPul5
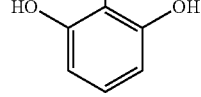
Other
BM1
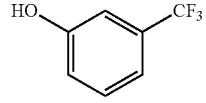

-continued

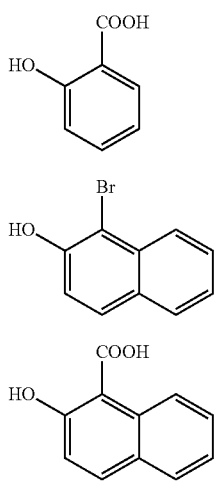

BM2

BM3

BM4

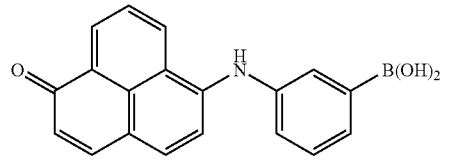

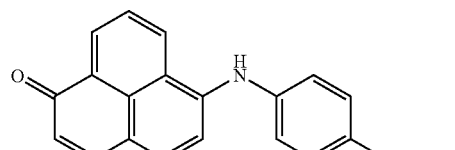

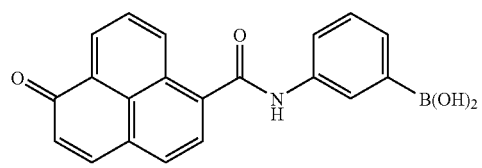

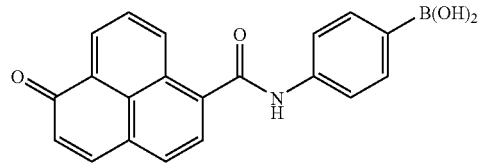

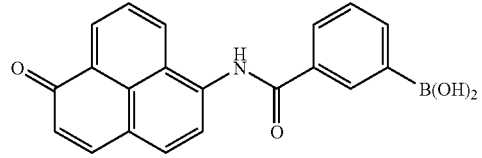

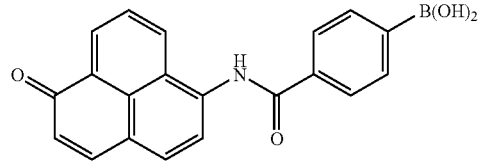

Summary of Design Strategy

This list comprises 15 A components, 18 B components. Combination of these materials would result in 270 xanthene dyes.

The list of components is

| A Components | |
|---|---|
| Fluoresceins: | AF1; AF2 |
| Rhodamines: | AR1 |
| Thio derivatives: | AT1; AT2 |
| Rigidified xanthenes: | ARg1; ARg2 |
| Quinoid chromophores: | AQ1 |
| Push-Pull xanthenes | |
| Push: | APus; APus2 |
| Pull: | APull1; APul2 |
| Naphtho xanthenes: | AN1; AN2 |
| Miscellaneous: | AM1 |
| Xanthene analogs: | AX1; AX2 |
| B Components | |
| Fluoresceins: | BF1 |
| Rhodamines: | BR1; BR2; BR3 |
| Thiol derivatives: | BT1; BT2 |
| Heterocyclic analogs: | BN1; BN2; BN3 |
| Naphtho xanthenes: | BNap1; BNap2 |
| Push-Pull derivatives | |
| Push: | BPus1; BPus2 |
| Pull: | BPul1; BPul2 |
| Other: | BM1; BM2; BM3; BM4 |

Example 7

Phenalene-1-one Dyes Used as Glucose Reporters

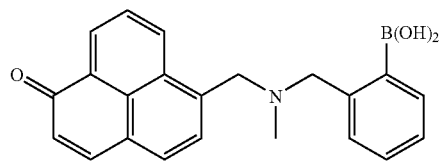

Example 8

Coumarin Derivatives Used as Glucose Reporters

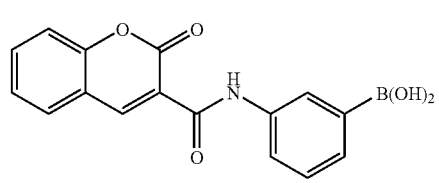

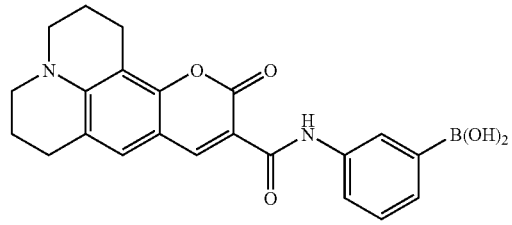

-continued

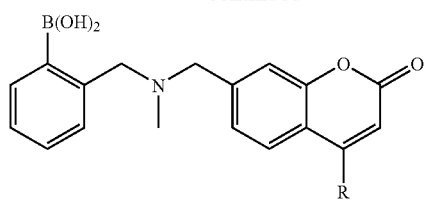

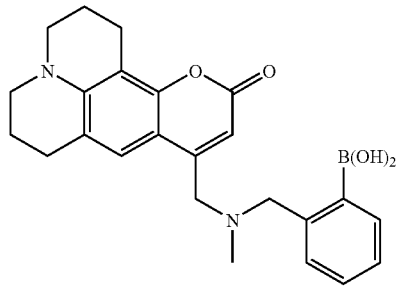

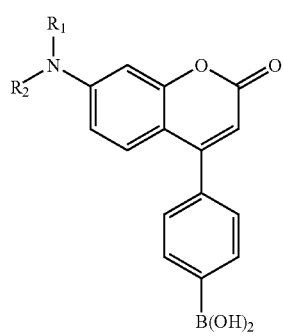

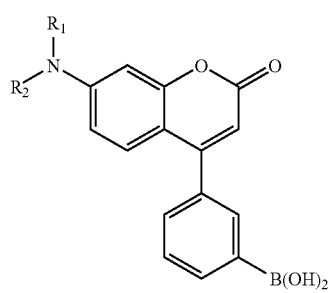

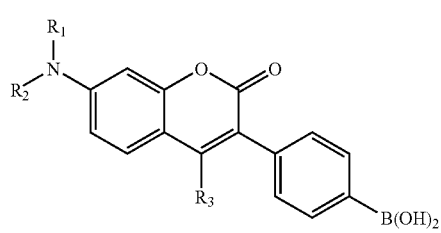

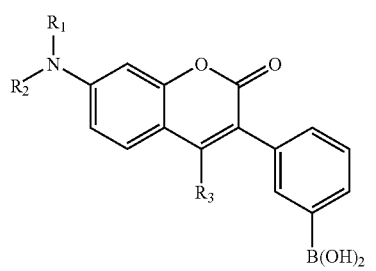

-continued

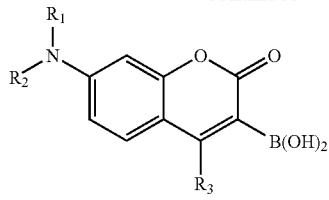

Example 9

Use of Coumarin-Boronic Acid SMMRs to Report Glucose in Plasma, Interstitial Fluid, or Other Body Fluids The structure of the glucose sensing deprotected compound referred to for this invention as (Argofluor-327d) is given here. The protecting group must be removed before the interaction of the compound with glucose can be examined.

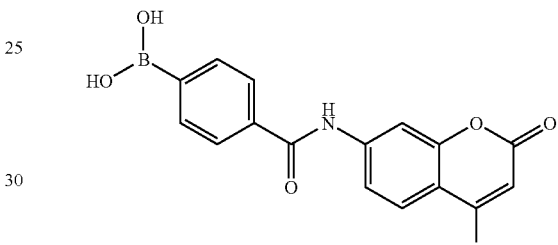

Argofluor-327d

The compound has been prepared by leaving an ethanol solution of the parent compound to stand overnight at room temperature in the dark. While not intending to be bound by theory, it is believed that ethanol replaces the pinacol-protecting group in an equilibrium driven by the overwhelming concentration of ethanol. Dilution of this stock solution into aqueous (pH 8) buffer shows that the largest change in the absorption spectrum within about 20 minutes, as water displaces the ethanol forming the deprotected boronic acid. Smaller changes in the spectrum are observed up to 90 minutes later.

Figure 50:
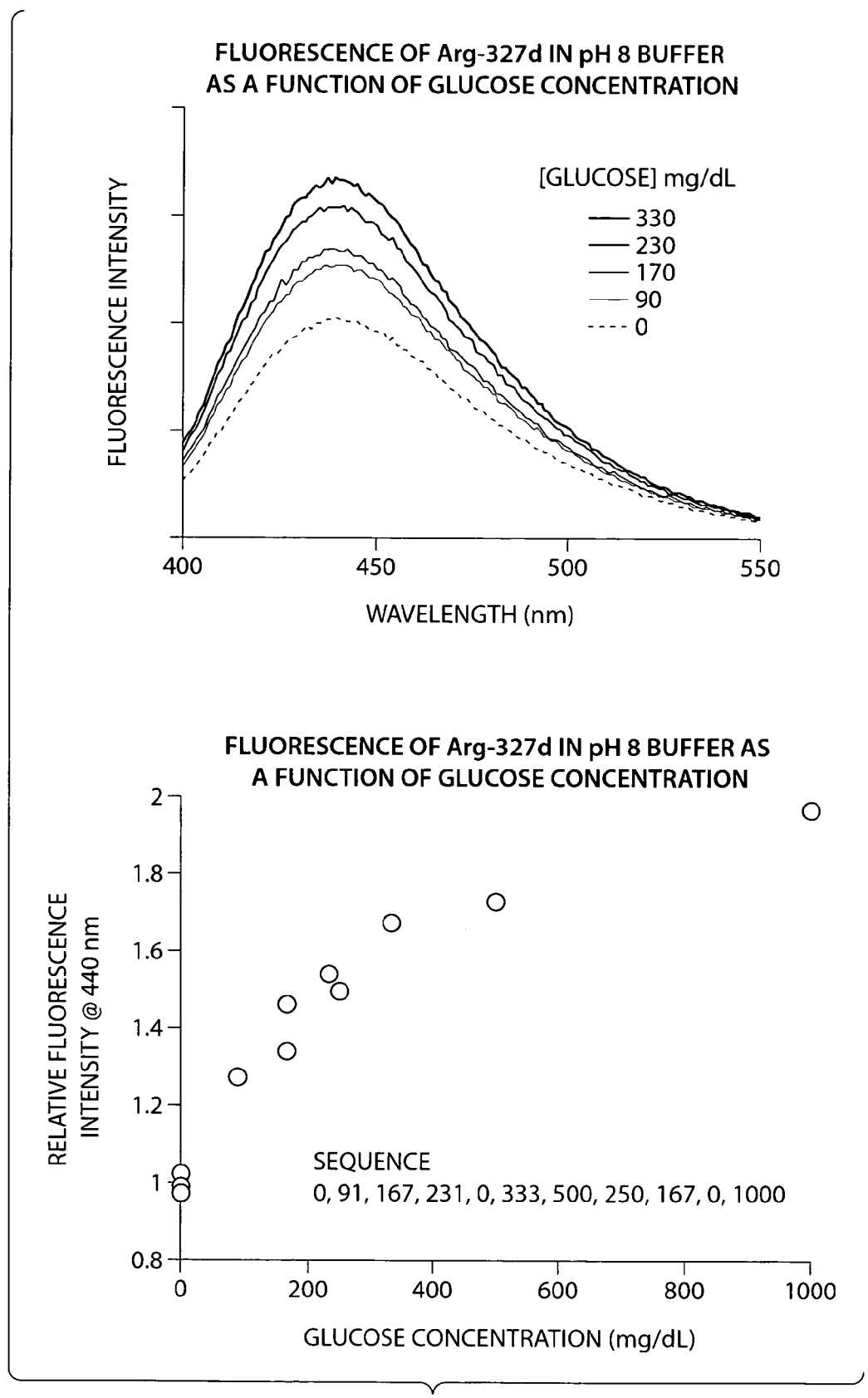
FIG. 50. Absorption and fluorescence spectra of Argofluor-327d obtained as a function of glucose concentration.

The absorption and fluorescence spectra of Argofluor-327d were obtained as a function of glucose concentration. The absorption spectrum changed by less than 10% at the excitation wavelength. A plot of the fluorescence intensity from 400 nm to 550 nm as a function of glucose concentration is shown in FIG. 50. There is no apparent shift in the wavelength maximum. The excitation wavelength was 375 nm. The long wavelength absorption maximum was found to be 333 nm. Note for this compound the fluorescence intensity increases by at least 40% over a glucose range of 200 mg/dL. A 60% rise in fluorescence intensity was observed on addition of glucose for a physiological glucose concentration range of 300 mg/dL. The maximum emission wavelength position remained constant at all glucose concentrations tested (i.e., no wavelength EM maximum shift).

In Vitro Experiment (3 mL Total Volume in Buffer Solution)

While not intending to be bound by theory, it is believed that the mechanism by which the intensity of fluorescence is affected by glucose, but not the emission wavelength, involves modulation of electron density in the coumarin moiety. Calculations have shown that the electron affinity of bound and free boronic acid is very different. Free boronic acid is strongly electron withdrawing while complexed boronic acid is neutral or even electron donating.

In light of the magnitude of the effect observed, other compound analogs are prepared to look for wavelength shift as well as a strong effect on binding glucose.

An effect of glucose on the complexation of phenyl boronic acid with esculetin, i.e.

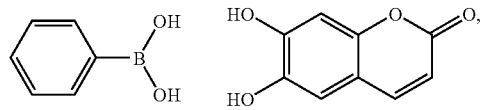

has also been observed.

Figure 51:
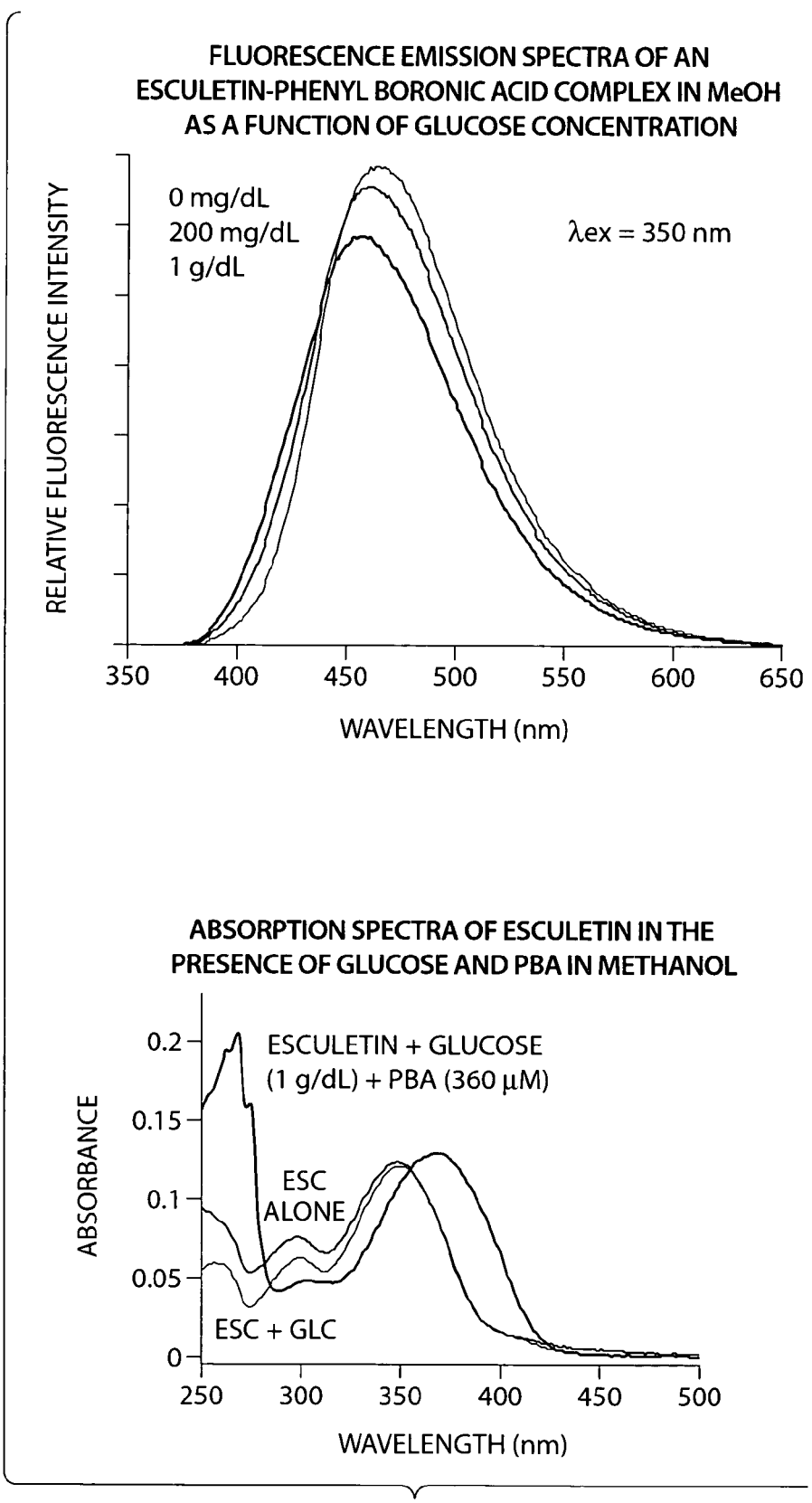
FIG. 51. Fluorescence and absorption spectra showing effect of glucose on the complexation of phenyl boronic acid with esculetin.

These two compounds form a complex when the phenyl boronic acid is present at high concentration. In the presence of glucose, the complex is disrupted with a change in the fluorescence and absorption spectra. FIG. 51 shows the fluorescence spectra on top; and the absorption spectra below. The purpose of an experiment such as this is that if a complexed pair showed a large spectral change with glucose concentration then a tethered pair would be synthesized that would then reasonably be expected to show a large change in their spectral properties in the presence of glucose.

NMR Observation of Hydrolysis of Protected Boronic Acids

The timeframe in which a pinacol-protected boronic acid derivative hydrolyzes and converts into the free boronic acid, which then could be complexed with glucose can be determined using NMR.

was conducted using the protected 3-phenol-boronic acid. It gave essentially the same results. Understanding the removal of the protecting group is an important step in the synthesis of boronic acid analogs.

In-Vivo Glucose Detection Using Coumarin-Boronic Acid-Based Reporter

Three separate test series were performed in rats by injecting 100 microliter of a 1 mM compound solution, followed by injection of 100 microliter of buffer solution, with and without glucose at 300 mg/dL concentration. Fluorescence was measured by excitation at 355 nm and detection of emission at 440 nm. The typical experiments showed a decreasing baseline of tissue autofluorescence. Micro-injected dye spots exhibited fluorescence intensity of more than 10× the autofluorescence background, under the experimental conditions. Injected spots also showed changing fluorescence intensity (usually declining as the compound was transported into cells). No effect of glucose could be discerned in the experimental setup, due to positional sensitivity, and unknown mechanical factors in acquiring the dye spot and referencing the intensity.

In-Vitro Detection Using Coumarin-Boronic Acid-Based Reporter

PHK cells were loaded with AF-327d reporter, at 50 micromolar concentration, in buffer. Fluorescence was measured using a two-photon fluorescent imaging system at approximately EM 440 nm, and excitation at (2P) 705 nm. Pictures taken 10 minutes apart show a slight change in fluorescence intensity upon increasing the glucose concentration to 300 mg/dl in the cell buffer medium. This is seen clearly, as a 20% decrease in time course of fluorescence.

Scheme 8.

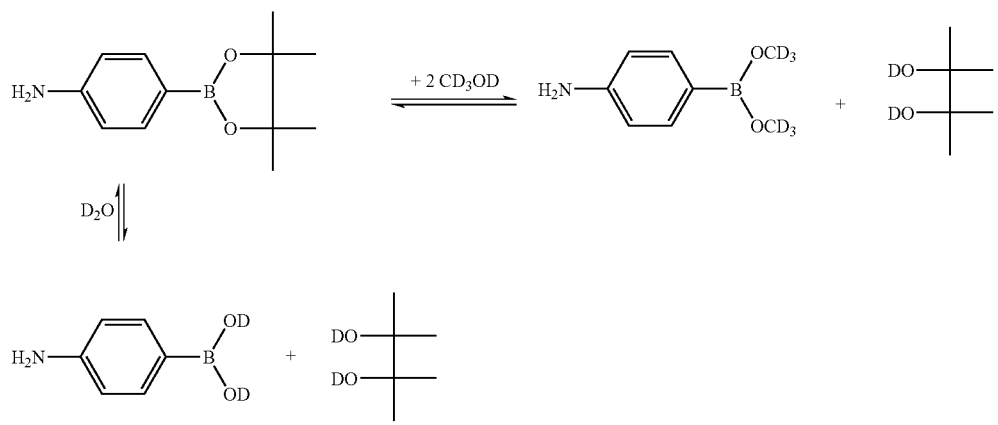

Figure 52:
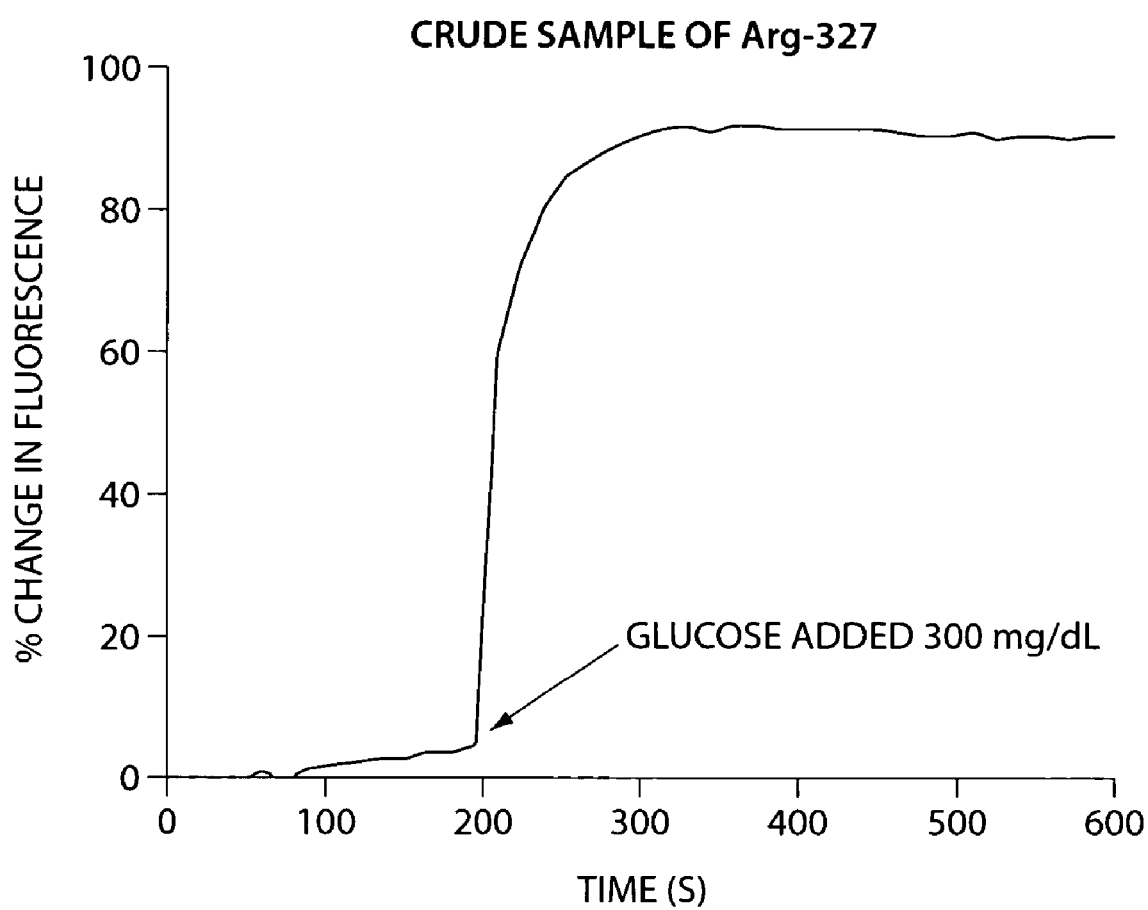
FIG. 52. Glucose response rate using coumarin-boronic acid-based reporter.

15 mg protected 4-amino-phenylboronic acid was dissolved in 0.75 ml CD$_3$OD and the $^1$H-NMR spectrum was recorded immediately. A clear spectrum was obtained. The sample was measured again after 1 h and 15 h. The spectrum was essentially unchanged, which means, that the pinacol-group is still attached to the boron. After 15 h two drops of D$_2$O (ca. 20 mg) were added into the NMR-sample and the spectrum recorded. This spectrum and a spectrum after 4 h were also almost unchanged, which means, that the protecting group is very stable in these media. The same kind of test Glucose Response Rate Using Coumarin-Boronic Acid-Based Reporter Arg-327 unprotected batches were prepared. One batch was supplied as a yellow powder and the other as a concentrated solution in deuterated methanol. A small sample of these materials was taken and dissolved in 3 ml of pH 8 phosphate buffer. The fluorescence of these materials was excited at 340 nm and the emission monitored at 440 nm. The fluorescence was monitored every 15 seconds in a stirred cuvette. After about 3 minutes 100 μL of 300 mg/dL glucose in pH 8 buffer was added. The change in glucose increased immediately on this timescale and a plot of the fluorescence intensity as a function of time is shown in FIG. 52. Similar results were obtained for both samples.

Laboratory Synthesis of Boronic-Acid-Based Glucose Reporters

Preparation of Designation #AF-332: Coupling of a Protected 4-aminophenylboronic Acid with 6-Methoxy-2-naphthoic Acid

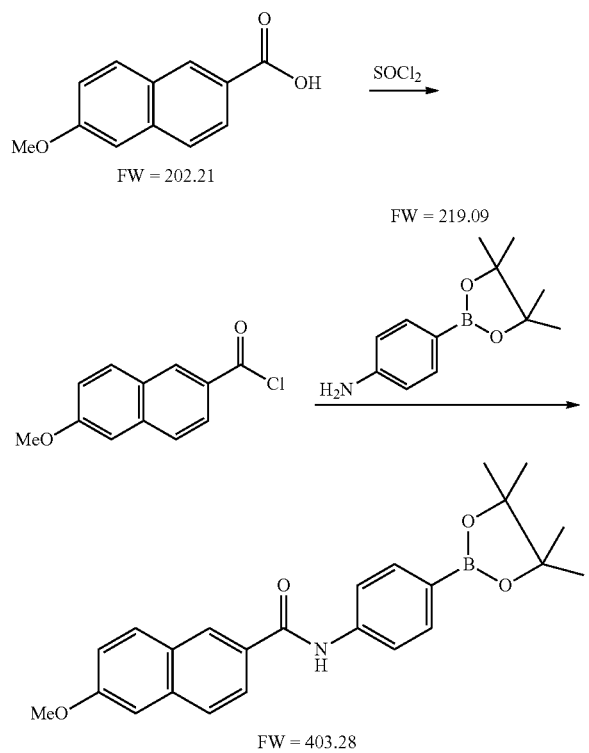

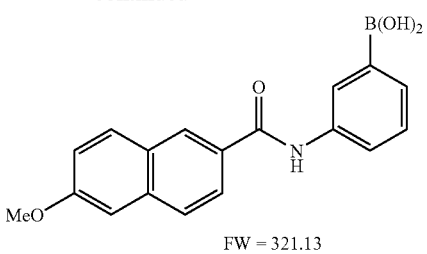

NMR spectrum of the isolated product is consistent with the proposed structure

Preparation of Designation #AF-327 (ZW-17-41)

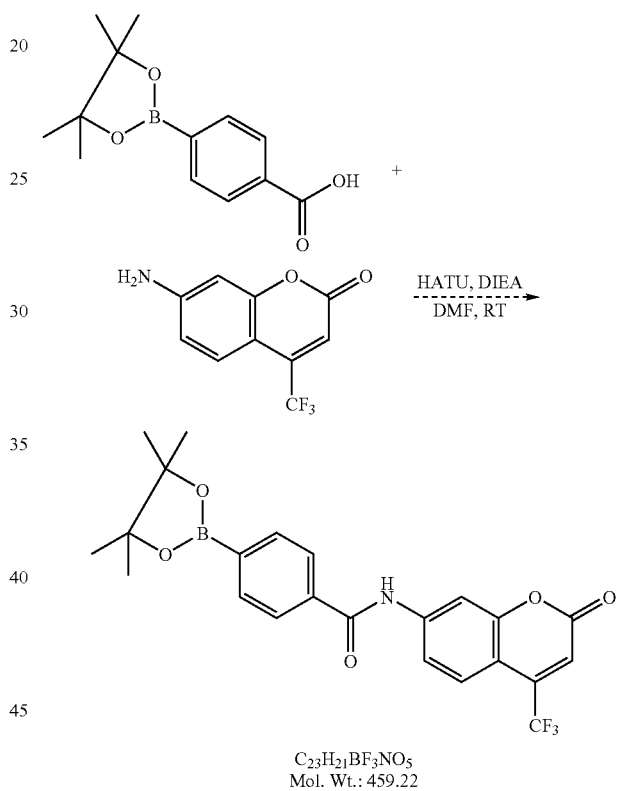

NMR and MS analyses are consistent with the proposed structure.

Preparation of Designation #AF-333: Coupling of 3-Aminophenylboronic Acid with 6-Methoxy-2-naphthoic Acid

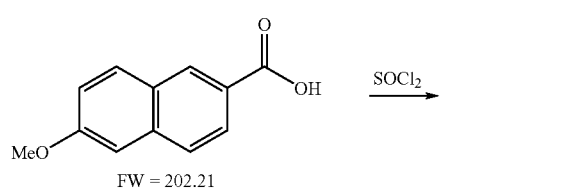

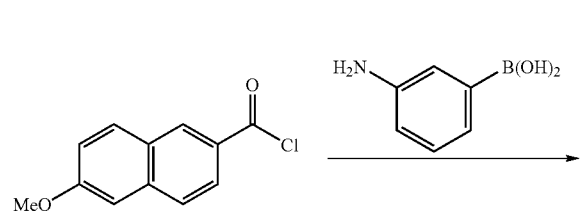

NMR if the isolated compound is consistent with the proposed structure.

Preparation of Designation #AF-327d (HN-2-58): Synthesis A, Coupling of 4-Chlorocarbonylphenylboronic Anhydride with Coumarin 151

This reaction gives a higher yield of the desired product in contrast to other experiments using a coupling agent, in which the isolated yields were less than 5%. A major spot was found in TLC, which appears to be the desired boronic acid. This compound is responsive to glucose, again exhibiting a 60% increase in fluorescence intensity in vitro, when [glucose] is changed from zero to 300 mg/dL. The NMR is consistent with the proposed structure.

Preparation of Designation #AF-327d (HN-2-58 and HN-2-64) Resynthesis: Coupling of 4-Chlorocarbonylphenylboronic Anhydride with Coumarin 151

Preparation of Designation #AF-327d (HN-2-59): Synthesis B, Coupling of 4-Chlorocarbonylphenylboronic Anhydride with Coumarin 120

Resynthesis of AF-327d (HN-2-78): Additional Supply of AF-327d was Prepared According to the Methods Previously Reported.

Approximately 100 mg (13% yield) of pure product and 250 mg unreacted Coumarin-151 were recovered. Em=440 nm; ex=340 nm.

Preparation of Designation #AF-329 (ZW-17-51)

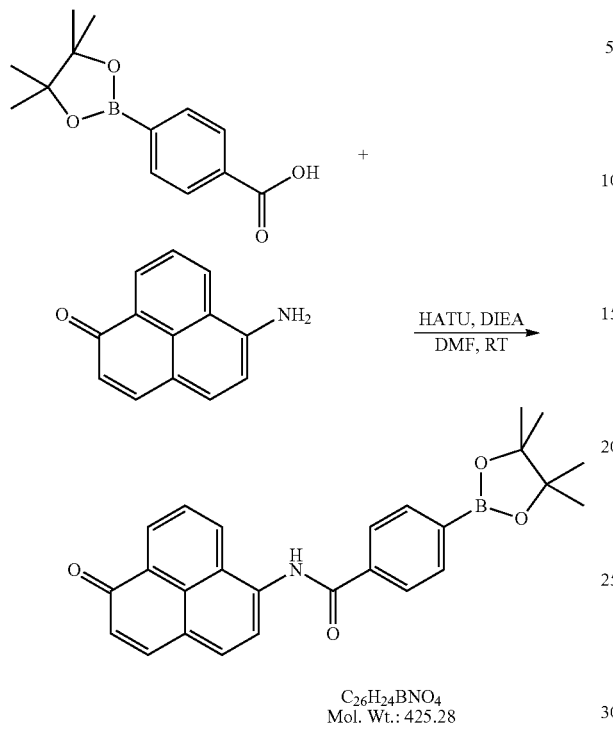

NMR of the purified compound is consistent with the assigned structure.

Preparation of Designation #AF-329d (HN-2-71) Preparation: Reaction of 4-Chlorocarbonylphenylboronic Anhydride with 6-Amino-1H-phenalene-1-one

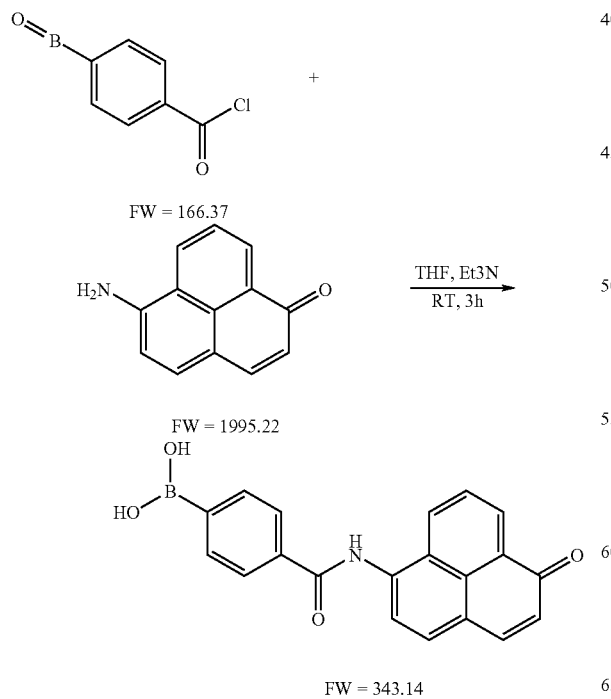

TLC shows some new bright yellow spots. The crude mix shows a huge Stokes shift. No response to the addition of Glucose could be observed.

Preparation of Designation #AF-330 (ZW-17-54)

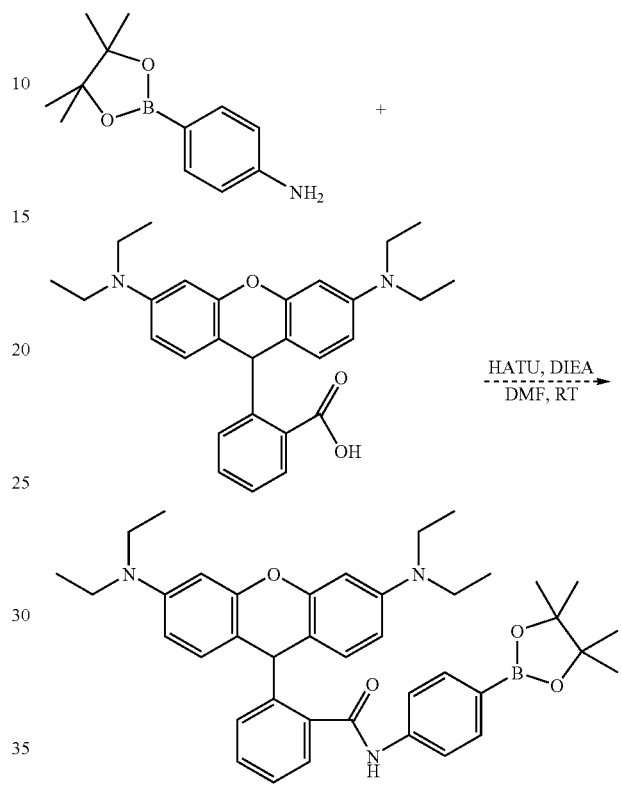

A product was isolated by column purification. It is being analyzed for identity and properties. Paradoxically, it appears colorless in the bottle.

Preparation of Designation #AF-333-1 (ZW-17-55)

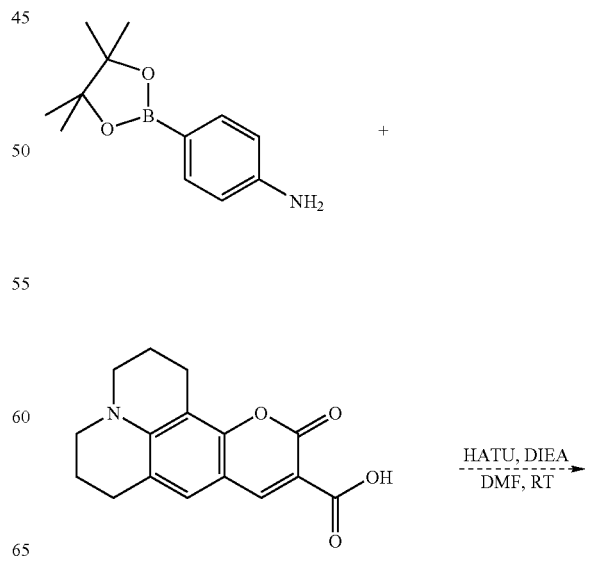

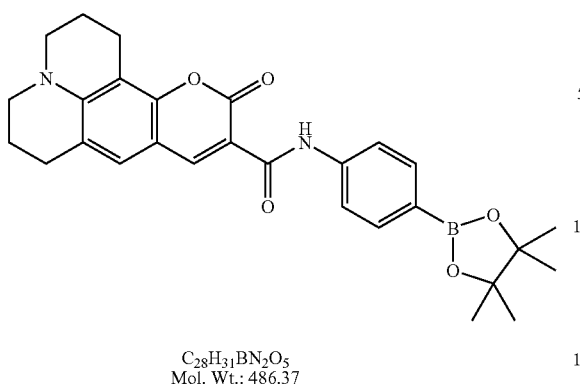

C28H31BN2O5
Mol. Wt.: 486.37

A pure product has been obtained. Characterization is in process.

Preparation of Designation #AF-334 (HN-2-47): Coupling of the Acid Chloride of Coumarin-343 with 3-aminophenyl-boronic acid.

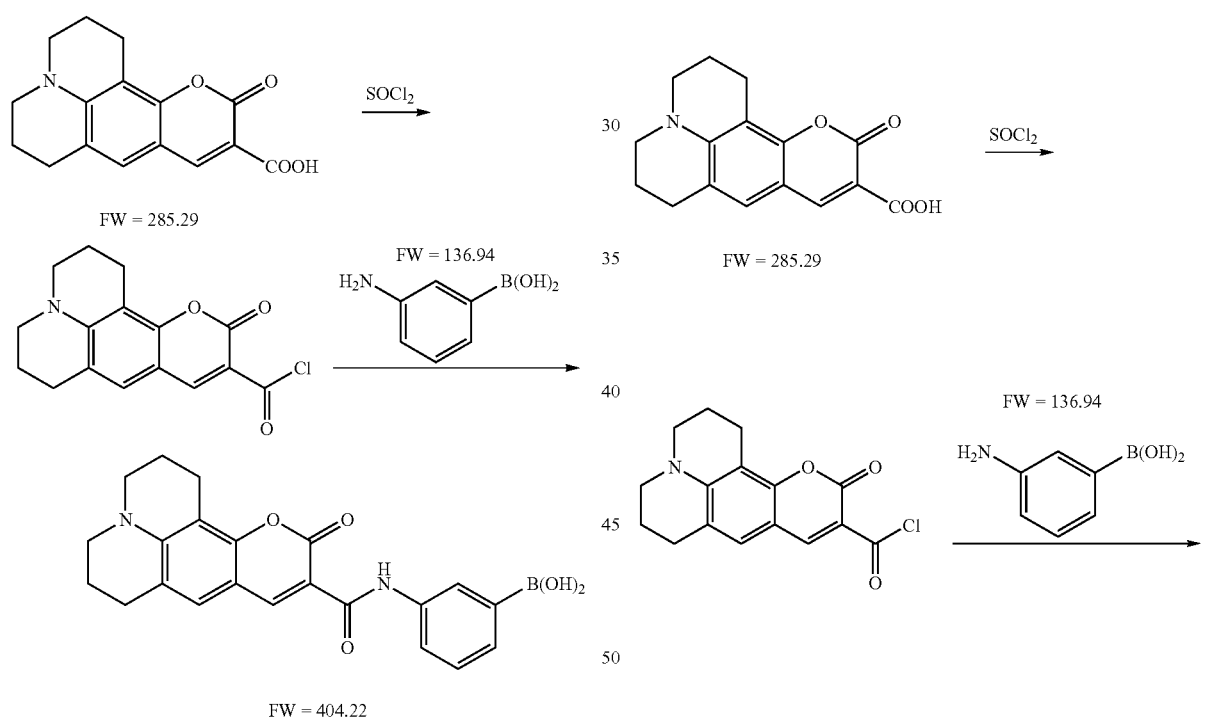

Preparation of Designation #AF-334 (HN-2-48): Coupling of the Acid Chloride of Coumarin 3-carboxylic Acid with 3-aminophenylboronic Acid.

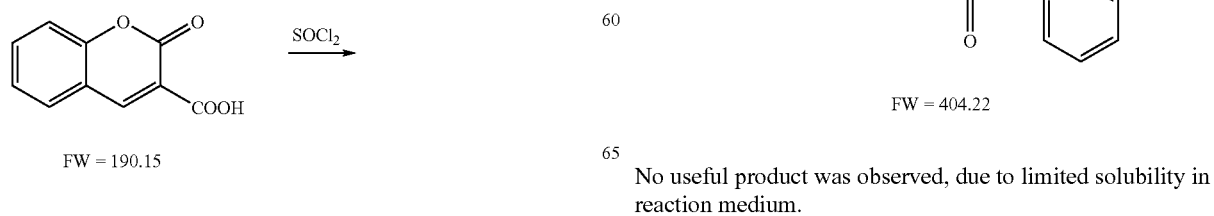

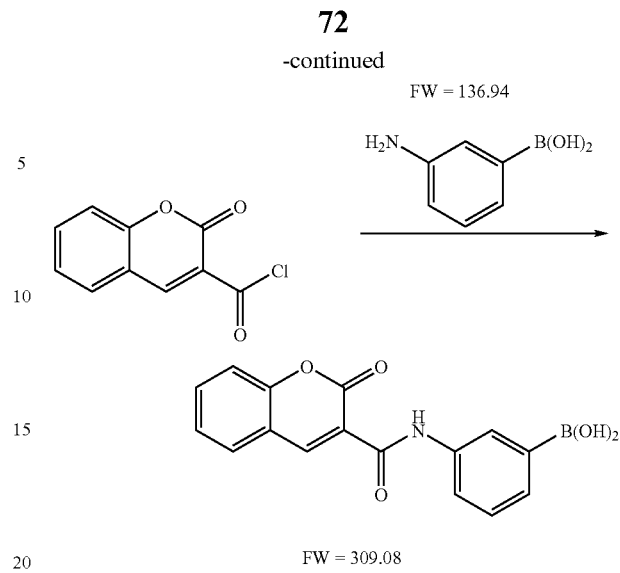

Preparation of Designation #AF-335 (HN-2-47): Coupling of Coumarin-343 with 3-Aminophenyl-boronic Acid No useful product was observed, due to limited solubility in reaction medium.

Preparation of Designation #AF-336 (HN-2-50): Preparation of a Fluorescein-Like Xanthyl-Boronic Acid

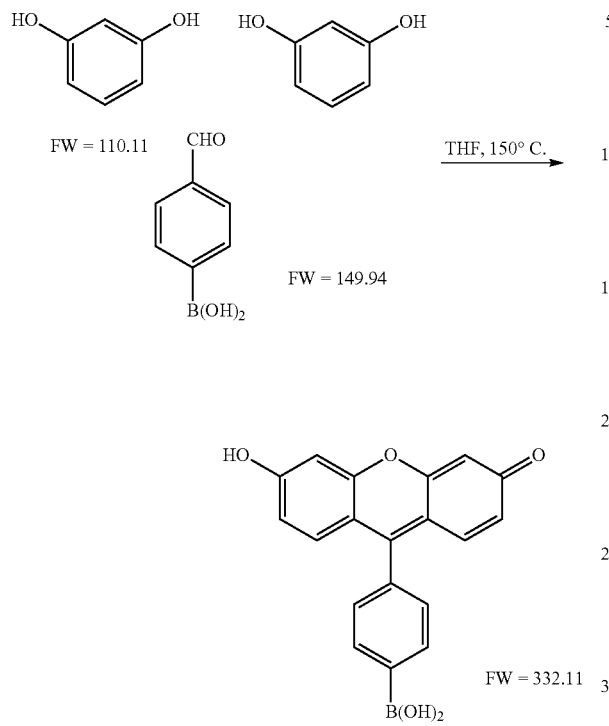

Preparation of Designation #AF-337 (HN-2-52): Preparation of a Rhodamine-Like Xanthyl-Boronic Acid:

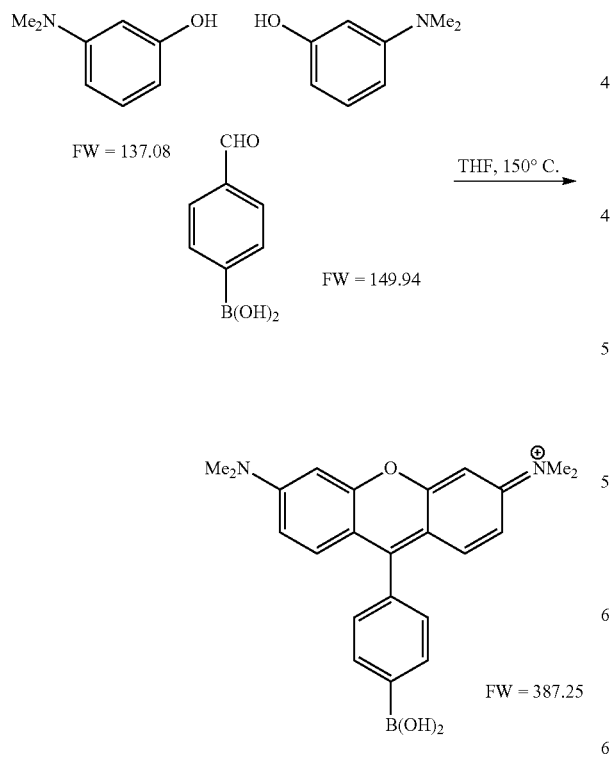

Crude reaction mixture is deep red.

Preparation of Designation #AF-337 (HN-2-77) Preparation of a Rhodamine-Like Xanthyl-Boronic Acid:

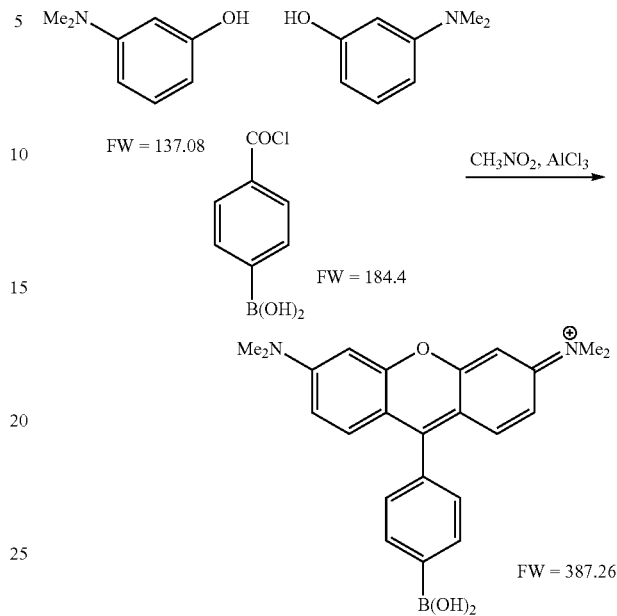

Reaction carried out at room temperature, or with heating to reflux, showed no indication of product formation.

Preparation of Designation #AF-338 (HN-2-65): Reaction of 4-Chlorocarbonylphenylboronic Anhydride with Coumarin 500

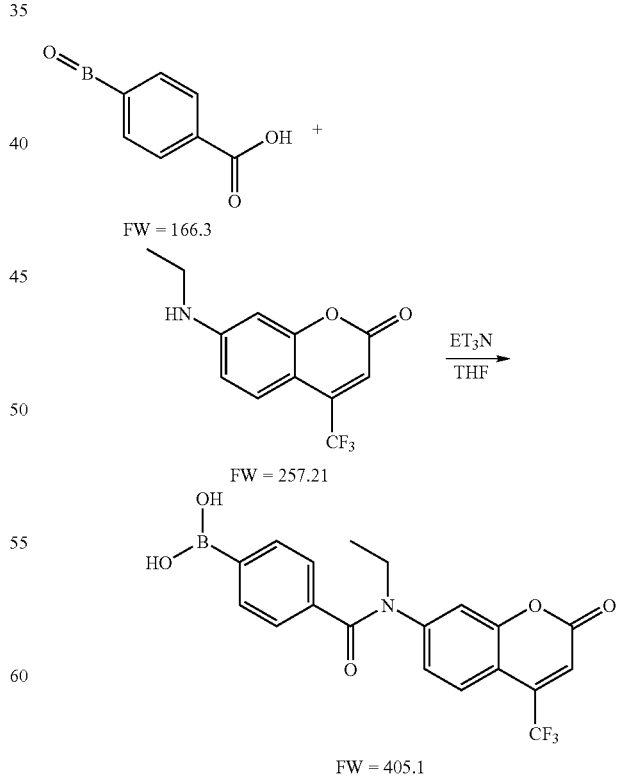

Two batches were combined and worked up to provide 45 mg of pure compound for additional experiments.

Preparation of Designation #AF-339 (HN-2-70) synthesis: Coupling of 4-Chlorocarbonylphenylboronic Anhydride with 4-nitroaniline

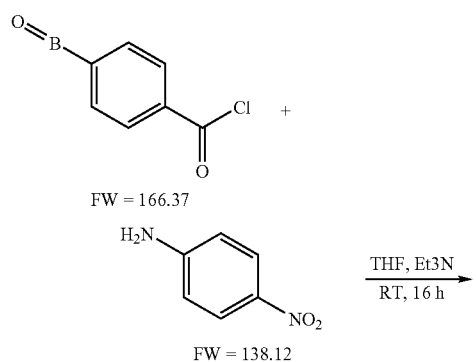

This model compound was prepared, to combine the solvatochromic effects of 4-nitroaniline with glucose binding capability of phenyl boronic acid. Response to glucose in vitro was weaker than AF-327.

Preparation of Designation #AF-340 (HN-2-72) Preparation: Coupling of Chlorocarbonylphenylboronic Anhydride with 8-Hydroxy-1,3,6-pyrenetrisulfonic Acid, Trisodium Salt. (Pyronin; D&C Green #8)

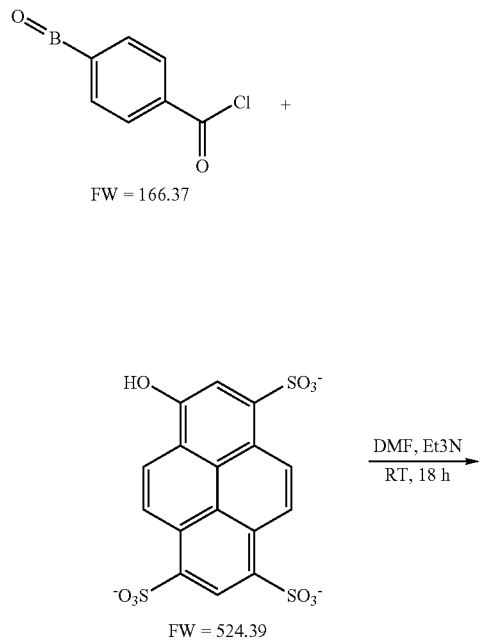

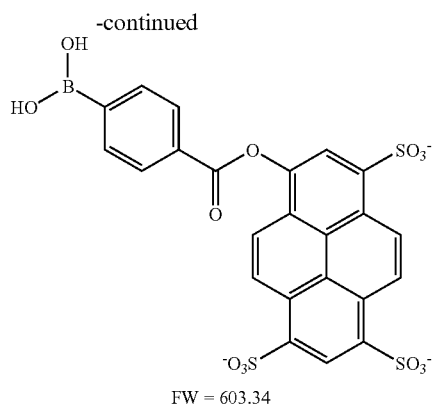

TLC shows a nonfluorescent spot at Rf=0.3 and a very fluorescent spot on the starting line. No product was isolated.

Preparation of Designation #AF-341 (HN-2-73) Preparation: Boronic-Acid Containing (Semi-Rhodafluor) Xanthene Structure.

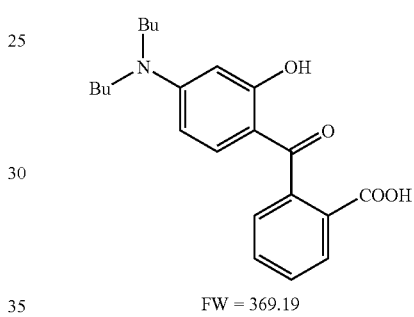

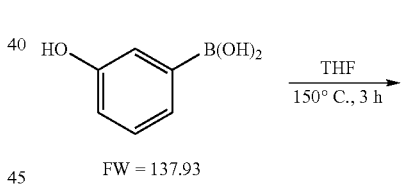

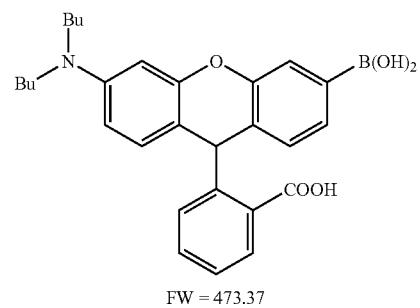

No evidence of product formation corresponding to xanthene structure.

Preparation of Designation #AF-342 (HN-2-69, 75, 76) Preparation: Boronic-Acid Containing Rhodamine 110 Structure.

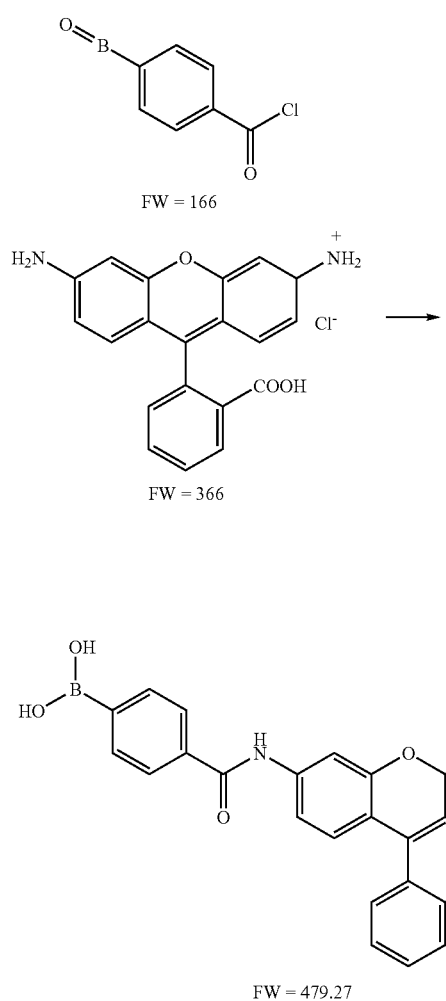

Reaction was attempted in THF; in Acetonitrile; and in DMF. In all cases, no new product was observed.

Preparation of Designation #AF-343 (EB-16-40): Preparation of a Coumarin-Boronic Acid Chalcone Compound:

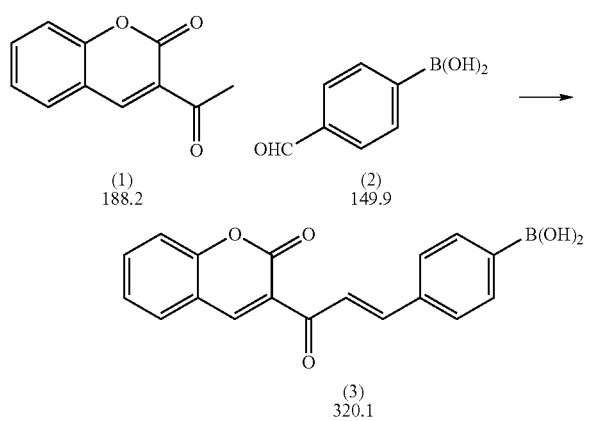

A rust-colored solid product was formed. No fluorescence or glucose effect was observed.

Preparation of Designation #AF-344 (EB-16-42): Preparation of a Coumarin-Boronic Acid Chalcone Compound

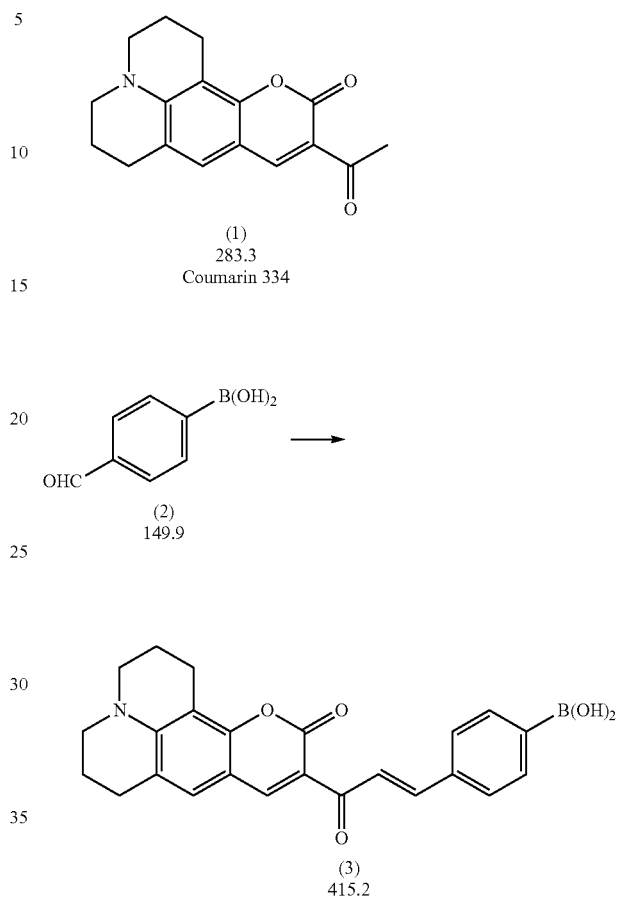

Besides starting material, a major red fluorescent spot at Rf=0.25 was observed in TLC. This compound was isolated and purified. There was no observed effect of glucose in vitro. NMR suggests that the compound is likely a dimer of Coumarin 334. By NMR, no spectral features corresponding to the boronic acid incorporation were observed. A minor orange fluorescent product, represented by a spot at Rf=0.1 was also inactive in regard to glucose addition.

Preparation of #AF-345 (EB-16-100): This Compound was Attempted to explore another fluorophore Family.

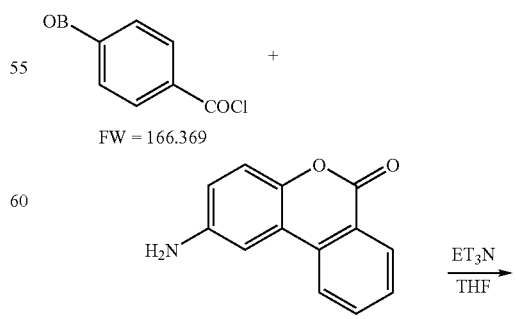

-continued

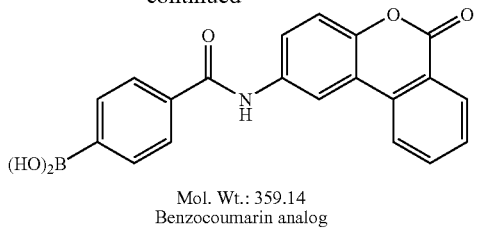

Mol. Wt.: 359.14
Benzocoumarin analog

This reaction proceeded in approximately 10 percent yield, following the procedure previously employed in AF-327d. 11 mg of pure product was recovered.

The AF-345 compound is fluorescent em=435 nm; ex=330 nm. Fluorescence intensity was observed to increase by 30% on addition of 300 mg/dl glucose concentration.

Comparison Materials

Designations #HN-2-32 and #HN-2-44: Preparation of 3-Phenylboronic acid 3-nitro-1,8-naphthalenedicarboximide (Ref. See Lakowicz, Organic Letters, 9, 1503 (2002))

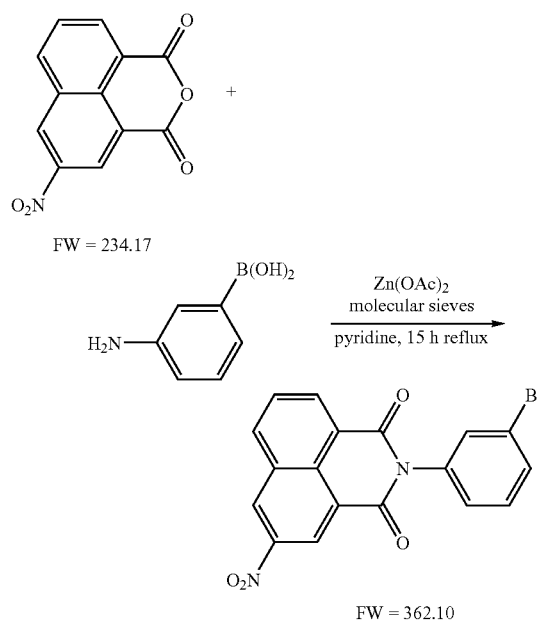

FW = 234.17

FW = 362.10

This compound was prepared for comparison to literature results on the spectroscopic detection of glucose reporting efficacy.

Designation #HN-2-42: Preparation of Protected 4-Phenylboronic Acid 3-nitro-1,8-naphthalenedicarboximide (Analog of the Lakowicz Compound Above)

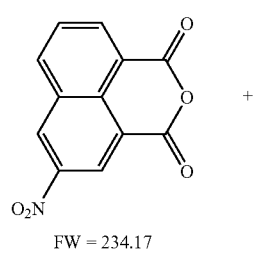

FW = 234.17

-continued

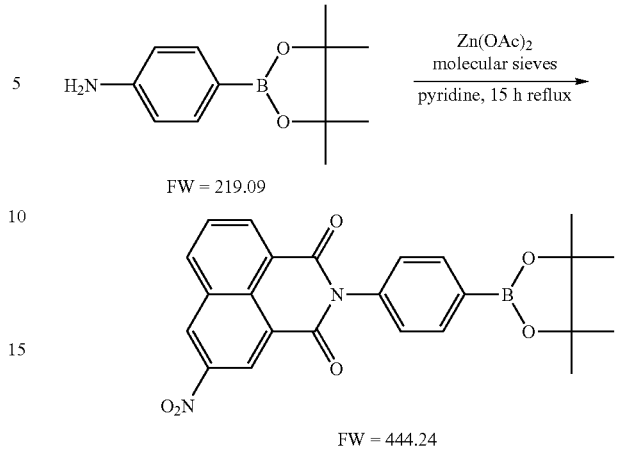

FW = 219.09

FW = 444.24

TLC of the reaction mixture shows multiple products.

Preparation of Designation #HN-2-44: Preparation of 3-Phenylboronic Acid 3-nitro-1,8-naphthalenedicarboximide (See Lakowicz. Organic Letters, 9, 1503 (2002))

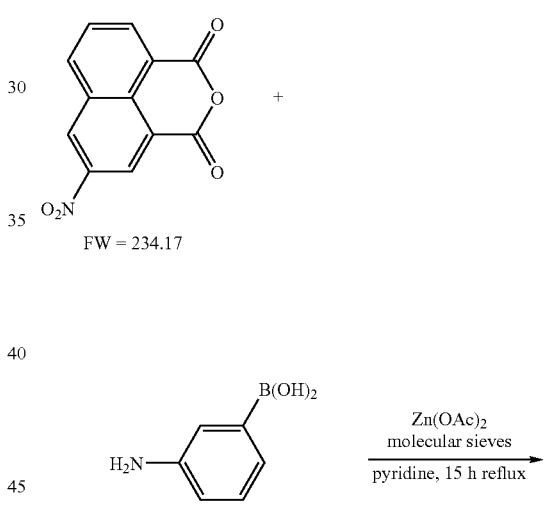

FW = 234.17

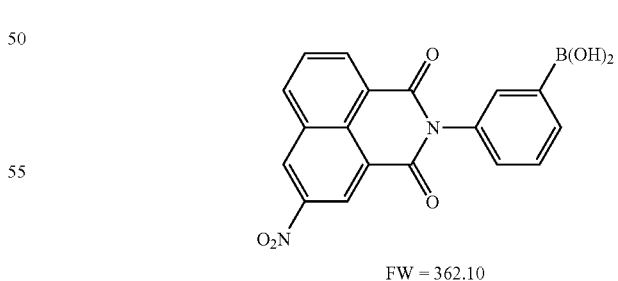

FW = 362.10

The major product isolated has NMR consistent with the reported structure, but UV which does not fit the literature. A minor product has the reported UV characteristics, but NMR inconsistent with the reported structure. It is likely that the material reported by Lakowicz is a mixture and not a pure compound.

Example 10

Carbostyril Derivatives Used as Glucose Reporters

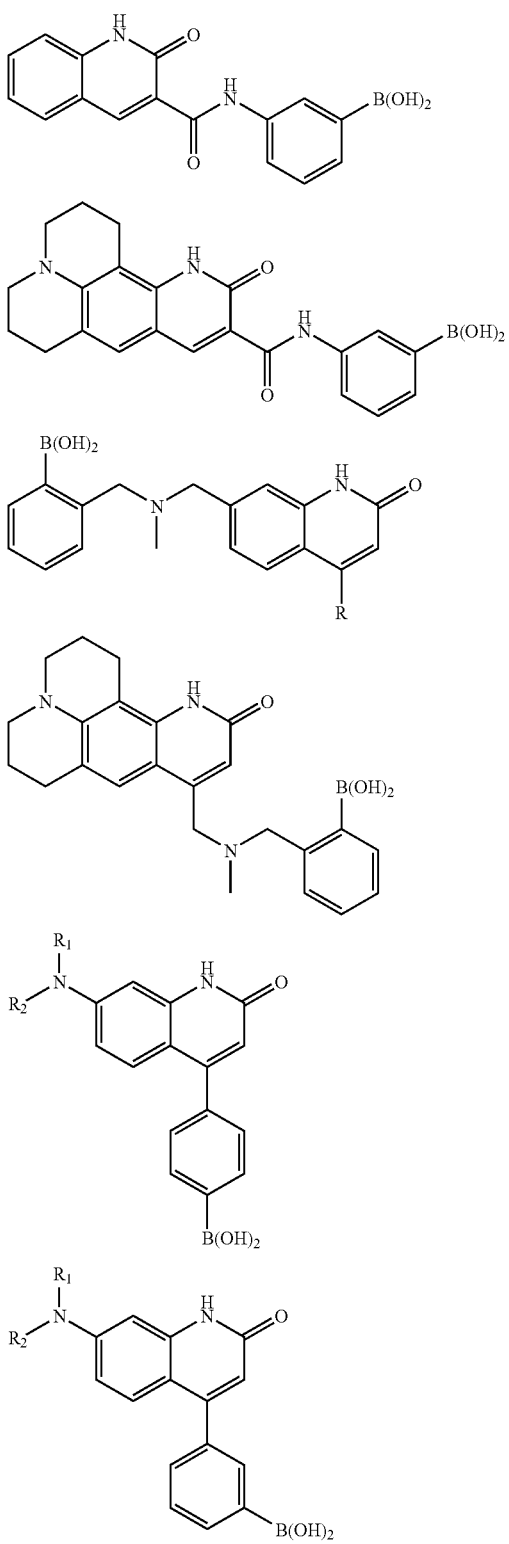

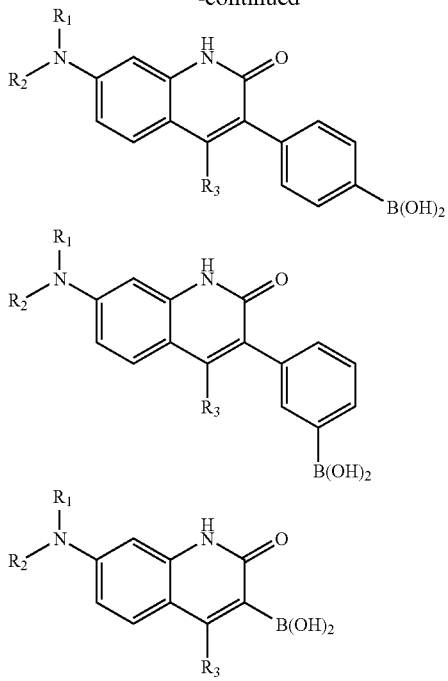

Example 11

Use of Tethered Molecules for Glucose Measurement

Suitable tethers include both ring structures and linear systems (example given in Scheme 8, below). The advantage of a ring system is that the structure is semi-rigid which limits the degree of entropy in the system. If the system is too flexible, the two chromophores will be less likely to approach each other. In order of complexity, cyclic tethers include cycloalkanes, crown ethers, cyclodextrins and cyclic peptides. The number of residues in the ring system is chosen so that the chromophores come close enough together to promote complex formation.

Scheme 8. An example of a cyclic tethered system

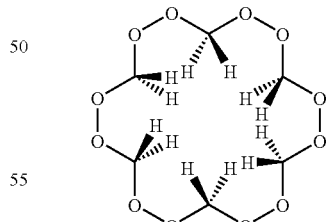

Example 12

Use of a Crown Ether for Glucose Detection

Substitution of the ring system may at a ring carbon position for cycloalkanes and crown ethers, at a hydroxyl group in cyclodextrins or on any of the amino acid residues in a cyclic peptide (example given in Scheme 9). The cyclic peptide may be designed to have some specificity for glucose by choosing a peptide sequence that mimics the binding site found in a protein such as glucose oxidase or glucose dehydrogenase.

Scheme 9. A ten saccharide cyclodextrin

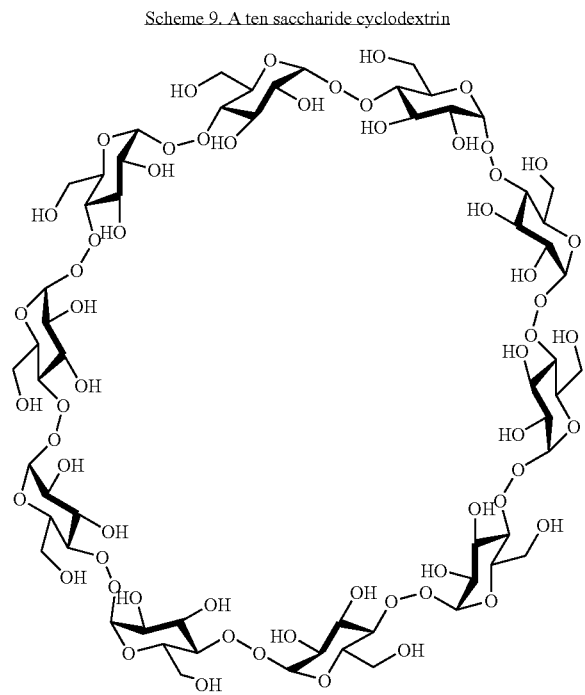

Example 13

Use of Cyclic Decapeptide Fluorophores for Glucose and Other Diol Sensing

This example describes a molecule for use in the detection and quantification of glucose. This glucose sensing occurs by means of a fluorescent reporter whose photophysical properties are modulated by direct binding with glucose or other diol molecules. Such reporters consist of three mechanistic parts:

1. A fluorophore with suitable photochemical characteristics;
2. A chemical affinity group that binds reversibly with glucose and similar molecular species (cyclic peptide);
3. Additional substructural features to favor specificity for Glucose over Fructose and other saccharides.

A cyclic peptide is proposed as a structural element that incorporates H-Bond donating and accepting atoms to provide affinity to glucose (and other biomolecules). Careful choice of amino acid residues forming the peptide will allow for adjusting specificity.

Two proof of concept compounds are demonstrated: Cyclic peptides "A" and "B" (Scheme 10).

Scheme 10. Proposed cyclic decapeptides for proof of concept experiments.

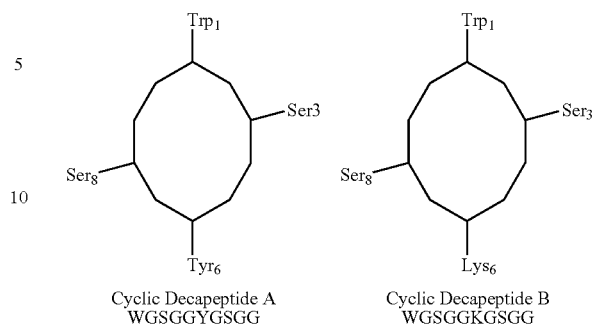

Cyclic Decapeptide A
WGSGGYGSGG

Cyclic Decapeptide B
WGSGGKGSGG

Cyclic Decapeptide "A"

Glucose binding to Peptide A is confirmed by: (1) examination of change in fluorescence polarization of Tryptophan, or (2) changes in energy transfer from Tyrosine to Tryptophan. Note: added serines will boost the binding affinity for Glucose by additional H-bonding sites.

Cyclic Decapeptide "B"

Glucose binding to Peptide B is confirmed by one or more of the following: (1) examination of change in fluorescence polarization of Tryptophan, (2) changes in fluorescent quenching of tryptophan by the nitrogen of Lysine, (3) change in fluorescence polarization of tryptophan, or (4) a change in fluorescence polarization or energy transfer of a fluorophore connected to the end of the Lysine side chain. Note: added serines will boost the binding affinity for Glucose by additional H-bonding Quantitation SMMR compounds have a number of quantifiable parameters in common. They have high molar absorption coefficients ($>50,000$ dm$^3$ mol$^{-1}$cm$^{-1}$), high fluorescence quantum yield ($>0.2$), and they interact only with components of the cell or biological system that are present in high concentration. This last requirement helps minimize the toxicity of the SMMR. Competitive inhibition of enzymatic processes and interference with cellular processes is minimized if the SMMR does not interact with a significant fraction of the cells metabolic pathways.

Rational Design for Novel SMMR Compounds

This section discloses the aspects important to intelligent design of SMMRs for glucose detection. There are several individual properties involved during the rational molecular design process and these are disclosed within the following text.

The fluorescence quantum yield ($\Phi_F$) of a molecule is given by equation (12).

$$\phi_F = \frac{k_r}{k_r + k_{nr}} \quad \text{(EQ. 12)}$$

Where $k_r$ is the radiative rate constant and $k_{nr}$ is the non-radiative rate constant. In this discussion, the term $k_{nr}$ includes all mechanisms for decay that does not lead to fluorescence. The $\Phi_F$ of BeXan type dyes is typically 0.2 or less.

The reasons the value is so low may include the flexibility which increases the number of vibrational modes available to the compound, intramolecular reactions or competing photophysical pathways such as intersystem crossing. All of these processes increase $k_{nr}$ for deactivation of the excited state. For BeXan it is unlikely that flexibility or intramolecular reactions contribute significantly to $k_{nr}$, other molecules of similar size and substitution have $\Phi_F$ values close to unity. It is more likely that intersystem crossing for the molecule is significant and is the cause for the low $\Phi_F$. If the BeXan structure is drawn as shown here then the molecule can be designed with two linked chromophores (Scheme 11, below):

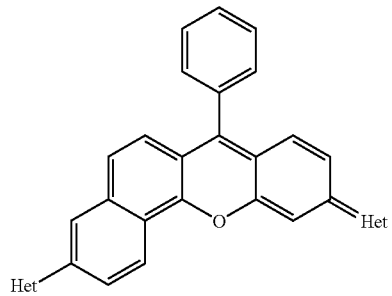

a quinoid type structure involving the heteroatom at position 9 and a substituted naphthalene structure involving the heteroatom at position 3. Het refers to a heteroatom, most commonly oxygen or nitrogen. The photochemistry may be interpreted as a combination of these two chromophores. The validity of this kind of interpretation is dependent on the fraction time the molecule may be considered in this configuration as opposed to a configuration involving a naphthoquinoid and a phenol type structure.

Figure 21A:
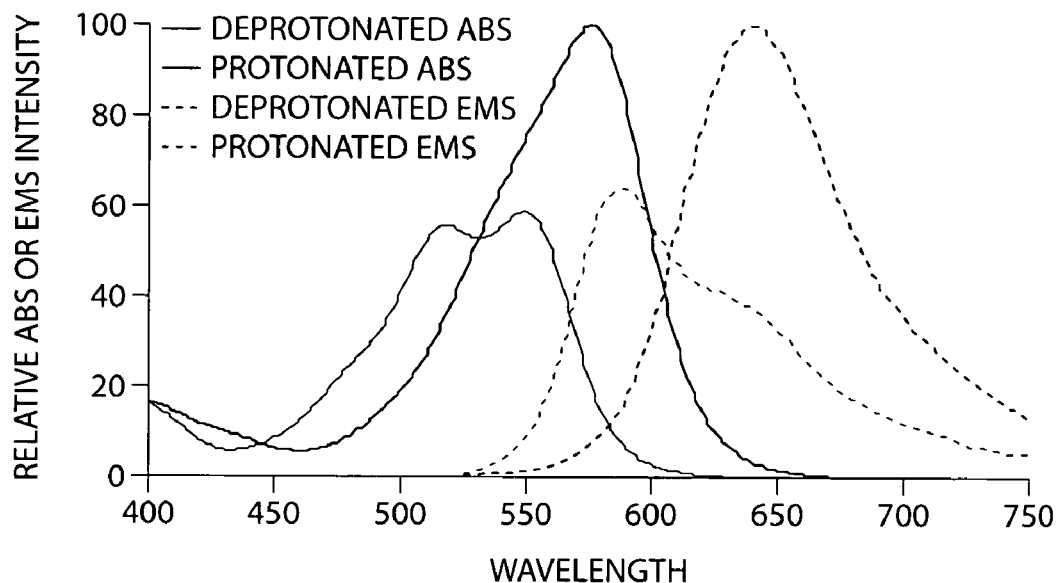
FIG. 21a. Absorption and emission spectra for BeXan type dyes.
Figure 21B:
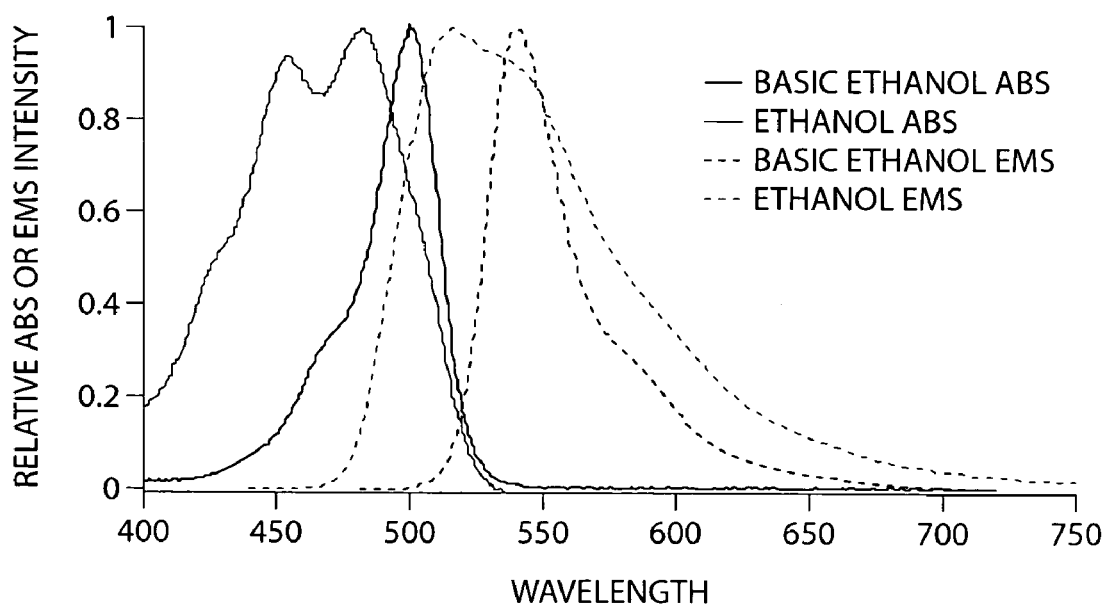
FIG. 21b. Absorption and emission spectra for fluorescein.

The configuration of the dye is strongly influenced by the nature of the heteroatom substitution. The structure of the dye responsible for the absorption may be estimated by consideration of the photophysical properties of related compounds and calculations on them. For example comparison of fluorescein and BeXan type dyes are shown in FIGS. 21a and 21b, with structures shown in Schemes 11 and 12, respectively.

Scheme 12. Structure of deprotonated BeXan dye shown with no delocalization

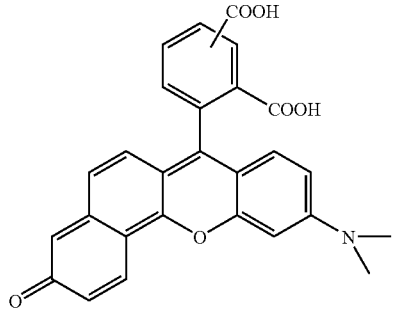

Scheme 13. Deprotonated and protonated forms of fluorescein shown delocalized

Table 4 demonstrates the absorption and emission maxima (i.e., wavelength in nanometers) with corresponding energies for fluorescein and BeXan visible spectral absorption bands. The table also demonstrates other spectral properties for a comparison of these two molecular structures.

TABLE 4

Absorption and emission position and energy data for fluorescein and BeXan

| | Absorption Wavelength (nm) | Emission Wavelength (nm) | Absorption Energy (kcal/mol) | Emission Energy (kcal/mol) |
|---|---|---|---|---|
| Fluorescein Protonated | 455, 483 | 516, 541 | 62.8, 59.2 | 55.4, 52.9 |
| Fluorescein Deprotonated | 501 | 540 | 57.1 | 53 |
| BeXan Protonated | 518, 549 | 586, 635 | 55.2, 52.1 | 48.8, 45 |
| BeXan Deprotonated | 576 | 640 | 49.6 | 44.7 |

| Difference in energy of protonated absorption bands | |
|---|---|
| Fluorescein | 3.6 kcal/mol |
| BeXan | 3.1 kcal/mol |
| Stokes shift for deprotonated bands | |
| Fluorescein | 4.1 kcal/mol |
| BeXan | 4.9 kcal/mol |
| Stokes shift for protonated bands | |
| Fluorescein | 3.8 kcal/mol |
| BeXan | 3.3 kcal/mol |

TABLE 4-continued

Absorption and emission position and energy data for fluorescein and BeXan

| Band positions relative to the high-energy protonated absorption band | Absorption | Emission |
|---|---|---|
| Fluorescein (kcal/mol) | | |
| High energy protonated band | 0 | 7.4 |
| Low energy protonated band | 3.6 | 9.9 |
| Deprotonated band | 5.7 | 9.8 |
| BeXan (kcal/mol) | | |
| High energy protonated band | 0 | 6.4 |
| Low energy protonated band | 3.1 | 10.2 |
| Deprotonated band | 5.6 | 10.5 |

These two compounds show very similar visible absorption and emission spectra. The absorption spectrum of the BeXan type dye is about 70 nm shifted to the red, probably as a consequence of extended conjugation compared with fluorescein. The emission spectrum of BeXan is shifted by as much as 100 nm compared to fluorescein. Despite this difference in the wavelengths the energy spacing of the visible bands is also similar. There is a slightly larger Stokes shift for BeXan, which may have been expected since the flexibility of the naphthoxanthene structure is likely to be greater than that for the xanthene ring.

The similarities in these spectra support the idea that in the BeXan ring system there is a high degree of delocalization both in the protonated and the deprotonated form of the dye as is observed for fluorescein. These similarities also support the idea that substitution of other heteroatoms onto the xanthene ring structure should not lead to significant changes to the spectral properties of the molecule. The parameter that cannot be accounted for in this kind of analysis is the quantum yield of fluorescence.

Comparison of the Structures of Two Dyes

Figure 22:
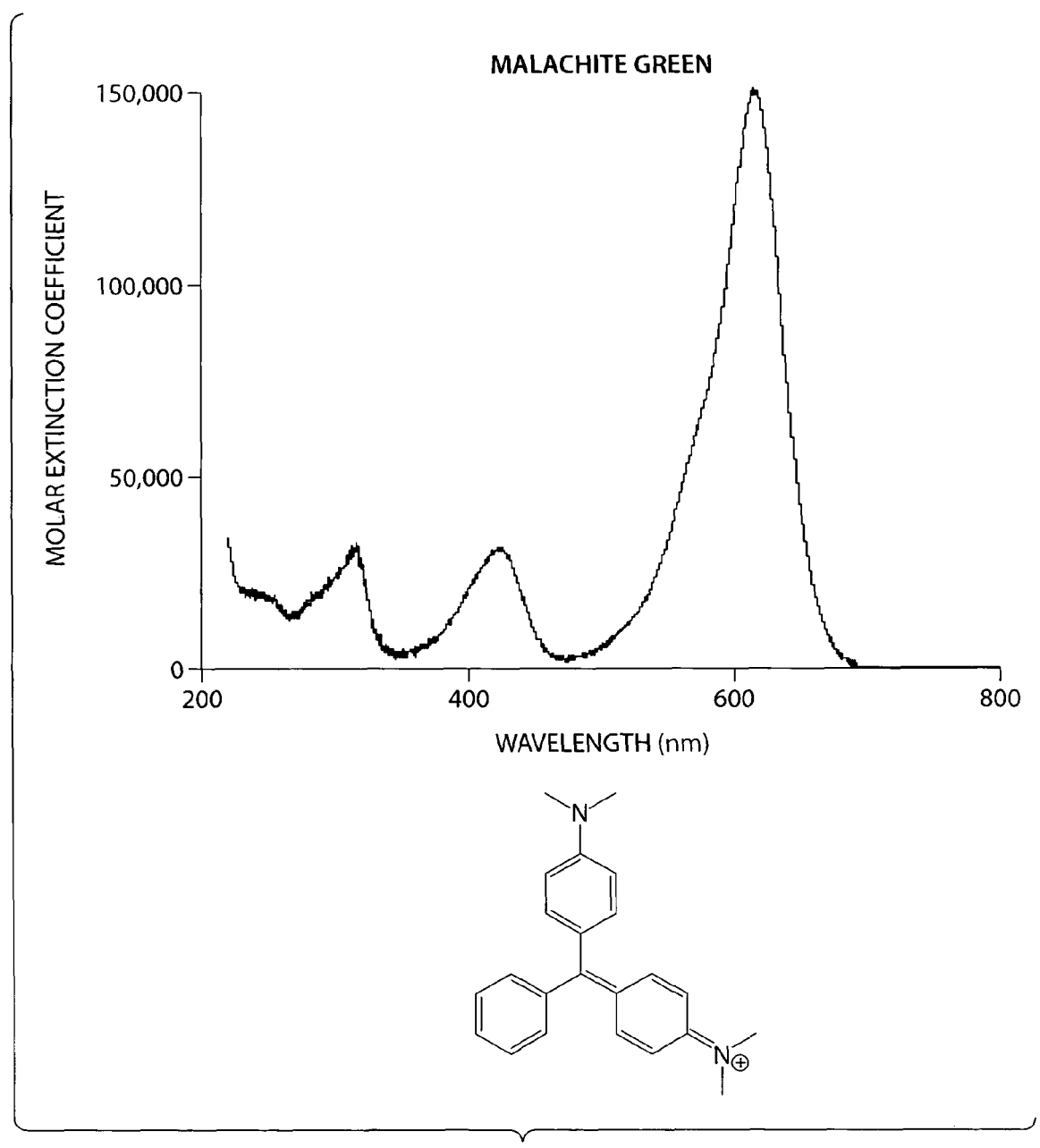
FIG. 22. Malachite green absorption spectrum (left), with molecular structure (right).
Figure 23:
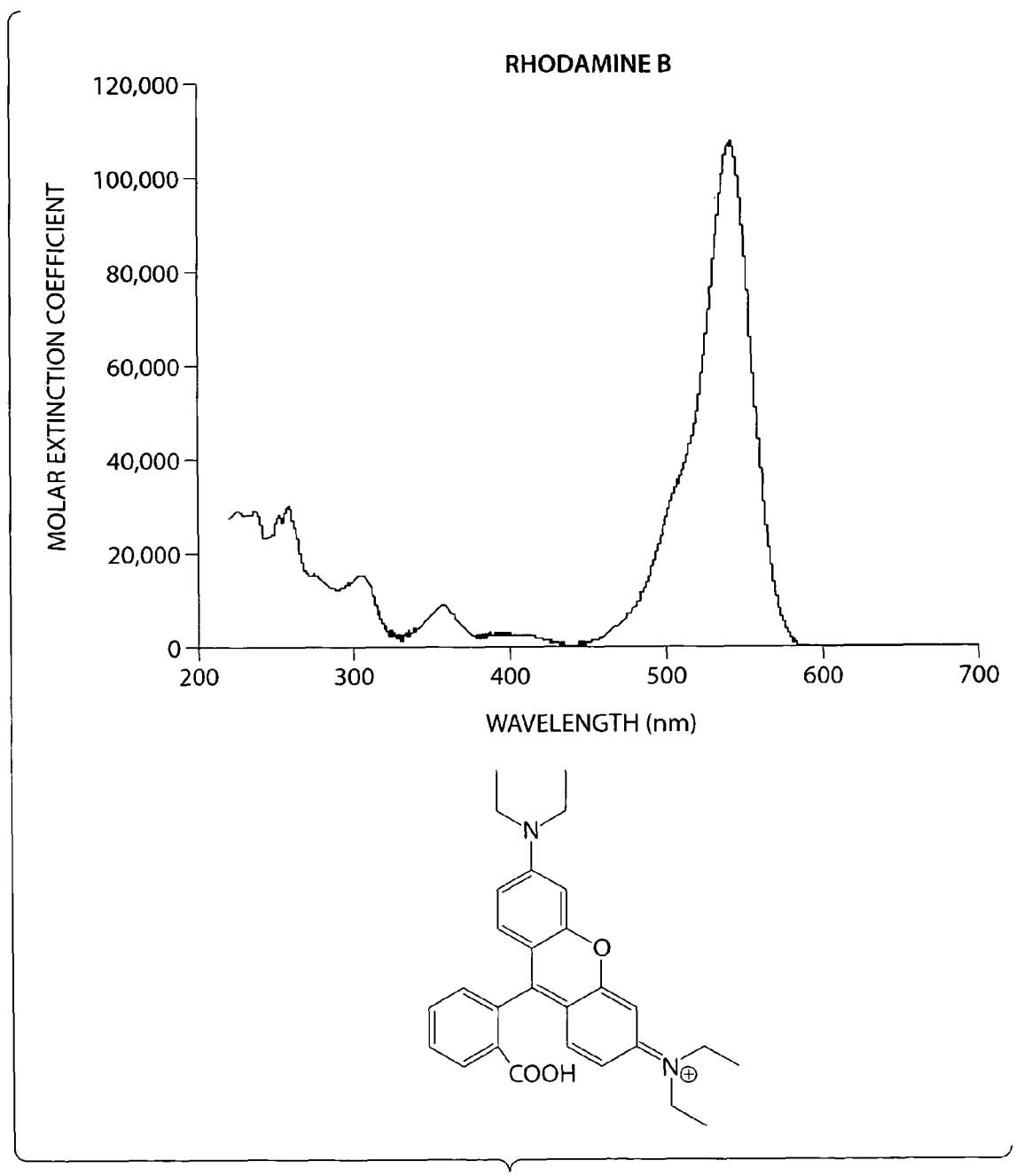
FIG. 23. Rhodamine B absorption spectrum (left), with molecular structure (right).

As an example of the principle, Malachite green is an aryl methine dye that absorbs strongly in the red region of the spectrum (150,000 $dm^3\ mol^{-1}\ cm^{-1}$). It is non-fluorescent. Conjugation in this molecule probably extends over the three phenyl rings with the positive charge located primarily on the two substituted rings [FIG. 22 shows the absorption spectrum (left), and the molecular structures (right)]. Comparison of this structure with that of Rhodamine B shows the two substituted rings tied together with an oxygen bridge [FIG. 23 shows the absorption spectrum (left), and the molecular structures (right)]. The molar absorption coefficient is 109,000 $dm^3\ mol^{-1}\ cm^{-1}$. Molecular modeling shows the phenyl ring twisted out of plane with respect to the xanthene ring. A consequence of this is that the molecule has an absorption maximum about 60 nm to the blue, supporting the view that the phenyl ring is not involved in the main xanthene chromophore. The molecule is also significantly more rigid than the aryl methine dye and the quantum yield of fluorescence is close to unity.

Consideration of the structures of these two compounds and their desirable photophysical properties leads to the design of a new chromophore that may well have a very high molar absorption coefficient and a high quantum yield of fluorescence, the structure of which is shown in Scheme 13.

Scheme 14. Design structure of a new chromophore proposed to have a very high molar absorption coefficient and a high quantun yield of fluorescence

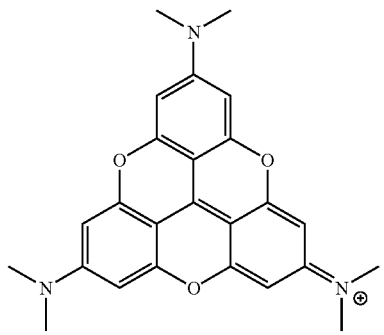

Molecular modeling of this compound shows it to be highly planar and from earlier arguments it would be expected to absorb at 600 nm or higher and to be highly fluorescent. There is little information concerning this type of structure in the literature but a synthesis has been published of a molecule 2,6,10-Tris(dialkylamino)trioxatriangulenium (2,6,10-Tris(dialkylamino)trioxatriangulenium ions. Synthesis, structure, and properties of exceptionally stable carbenium ions. B. W. Laursen, F. C. Krebs, M. F. Nielsen, K. Bechgaard, J. B. Christensen and N. Harrit. J. Am. Chem. Soc. (1998) 120 12255-12263). The rational behind its synthesis however extends to other molecules with heteroatom substitution including the carbonyl/hydroxyl derivative, the sulfur analog and mixed heteroatom analogs such as that proposed in Scheme 14.

Scheme 15. A rational design for heteroatom substitution for the molecule proposed in Scheme 14, including the carbonyl/hydroxyl derivative, the sulfur analog and mixed heteroatom analogs.

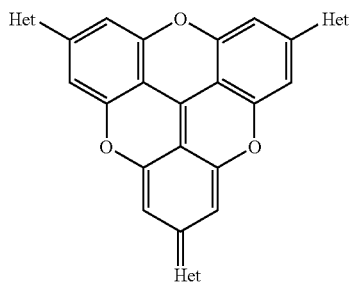

To the best of our knowledge there is no previous reference to the oxygen or sulfur analog as proposed in Scheme 15.

Scheme 16. An oxygen analog of the molecule as proposed in Scheme 15. Note that a sulfur analog would also be obvious to one skilled in the art from this description.

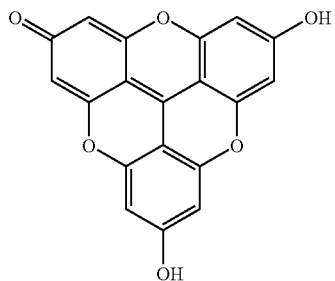

Enhancement of Cellular Retention and Quantum Yield

The problems that exist for the some dyes that make them unsuitable as SMMRs are low quantum yield of fluorescence, poor retention inside cells, and toxicity. These problems may be addressed to a certain extent by binding the dye to a controlled size metal particle. The fact that the quantum yield for fluorescence is determined by the balance between the radiative and non-radiative rate constants has already been discussed. For dyes that have low quantum yield of fluorescence the non-radiative rate constant dominates the radiative rate constant. In the presence of a strong electric field, the radiative rate constant may be increased to such an extent that it dominates in determining the quantum yield.

This phenomenon is will known near the surface of metals. If a fluorophore with a low quantum yield is placed within a certain distance from a metal surface then a dramatic shortening of the fluorescence lifetime and an enhancement of the fluorescence quantum yield may be observed. If very small (nm) beads are used to bind the dye, or the dye resides on the surface of the metal the dye may stop fluorescing completely. Selecting the optimum bead size and dye spacing from the surface of the metal has some important consequences:

If the bead is too small or if the dye is so close to the metal that it resides on the surface, the excited state of the dye is completely quenched. If the particle size is too large, the particle bound dye will not be taken up by the cell.

The optimum dye-to-particle spacing and particle size will lead to a SMMR system that has a quantum yield close to unity. Because the radiative rate constant is so high the fluorescent lifetime will be short and as a result there will be less time for excited state chemistry to take place, reducing phototoxicity. Since the dye is bound to a relatively large bead it cannot migrate away from the active site and overall toxicity is reduced. With a short excited state lifetime the photostability of the molecule will be improved for the same reason that the phototoxicity is reduced. The synthesis of these complexes is relatively simple. If the bead is made from gold then the dye will bind with a free thiol group. These molecules may be prepared starting with the chloromethyl BeXan dye. It is reacted at a 1:1 ratio with a dithioalkane. The free thiol terminus binds to the gold surface.

Effective concentrations of SMMRs to be applied in compositions and methods of the invention are in the range of at least 1 to 500 µg/ml, e.g. 5 to 150 µg/ml or 10 to 100 µg/ml. The concentration of SMMRs used is preferably from 10 to 500 µM, more preferably from 100 to 300 µM, and most preferably from 150 to 250 µM.

Design Strategy for Boronic Acid Glucose Reporters

Designing Ratiometric Direct Glucose Detection Probes

Figure 24:
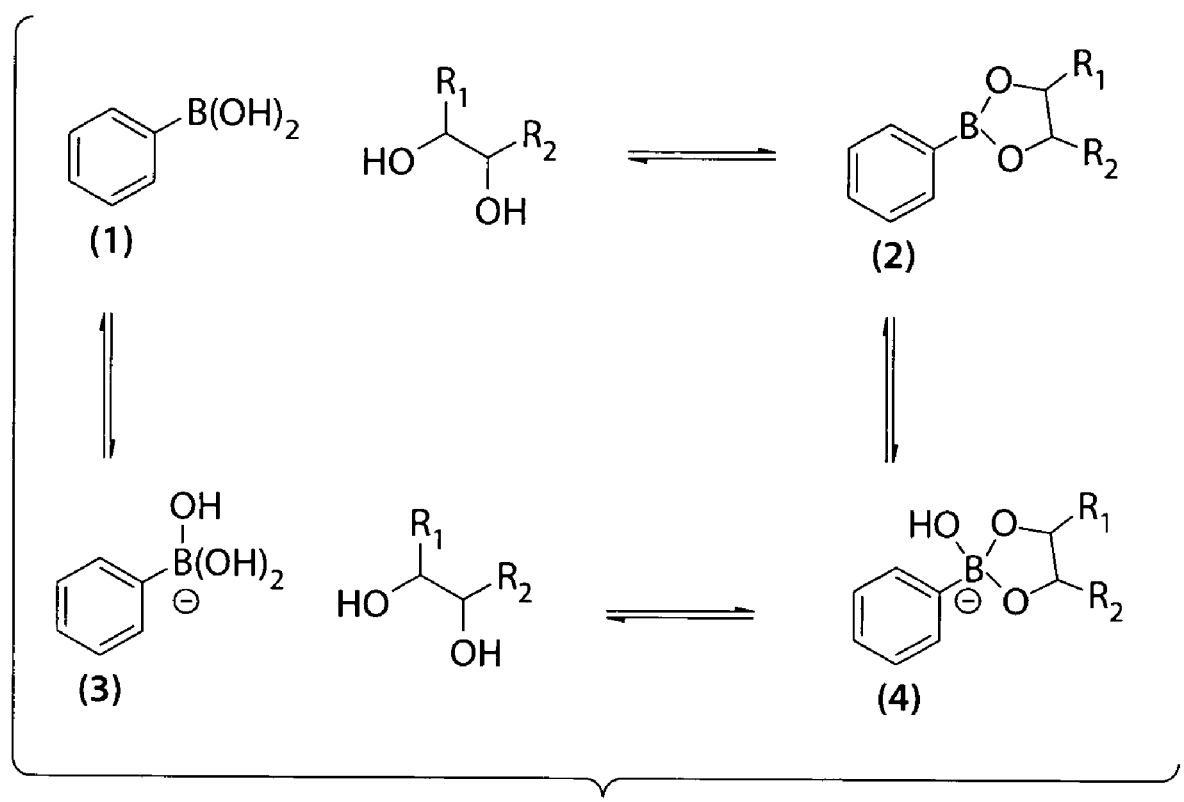
FIG. 24. The Boronic acid-diol equilibrium.

A phenyl-boronic acid and a diol, e.g. a molecule of glucose (or two equivalents of a monohydric alcohol) exist in a 4-way equilibrium in aqueous solution. This is shown schematically in FIG. 24 and has been discussed previously.

The pKa of Phenylboronic Acid Compounds and Their Interaction with Diols

Figure 25:
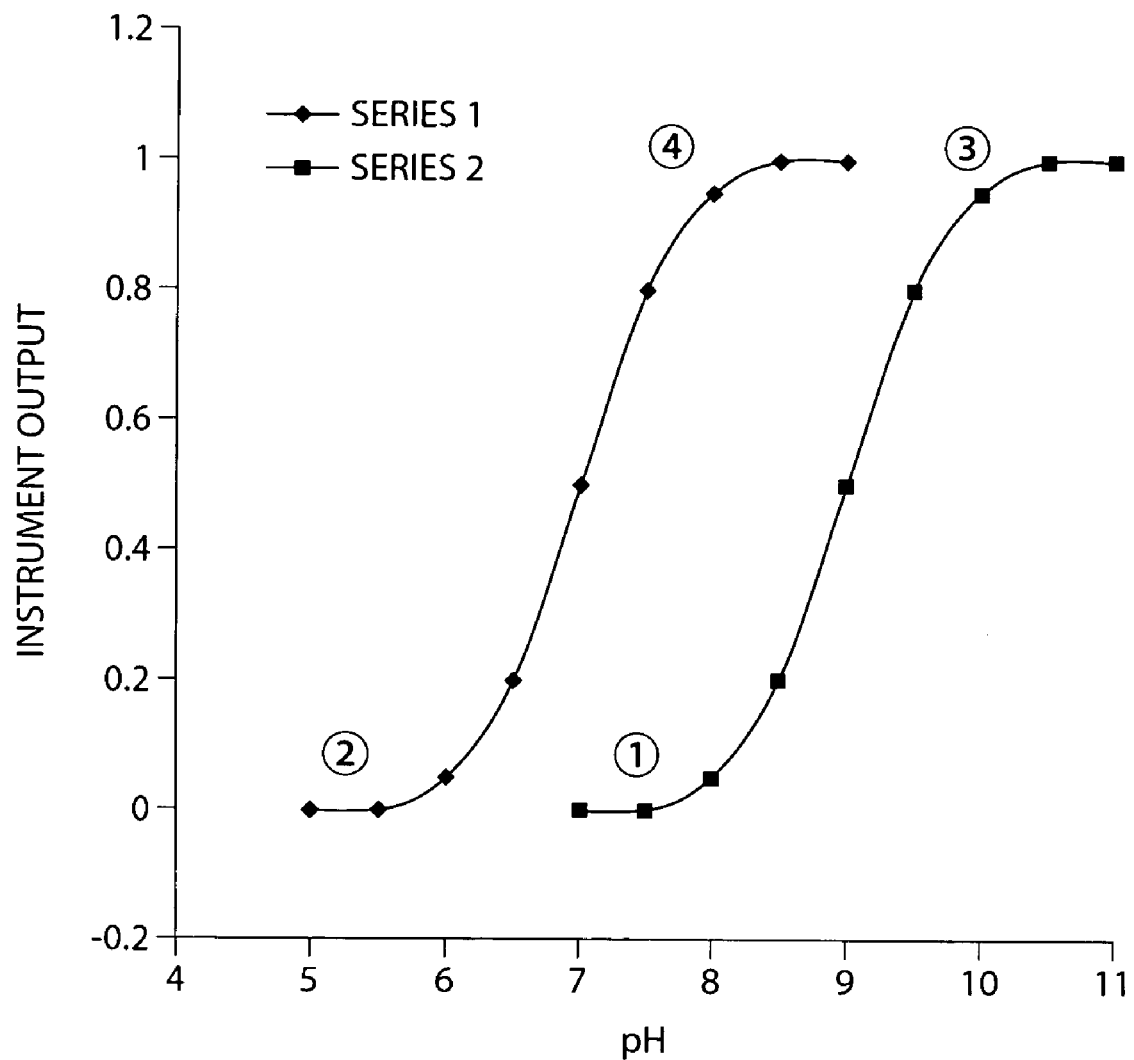
FIG. 25. Typical titration curves of a phenyl boronic analog (2-4 bound to diol; 1-3 unbound).

FIG. 25 shows typical schematic curves of the influence of pH on boronic acid-saccharide binding. In this conceptual example, the Y-axis represents percent present as the hydroxylated species. Actual examples are presented in the literature wherein the Y axis is denominated in terms of an instrument observation like fluorescence intensity.

The point illustrated here is that the pH dependent equilibrium of the "unbound" (1→2) boronic acid has a pKa of 1 to 2 units greater than the "bound" (3→4) (sugar-complex) form. [pKa of the boronic acid (a Lewis acid) is the pH value at which the titration curve is at 50% of maximum.]

A consequence of the difference in the curves is that at a given pH, (e.g. pH=7) the boronic acid-sugar complex exists mainly in the hydroxylated form (4), whereas the free boronic acid exists mainly in the neutral form (1).

For purposes of creating a biological sensor, the actual pKa of the bound and unbound forms can be adjusted by engineering the molecule to include electron-donating or electron-withdrawing atoms.

The practical importance of this observation comes into play when there is some observable property of a boronic acid-containing molecule that changes depending on the state of hydroxylation. For example, when a phenyl boronic acid is used in the signal transduction scheme of a glucose reporter molecule (see below) maximum dynamic range of the reporter signal may be obtained, when the pKa's of the boronic acid are adjusted, such that the bound form has pKa less than 7 and the unbound form has pKa greater than 7. In that case, at pH ~7 (normal physiological range) the glucose-bound complex exists primarily in the hydroxylated form, whereas, in the absence of glucose (or other saccharide) the neutral form predominates.

In the case of Argofluor-327d or other p-carboxamido-phenylboronic acids, the pKa (not measured for AF-327d) is close to optimal for this phenomenon to take place.

Figure 26:
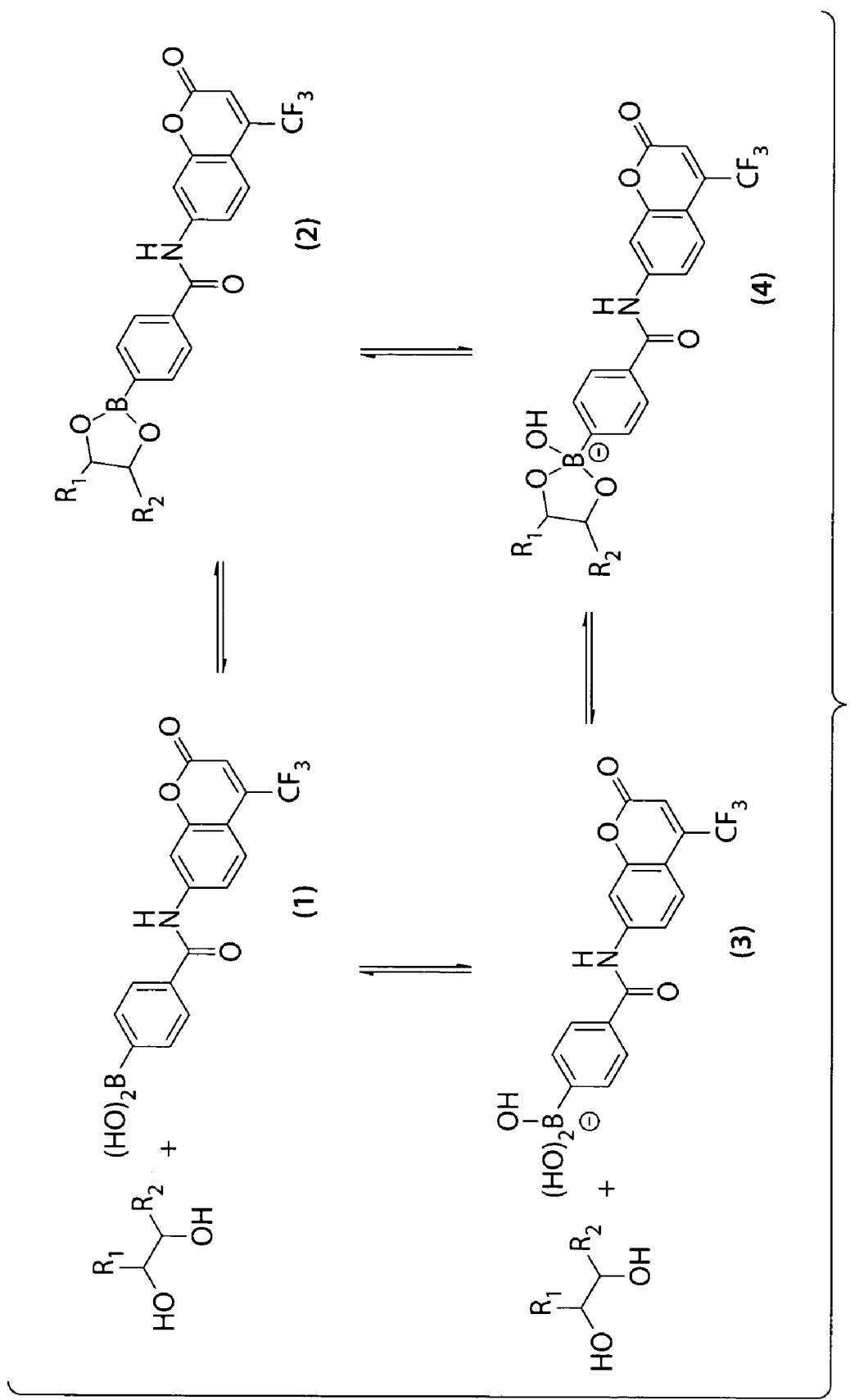
FIG. 26. Argofluor-327d in equilibrium with a diol.

Thus a large swing in fluorescence intensity has been observed due to the predominance of species 4, when glucose is present. The phenylboronic acid species 4 exerts an electron donating influence, whereas the species 1 is weakly withdrawing. In the context of an electronic "push-pull" fluorophore such as Coumarin-151, this translates into increased fluorescence intensity on hydroxylation. See FIG. 26.

In practice, AF-327d maintains a constant 440 nm emission wavelength with and without added glucose at pH=7, in our experimental measurements. The calculations herein to predict wavelength would have suggested a red-shift of as much as 79 nm (536 vs. 457) on hydroxylation—going from species 1 to 4.

A relatively large wavelength change between forms 1 and 4 would be a necessary precondition to observe resolved fluorescent emission peaks attributable to the two forms. This would become useful as a ratiometric probe, which could be accurately calibrated top glucose concentration. With this in mind, a number of synthetically accessible probe types were evaluated by calculating predicted emission wavelengths. Such compounds could form the basis for a; future chemical synthesis campaign.

Figure 27:
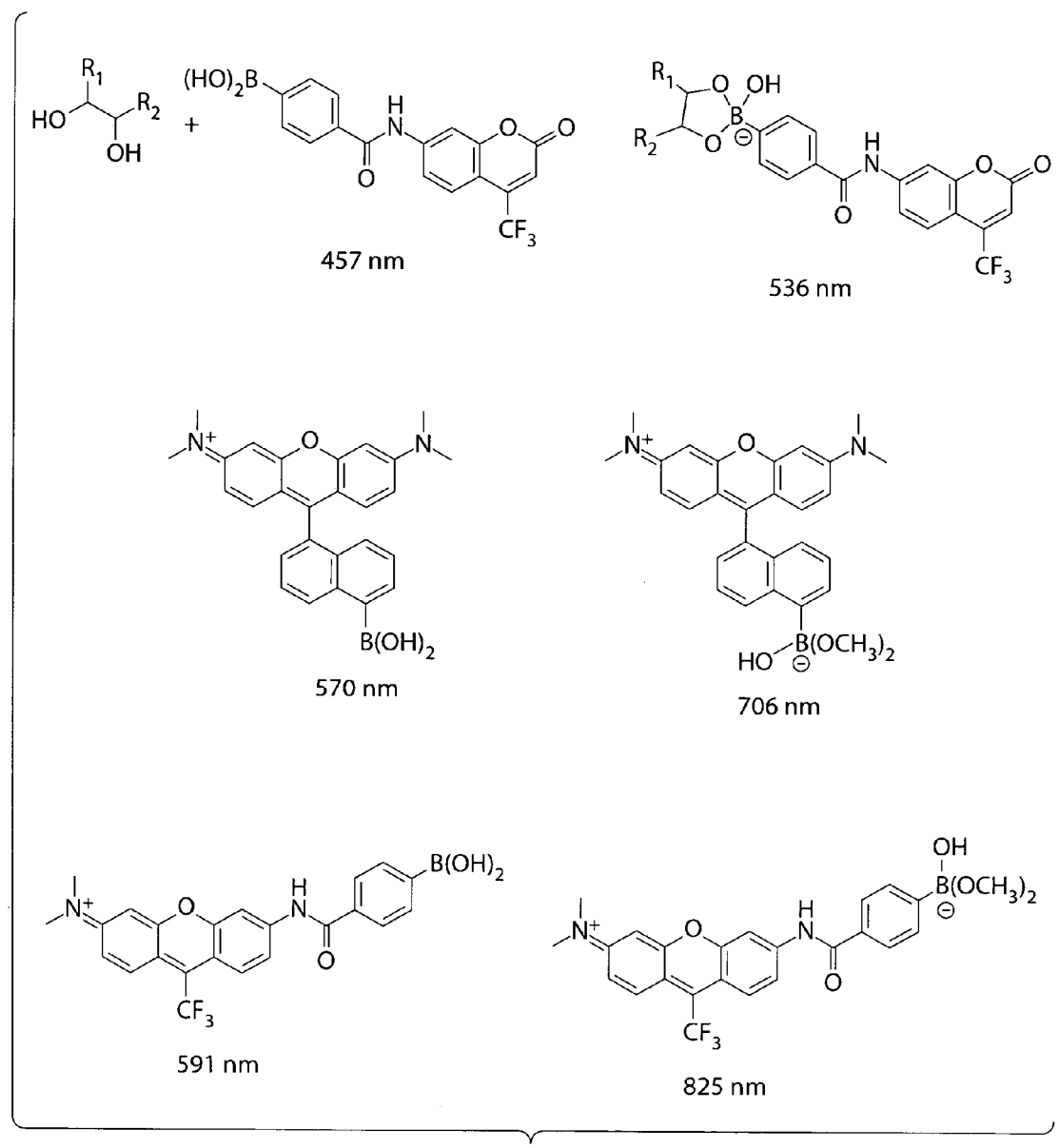
FIG. 27. Predicted emission wavelengths of several proposed fluorophores.

Other model compounds were analyzed to attempt to predict emission wavelength shift. Examples are presented in FIG. 27. Compounds such as these, wherein there is a very large predicted wavelength shift on hydroxylation would be a reasonable place to start on designing a fluorescent probe with ratiometric behavior.

Solvatochromism Using Aniline-Boronic Acid-Based Reporters

Comparison of the electron withdrawing properties of a nitro group and a boronic acid are similar. The absorption and fluorescence of p-nitro aniline and p-boronic acid aniline have been compared in a variety of solvents. These findings are useful for designing boronic acids that show a ratiometric change in absorption and or fluorescence in the presence of glucose. The nitro substituted material is a simpler model for the electron withdrawing properties of a boronic acid.

Figure 28A:
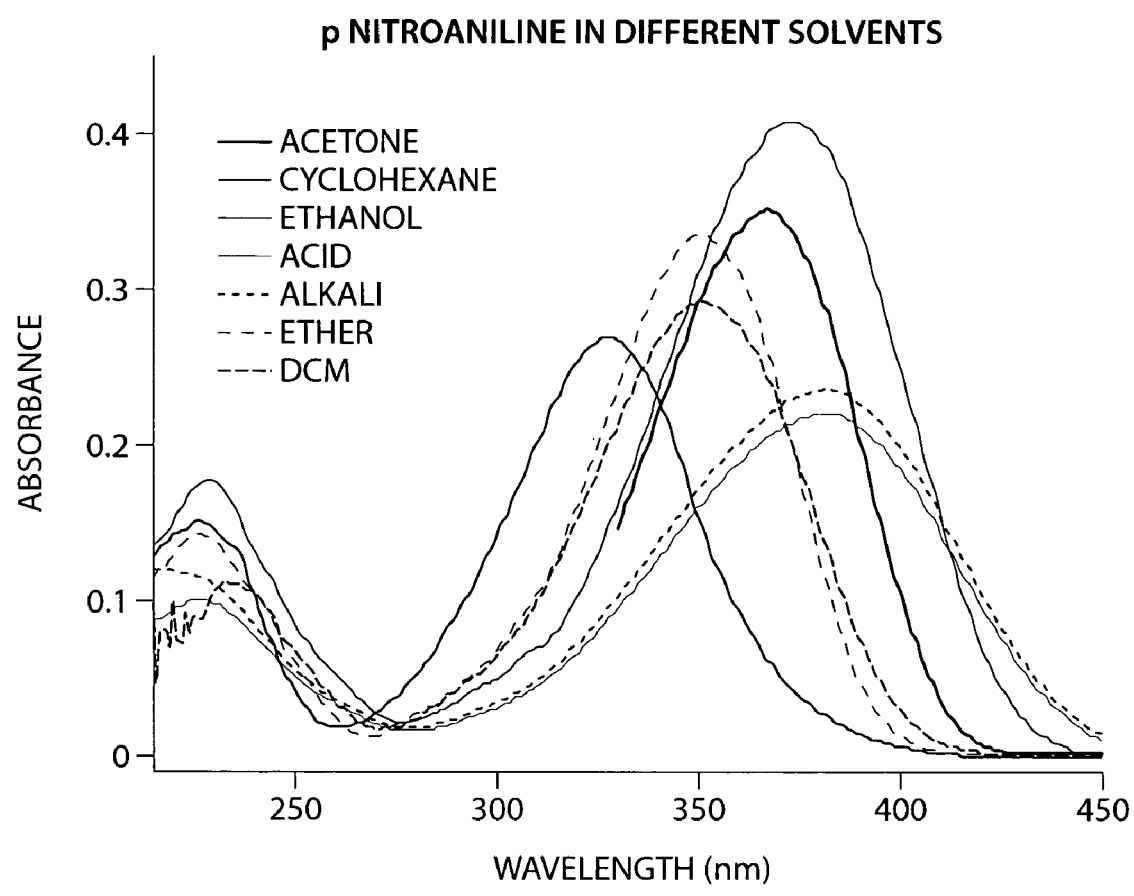
FIG. 28a. The absorption spectra of p-nitroaniline in different solvents.

The absorption spectra are shown above (FIG. 28(a)). The long wavelength band is a charge transfer band the position of which is sensitive to the solvent. This behavior is well known.

The material is not fluorescent. The absorption spectra are also virtually identical in acid and base.

Figure 28B:
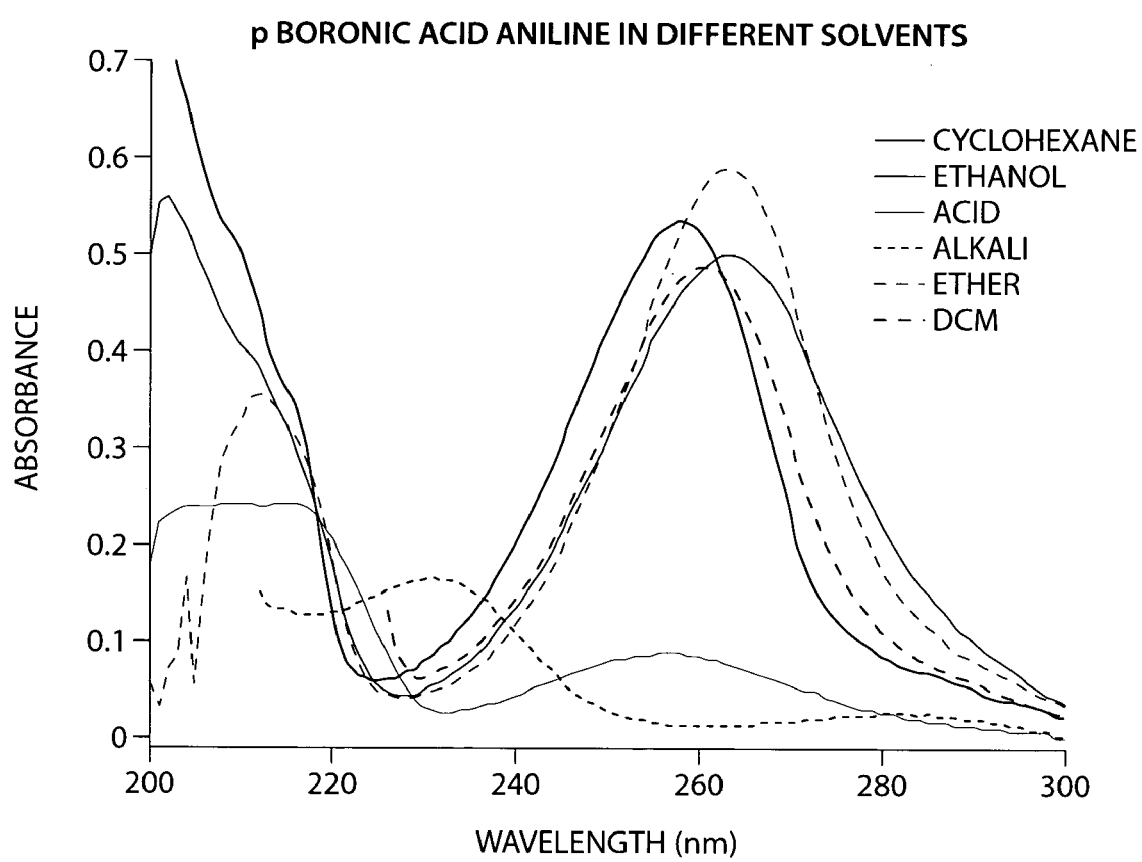
FIG. 28b. The absorption spectra of p-boronic acid aniline in different solvents.

The corresponding spectra for p-Boronic acid aniline are shown below (FIG. 28(b)). The p-boronic acid aniline was prepared from a derivative protected with a pinacol group by dissolving in ethanol. A small (20 μL) aliquot of this solution was then added to 3 mL of the solvent.

Figure 28C:
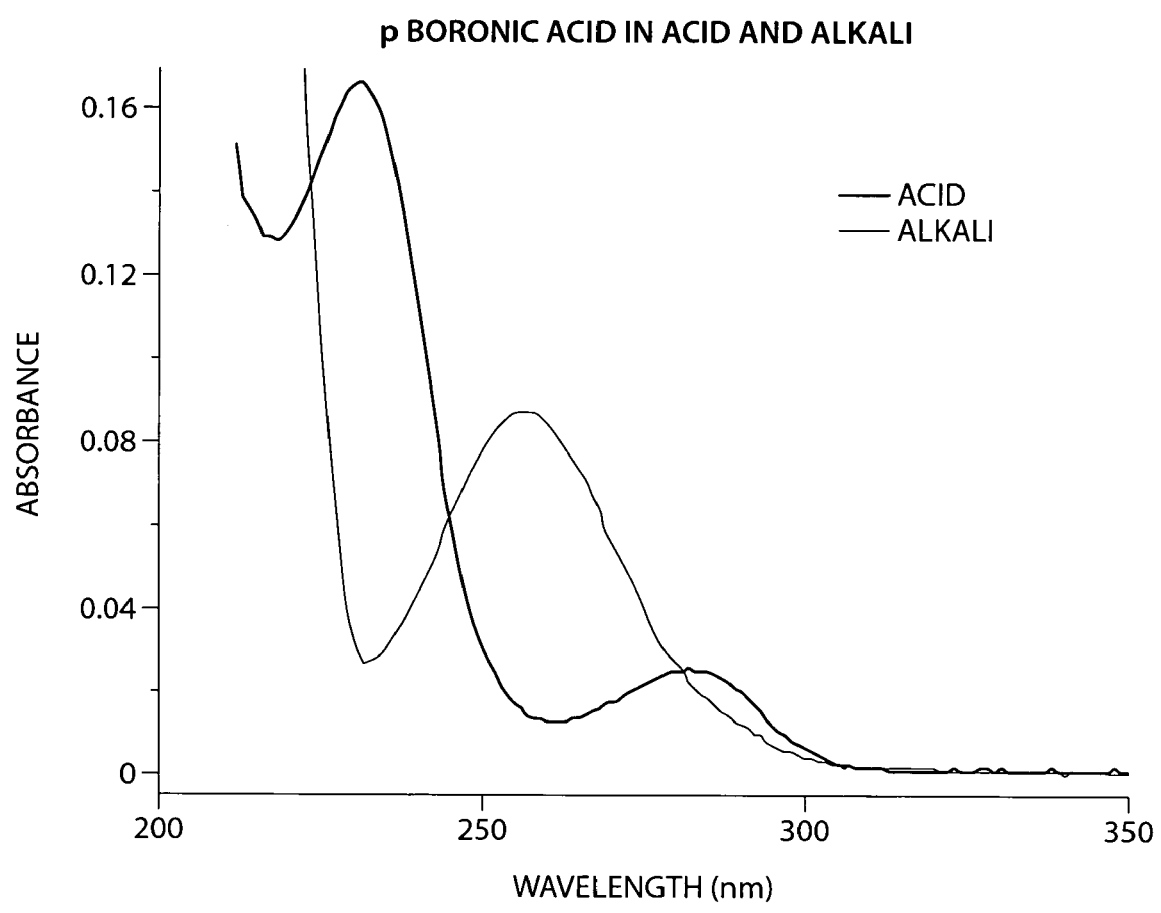
FIG. 28c. p-boronic acid spectra for acid (pH 2) and alkali (pH 12) conditions.

The material absorbs at a much shorter wavelength and the lowest energy band is much less solvent sensitive. The material is fluorescent. The absorption spectra are also sensitive to pH and the spectra for acid (pH 2) and alkali (pH 12) conditions are shown below (FIG. 28(c)).

Glucose Reporting Using Pyrene-Boronic Acid-Based Reporters

Figure 29A:
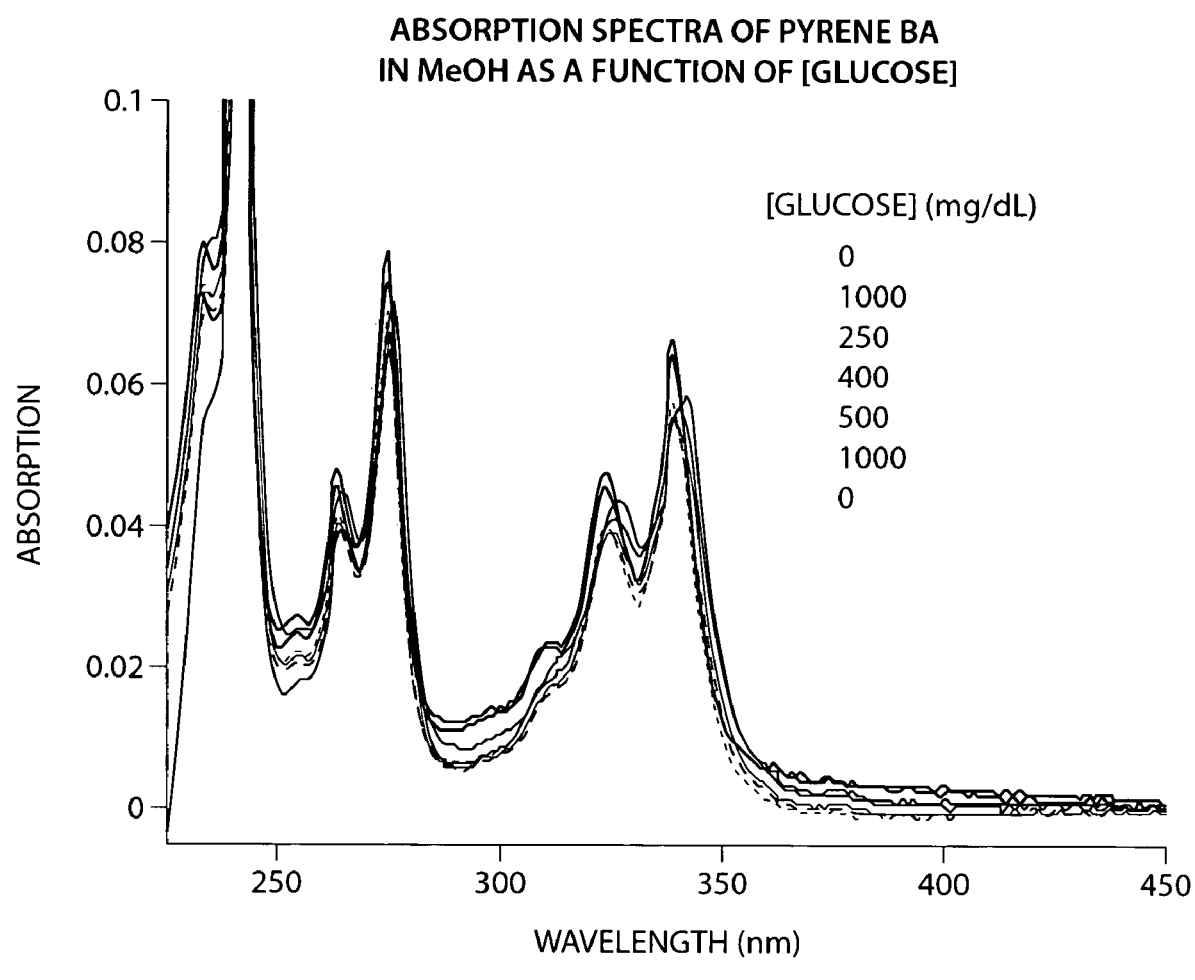
FIG. 29. Response of pyrene boronic acid fluorescence in the presence of glucose (methanol as solvent). Absorption spectra (top), fluorescence spectra (middle), and relative fluorescence intensity (bottom) as a function of glucose concentration.
Figure 29B:
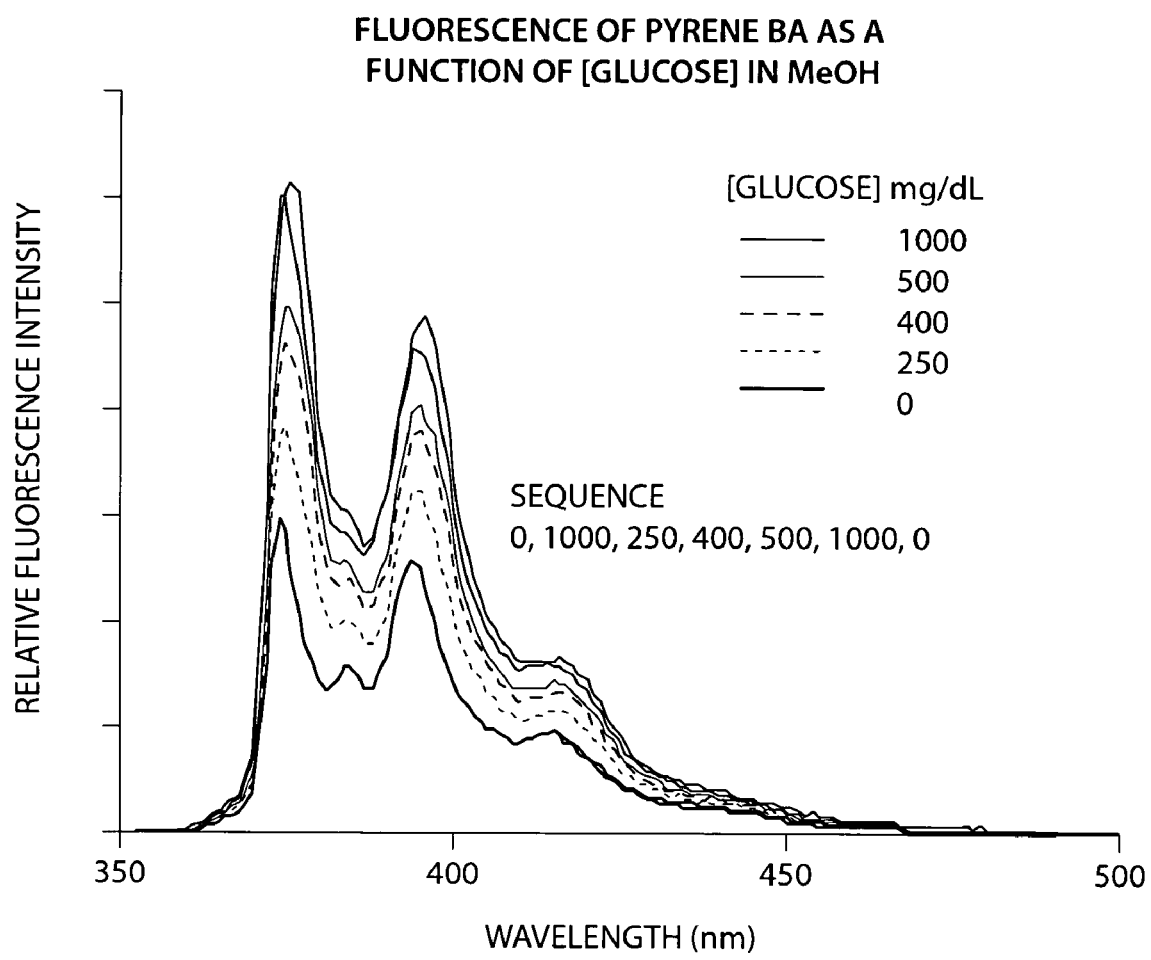
Figure 29C:
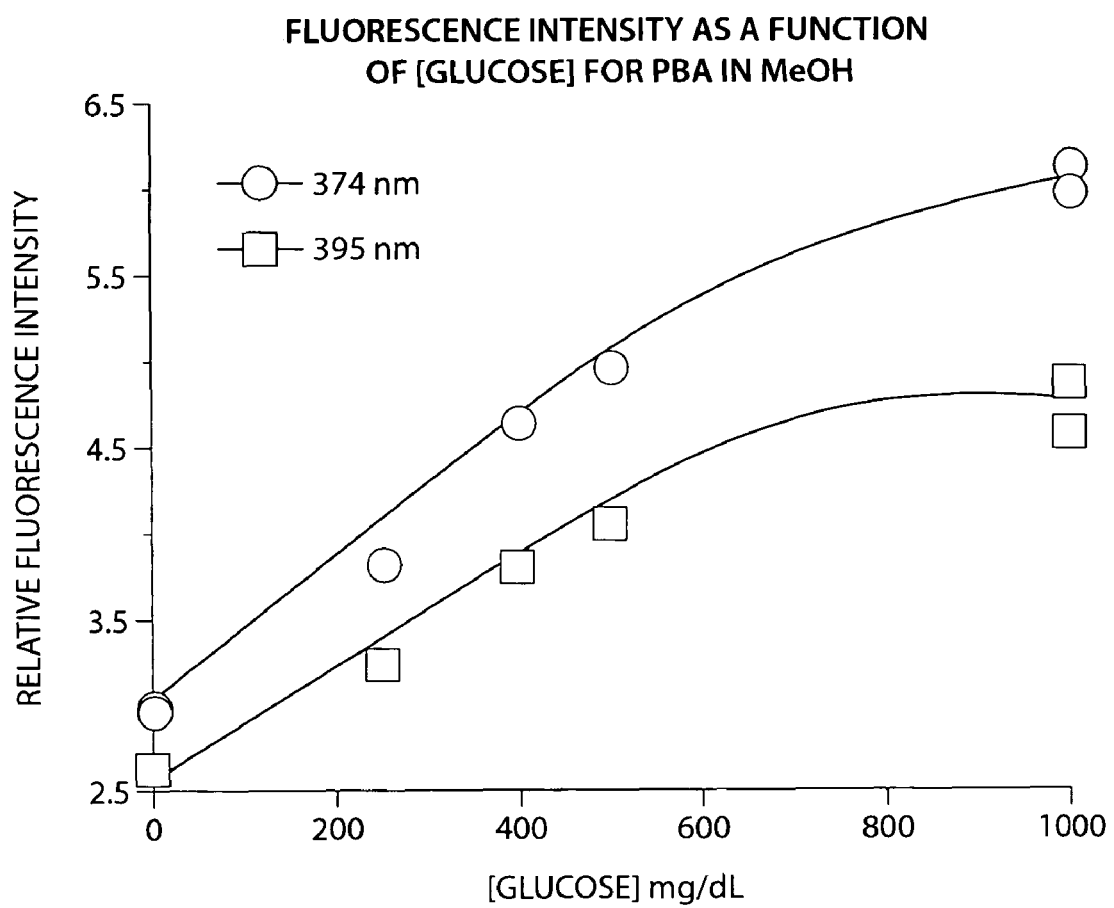

Pyrene boronic acid fluorescence increases in the presence of glucose, but this effect has only been observed in methanol and not in aqueous solutions (See FIG. 29).

For both coumarin-based and pyrene-based boronic acids the quantum yield of fluorescence increases with glucose. The fluorescence and the absorption spectra remain the same implying that there is no change in the electronic configuration of the ground and excited state.

Approaches to Enhance D-Glucose Specificity

Phenyl Boronic acid analogs bind reversibly to hydroxyl containing compounds to form a stable boronate ester. This equilibrium is established in solution, at room temperature with alcohols, in aqueous solution. The equilibrium is particularly favorable with diols and other polyhydroxy compounds, when binding to two vicinal hydroxyl groups allows for the formation of a highly favorable 5-membered-ring reaction product. Early on Boric Acid (1) and Phenyl Boronic Acid (2) were studied in relation to their binding with various sugar molecules.

Since the 1980's, many investigators have considered phenyl boronic acids as a suitable reactive moiety to bind to glucose and other saccharides. Derivatives of Phenylboronic acid have been invoked in many schemes for the direct measurement of the concentration of Glucose and other sugars. In particular, phenylboronic acid has formed a key element in signal transduction in fluorescence-based glucose assays. (3)

The majority of the schemes employ boronic acid to bind to the target saccharide and to modulate photophysical properties of the fluorophore through a quenching mechanism or direct effect on the electronic configuration of the fluorophore itself. The observable effect of saccharide binding manifests itself through changes in wavelength and/or intensity.

The boronic acid—sugar detection schemes are specific for diol-containing compounds. Phenylboronic acid shows a small but observable specificity in its bonding affinity to various sugars. The order Fructose>Arabinose, Ribose>Galactose>Glucose has been observed in the literature, although the relative specificity spans only 1 to 2 orders of magnitude. (4)

This is acceptable in the case of laboratory assays in the absence of interfering compounds. However, in-vivo, or with physiological samples, many additional saccharides, including glycoproteins are present in unknown large concentrations, which interfere with a satisfactory assay.

In nature, glucose and other individual saccharide molecules are recognized with exquisite specificity. In enzymes (glucose oxidase, hexokinase) and bacterial periplasmic binding proteins (PBP) (glucose binding protein; arabinose BP; ribose BP; etc) the individual sugar molecule is bound in a receptor or active-site by intermolecular forces, which achieve chemical complementarity with the molecule in question. This is a delicate balance of nonbonded, electrostatic, and H-bonding interactions, which exclude undesired molecules and provide strong affinity to the one native target molecule. The binding pockets of this family of proteins, favor H-bonding to the bound sugar by side chains of glutamates aspartates and asparagines. (5)

These features can be evaluated by visualization and inspection of the published crystal structures of the proteins, with their native saccharide-molecule ligand. All of these proteins and more particularly, all within a given family, share a common attribute for specificity-determination. The small saccharide molecule, i.e. glucose, etc., is bound (indeed almost totally surrounded) in a concave binding pocket, which effectively excludes molecules above a size threshold.

Hellinga has reported and patented protein-mediated assay systems, based on a environmentally-sensitive fluorophore attached to the appropriate the binding protein (6). For example, a sensitive and selective glucose reporter is based on glucose-binding protein, conjugated to NBD, Fluorescein, pyrene, and other fluorophores. This study also demonstrated that specificity can be tailored to accommodate man-made small molecules, by site-directed mutagenesis of the residues that line the putative monosaccharide binding pocket.

Thus, the specific reporting of glucose is solved, for small in-vitro assays. The concept faces practical barriers to in-vivo implementation, such as that of delivering a relatively large protein molecule.

Specificity with Small-Molecule Synthetic Reporters

Figure 30:
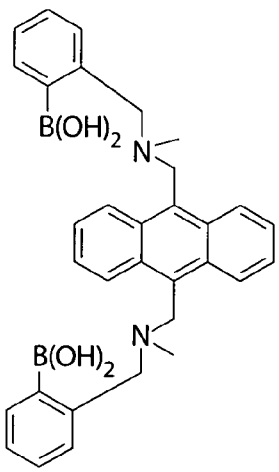
FIG. 30. Some Bidentate Glucose reporter molecules.
Figure 30:
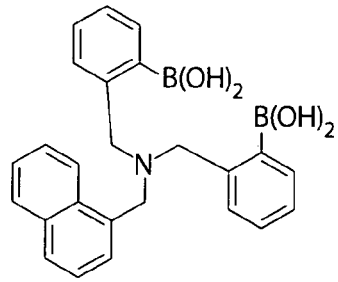
Figure 30:
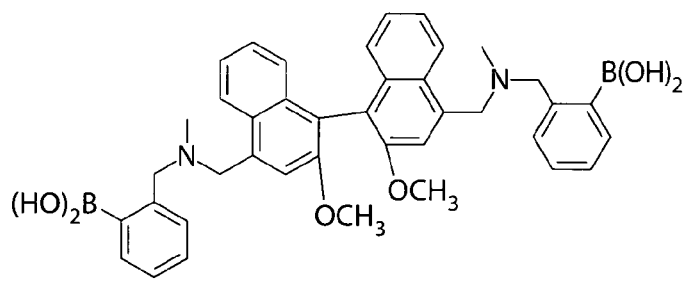
Figure 30:
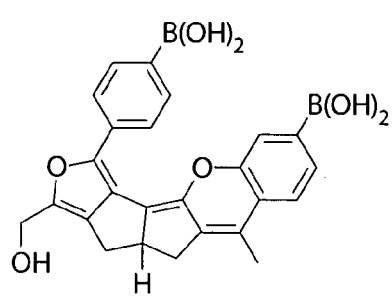
Figure 30:
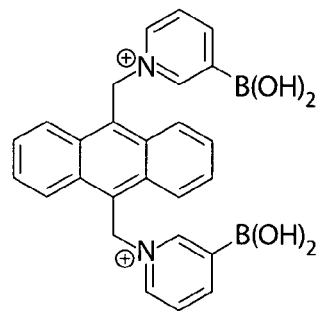

In a small-molecule reporter context, strategies may be enumerated for achieving specificity for glucose (ratio of binding equilibrium constants) over larger saccharide-containing species:
  1. Bidentate (or polydentate) reporters, that restrict the preferred saccharide ligand by size and accessible orientations.
  2. Reporters with additional auxiliary side chains to simulate a binding-pocket environment.
  3. Reporters incorporating a semi-rigid small binding pocket environment to complement the boronic acid and other "side chains"
  4. Repulsion of the larger molecules by placement of functionality similar to silicone polymer Bidentate Reporters Attempts have been made to improve glucose specificity by engineering boronic acid based fluorescent sensors that favor one sugar over another. This has been accomplished by adjusting the distance of an intramolecular linker, between two boronic acid groups, thus constraining the geometry into which a sugar molecule can fit. (7) Several examples from the literature are given in FIG. 30.

Boronic-Acid Reporters with Auxiliary Side Chains

A similar concept is proposed, using one boronic acid group and other molecular fragments which provide intermolecular attraction and constrain the space into which a sugar molecule can bind. Molecular fragments to be employed in this regard are selected with a preference for the amino acid side chains that comprise the binding site of the PBP's (Asp, Asn, Glu, Gln, Ser, etc). As an initial attempt, neutral fragments (like Asn, Gln, or Ser) are most likely due to molecular property considerations. Such a "small molecule" multi-domain reporter (SMMDR) is advantageous in its ready assembly by general methods of synthetic organic chemistry and its small size, which facilitates transdermal delivery, in-vivo.

Figure 31:
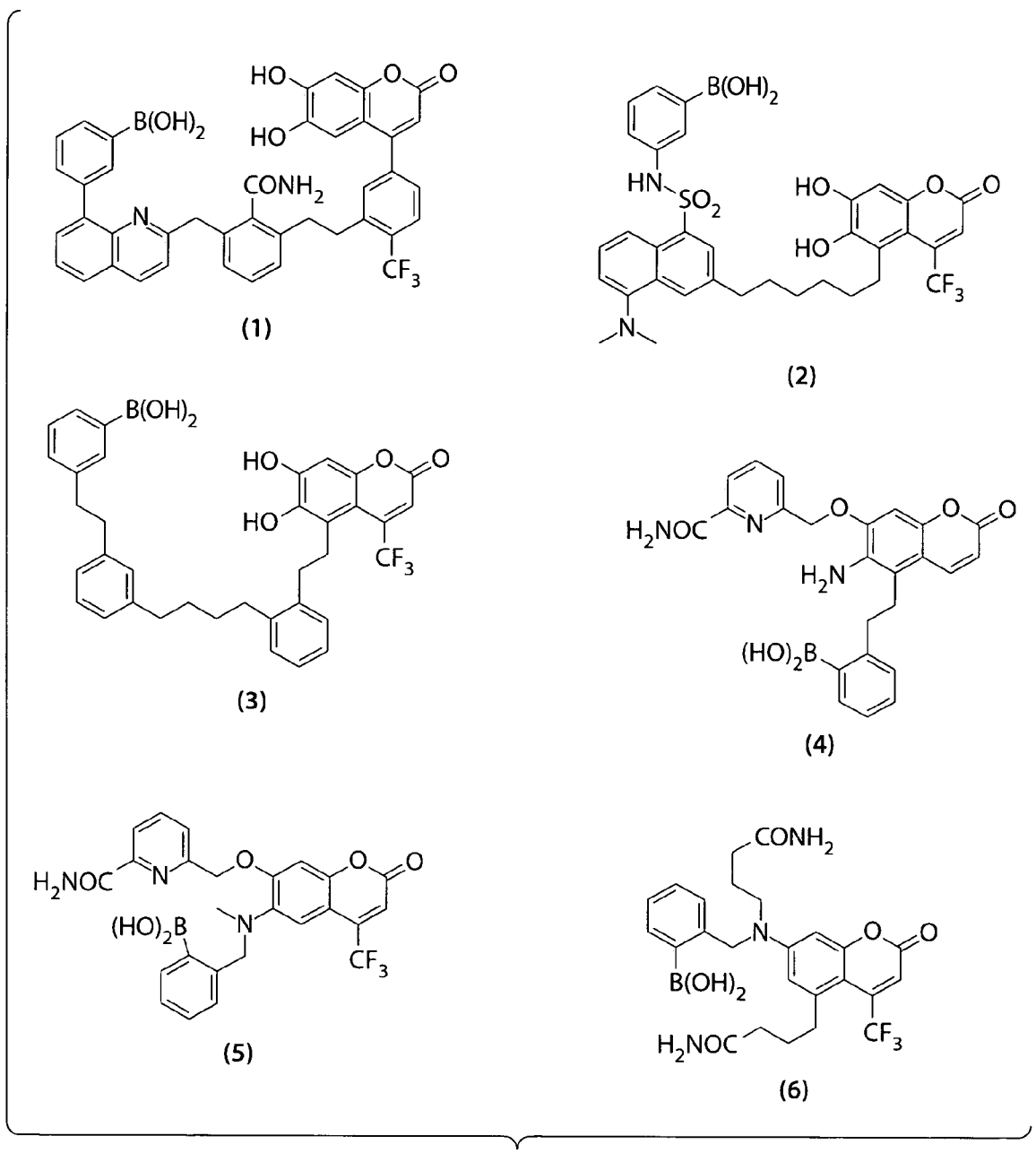
FIG. 31. Illustrative examples of SMMDR molecules.

FIG. 31 shows illustrative examples of SMMDR concepts. Compounds 1, 2, and 3 modulate fluorescence by sugar displacing the dihydroxy coumarin fluorophore from the boronic acid group. Compounds 3, 4, and 5 modulate fluorescence by a photochemically induced electron transfer mechanism, wherein sugar binds to boron, displacing the nitrogen proximal to the fluorophore, making its electron pair available for quenching.

Figure 32:
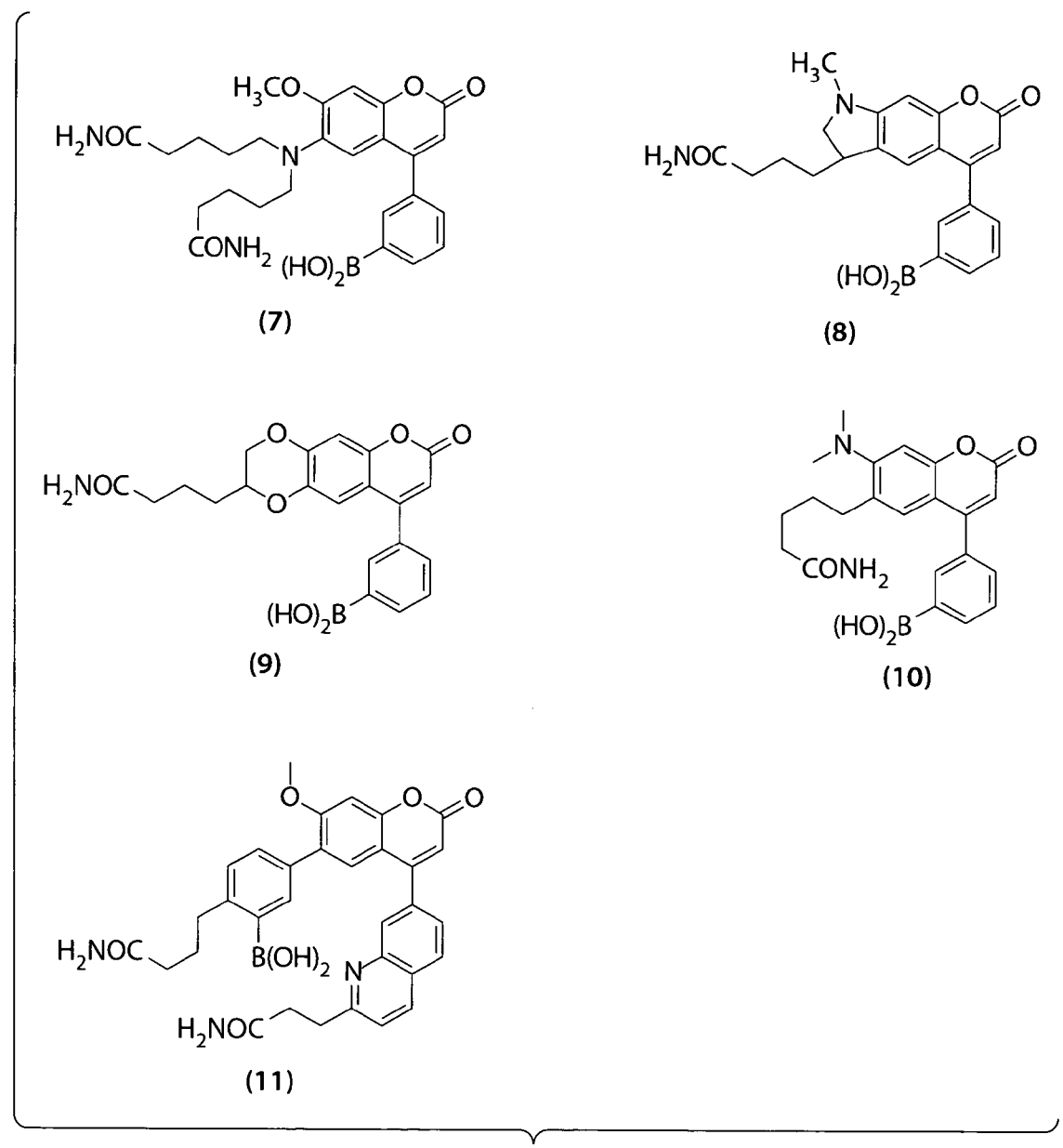
FIG. 32. SMMDR molecule concepts in which phenylboronic acid is part of a push-pull fluorophore. Carboxamide groups provide auxiliary binding.

FIG. 32 shows examples of SMMDR concepts in which compounds 7 thru 11 incorporate phenylboronic acid as an element of a push-pull fluorophore. Fluorescence intensity and/or wavelength are modulated by change of the boronic substituent from electron-withdrawing to electron-donating in the glucose binding equilibrium. Additional carboxamide H-bonding groups (based on Asn) are appended in the vicinity of the boronic acid to increase affinity and geometry-induced selectivity for the sugar of interest.

In practice such concept compounds would be refined by molecular modeling techniques to assure that dimensions and geometry are optimal for selectivity with the sugar molecule of interest, and that the auxiliary binding groups provide the maximum affinity on binding.

Reporters Incorporating a Semi-Rigid Binding Pocket Environment

An additional refinement of the multi-domain concept is to add a natural molecular binding pocket, which is an integral part of the reporter molecule structure. This general concept has been employed in a number of selective ionophores and used in ion assay systems. The basic notion is to create a ring or pocket-like structure, of optimal size, which also possesses some natural binding affinity toward the analyte of interest. Overall binding affinity is enhanced over a non rigid analog, due to a diminished entropy eanalty on binding. In the case of glucose binding, crown ethers and cyclic peptides are a logical starting point. These molecules are advantageous in a) synthetic accessibility, b) adjustable size, c) general biocompatibility, and d) ability to attach additional side chains to enhance binding or steric exclusion.

Figure 33:
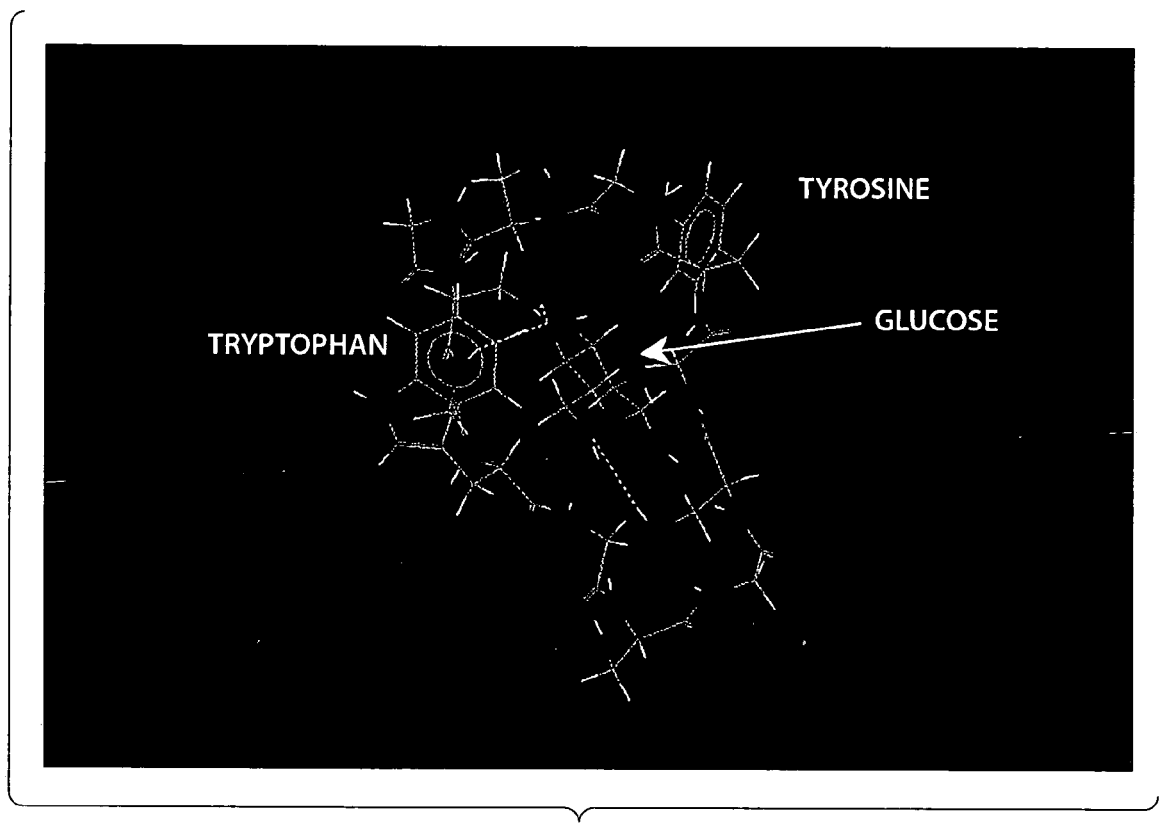
FIG. 33. In this image, the glucose interacts with a cyclic peptide that contains four serine residues, eight glycine structures, and a tryptophan and a tyrosine residue. The dotted lines represent hydrogen bonds. The two aromatic residues are above the plane of the peptide ring and in this conformation would be expected to undergo efficient energy transfer. The model simply represents a starting point from which a small glucose binding peptide might be built.
Figure 34:
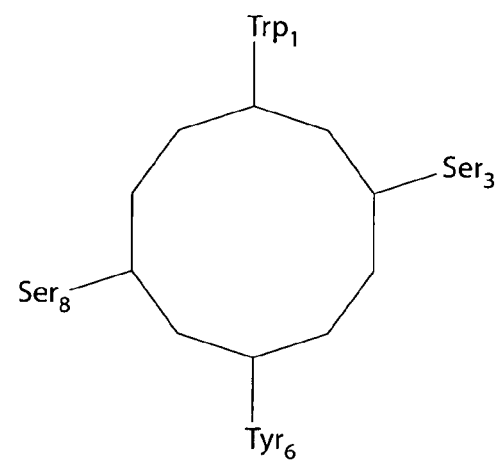
FIG. 34. Compounds to test cyclic peptide and crown-ether recognition of glucose.
Figure 34:
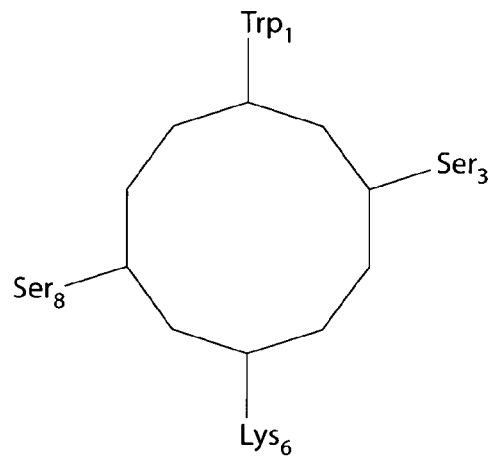
Figure 34:
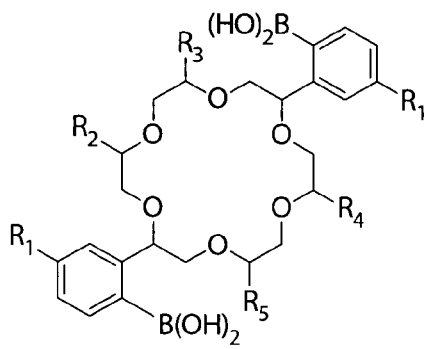
Figure 34:
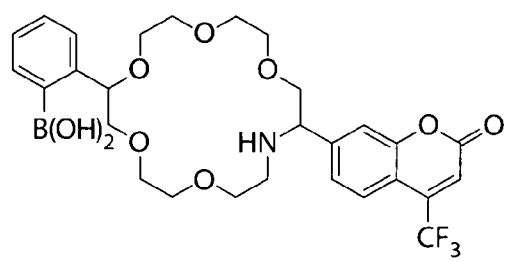

The first iteration of such a cyclic peptide might contain tyrosine and tryptophan residues. The binding of glucose could then be detected by a change in the efficiency of energy transfer from tyrosine to tryptophan. Some preliminary modeling of the interaction of the cyclic peptide with glucose has been done. (FIG. 33). Additional general concepts are illustrated in FIG. 34.

Repulsion and/or Size Exclusion of Larger Molecules

Figure 35:
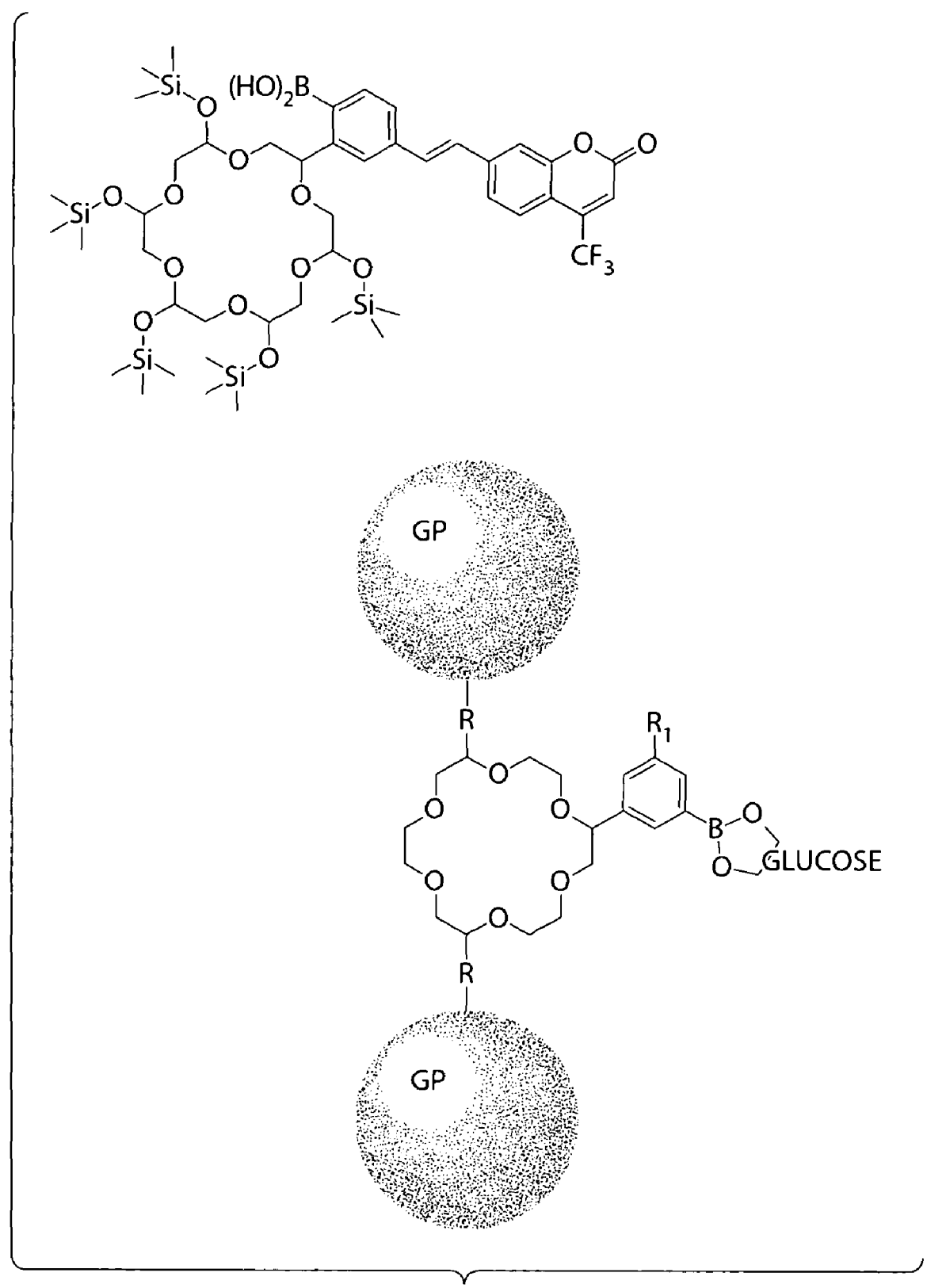
FIG. 35. Conceptual illustration of glucose-binding reporters that operate by repulsion and size exclusion.

In the context of the small binding pocket concept proposed above, compounds could be designed and prepared, in which reporting of glycoproteins is minimized or eliminated. Two concepts are proposed to solve this problem: a) incorporating functional groups that repel the hydrophilic surface of a protein, e.g. the functionality of a silicone polymer; and b) establishment of sham binding sites, which when occupied, exclude binding of large species to the reporter binding site. See FIG. 35.

Combinatorial/Iterative Design Approach

Figure 36:
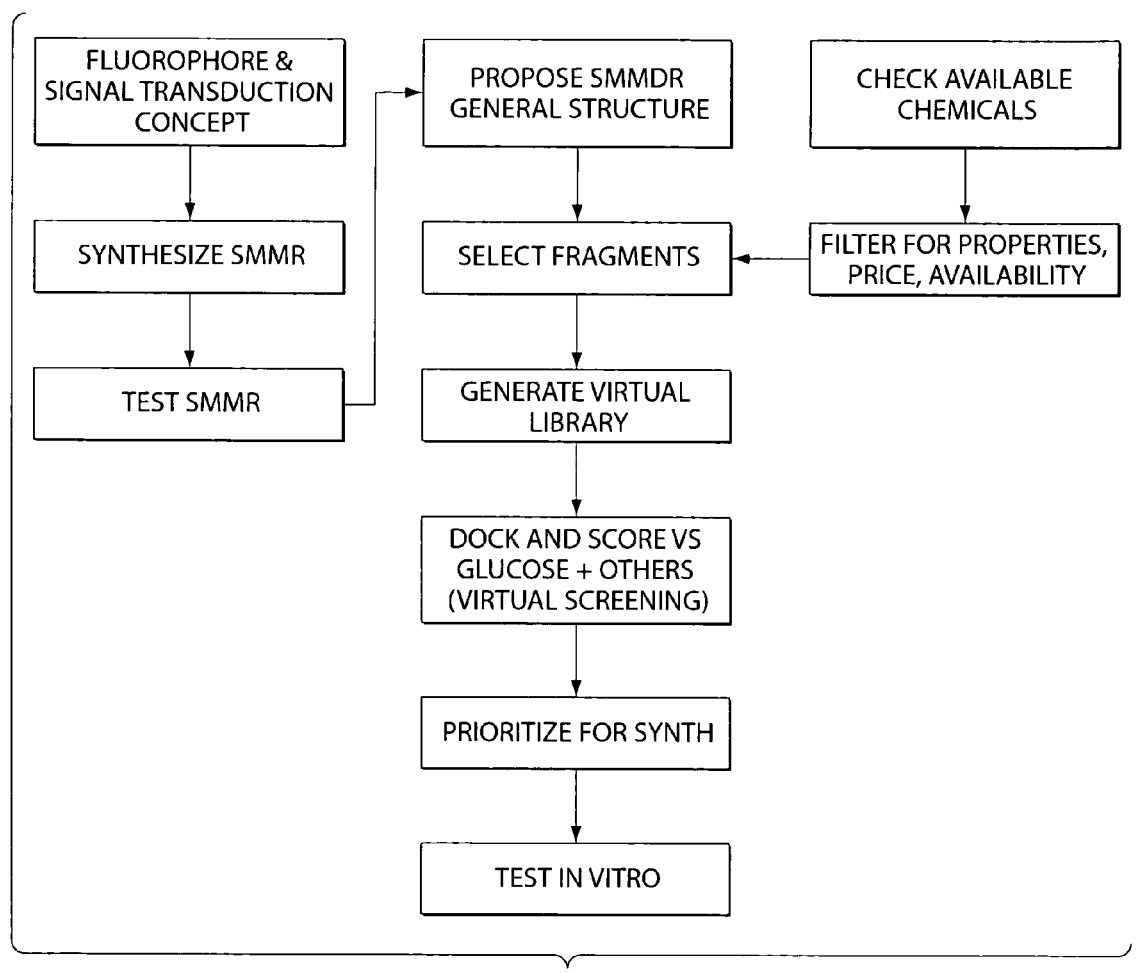
FIG. 36. SMMDR Development strategy: Library generation and virtual screening.

Due to the subtle distinctions required in molecular recognition amongst different sugar molecules, the most fruitful approach to creating and improving ligand-binding specificity is an evolutionary/combinatorial paradigm. The desired SMMDR structure is treated as modular and assembled from molecular building blocks. SMMDR molecules thus conceived are pre-screened and scored by analysis in-silico, prior to beginning synthetic chemistry efforts. A general flow chart for addressing this problem is illustrated in FIG. 36.

This method is applicable to the series of discrete molecules illustrated above, as well as a series of combinatorially-generated compounds.

The library generation/dock and score/virtual screening paradigm is applicable to any arbitrary set of candidate chemical compounds. A known chemical synthesis method is not necessary to conduct this in-silico analysis, however a ready means to construct target structures is advantageous when new compounds are proposed for testing.

Figure 37:
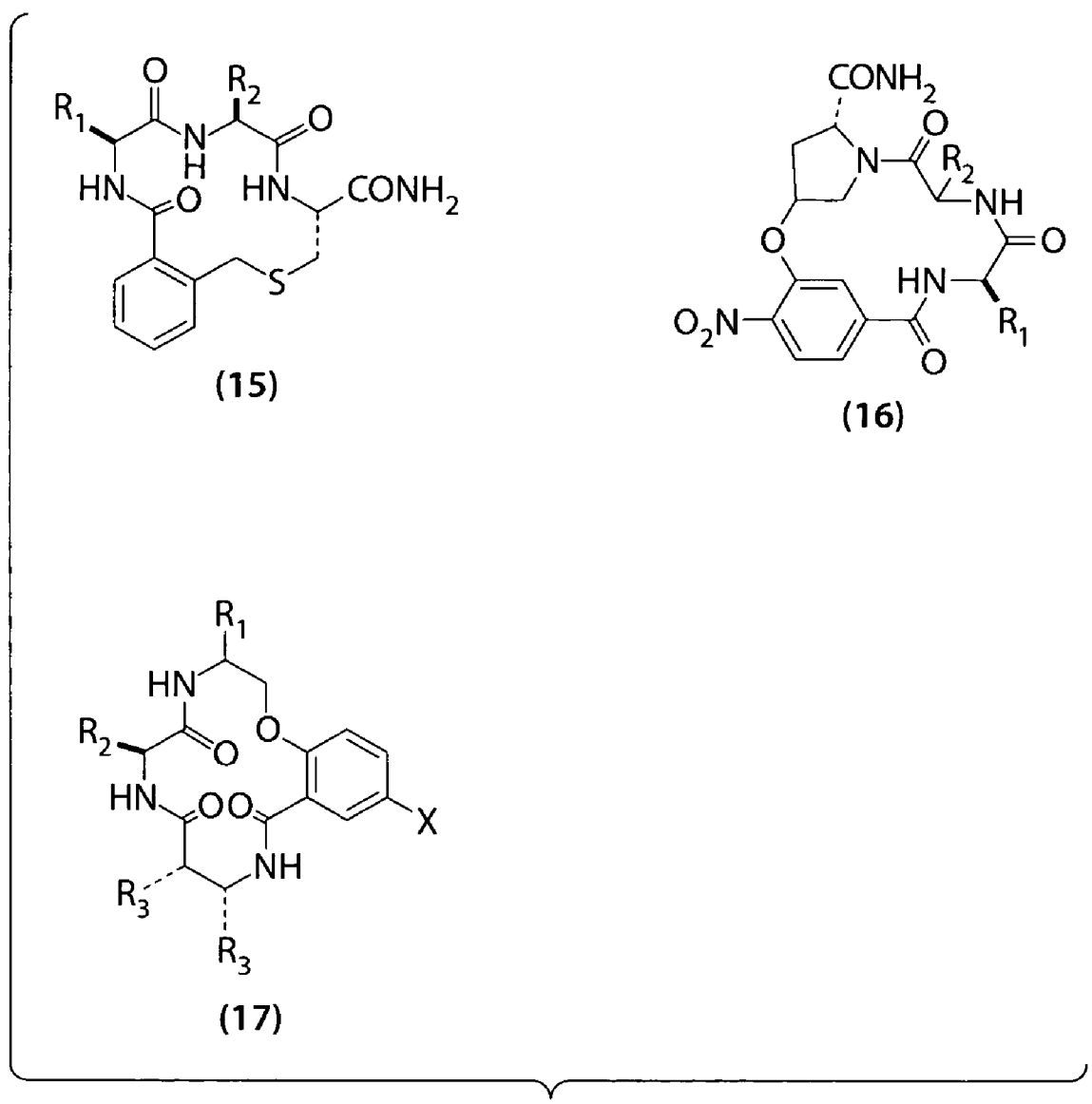
FIG. 37. Combinatorial Libraries based on small cyclic peptides.

Over the last decade there has developed a rich literature on synthesis of diverse combinatorial libraries comprising 3 or more points of diversity, and considerable stereochemical variability. Thus, some of the basic library structural types from the literature may be evaluated to form the basis for SMMDR libraries. (7) Several concept examples are presented in FIG. 37.

The ordinary paradigm of drug development relies on modification of a "small-molecule" to enhance its fit into a relatively "fixed" receptor, active site, or binding pocket. Specificity in this interaction (vs. other similar receptors) is accomplished by adjusting the chemical functionality, size, and geometry of the small molecule, to enhance non-bonded interactions (charges, van der Waals interactions, dipoles, etc.) such that the interaction energy with the target of interest is more favorable than with other targets.

One way to consider the specificity problem is that the small molecule (i.e. glucose) is fixed and a synthetic "receptor" (SMMR) is adjusted in ways to exclude larger and undesired saccharides, while enhancing the binding energy between our SMMR and glucose. By way of non-limiting example, several approaches are suggested:

1. Bidentate and multi-dentate phenylboronic acid—SMMR's
2. Artificial binding pockets based on crown ethers, cyclic peptides, etc.
3. Multi-dentate SMMR's with Boronic acid and other interacting side chains based on precedent from naturally occurring proteins and other literature. A Nature has solved the specificity problem in enzymes (hexokinase, glucose oxidase, etc.); Periplasmic binding proteins, and lectins, by creating a relatively constrained binding pocket within a large protein molecule.

There is a trade-off of size and specificity. For example, a very small SMMR does not embody sufficient molecular features (information content) for good specificity. A feature-rich large molecule can be very specific, but may suffer from multiple practical and economic drawbacks.

Alternate Fluorophores

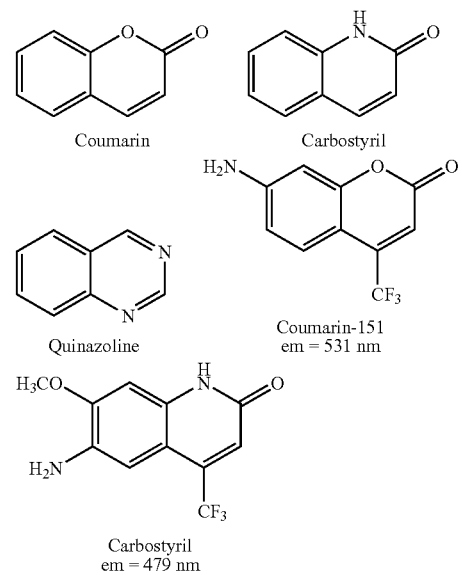

Coumarin

Carbostyril

Quinazoline

Coumarin-151
em = 531 nm

Carbostyril
em = 479 nm

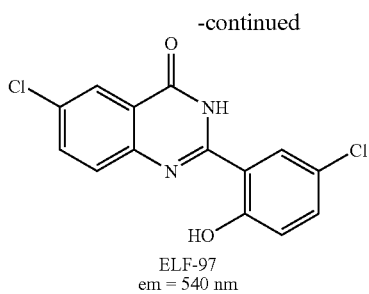

ELF-97
em = 540 nm

Alternate fluorophores based on carbostyril and quinazoline have been identified. Characteristics of these alternate fluorophores include:

Carbostyrils—Similar structure-activity relationship (SAR) to coumarins, long-wavelength examples, known SAR to get high quantum yield.

Quinazolines—opportunity for enzymatic activation in situ; and examples with large stokes shift.

A number of quinazoline derivatives have been reported in the literature, as fluorescent reporters. They offer the advantage of facile synthesis of diverse analogs, high quantum yield and large Stokes shift. The Quinazolin-4(3H)-one analog ELF-97 in particularly interesting in enzymatic assays. For example, the weakly-fluorescent, phosphate ester of ELF-97 is hydrolyzed by acid and alkaline phosphatase enzymes, to yield the insoluble alcohol. Interestingly, the hydrolyzed form is strongly fluorescent, with a very large stokes shift and is insoluble in aqueous solution.

Figure 38:
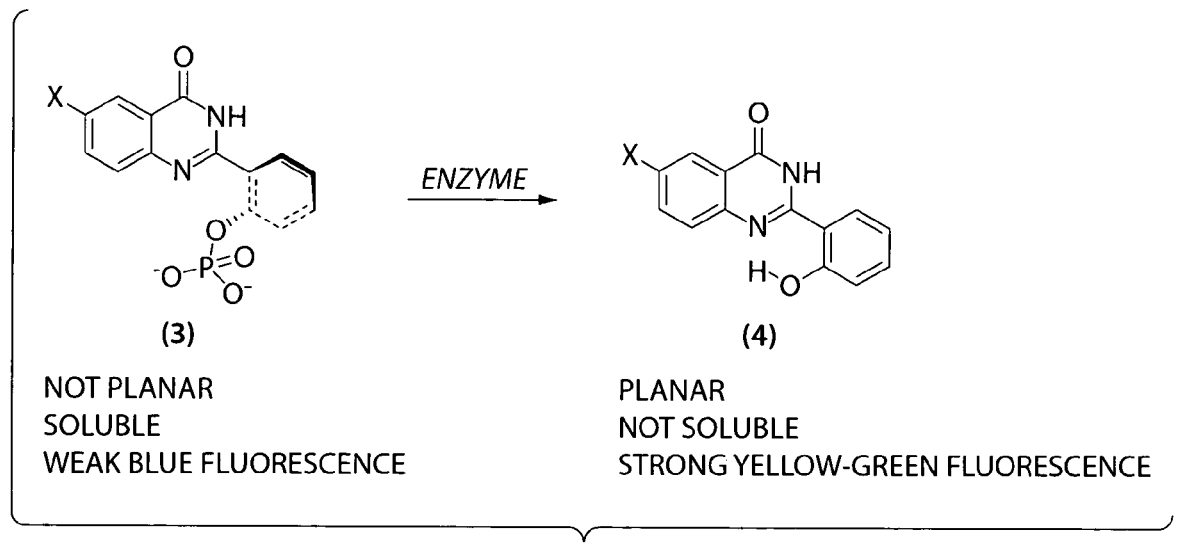
FIG. 38. Illustration of the action of the 2-phenylquinazolin-4(3H)-one compounds.

The fluorescence of these compounds arises from the ability of the molecule to adopt a planar conformation, stabilized by an intramolecular Hydrogen bond when the bulky phosphate group is hydrolyzed away (FIG. 38).

It is likely that an ester or amide of a similar SMMR could be created, such that the compound would be activated by esterases or proteases in the interstitial medium of the epidermis. The resulting insoluble, fluorescent compound may be less likely to move by diffusion.

Figure 39:
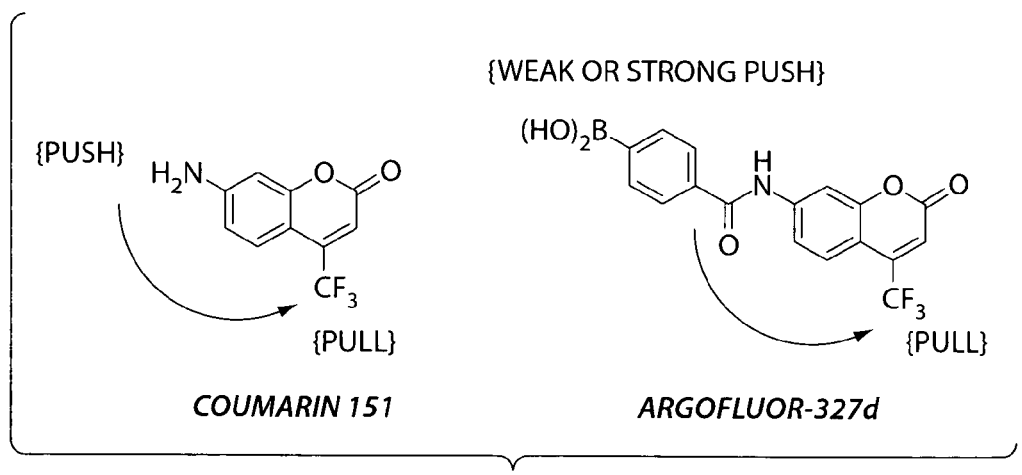
FIG. 39. "Push-Pull" Fluorophores.

One compound for direct glucose detection, AF-327d, is a boronic acid analog, based on Coumarin-151. It derives its fluorescence from a push-pull fluorophore, whose donating/withdrawing properties are modulated through the acid-base equilibrium that occurs on the boronic-acid moiety (FIG. 39). This compound exhibits a stronger response to glucose than other published compounds. The following characteristics of this compound can be modified:

1. Specificity—modifications to distinguish glucose from other non-glucose saccharides.
2. Wavelength—a longer wavelength is desirable, to avoid interference of auto-fluorescence in vivo
3. Calibration—Ratiometric self-referencing is will be helpful.

Computational Studies
Wavelength

Using the correlation of wavelength vs. computed HOMO-LUMO energy gap, it is possible to predict the fluorescent wavelength of candidate compounds. Substituent patterns on coumarin, carbostyril, and xanthene analogs were evaluated. Additional studies assessed the predicted effects of annellation to the corresponding naphtho-analogs, and alternate linkages between the fluorophore and boronic acid units analogous to AF-327d.

Conclusions from the computational predictions are presented as relative change in predicted wavelength—

Figure 40:
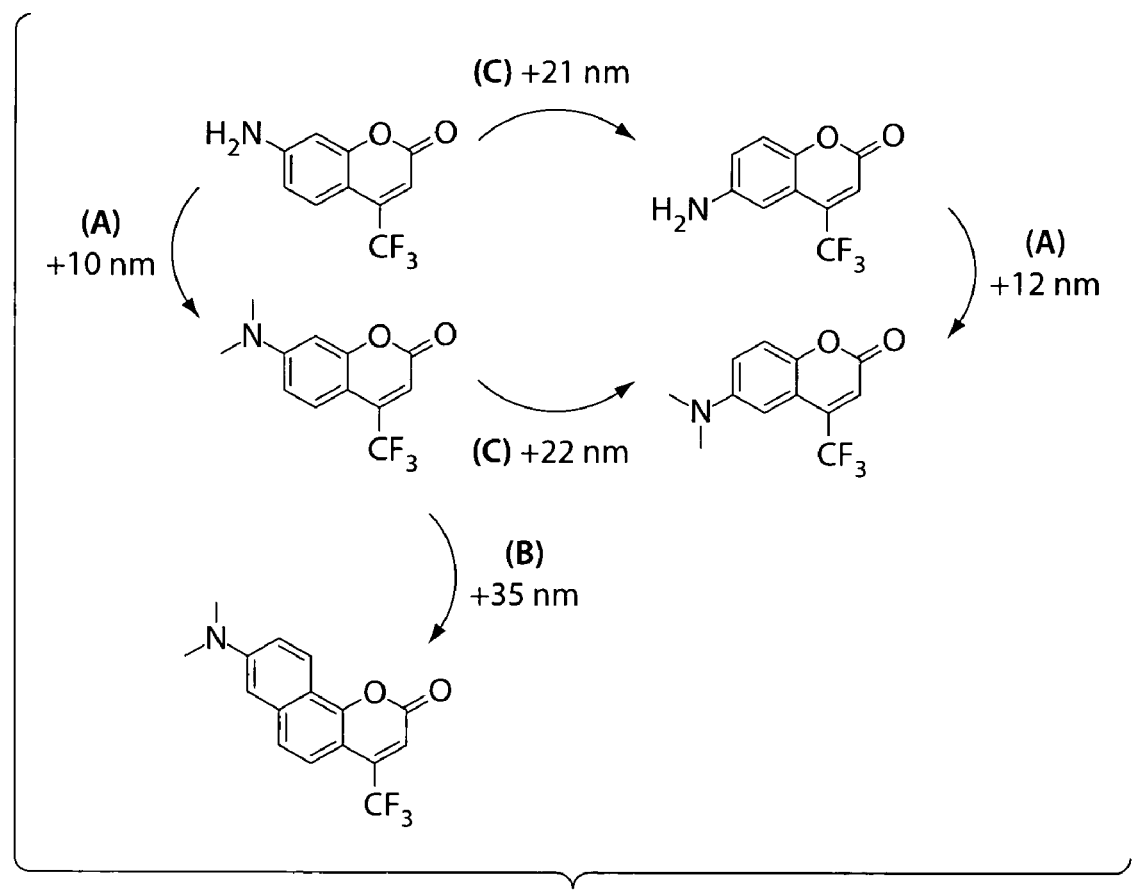
FIG. 40. Predicted wavelength changes due to annellation and substitution.

1. N,N-dimethyl substituent increases predicted wavelength about +10 to +12 nm vs.-NH$_2$ in coumarin analogs, FIG. 40 (A).
2. Annellation to form a naphthocoumarin can increase wavelength dramatically FIG. 40 (B).
3. Wavelength is sensitive to substitution pattern, which affects the strength of the push-pull interaction, FIG. 40 (C).

Figure 41:
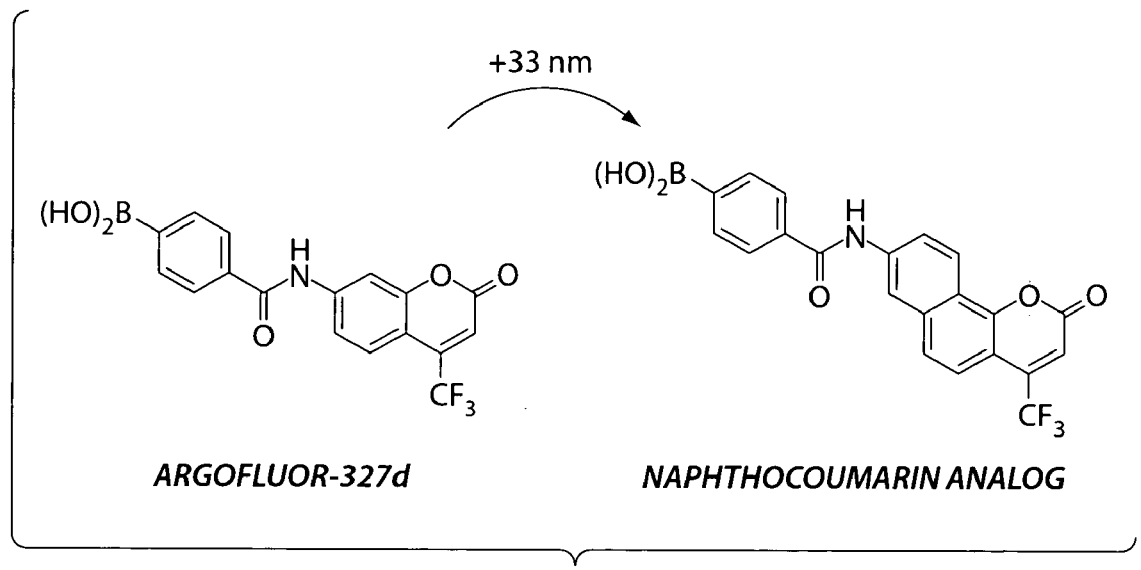
FIG. 41. Predicted Wavelength effect of ring annellation in a boronic acid probe compound.

This wavelength effect is predicted to carry over to a Naphtho-coumarin analog of AF-327d, as shown in FIG. 41.

Figure 42:
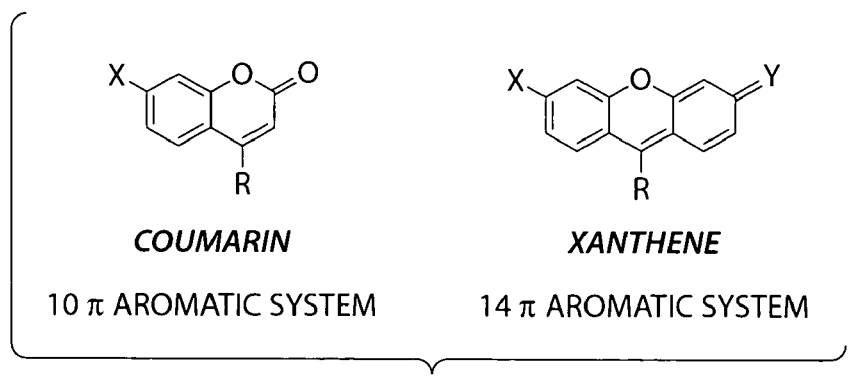
FIG. 42. Comparison of Coumarins and Xanthenes.

The general influence of ring annellation is also observed in the case of xanthenes, which can be viewed as a "benzocoumarin" or a 14-$\pi$ electron homolog of the coumarin ring system (FIG. 42).

Figure 43:
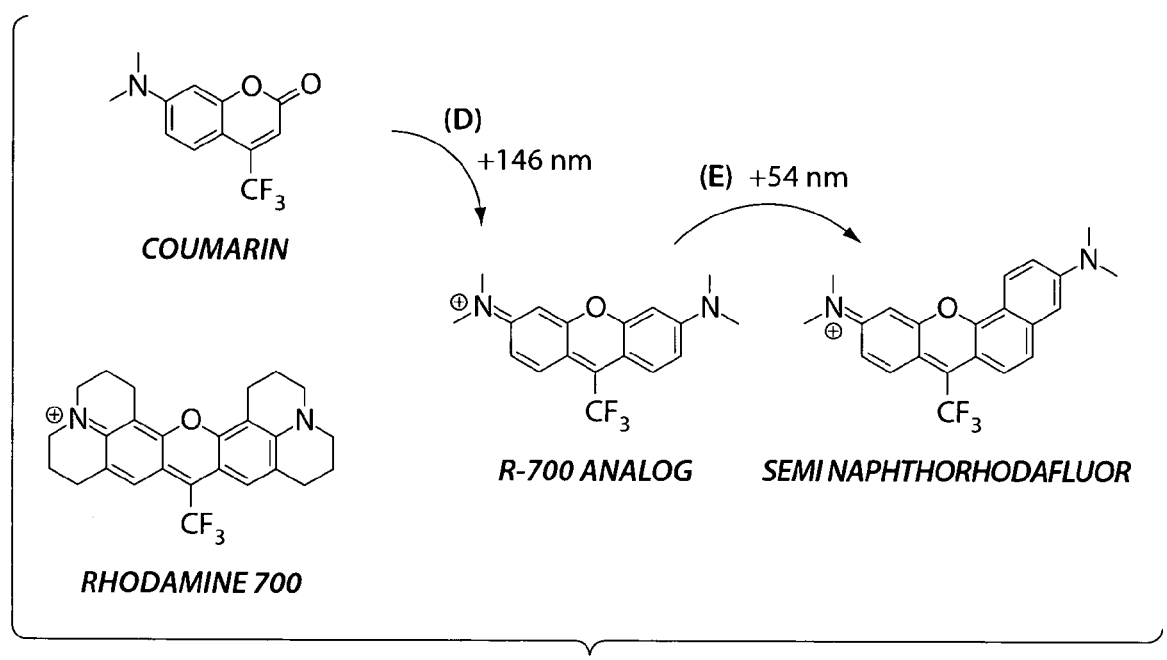
FIG. 43. Comparison of Coumarin, Xanthene, and Seminaphthorhodafluor analogs.

Starting from a relatively long wavelength analog of Rhodamine 700, conversion to the semi-naphthorhodafluor provides an additional dramatic increase in predicted wavelength over the corresponding coumarin analog (FIG. 43).

These predictions provide an ideal roadmap for elaboration of longer-wavelength analogs for our direct glucose probes. The synthesis of R-700 and a few naphthocoumarin analogs is known in the literature. Semi-naphthorhodafluors have also been made. Thus future long wavelength (and near-IR) analogs in these three families are synthetically accessible through straightforward reaction schemes.

Ratiometric Behavior

The ratiometric pH dependent fluorescence of SNARF is well known. The dual wavelength spectrum around pH=7 is due to the —OH and —O$^-$ species respectively. In this example, the OH and O— are the electron donors in a push-pull system, where deprotonation increases the strength of the donation in a push-pull fluorophore and allows for additional tautomeric forms.

Calculations on several analogs with a variety of substituents at the bottom of the molecule demonstrated a strongly electron-donating ring that appears to provide a larger wavelength shift on deprotonation of the hydroxyl group. Examination of Hammett constants revealed that the carboxylate anions on SNARF would also be slightly electron donating.

Figure 44:
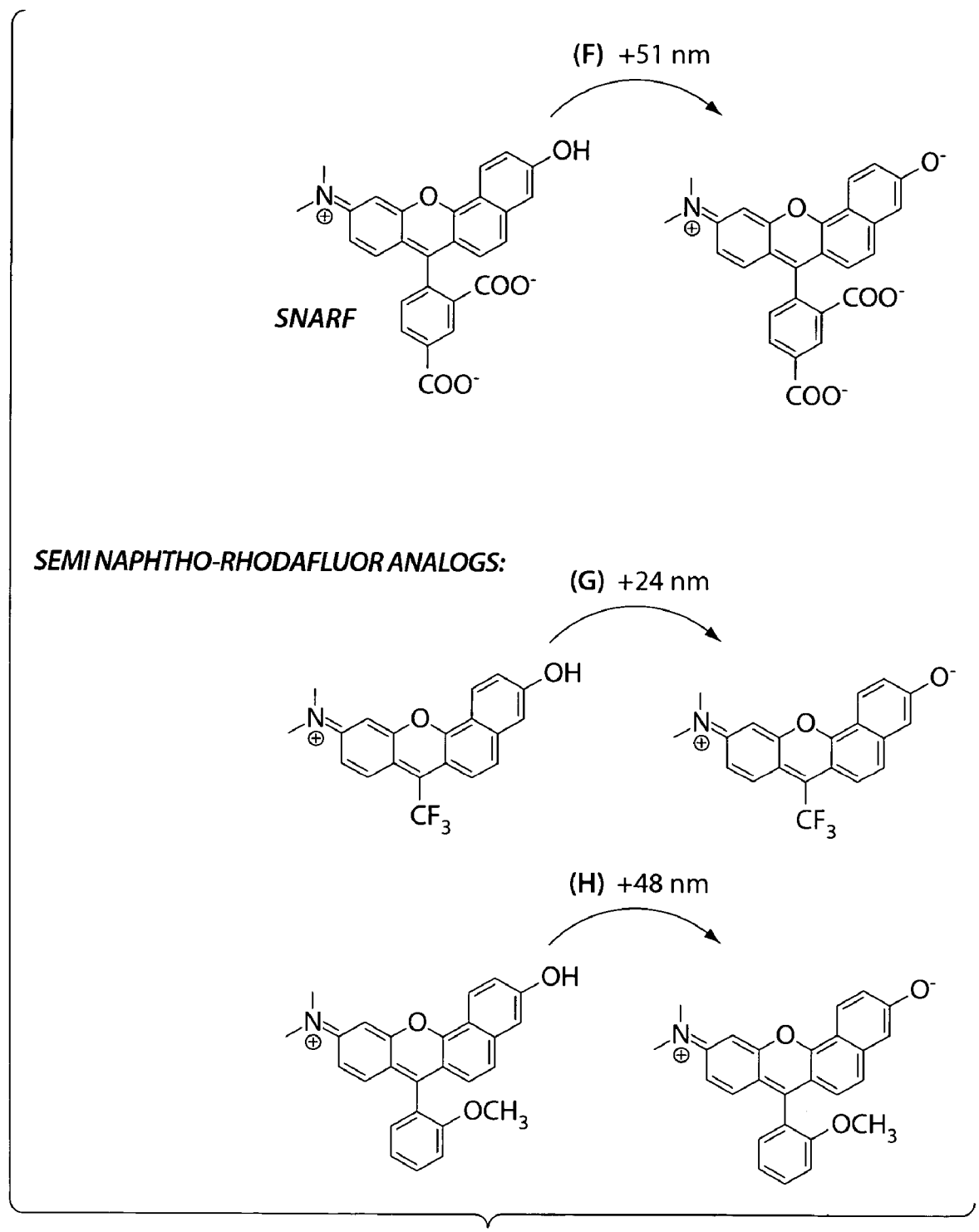
FIG. 44. Novel Seminaphthorhodafluor compounds with predicted long wavelength and ratiometric pH properties.

This knowledge can be used in creating a "ratiometric" glucose probe, to satisfy the internal referencing situation (FIG. 44).

Design Strategy for pH-Based Glucose or Lactate Reporters

Esculetin (6,7 dihydroxycoumarin) pH Dependency

Figure 45A:
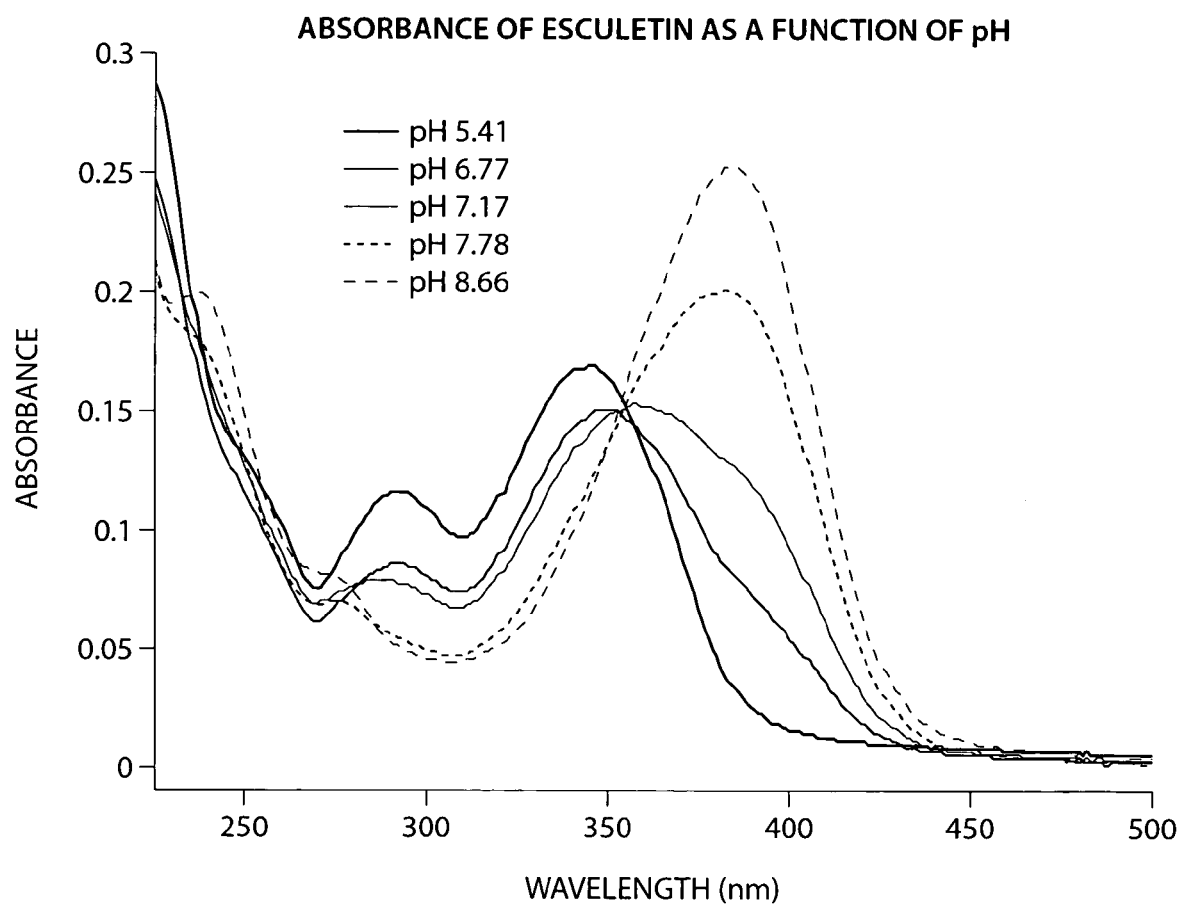
FIG. 45. Spectra of esculetin demonstrating absorbance (top), fluorescence (middle), and absorption ratio at 384 nm/344 nm (bottom) as a function of pH.
Figure 45B:
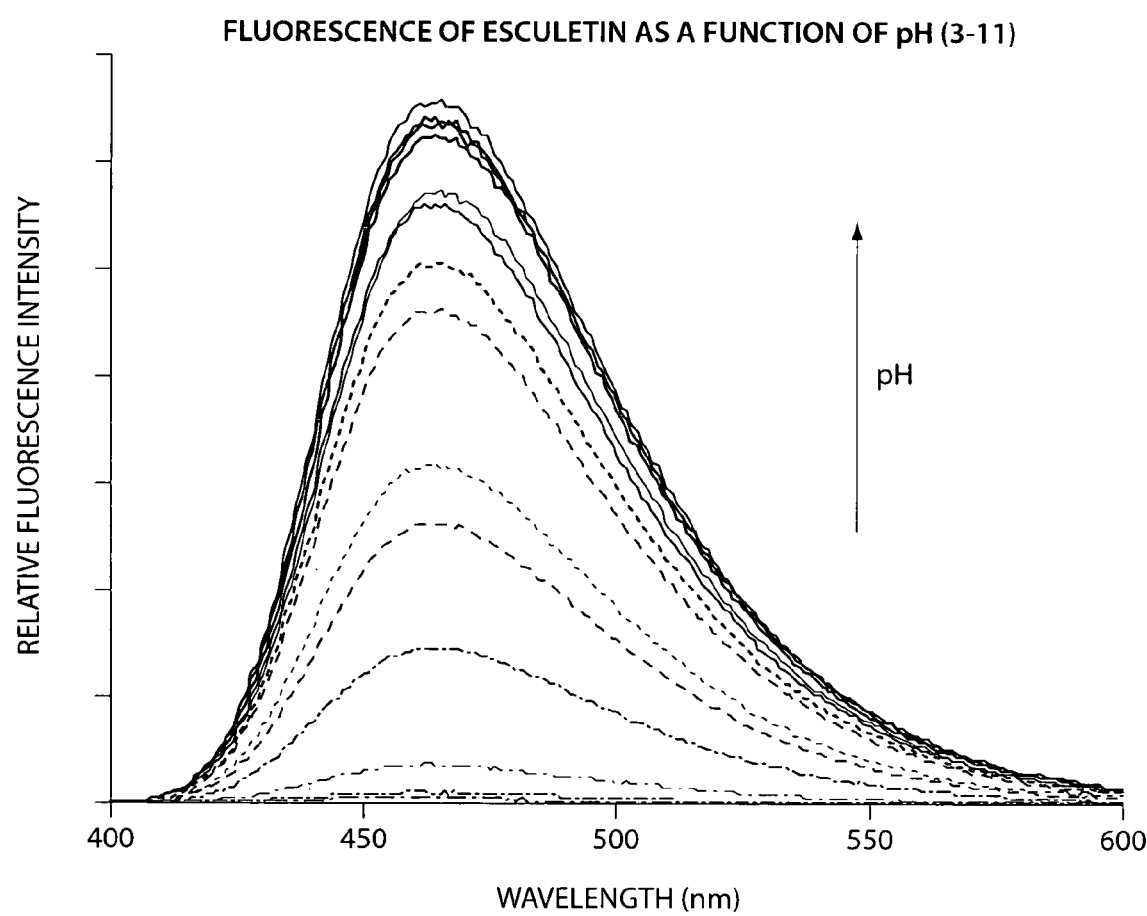
Figure 45C:
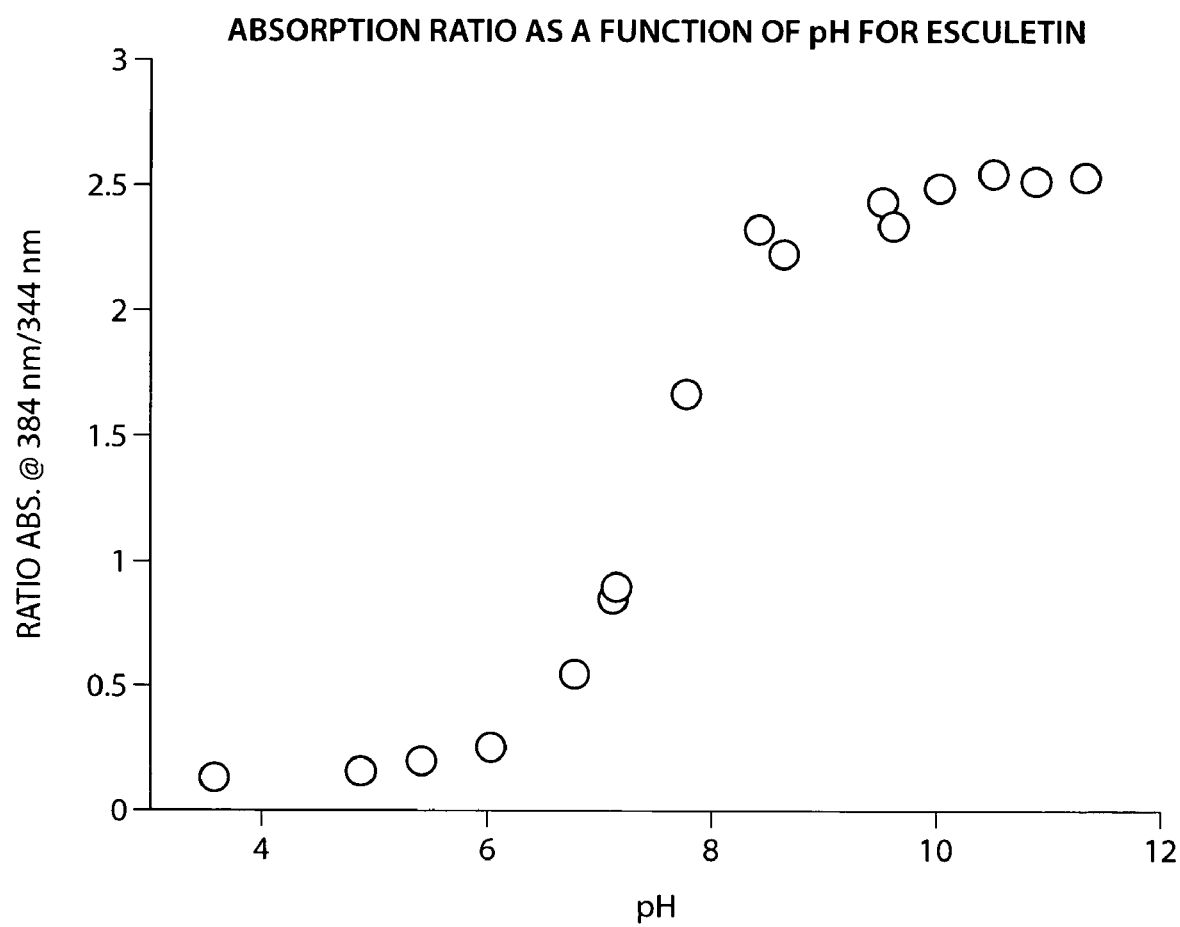

The pKa of esculetin was determined to be 7.5. The intensity of the fluorescence varies with pH but not the emission wavelength. The absorption spectrum did change with pH, implying the molecule could be used ratiometrically to measure pH using one monitoring wavelength and two excitation wavelengths. The relevant spectra are shown here together with a plot of absorption ratio as a function of pH (FIG. 45).

Design Strategy for Other Glucose Reporting Structures

Crown Ethers

The molecular structure shown immediately below is a boron derivative of a crown ether. Provided the boron still has affinity for alcohols, the structure might be expected to bind with monosaccharide. Modeled molecular mechanics of a crown ether with a fluorescein and rhodamine dye tethered to opposite sides of the ring. In one embodiment, the crown ether is in a conformation in which the two dyes are brought into close proximity to one another.

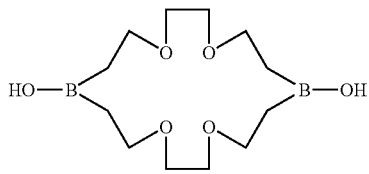

For the molecule drawn above, the electron density is compared with a conventional boronic acid. Calculations are run with ZINDO using HyperChem. Calculations with crown ethers and glucose seem to position the glucose above the plane of the crown ether.

It is well known that such compounds have been used to detect the presence of metal ions. Crown ethers are often used as phase transfer catalysts in organic chemistry. No reports of interactions between glucose or monosaccharides with crown ethers were identified. While not intending to be bound by theory, it is suggested that modifying the ring with boron as previously described or by synthesis of a more conventional boronic acid crown ether derivative would be expected to improve the affinity of the ether for the saccharide.

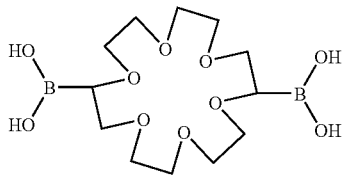

Techniques for Placement of SMMRs into the Epidermis

For any of the embodiments described herein, a series of techniques exist that allow the placement of specialized fluorescent or absorptive molecules (SMMRs) into the epidermis, epithelial cells, or peripheral cells (for organs or muscle tissue during invasive surgery). Penetration of the sensor composition can be accomplished using an active transport technique, such as, for example, electroporation, laser poration, sonic poration, ultrasonic poration, iontophoresis, mechanical poration, solvent transport, direct application by painting, tattooing methods involving application by needle, an equivalent electrical tattooing technique; or most preferably by using passive transport using special solvent and reporter molecule mixtures. Passive transport may be used to allow small molecules of typically 100 Daltons (Da) to 1000 Da to enter tissues and cells.

Exemplary methods for passive transport are pressurized delivery and wicking. The method is comprised of a direct measurement of the fluorescence of SMMRs placed within epidermal cells, i.e., keratinocytes. This fluorescence is measured using molecules with specific properties for defining glucose metabolism in epidermis and for inferring the magnitude of the change in fluorescence signal to blood glucose concentrations.

Incorporation of a reporter into the tissue without use of an external device is preferred, due to the reduced cost, convenience, and ease of use. Such a passive transdermal delivery solvent system must be accurate and safe. Thus, a more elaborate solvent regime must be applied than that used for the active mechanisms such as tattooing, electroporation, and ultrasonic poration. Suitable solvent systems useful for passive transdermal delivery include creams, emulsions, and oils. These solvent systems provide passive transdermal stain delivery into the tissue at a depth of less than 50 microns. The following additives aid the process of tissue penetration for SMMR and create a diffusion rate enhancing solvent system: Soybean Oil, Hazelnut Oil, Jojoba Oil, Sweet Almond Oil, Olive Oil, Calendula Oil, Apricot Kernel Oil, Grapeseed Oil, Wheat Germ Oil, refined Light Mineral Oil, Triundecanoin (Akomed C), Undecanoic acid, Caprylic/Capric Glycerides (Akoline MCM), Caprylic/Capric Triglycerides, Propylene glycoldiester of caprylic-/capric acid, Emu oil, all as low viscosity mixtures, preferably less than 35 cSt at 35° C. In addition, mixtures of one or more of the above oils in combination with a non-polar dilution solvent can also be used. The solvent system is allowed to passively penetrate the tissue for from about 1 minute, about 5 minutes, about 10 minutes, about 30 minutes to about 2 hours to allow diffusion of the SMMR into the appropriate tissue layer(s).

In addition, penetration of the sensor composition to the desired depth can be accomplished by combining the composition with various molecular size attachments.

After the reporters are injected into, or applied to the surface of the tissue, they are allowed to penetrate in proximity to superficial cells of tissues and organs at a depth from the surface of the cells of from about 10 μm to about 1500 μm. For measurement of specific metabolites, the preferred placement of the reporters should be near the surface of the tissue (i.e., about 10 to about 175 μm) yet be representative of the overall metabolic state of the tissue in which the reporters are placed. The reporters may also be placed at a greater depth into the tissue. The precise placement of the reporters is controlled by the combination of its molecular properties, including: specific molecular size (i.e., 100 daltons to 100 kilodaltons), polarity, charge, structure, pKa, solubility, the size and type of molecular attachments or anchors, the solvent system used, as well as the specific conditions used for poration (if required). A combination of these factors provides the ability to control the location, diffusion rate, and duration or lifetime of the SMMR within the tissue or organ layers.

The dyes may be introduced into the skin by passive diffusion over a period of 24-48 hours, more preferably over a period of 2-6 hours, and most preferably in 10 seconds to 5 minutes. Contemplated diffusion times include periods less than 48 hrs, 24 hrs, 10 hrs, 6 hrs, 2 hrs, 1 hr, 30 min, 15 min, 10 min, 5 min, 1 min, 30 sec, 10 sec, or 1 sec. With passive absorption, a molecule is placed on the surface of the skin and allowed to penetrate in proximity to the epidermal cells (keratinocytes) directly above the basal layer (stratum basale) at a depth from the surface of skin from 10 μm to 50 μm and up to 175 μm in the pits of the stratum basale extending into the dermis between the dermal papillae. For measurement of glucose, the placement of the SMMR is below the stratum corneum yet above the dermis, more specifically in the stratum spinosum or stratum basale immediately above the upward extensions of the dermal papillae. This SMMR placement is accomplished by varying the combination of the polarity and charge on the SMMR, the size of molecular attachments or anchors, as well as by the polarity and hydrophilicity characteristics of the solvent system. The specific conditions for poration or passive diffusion for placement of the SMMR in the skin are controllable factors. Using any combination of these factors, it is possible to control the localization of the dye within the skin layers and target cells.

Another embodiment of the reporter application involves the use of a reservoir containing reporter, which is used to automatically or manually dispense a dose of the reporter mixture topically prior to poration or passive transport. For measurement of metabolites and precursors the reporter is placed in the tissue at a depth of up to 300 µm. A solution of 10-400 µL volume made from 1-50 µM SMMR in a solvent system penetrates into the tissue for some period of time to allow activation following passive diffusion kinetics. Once activated the change in fluorescence or absorption response of the tissue cells to changes in extracellular and intracellular metabolite or precursor concentrations is monitored directly using an optical reader. Irritant chemicals such as salicylic acid can be used to facilitate the penetration of reporters into skin or peripheral tissue.

In another embodiment, a small disposable film patch composed of polyolefin, polyester, or polyacrylate and having an SMMR dispersed into a transfer gel applied to the transfer side of the film patch, is used for SMMR application. The patch is applied with the gel side toward the skin and the gel contacts the external surface of the skin. Following the gel application, a poration or passive transfer technique is used to introduce the mixture into the appropriate skin layer(s) (as described above). Another embodiment of the SMMR application involves the use of a reservoir containing molecular tag or SMMR. This reservoir is used to either automatically or manually dispense a dose of the SMMR mixture topically prior to poration or passive transport. A non-limiting example of a topical dose is a small dot or spot from 100 µm to 5 mm. A smaller area is preferred in most embodiments, but a larger area is also contemplated. For measurement of glucose, the SMMR is placed in the keratinocytes at 30 µm to 50 µm and up to 175 µm so that placement is precisely in the specific layer of the epidermis (e.g., above the dermal papillae and within or above the stratum basale), within a comparatively homeostatic keratinocyte stratum. The molecular tag or SMMR penetrates into the skin for some period of time (depending upon molecular size and solvent mixture used) to allow activation following passive diffusion kinetics (i.e., mass transport). Once activated, the change in fluorescence response of the skin cells to changes of extracellular and intracellular glucose is monitored directly using an optical reader.

An active mechanism utilizing tissue permeation, electroporation, laser poration, or ultrasonic poration is another procedure for introducing SMMRs into the skin. Pulse lengths for poration technologies are provided below. An example of an ultrasonic poration device includes those manufactured by Sontra Medical Corporation, Cambridge Mass. Sontra and other commercial manufacturers of devices useful for this application have previously described a method for sensing glucose directly in the interstitial fluid surrounding the skin cells by removing fluid or gaining access to removed fluid for analysis. See e.g., J A Tamada, M Lesho and M J Tierney, "Weekly Feature: Keeping Watch on Glucose—new monitors help fight the long-term complications of diabetes." IEEE Spectrum Online, Jun. 10, 2003 at website: <http://www.spectrum.ieee.org/WEBONLY/publicfeature/apr02/glu.html> (last visited Jun. 26, 2003). The methods and compositions of the invention do not remove fluid but, rather, place small quantities of solution containing low concentrations of SMMRs into the skin for direct reading of the SMMR fluorescence spectral characteristics as an indication of both epidermal skin and blood glucose levels.

For some reporters above 1,000 daltons in size, electroporation may be used to introduce reporter into tissue. Electroporation has been utilized for introducing chemotherapy treatments, for introduction of DNA into living cells and tissues, and broadly recommended for introducing materials into tissues for cosmetic or medical treatment applications. If poration schemes are used, the optimized settings for an electroporation device are achieved by commercially available or by a customizable device having settings that provide conditions as described within this invention. Commercial systems utilizing a square wave voltage pulse have been described within the literature, such as those available from Genetronics Biomedical Corporation, 11199 Sorrento Valley Road, San Diego, Calif. 92121. Such a small device can be inexpensively made to have one or more constant settings for the optimized conditions disclosed for this invention.

Electroporation uses a short pulse electrical field to alter cell membrane permeability. Micro-pores form in the membrane of skin cells allowing the introduction of various molecular size mixtures into the cells at an appropriate depth of penetration for this specific inventive application. When the electric field is discontinued, the cells return to normal and one or more SMMRs introduced into the cell using the technique remains at the cellular site specifically within the epidermal cell until either the dye is chemically degraded and disposed of within the tissue or is sloughed off in a normal desquamating cycle. The process of sloughing off (or desquamation) follows a normal ten-day to twenty-day (typically fourteen-day) cycle as the residence time of epidermal keratinocytes moving from the basal layer (stratum basale) to the desquamating layer of the stratum corneum.

When employed, electroporation is optimized for use in this invention by selection of voltage range (from about 40 to 90 Volts), gap distance (from about 0 to 2 mm), pulse length (from about 150 to 250 ms), number or pulses (from about 1-10), pulse interval (from about 5 to 60 s), specific electrode design, and desired field strength (from about 40 to 60 V/cm). In addition, the selection of molecular tag molecules, solvent molecules, concentration, and lag times relative to measurement onset is determined as precisely as possible. In certain embodiments, specific parameters are determined empirically using specific solvent and SMMR selection. For example, optimization of electroporation involves the following specifications:

1. Output voltage range: 0 to +200 VDC;
2. Discharge capacitor (Cdis) values in microfarads are on or about: 200, 500, 700, 1000, 1200, 1500, 1700 µF;
3. Pulse type: exponential decay;
4. Pulse RtCdis decay time constant where Rt (total)=5+ Rskin in parallel with 50 ohms. If Rskin>>50 ohms then Rt=55 ohms and Rt×Cdis=11, 27.5, 38.5, 55, 66, 82.5, 93.5 milliseconds (ms).

Electroporation also facilitates the delivery of dyes bound to large molecules that serve as anchors such as polymer beads, large polysaccharides, or colloidal particles. These approaches are contemplated as being within the invention, but are less advantageous in that the particles are often too massive to pass through the stratum corneum without active poration or mechanical injection. Once in the skin, they do not readily dissolve or organically reabsorb into the body. Such less desirable approaches would create undesirable particles that would either remain in place indefinitely or accumulate in lymph nodes, in other circulatory cavities and/or in other organ sites.

Reporters of the invention can be made with specific properties such that they are retained only within skin cells (keratinocytes) where they report on glycolytic activity and do not harm or affect cellular metabolism. These reporter compounds are sloughed off after a few days, even when permanently integrated into, or attached to, keratinocyte cells. The small quantity of reporter(s) that diffuse away from the epidermis are rapidly degraded within the body and are completely eliminated within a few days. In preferred embodiments, reapplication of the reporter(s) is relatively easy to perform. The process of sloughing off (or desquamating) follows a normal ten-day to twenty-day (typically fourteen-day) cycle as the residence time of epidermal keratinocytes moves from the basal layer (stratum basale) to the desquamating layer of the stratum corneum. Thus, reporters are developed to be applied once every 2 to 3 days, preferably every 3 to 4 days, and more preferably every 5 or more days.

More advanced solvent systems useful for passive transdermal delivery include, but are not limited to, e.g., creams, emulsions (both oil-in-water and water-in-oil), oils (ointments), gel film patches, a reservoir device, paints, polar solvents and non-polar solvents. Non-polar solvents are preferred, as these are most miscible with the SMMRs of the invention and the stratum corneum lipids cementing the keratinocyte lamellae in place. "Lipid solvent systems" have been reported in the literature for use in transdermal drug delivery, and are composed to resemble the chemistry of stratum corneum lipids. Such a mixture may also be used to place the SMMRs into the appropriate point within the epidermis. Such a suggested mixture includes: (w/w): ceramide (50%), cholesterol (28%), palmitic acid (17%) and cholesteryl sulfate (5%). See, e.g., Downing et al.: Partition of dodecyl sulfate into stratum corneum lipid liposomes. *Arch. Dermatol. Res.* 1993, 285:151-157.

The objective of each of these solvent systems is to provide passive transdermal SMMR delivery into the skin at a preferred depth of from about 10 to 175 μm (microns), more preferred from about 20 to 100 microns, and most preferred from about 20 to 50 microns. For example, the following solvents as additives to the final SMMR mixtures are added to the skin to initiate passive transport of the SMMR to the target cellular site. The materials listed aid the process of skin penetration for SMMRs and create a diffusion rate enhancing solvent system for transdermal delivery: dimethyl sulfoxide, ethanol, isopropanol, chloroform, acetic acid, saturated hydrocarbon solvent (with from 10 to 40 carbons as linear or branched chained molecules), soybean oil, hazelnut oil, jojoba oil, sweet almond oil, olive oil, calendula oil, apricot kernel oil, grapeseed oil, wheat germ oil, refined light mineral oil and mineral oil spirits, triundecanoin (akomed C), undecanoic acid, caprylic/capric glycerides (akoline MCM), caprylic/capric triglycerides, propylene glycoldiester of caprylic-/capric acid, and emu oil. All are low viscosity mixtures, preferably less than 35 cSt at 35° C. In certain embodiments, mixtures of one or more of the above oils are used in combination with a non-polar dilution solvent.

Factors that control the depth of penetration of the SMMR and its compartmentalization into the cells and domains of the epidermis include the polarity and partition coefficient of the SMMR as well as the solvent and the molecular size. The SMMR compound may also be derivatized so that it is readily taken up by the cell and then acted upon by enzymes that chemically alter the SMMR to prevent it from leaking out of the cell. One advantage of this type of approach is that the SMMR is only taken up in its active form by viable cells. Predictive schemes for determining appropriate derivatization of SMMR compounds are provided below. Alternative methods of derivatization well known to those skilled in the art are also contemplated as part of the invention.

The physical properties of the solvent system that strongly influence permeability in the skin include the molecular size, the vapor pressure, the water solubility, and the octanol water coefficient. Smaller molecular size increases the diffusion coefficient. The vapor pressure controls the balance between diffusion into the skin and evaporation from the surface. The water solubility and the octanol water partition coefficient determine the miscibility of the SMMR solution between aqueous interstitial fluid and hydrophobic core of the cell membrane.

For a passive solvent delivery system, the depth of penetration of the SMMR is strongly dependent on the volume of solvent added. Typically, the volume of SMMR used is from 10 μL to less than about 100 μL. Preferably, the concentration of SMMR is from 10 to 500 μM, more preferably from 100 to 300 μM, and most preferably from 150 to 250 μM. Target cells are exposed to extracellular concentrations in the range of 1 to 10 μM. Dilution of the SMMR concentration arises because of the diffusion properties from the surface of the tissue to the target cell site.

The proposed volume range added to the skin or other tissue is preferably from 1 to 50 μL, more preferably from 5 to 20 μL, and most preferably from 5 to 15 μL. Alternatively, a gel patch is used containing an SMMR coated surface of approximately 6 mm in diameter consisting of a concentration of SMMR preferably from 10 to 500 μM, more preferably from 100 to 300 μM, and most preferably from 150 to 250 μM.

Solvent systems used for SMMRs may be adjusted depending upon their molecular properties and compatibility with the specific SMMR being delivered. For example, solvent hydrophobicity and polarity are noted along with the solubility properties of the SMMR, which will all have an effect on the movement of the SMMR into the tissue. Each SMMR has a certain affinity for the solvent and the tissue. The solvent's activity for delivering the SMMR directly to target tissue is a matter for empirical testing. One preferred embodiment of the invention uses an SMMR dissolved in DMSO (dimethyl sulfoxide) and further diluted in a saturated hydrocarbon solvent (with from 10 to 40 carbons as linear or branched chained molecules), or an alcohol (with from 2 to 4 carbons) at a volume ratio of 5:95 to 20:80, respectively. The optimum volume of DMSO in the delivery solvent is less than 20 percent, as the DMSO is used to facilitate dissolution of the SMMR into the carrier hydrocarbon mixture. The mixture is added to the tissue in the concentrations and volumes described above.

A gel patch may be used to apply the SMMR. In one embodiment, a gel contains the SMMR in a volatile hydrocarbon solvent in suspension with a polymer such as PVA (polyvinyl alcohol). When placed against the skin or other living tissue, the heat of the skin causes the SMMR (dissolved in the PVA-hydrocarbon solvent) to diffuse into the skin. The final diffusion depth is controlled by length of application time. Volumes below 100 μL minimize extraneous transdermal delivery and maximize delivery into the epidermis target area. Optimum passive solvent delivery is attained by using a solvent mixture or emulsion that facilitates the movement of SMMR across the stratum corneum into the epidermis, but then dissipates rapidly to limit movement of the SMMR away from the target area. Solvent systems that have the lowest toxicity include water, saturated hydrocarbon oils, polyethylene glycols and glycerol. Solvents systems that include alcohols and dimethyl sulfoxide are less favored in this application since these solvents are less biologically inert.

The SMMRs are applied directly to the surface of the skin and then passively allowed to penetrate the skin for a period of 1 minute to 5 hours, more preferably less than 4 hours, and most preferably less than 1 hour. Ideally, a solvent delivery system would be developed to provide SMMR delivery to the target tissue in less than 1 hour, more preferably less than 30 minutes, and most preferably in less than 5 minutes. This time period allows the passive diffusion of the SMMRs into the appropriate epidermal cells.

Once the one or more SMMRs are activated as a result of placement within the skin, measuring fluorescence monitors the response of the skin cells to glucose. As described herein, the fluorescence mechanism used is either a direct or indirect indication of the glucose concentration in the target cell environment. Fluorescence is typically measured using an optical reader. The optical reader calculates the skin response to glucose, applies first principles mathematical models to the response (as described below and shown in FIG. 7), and provides a determination of the blood glucose levels (See FIGS. 3, 8-9). The choice of the particular commercially available or custom designed optical reader that is compatible for use with the methods and compositions of this invention is within the ability of one skilled in the art of the invention.

Apparatus and Methodology for Glucose Detection Using SMMRs

Instrumentation Required for Reporter Monitoring

The instrumentation required to detect changes in reporter signal may consist of simple light emitting diode sources combined with low-cost solid-state detectors. The mechanism of signal extraction relating to a biochemical or physiological process is derived from the elucidation and measurement of key metabolic pathways. The reporters are excited, and the remitted energy detected over the wavelength region of 190 nm to 850 nm (See FIG. 38). The three mechanisms of measurement for metabolites or precursors using the reporters of the invention include (1) using reporters to increase the signal-to-noise of native autofluorescence signals indicative of human reductive metabolism [$FADH_2$, NADH, and NAD(P)H], (2) using reporters for selection and enhancement of specific metabolite and precursor signals in tissue that are indicative of metabolic state and allow determination of changes in metabolism [$Ca^{2+}$, lactate, oxygen], and (3) using reporters to directly measure the presence of intracellular or extracellular molecular metabolites [protein-FL, and protein-$^3$FAD*].

All three mechanisms of signal identification and enhancement allow utilization of low-cost, hand held spectrophotometric equipment (e.g., LED excitation and diode detectors) that is simple in design and does not require advanced or complicated computational algorithms. Such equipment is not harmful to subjects and requires just an additional disposable component (other than a calibration strip) to prepare the subject for metabolite monitoring. A measurement device approximately the size of a personal cell phone having quality features, such as those which allow the user to determine whether a specific measurement is valid, or whether a repeat measurement is required, can be used. Such a hand-held, battery powered device is intended to be used either occasionally, or on a continuous, real-time monitoring basis for subjects requiring serious health management regimes. A single calibration allows continuous monitoring for up to several hours. A calibration technology that utilizes a calibration strip, which mimics the optical response of the subject and allows freedom from continuous correction using primary analysis devices, can be used. Other calibration technologies contemplated by the invention will be readily discerned by those skilled in the art.

As an example, to use the device, the subject or physician prepares the area to be measured using the enhancement technology, which is painless and requires a patch (similar in appearance to a Band-Aid® bandage), paint, or spray to be applied to the targeted tissue area. This treatment conditions the tissue area for from a few minutes up to 30 days, depending upon the SMMR properties selected and the depth at which it has been deposited in the subject tissue. The device is then calibrated using a calibration strip and is ready to make measurements for up to 2 hours or more, without requiring additional calibration. The subject or physician examines the conditioned area with the sensor and makes a measurement. Typically, the measurement takes less than about 5 seconds, and the sensor provides the appropriate metabolite concentration or reports that a repeat measurement is required.

In another embodiment, if the photophysics of fluorescent dyes are considered, the fluorescence changes associated with the SMMR and the analyte may also be monitored using fluorescence lifetime technology. One preferred embodiment for such a hand held device capable of measuring lifetime changes is to use a phase and modulation spectrometer, which is a device constructed from a radio frequency modulated light emitting diode and a miniature photomultiplier or photodiode, whose signal is amplified by a phase sensitive amplifier. Such devices have been well characterized in the literature and are commercially available in a variety of forms. Manufacturers of such devices include: Photon Technology International, Inc., 1009 Lenox Drive, Lawrenceville, N.J. 08648; PicoQuant GmbH, Rudower Chaussee 29 (IGZ) 12489 Berlin, Germany; Tecan Systems Inc., 2450 Zanker Road, San Jose, Calif. 95131; Thermo Oriel, 150 Long Beach Blvd., Stratford, Conn. 06615. These devices measure both the degree of modulation of the fluorophore and the phase shift of the emission relative to the excitation light, and these two parameters are then related to the lifetime of the dye. Determination of these parameters at a number of frequencies increases the accuracy of the device.

Phase Sensitive Flash Photolysis Apparatus

Figure 46:
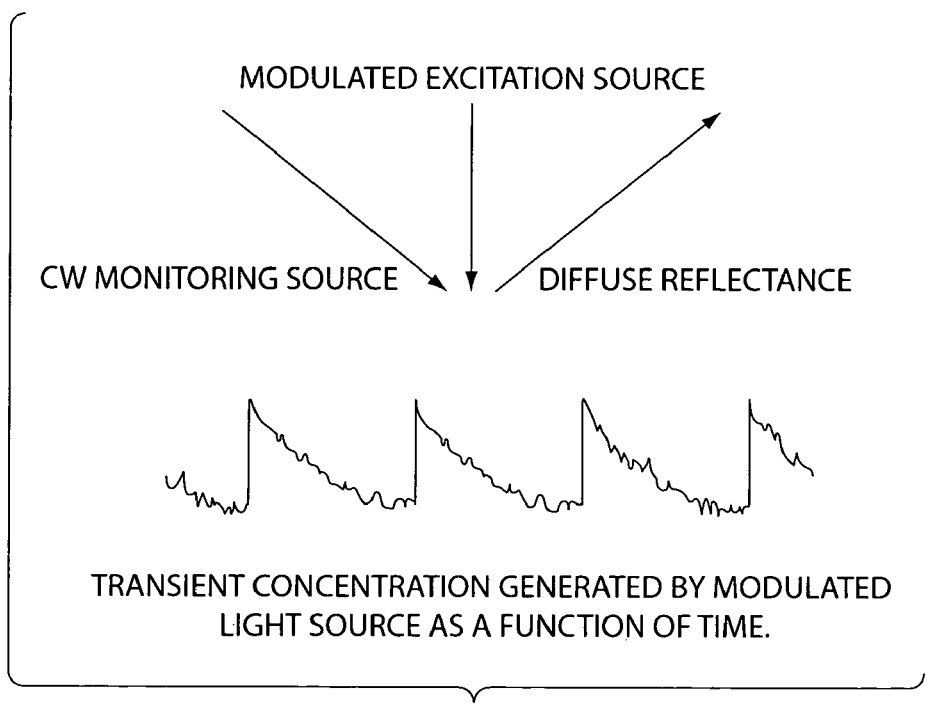
FIG. 46. Illustration of the excitation scheme and signal generated by a phase sensitive flash photolysis apparatus.

A suggested sensing apparatus can be miniaturized and measurement of the phase shift gives an indication of the lifetime of the transient species. This is an advantage over single pulse flash photolysis apparatus that typically require mJ pulse energies to generate transient species with sufficiently high concentration to be observed. In one embodiment, the apparatus described here is capable of detecting transients with a change in absorption of $10^{-5}$ (FIG. 46).

This apparatus is miniaturisable and the phase shift gives an indication of the lifetime of the transient. This is an advantage over single pulse flash photolysis apparatus that typically require mJ pulse energies to generate transient species with sufficiently high concentration to be observed. In one embodiment, the apparatus described here is capable of detecting transients with a $\Delta$ absorption of $10^{-5}$.

The diffuse reflectance light is modulated by the absorption of the transient therefore the instrument will reject scattered light. Selectivity is improved over a conventional spectrometer because the requirements for a transient to be detected are that the ground state has absorb at the correct wavelength, the transient species generated has to absorb at the correct wavelength and the transient generated has to have a defined lifetime. Triplet states typically have very different absorption spectra than ground state species and may occur at longer or shorter wavelengths than the ground state. This is an advantage over fluorescent molecules with small Stokes shift.

Dual processor, 1 GHz computer set up with Spartan.

The idea of using light to drive enzymatic reactions is not new (see for example http://chem.ch.huji.ac.il/~eugeniik/photo_enzymes3.htm). However, taking the cofactor from an enzyme and designing a small molecule system that can be driven to carry out the same reaction in the presence of light has not been reported. Enzymatic reactions are catalyzed essentially by shifting the position of equilibrium when the reactants are brought into close proximity. Photochemical reactions are powered by the energy supplied by photons.

This is considerable; to generate the same number of excited states in a sample with an absorption of 1 and molar absorption coefficient of $10^5$ $dm^3$ $mol^{-1}cm^{-1}$, with 1 mJ of 400 nm light would require a temperature of nearly 30,000 degrees Celsius!

The Brunet paper [Brunet, 2002 #562] refers to some theoretical studies that show, in the excited state there is an increase in the dipole moment. This change is brought about by an increase of electron density on the carbonyl groups. The magnitude of this change is not sufficient to generate a charge transfer state but it is obvious if the binding of an analyte interferes with the charge distribution of the excited state then this would provide a sensitive transduction mechanism. A change in electron density with the binging of glucose is caused by the use a boronic acid. The Brunet behavior can be modeled using Spartan.

Measured the repetition rate of the nanolase 355 nm tripled YAG. Using the 500 MHz Tektronix scope and a photodiode the frequency is 9 kHz. This is consistent for a transient with a lifetime of about 40 μs.

Set up the flash photolysis. Calculated using a 5 mJ laser at 9 kHz, an OD of 1 and a difference absorption coefficient of 45000, then for a 1 cm pathlength an OD should be 0.006. This should be simple to measure. A change in oxygen concentration with a porphyrin can also be detected. Subsequent experiments involve glucose oxidase.

Figure 47:
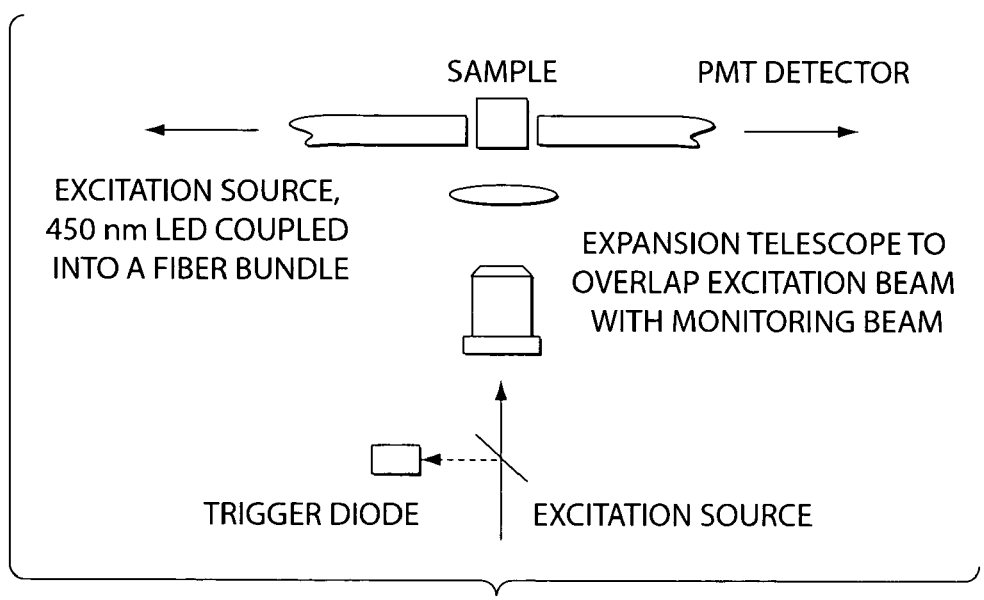
FIG. 47. Schematic overview of a phase sensitive flash photolysis apparatus.

Apparatus set up. The apparatus has been set up as follows: The monitoring light wavelength is chosen where there is maximum difference between the excited state absorption and the ground state absorption. The excitation wavelength is chosen where there is maximum absorption of the ground state. The photomultiplier is coupled to a lock-in amplifier. The trigger diode generated the signal for the reference channel. The excitation source used in this experiment was a nanolase tripled YAG that has repetition frequency of 9 kHz. A telescope was made from a microscope objective and a cylindrical lens (FIG. 47).

The experiment was carried out with a solution of deuteroporphyrin in ethanol. The sample was flushed with nitrogen first to remove dissolved oxygen. Under these conditions, the lifetime of the excited triplet state should be about 100 μs. The difference molar absorption coefficient is about 40,000 $dm^3$ $M^{-1}$ $cm^{-1}$. The laser energy was measured at the sample to be 1.8 mJ. With these figures, it was calculated that the sample should generate a transient with a difference absorption of about 0.006. Although the lock-in amplifier detected a signal, the phase shift of this signal did not change when oxygen was readmitted into the sample and is probably residual fluorescence.

Instead of using the lock-in amplifier, the signal from the PMT was coupled to a Tektronix 500 MHz digital scope. Averaging 512 pulses, it is possible to observe a change in absorption of about 0.01% that corresponds to an absorption change of about $4 \times 10^{-5}$. No transient at all was observed under these conditions; however, such a small transient can be measured using this device. It would be expected that even smaller signals could be observed with the lock-in amplifier. The sensitivity of the system would be sufficient to observe electron transfer in glucose oxidase in the presence of glucose.

Chromatography on Saccharide Solutions Containing Glucose

The purpose of this experiment is to set up a chromatography system that can be used to separate glucose from other saccharides and to detect glucose using Arg-327. To set the chromatography system up we need a rapid reliable test for glucose. HPLC methods use amperometric methods or refractive index changes to monitor saccharides. Two well known methods are the Fehling's test for reducing sugars and to use enzyme activity.

The Fehling's method uses two solutions commonly known as Fehling's A and B. Fehling's A consists of 7 g of hydrated copper(II) sulfate dissolved in 100 mL of distilled water. Fehling's B is made by dissolving 35 g of potassium sodium tartrate and 10 g of sodium hydroxide in 100 mL of distilled water. The Fehling's reagent is made from equal volumes of Fehling's A and Fehling's B are mixed to form a deep blue solution. The test is really one for aldehydes and since a small percentage of solvated glucose exists in an open chain, aldehyde form, it gives a positive result to the test.

The cupric ion in the Fehling's A solution acts as a mild oxidizing agent, the tartrate complexes with the cupric ion and prevents copper hydroxide from precipitating from solution. The overall reaction is:

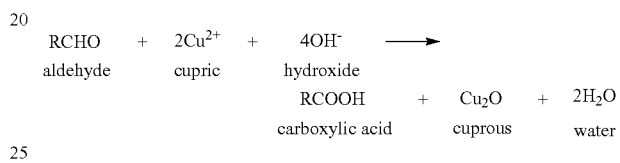

Cuprous oxide is insoluble in water and forms a brick red precipitate. The oxidation of glucose could be carried out photochemically to generate fluorescent products.

The method chosen to develop the chromatographic system is an enzymatic one. The method is quantitative and relatively specific:

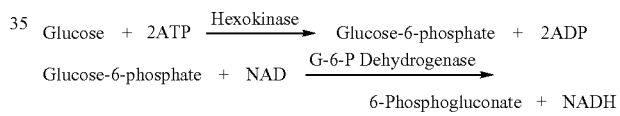

An equimolar amount of NADH is generated for the amount of glucose consumed. The NADH may be monitored by either its absorption at 340 nm or its emission at 450 nm.

The proposed experiment is to set up a number of small packed columns and to determine the optimum conditions for viewing of the glucose eluting from the column.

In Vitro Glucose Probe not Requiring Strip Use

Figure 48:
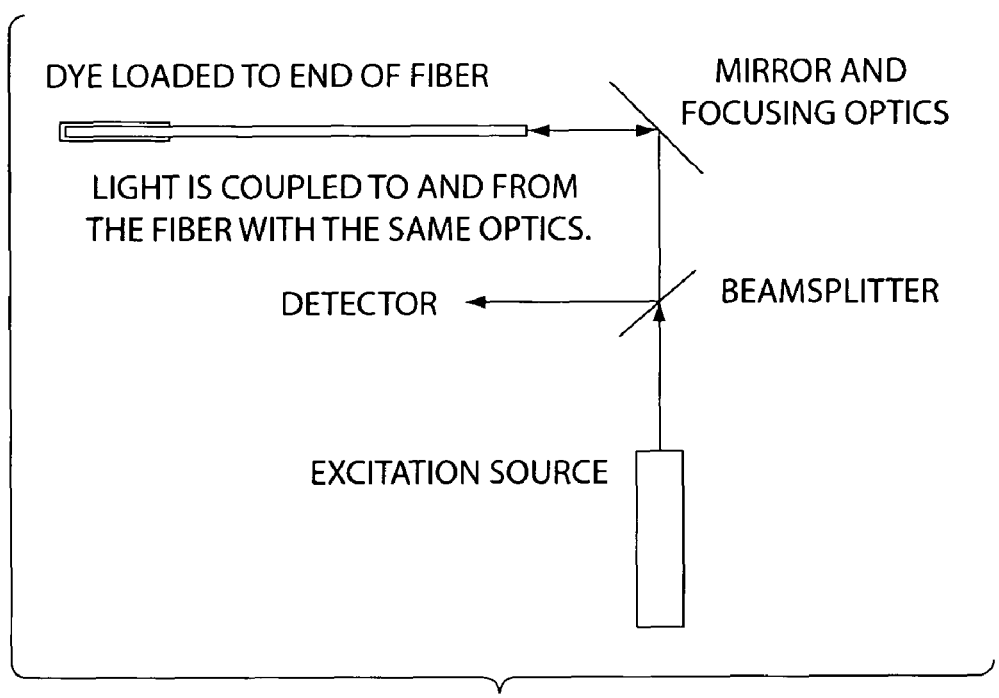
FIG. 48. Schematic overview of an in vitro glucose probe not requiring strip use.

This probe is made by attaching Arg-327 to the end of fiber optic and monitoring the fluorescence of this material using the following apparatus (FIG. 48).

The device is calibrated by dipping the end of the fiber in glucose free medium and a known concentration of glucose. Dipping the fiber into an unknown glucose solution then gives a fluorescence response that is correlated with the glucose concentration. A suitable dye to carry out this experiment is Arg-327.

To develop a strip type of device two approaches were used. First, slurries of materials that may be used as TLC plates were made and secondly different materials were tried in order to image spots of glucose placed on the plates.

Plates were made up by dipping clean microscope slides in slurries of Silica, $TiO_2$ and Carbomer 981 in methanol. Of these, the plates made with $TiO_2$ came out the most uniform. If the silica used for these plates is too coarse, commercial plates can be used. The Carbomer 981 slurry that dries to a clear film is a commercial material that is used to control viscosity in cosmetics.

To view glucose spotted onto commercial silica plates 10% (w/v) solutions of chloranil and phenyl boronic acid were co-spotted with the glucose (300-mg/dL) and the result viewed under UV light. Chloranil was used because it is an oxidant and is known to undergo a color change when it is reduced. Phenyl boronic acid was used as a model compound for Arg-327 since it can be viewed under UV light. There is some indication that the chloranil reacted with the glucose.

The experiment was repeated with alkaline glucose.

Used Arg-327 as one of the visualizing materials. Compared chloranil and Arg-327 at a concentration of 1% (w/v) with and without glucose. There is visually little difference between the spot with and without glucose. A dark spot can be seen with chloranil and glucose. Also spotted the plate with 1%, 0.1% and 0.01% Arg-327. All three spots are visible but the dynamic range that can be judged with the eye is poor.

A sample of Rose Bengal was made up and run on the apparatus to observe transient absorption.

Measured fluorescence with fluorolog. Fitted the fluorolog with the 3 mm fiber bundle. The fluorescence of the Arg-327 decreases by about 30% in the presence of glucose. This is the opposite of what happens in solution. Plates can be pretreated with the Arg-327 and/or a gel can be used as the stationary phase.

Strip Technology

To build a monitor using strip technology different chemistry to be applied. Molecules bound to gold surfaces can be used to increase the fluorescence quantum yield. Applying this idea to strip technology allows one to link fluorophores to a gold surface. The fluorophore gold linkage is synthesized by incorporating a thiol group on the chromophore, i.e.

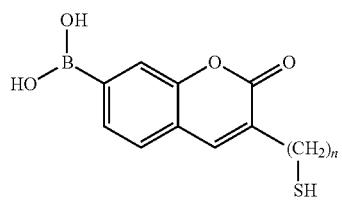

The hydrocarbon chain —(CH$_2$)$_n$— is of such a length that the fluorescence of the dye is enhanced by the proximity of the gold surface [see for example, "Intrinsic fluorescence from DNA can be enhanced by metallic particles." *Biochem. Biophys. Res. Comm.* Lakowicz, J. R., Shen, B., Gryczynski, Z., D'Auria, S. and Gryczynski, I. (2001) 286 875-879 and references therein.]. The correct length for the chain is determined experimentally. If the chain is too short then the fluorescence of the molecule is quenched completely, if the chain is too long then there is no surface effect. This phenomenon allows molecules to be designed that have a sensitive transduction mechanism for the presence of glucose; their fluorescence properties are dependent on the presence of the gold surface. Such technology may be incorporated either into a strip type device or into a MEMS type device. If a fiber tip was coated with a film of gold then this type of molecule could be bonded to the fiber by the interaction of the SH and the gold film.

Compounds Used for Glucose Fluorescent Strip Demonstration

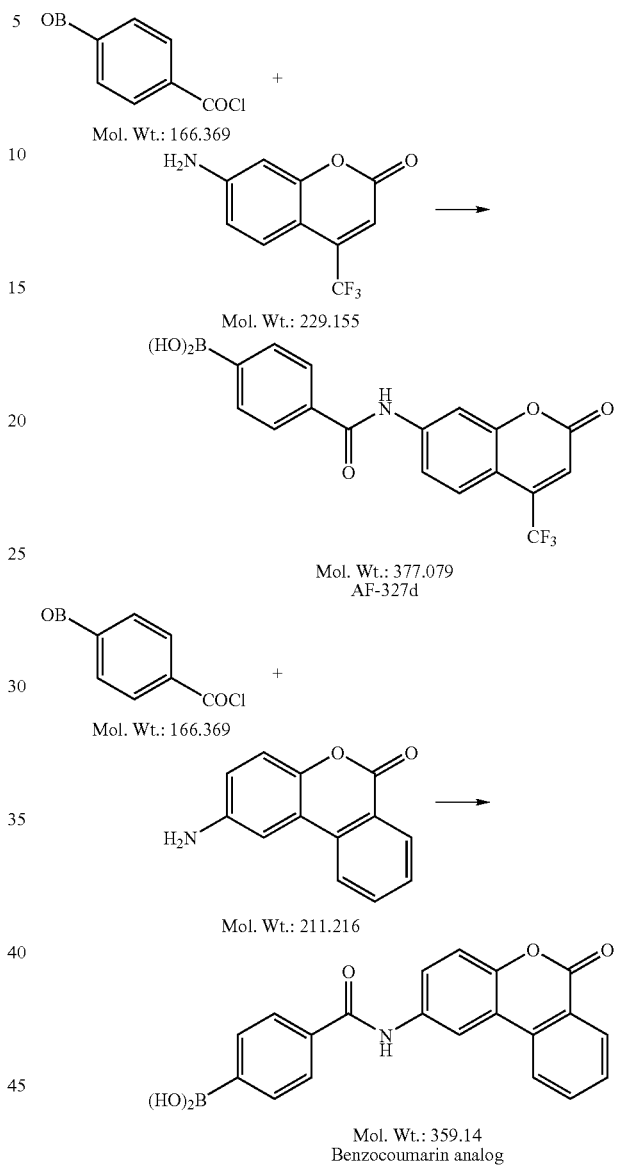

AF-327d is a re-synthesis. In parallel, we will make and test the Benzocoumarin analog, due to the expectation that it may have a longer emission wavelength, if it's fluorescent.

Strip Design

The use of strip type technology opens up a number of possibilities that are not available to non-invasive technologies. Patents that have been published for strip technology include features to facilitate blood flow on the strip and to remove confounding factors such as red blood cells.

For example, U.S. Pat. No. 5,708,247 issued to Lifescan includes features such as a silica filter to remove red blood cells and a mesh to guide the liquid sample to the electrodes on the strip.

Figure 49:
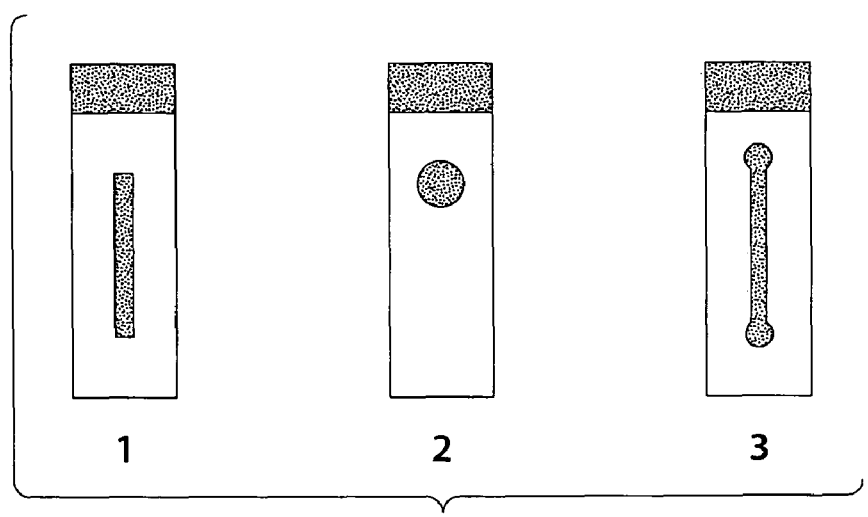
FIG. 49. Strip technology designs when using direct fluorescence molecules.

The construction of a strip for a spectroscopic sensor uses some of these features to improve selectivity and to ensure rapid mixing of the blood glucose and the sensor material (FIG. 49). Prototype substrates have been manufactured from glass, which may be difficult to engineer but is convenient to use as a reusable prototyping breadboard in testing.

The following patterns have been milled in glass. Each of the patterns described is 0.6 mm deep. Each substrate is 75 mm×25 mm×1 mm.

The gray strips are an area where the prototype can be labeled; the green area is the cutout to a depth of 0.6 mm. Other shapes were also generated but these were the most accurate and reproducible to be made. The green portion of each slide may be filled with aqueous or alcoholic gels, with silica and the third slide also has a region to apply solvents.

For the experiments that were carried out with these systems a silica derivatized with a four carbon chain was used. The silica was applied in a methanol slurry and the solvent allowed to dry. The derivatization prevents interaction of the silica with the boronic acid sensor.

The technology is using chromatography to separate glucose in the blood from proteins and cellular material. The development time for the strip is dependent on the dimensions of the cutout. The sample is applied at one end of the strip and interaction between the glucose and the sensor occurs at the other end. Prototype 2 may be used to look simply at the interaction of the sensor molecule and glucose.

Using this type of approach, molecules that have a large response to the presence of glucose but poor selectivity may be used as the sensor with interfering substances being removed by the material on the substrate.

Silica gels were the only material tried on these plates but other materials that would be suitable include aqueous and methanolic gels. The physical dimensions of the strip and the nature of the gel or silica determine how rapidly the strip responds to the presence of glucose.

If the solutions are brought together on plate 2, with no mixing then the response time may be as much as 100 seconds. By filling the cavity with small beads or silica, capillary action can greatly speed up the mixing time.

This type of technology also lends itself to the use of fluorescent sensors on gold films. By controlling the distance between the gold surface and the fluorophore the quantum yield of the material can be increased to unity. This phenomenon has been described many times in the literature. The advantage of this kind of approach to us is that the chemical synthesis of the molecule can concentrate on the transduction mechanism by which the binding of the glucose causes a change in the molecule. The quantum yield of the system is controlled by the gold surface.

REFERENCES

1. J. Boeseken, Advan. Carbohydrate Chem., 4, 189 (1949), C. A. Zittle, Advan. Enzymology, 12, 493 (1951).
2. H. G. Kuivila, et al., J. Org. Chem., 19, 780 (1954); J. P. Lorand and J. O. Edwards, J. Org Chem., 24, 769 (1959).
3. Lakowicz; Sinkurai; Shinkai; Wang; Singaram; James;
4. G. Springsteen and B Wang, Tetrahedron, 58, 5291 (2002)
5. Arabinose Binding Protein, 1ABE: N. K. Vyas, et al., Nature, 310, 381 (1984); Galactose/Glucose Binding Protein 1GLG; Ribose Binding Protein 2DRI.
6. "Biosensor" H. W. Hellinga, U.S. Pat. No. 6,277,627; Aug. 21, 2001; R. M. Delorimer, et al., Protein Science, 11, 2655 (2002); J. S. Marvin and H. W. Hellinga, J. AM Chem Soc., 120, 7 (1998); L. L. Looger, M. A. Dwyer, J. J. Smith, and H. W. Hwllinga, Nature, 423, 185 (2003).
7. W. Yang, et al., Angew. Chem. Int. Ed., 40, 1714 (2001). H. Eggert, et al., J. Org. Chem., 64, 3846 (1999). G.

Deng, et al., J. Amer. Chem. Soc., 116, 4567 (1994). T. D. James, et al., J. Amer. Chem. Soc., 117, 8982 (1995).
8. R. E. Dolle, J. Combinatorial Chem., 2, 383 (2000).

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A small molecule metabolite reporter compound of the following formula:

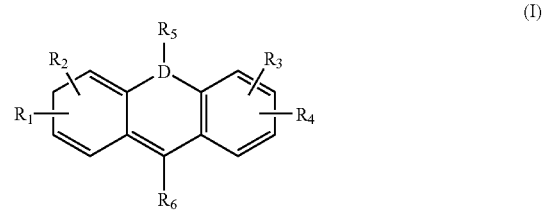

(I)

wherein
D is a heteroatom other than O;
$R_1$ and $R_2$ are different and are selected from the group consisting of H, OH, $NO_2$, $OCH_3$, A, or, $R_1$ and $R_2$, taken together with the ring to which they are attached, form $R_7$;
$R_3$ and $R_4$ are different and are selected from the group consisting of H, $$\overset{O}{\underset{\|}{}}$$

OH, $B(OH)_2$, M, or $R_3$ and $R_4$ taken together with the ring to which they are attached, form $R_8$;
$R_5$ and $R_6$ are different and are selected from the group consisting of H or

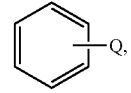

wherein Q is H, COOH, or $B(OH)_2$;
A is OH, or $$\overset{O}{\underset{\|}{}};$$

$R_7$ is

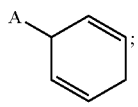

$R_8$ is

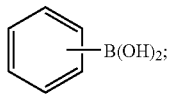

M is

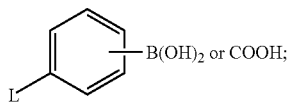

L, when present, is an amino-containing linking moiety;
$R_1$ and $R_2$, and $R_3$ and $R_4$, are adjacent to each other on the rings on which they reside; and
at least one boronic acid moiety is present; and salts thereof.

2. The reporter compound of claim 1, wherein D is N.
3. The small molecule metabolite reporter compound of claim 1, wherein:
D is N;
$R_1$ and $R_2$ are different and are selected from the group consisting of H and OH;
$R_3$ and $R_4$ are different and are selected from the group consisting of H,

and OH; and
$R_5$ and $R_6$ are different and are selected from the group consisting of H or

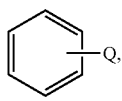

wherein Q is H, COOH, or $B(OH)_2$.

4. A small molecule metabolite reporter compound of the following formula:

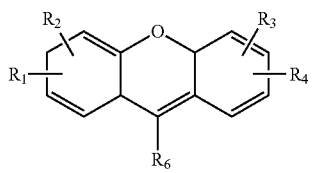

(VI)

wherein $R_1$ and $R_2$ together form $R_7$;
$R_3$ and $R_4$ are different and are selected from the group consisting of H, $B(OH)_2$, or $R_3$ and $R_4$ taken together with the ring to which they are attached, form $R_8$;
$R_6$ is selected from the group consisting of H or

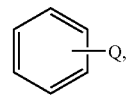

wherein Q is H, COOH, or $B(OH)_2$;
A is $NH_3$,

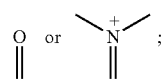

$R_7$ is

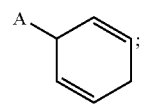

$R_8$ is;

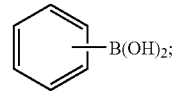

at least one boronic acid moiety is present; and
$R_1$ and $R_2$, and $R_3$ and $R_4$, are adjacent to each other on the rings on which they reside; and salts thereof.

5. The small molecule metabolite reporter compound of claim 4, wherein:
A is

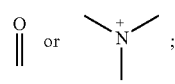

$R_3$ and $R_4$ are different and are selected from the group consisting of H and $B(OH)_2$; and
$R_6$ is

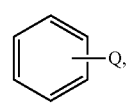

wherein Q is H or COOH.

6. A topical sensor composition comprising a compound of any one of claims 1, 2, 4, 5, and 3, and a carrier or binder.

* * * * *